US011466075B2

(12) United States Patent
Feng et al.

(10) Patent No.: US 11,466,075 B2
(45) Date of Patent: Oct. 11, 2022

(54) YEAST-BASED IMMUNOTHERAPY AGAINST CLOSTRIDIUM DIFFICILE INFECTION

(71) Applicants: Hanping Feng, Ellicott City, MD (US); James Eugene Galen, Eldersburg, MD (US); Kevin Chen, Baltimore, MD (US); Yixuan Zhu, Ellicott City, MD (US)

(72) Inventors: Hanping Feng, Ellicott City, MD (US); James Eugene Galen, Eldersburg, MD (US); Kevin Chen, Baltimore, MD (US); Yixuan Zhu, Ellicott City, MD (US)

(73) Assignee: University of Maryland, Baltimore, Baltimore, MD (US)

( * ) Notice: Subject to any disclaimer, the term of this patent is extended or adjusted under 35 U.S.C. 154(b) by 52 days.

(21) Appl. No.: 15/768,331

(22) PCT Filed: Oct. 13, 2016

(86) PCT No.: PCT/US2016/056875
§ 371 (c)(1),
(2) Date: Apr. 13, 2018

(87) PCT Pub. No.: WO2017/066468
PCT Pub. Date: Apr. 20, 2017

(65) Prior Publication Data
US 2018/0319872 A1 Nov. 8, 2018

Related U.S. Application Data

(60) Provisional application No. 62/240,810, filed on Oct. 13, 2015.

(51) Int. Cl.
*C07K 16/12* (2006.01)
*A61P 31/04* (2006.01)
*A61K 9/00* (2006.01)
*A61K 36/064* (2006.01)
*A61K 45/06* (2006.01)
*C12N 1/18* (2006.01)
*G01N 33/569* (2006.01)
*A61K 39/00* (2006.01)

(52) U.S. Cl.
CPC ........ *C07K 16/1282* (2013.01); *A61K 9/0031* (2013.01); *A61K 9/0043* (2013.01); *A61K 9/0053* (2013.01); *A61K 36/064* (2013.01); *A61K 45/06* (2013.01); *A61P 31/04* (2018.01); *C12N 1/18* (2013.01); *G01N 33/56961* (2013.01); *A61K 2039/505* (2013.01); *C07K 2317/14* (2013.01); *C07K 2317/21* (2013.01); *C07K 2317/22* (2013.01); *C07K 2317/31* (2013.01); *C07K 2317/35* (2013.01); *C07K 2317/52* (2013.01); *C07K 2317/569* (2013.01); *C07K 2317/64* (2013.01); *C07K 2317/76* (2013.01); *C07K 2317/94* (2013.01)

(58) Field of Classification Search
USPC ...................................................... 424/195.16
See application file for complete search history.

(56) References Cited

U.S. PATENT DOCUMENTS

| | | | |
|---|---|---|---|
| 2002/0018749 A1 | 2/2002 | Hudson et al. | |
| 2003/0228665 A1* | 12/2003 | Gautvik | C07K 14/635 435/69.4 |
| 2010/0272698 A1 | 10/2010 | Stateva et al. | |
| 2012/0237496 A1 | 9/2012 | Birkenfeld et al. | |
| 2013/0058962 A1 | 3/2013 | Shoemaker et al. | |
| 2014/0294826 A1* | 10/2014 | Shoemaker | C07K 16/1282 424/134.1 |

FOREIGN PATENT DOCUMENTS

| | | |
|---|---|---|
| WO | 2015/100409 | 7/2015 |
| WO | 2016/127104 | 8/2016 |

OTHER PUBLICATIONS

Yang et al. JID vol. 210, pp. 964-972, Sep. 2014 (Year: 2014).*
Hudson et al. PLOS One vol. 9, issue 1, Nov. 2014. (Year: 2014).*
Hudson et al. (PLOS One vol. 9, issue 1, Nov. 2014. All art of record. (Year: 2014).*
International Search Report and Written Opinion of the International Searching Authority, dated Feb. 3, 2017 in corresponding International Application No. PCT/US2016/056875.
Vickers et al., "Dual gene expression cassette vectors with antibiotic selection markers for engineering in *Saccharomyces cerevisiae*", Microbial Cell Factories, 12(96): 1-10 (2013).
Yang et al., "A Novel Multivalent, Single-Domain Antibody Targeting TcdA and TcdB Prevents Fulminant *Clostridium difficile* Infection in Mice", Journal of Infectious Diseases, 210: 964-972 (2014).

(Continued)

*Primary Examiner* — Jana A Hines
*Assistant Examiner* — Khatol S Shahnan Shah
(74) *Attorney, Agent, or Firm* — Foley & Lardner LLP

(57) ABSTRACT

Antibody-based binding agents derived from human and camelid immunoglobulins are described, as well as strains of yeast engineered to secrete the binding agents, and methods of treating and preventing *Clostridium difficile* infections using the engineered strains of yeast. These binding agents recognize and bind with specificity to *Clostridium difficile* toxin A and/or toxin B and in some cases exhibit toxin neutralizing activity. The binding agents include camelid $V_HH$ peptide monomers, linked groups of $V_HH$ peptide monomers, $V_HH$ peptide monomers joined to antibody Fc domains, and $V_HH$ peptide monomers joined to IgG antibodies.

12 Claims, 21 Drawing Sheets
Specification includes a Sequence Listing.

(56) References Cited

OTHER PUBLICATIONS

Feng, Hanping, "Multispecific single domain antibody for treatment of Clostridium difficile infection," BIT'S 5th international Congress of Antibodies, 2013, Hangzhou, China, 186.

Hamedi et al., "Generation of a Uracil Auxotroph Strain of the Probiotic Yeast *Saccharomyces boulardii* as a Host for the Recombinant Protein Production," Avicenna J. Med. Biotech., 2013. 5(1):29-34.

Hudson et al., "Functional Heterologous Protein Expression by Genetically Engineered probiotic Yeast *Saccharomyces boulardii*," PLoS ONE, Nov. 12, 2014, 9(11):e112660, 1-12.

Liu et al., "Single domain antibody-alkaline phosphatase fusion proteins for antigen detection—Analysis of affinity and thermal stability of single domain antibody," Journal of Immunological Methods, 2013, 393:1-7.

Office Action and Search Report dated Feb. 23, 2021 in CN 201680072004.8.

Office Action dated Nov. 26, 2021 in CN 201680072004.8, with English translation.

Office Action dated Nov. 9, 2021, in JP 2018-519059, with English translation.

Palma et al., "Probiotic *Saccharomyces cerevisiae* strains as biotherapeutic tools: is there room for improvement?", Appl. Microbiol. Biotechnol., 2015, 99:6563-6570.

Schmidt et al., "A Tetraspecific VHH-Based Neutralizing Antibody Modifies Disease Outcome in Three Animal Models of Clostridium difficile Infection," Clin. Vaccine Immunol., Sep. 2016, 23(9):774-784.

Search Report dated Nov. 21, 2021 in CN 201680072004.8.

Spiess et al., "Alternative molecular formats and therapeutic applications for bispecific antibodies," Molecular Immunology, 2015, 67:95-106.

Von Heijne et al., "Species-specific variation in signal peptide design, Implications for protein secretion in foreign hosts," FEBS Letters, Feb. 1989, 244(2):439-446.

Yang et al., "The protective effect of recombinant Lactococcus lactis oral vaccine on a Clostridium difficile-infected animal model," BMC Gastroenterology, 2013, 13:117, 13 pages.

Office Action dated Jul. 5, 2022 in JP 2018-519059, with English translation.

Shi et al,. "Engineering of Chromosomal Wax Ester Synthase Integrated Saccharomyces Cerevisiae Mutants for Improved Biosynthesis of Fatty Acid Ethyl Esters," Biotechnol. Bioeng., 2014, 111(9):1740-1747.

\* cited by examiner

Figure 9A

Coat TcdA to detect TcdB

- TcdB=1000ng/ml
- TcdB=200ng/ml
- TcdB=40ng/ml
- TcdB=8ng/ml
- TcdB=1.6ng/ml

X-axis: Habab (ng/ml)
Y-axis: OD450

Figure 9B

Coat TcdB to detect TcdA

- TcdA=1000ng/ml
- TcdA=200ng/ml
- TcdA=40ng/ml
- TcdA=8ng/ml
- TcdA=1.6ng/ml

X-axis: Habab (ng/ml)
Y-axis: OD450

A

B

A

B

A

B

A

B

C

A

B

C

A

B

C

A

B

A

B

C

SEQUENCE LISTING

```
<160> NUMBER OF SEQ ID NOS: 111

<210> SEQ ID NO 1
<211> LENGTH: 127
<212> TYPE: PRT
<213> ORGANISM: Artificial Sequence
<220> FEATURE:
<223> OTHER INFORMATION: Codon-optimized VHH peptide monomer 5D

<400> SEQUENCE: 1

Gln Val Gln Leu Val Glu Ser Gly Gly Gly Leu Val Gln Pro Gly Gly
1               5                   10                  15

Ser Leu Arg Leu Ser Cys Glu Ala Ser Gly Phe Thr Leu Asp Tyr Tyr
            20                  25                  30

Gly Ile Gly Trp Phe Arg Gln Pro Pro Gly Lys Glu Arg Glu Ala Val
        35                  40                  45

Ser Tyr Ile Ser Ala Ser Ala Arg Thr Ile Leu Tyr Ala Asp Ser Val
    50                  55                  60

Lys Gly Arg Phe Thr Ile Ser Arg Asp Asn Ala Lys Asn Ala Val Tyr
65                  70                  75                  80

Leu Gln Met Asn Ser Leu Lys Arg Glu Asp Thr Ala Val Tyr Tyr Cys
                85                  90                  95

Ala Arg Arg Arg Phe Ser Ala Ser Ser Val Asn Arg Trp Leu Ala Asp
            100                 105                 110

Asp Tyr Asp Val Trp Gly Arg Gly Thr Gln Val Ala Val Ser Ser
        115                 120                 125

<210> SEQ ID NO 2
<211> LENGTH: 381
<212> TYPE: DNA
<213> ORGANISM: Artificial Sequence
<220> FEATURE:
<223> OTHER INFORMATION: Codon-optimized VHH peptide monomer 5D

<400> SEQUENCE: 2
caggtgcaac tggttgaatc tggggggaggc ttggtacaac ctgggggatc cctgagactc          60
```

```
tcttgcgagg cctccggatt caccttggac tactatggca tcggctggtt ccgccagccc    120
ccagggaagg agcgggaggc cgtttcatac attagtgcca gtgcccggac catactgtac    180
gcagactctg tgaagggacg ctttaccatc tctagggaca tgccaaaaa tgctgtgtac    240 ctgcaaatga acagcctcaa gcgggaggat accgcagtgt actactgcgc gagacggcgc    300
ttctccgctt ctagcgtgaa tagatggctg gccgacgact acgacgtgtg gggacggggc    360
acacaggtgg ctgtctcgag c                                              381

<210> SEQ ID NO 3
<211> LENGTH: 111
<212> TYPE: PRT
<213> ORGANISM: Artificial Sequence
<220> FEATURE:
<223> OTHER INFORMATION: Codon-optimized VHH peptide monomer E3

<400> SEQUENCE: 3

Gln Val Gln Leu Val Glu Ser Gly Gly Gly Leu Val Gln Thr Gly Gly
1               5                   10                  15

Ser Leu Arg Leu Ser Cys Ala Ser Ser Gly Ser Ile Ala Gly Phe Glu
            20                  25                  30

Thr Val Thr Trp Ser Arg Gln Ala Pro Gly Lys Ser Leu Gln Trp Val
        35                  40                  45

Ala Ser Met Thr Lys Thr Asn Asn Glu Ile Tyr Ser Asp Ser Val Lys
    50                  55                  60

Gly Arg Phe Ile Ile Ser Arg Asp Asn Ala Lys Asn Thr Val Tyr Leu
65                  70                  75                  80

Gln Met Asn Ser Leu Lys Pro Glu Asp Thr Gly Val Tyr Phe Cys Lys
                85                  90                  95

Gly Pro Glu Leu Arg Gly Gln Gly Ile Gln Val Thr Val Ser Ser
            100                 105                 110

<210> SEQ ID NO 4
<211> LENGTH: 333
<212> TYPE: DNA
<213> ORGANISM: Artificial Sequence
<220> FEATURE:
<223> OTHER INFORMATION: Codon-optimized VHH peptide monomer E3

<400> SEQUENCE: 4
caagttcagc tggtcgaatc cggggggcgga ctggtccaga caggggggctc cctgaggctc     60 tcctgtgcat cttccggaag catcgccggc ttcgagaccg tgacctggtc tcgccaggct    120
cccgggaagt ctctgcagtg ggtcgcttcc atgactaaga ctaacaacga gatctactct    180
gactcagtga aggccgcctt catcatttct agagataacg ctaaaaacac agtgtatctg    240
cagatgaata gtctcaaacc tgaagacaca ggcgtgtatt tctgtaaggg tcctgagctg    300
aggggccagg gcatccaggt aacagtctcg agt                                  333

<210> SEQ ID NO 5
<211> LENGTH: 121
<212> TYPE: PRT
<213> ORGANISM: Artificial Sequence
<220> FEATURE:
<223> OTHER INFORMATION: Codon-optimized VHH peptide monomer AA6

<400> SEQUENCE: 5

Gln Leu Gln Leu Val Glu Thr Gly Gly Gly Leu Val Gln Pro Gly Gly
1               5                   10                  15

Ser Leu Arg Leu Ser Cys Ala Ala Ser Gly Phe Thr Phe Ser Asp Tyr
```

```
                20                  25                  30
Val Met Thr Trp Val Arg Gln Ala Pro Gly Lys Gly Pro Glu Trp Ile
            35                  40                  45

Ala Thr Ile Asn Thr Asp Gly Ser Thr Met Arg Asp Asp Ser Thr Lys
        50                  55                  60

Gly Arg Phe Thr Ile Ser Arg Asp Asn Ala Lys Asn Thr Leu Tyr Leu
65                  70                  75                  80

Gln Met Thr Ser Leu Lys Pro Glu Asp Thr Ala Leu Tyr Tyr Cys Ala
                85                  90                  95

Arg Gly Arg Val Ile Ser Ala Ser Ala Ile Arg Gly Ala Val Arg Gly
            100                 105                 110

Pro Gly Thr Gln Val Thr Val Ser Ser
            115                 120

<210> SEQ ID NO 6
<211> LENGTH: 363
<212> TYPE: DNA
<213> ORGANISM: Artificial Sequence
<220> FEATURE:
<223> OTHER INFORMATION: Codon-optimized VHH peptide monomer AA6

<400> SEQUENCE: 6
caactgcagc tggtagagac aggggggcgc ttagttcagc ctggagggtc tctcagactg      60
tcatgcgctg cctctggctt taccttcagt gactacgtga tgacatgggt ccgccaagct     120
ccagggaagg ggcctgagtg gatcgctact attaatacag atggcagcac aatgcgggac     180
gactccacaa aggggcggtt caccatttcc agagacaacg ccaagaatac tctgtacctt     240
cagatgacca gtctgaaacc cgaggacact gctctgtact attgtgcaag aggccgggtg     300
atctctgctt ccgctatcag aggcgcagta agggggccctg aacacaagt aactgtctcg     360 agc                                                                   363

<210> SEQ ID NO 7
<211> LENGTH: 126
<212> TYPE: PRT
<213> ORGANISM: Artificial Sequence
<220> FEATURE:
<223> OTHER INFORMATION: Codon-optimized VHH peptide monomer AH3

<400> SEQUENCE: 7

Gln Val Gln Leu Val Glu Thr Gly Gly Leu Val Gln Pro Gly Gly Ser
1               5                   10                  15

Leu Arg Leu Ser Cys Ala Ala Ser Gly Phe Thr Leu Asp Tyr Ser Ser
            20                  25                  30

Ile Gly Trp Phe Arg Gln Ala Pro Gly Lys Glu Arg Glu Gly Val Ser
        35                  40                  45

Cys Ile Ser Ser Ser Gly Asp Ser Thr Lys Tyr Ala Asp Ser Val Lys
    50                  55                  60

Gly Arg Phe Thr Thr Ser Arg Asp Asn Ala Lys Asn Thr Val Tyr Leu
65                  70                  75                  80

Gln Met Asn Ser Leu Lys Pro Asp Asp Thr Ala Val Tyr Tyr Cys Ala
                85                  90                  95

Ala Phe Arg Ala Thr Met Cys Gly Val Phe Pro Leu Ser Pro Tyr Gly
            100                 105                 110

Lys Asp Asp Trp Gly Lys Gly Thr Leu Val Thr Val Ser Ser
        115                 120                 125
```

```
<210> SEQ ID NO 8
<211> LENGTH: 378
<212> TYPE: DNA
<213> ORGANISM: Artificial Sequence
<220> FEATURE:
<223> OTHER INFORMATION: Codon-optimized VHH peptide monomer AH3

<400> SEQUENCE: 8
caggtacagc tggtggagac gggggggctg gtacaaccag gcgggtcact gaggctttcc      60
tgtgccgcat ctgggttcac actggattat tcgtccatag ggtggtttcg gcaggctcct     120
ggcaaagagc gtgaggggt ctcatgtatt agtagtagtg gtgatagcac aaagtacgcc      180
gattccgtaa agggccggtt tacaacctcc agggataatg ctaagaacac cgtatatctc     240
cagatgaact ctctgaagcc cgacgatacg gccgtatatt actgtgcggc tttcagggcg     300
actatgtgcg gcgtgttccc tctgagccct tacggcaagg acgactgggg caaggggacc     360
ctggtgaccg tctcgagt                                                   378

<210> SEQ ID NO 9
<211> LENGTH: 15
<212> TYPE: PRT
<213> ORGANISM: Artificial Sequence
<220> FEATURE:
<223> OTHER INFORMATION: Codon-optimized flexible linker 1

<400> SEQUENCE: 9

Gly Gly Gly Gly Ser Gly Gly Gly Gly Ser Gly Gly Gly Gly Ser
1               5                  10                  15

<210> SEQ ID NO 10
<211> LENGTH: 45
<212> TYPE: DNA
<213> ORGANISM: Artificial Sequence
<220> FEATURE:
<223> OTHER INFORMATION: Codon-optimized flexible linker 1

<400> SEQUENCE: 10
ggcggtggag ggtctggtgg gggaggctca ggggtggag gcagc                       45

<210> SEQ ID NO 11
<211> LENGTH: 16
<212> TYPE: PRT
<213> ORGANISM: Artificial Sequence
<220> FEATURE:
<223> OTHER INFORMATION: Codon-optimized flexible linker 2

<400> SEQUENCE: 11

Gly Gly Gly Ser Gly Gly Gly Ser Gly Gly Gly Ser Gly Gly Gly Ser
1               5                  10                  15

<210> SEQ ID NO 12
<211> LENGTH: 48
<212> TYPE: DNA
<213> ORGANISM: Artificial Sequence
<220> FEATURE:
<223> OTHER INFORMATION: Codon-optimized flexible linker 2

<400> SEQUENCE: 12
ggtggcggaa gcggaggggg cagcgggggt gggagcggtg ggggcagc                   48

<210> SEQ ID NO 13
<211> LENGTH: 15
<212> TYPE: PRT
<213> ORGANISM: Artificial Sequence
<220> FEATURE:
```

<223> OTHER INFORMATION: Codon-optimized flexible linker 3

<400> SEQUENCE: 13

Gly Gly Gly Gly Ser Gly Gly Gly Gly Ser Gly Gly Gly Gly Ser
1               5                   10                  15

<210> SEQ ID NO 14
<211> LENGTH: 45
<212> TYPE: DNA
<213> ORGANISM: Artificial Sequence
<220> FEATURE:
<223> OTHER INFORMATION: Codon-optimized flexible linker 3

<400> SEQUENCE: 14
gggggaggcg gttcaggcgg tgggggatct ggcggggtg gatcc                45

<210> SEQ ID NO 15
<211> LENGTH: 269
<212> TYPE: PRT
<213> ORGANISM: Artificial Sequence
<220> FEATURE:
<223> OTHER INFORMATION: AH3-5D heterodimer

<400> SEQUENCE: 15

Gln Val Gln Leu Val Glu Thr Gly Gly Gly Leu Val Gln Pro Gly Gly
1               5                   10                  15

Ser Leu Arg Leu Ser Cys Ala Ala Ser Gly Phe Thr Leu Asp Tyr Ser
            20                  25                  30

Ser Ile Gly Trp Phe Arg Gln Ala Pro Gly Lys Glu Arg Glu Gly Val
        35                  40                  45

Ser Cys Ile Ser Ser Ser Gly Asp Ser Thr Lys Tyr Ala Asp Ser Val
    50                  55                  60

Lys Gly Arg Phe Thr Thr Ser Arg Asp Asn Ala Lys Asn Thr Val Tyr
65                  70                  75                  80

Leu Gln Met Asn Ser Leu Lys Pro Asp Asp Thr Ala Val Tyr Tyr Cys
                85                  90                  95

Ala Ala Phe Arg Ala Thr Met Cys Gly Val Phe Pro Leu Ser Pro Tyr
            100                 105                 110

Gly Lys Asp Asp Trp Gly Lys Gly Thr Leu Val Thr Val Ser Ser Gly
        115                 120                 125

Gly Gly Gly Ser Gly Gly Gly Ser Gly Gly Gly Gly Ser Gln Val
    130                 135                 140

Gln Leu Val Glu Ser Gly Gly Gly Leu Val Gln Pro Gly Gly Ser Leu
145                 150                 155                 160

Arg Leu Ser Cys Glu Ala Ser Gly Phe Thr Leu Asp Tyr Tyr Gly Ile
                165                 170                 175

Gly Trp Phe Arg Gln Pro Pro Gly Lys Glu Arg Glu Ala Val Ser Tyr
            180                 185                 190

Ile Ser Ala Ser Ala Arg Thr Ile Leu Tyr Ala Asp Ser Val Lys Gly
        195                 200                 205

Arg Phe Thr Ile Ser Arg Asp Asn Ala Lys Asn Ala Val Tyr Leu Gln
210                 215                 220

Met Asn Ser Leu Lys Arg Glu Asp Thr Ala Val Tyr Tyr Cys Ala Arg
225                 230                 235                 240

Arg Arg Phe Ser Ala Ser Ser Val Asn Arg Trp Leu Ala Asp Tyr
                245                 250                 255

Asp Val Trp Gly Arg Gly Thr Gln Val Ala Val Ser Ser
            260                 265

<210> SEQ ID NO 16
<211> LENGTH: 807
<212> TYPE: DNA
<213> ORGANISM: Artificial Sequence
<220> FEATURE:
<223> OTHER INFORMATION: AH3-5D heterodimer

<400> SEQUENCE: 16

```
caggtacagc tggtggagac ggggggaggg ctggtacaac caggcgggtc actgaggctt      60
tcctgtgccg catctgggtt cacactggat tattcgtcca tagggtggtt tcggcaggct     120
cctggcaaag agcgtgaggg ggtctcatgt attagtagta gtggtgatag cacaaagtac     180
gccgattccg taaagggccg gtttacaacc tccagggata atgctaagaa caccgtatat     240
ctccagatga actctctgaa gcccgacgat acggccgtat attactgtgc ggctttcagg     300
gcgactatgt gcggcgtgtt ccctctgagc ccttacggca aggacgactg ggcaagggg     360
accctggtga ccgtatcctc aggcggtgga ggtctggtg ggaggctc aggggggtgga     420
ggcagccagg tgcaactggt tgaatctggg ggaggcttgg tacaacctgg ggatccctg     480
agactctctt gcgaggcctc cggattcacc ttggactact atggcatcgg ctggttccgc     540
cagcccccag ggaaggagcg ggaggccgtt tcatacatta gtgccagtgc ccggaccata     600
ctgtacgcag actctgtgaa gggacgcttt accatctcta gggacaatgc caaaaatgct     660
gtgtacctgc aaatgaacag cctcaagcgg gaggataccg cagtgtacta ctgcgcgaga     720
cggcgcttct ccgcttctag cgtgaataga tggctggccg acgactacga cgtgtgggga     780
cggggcacac aggtggctgt ctcgagc                                         807
```

<210> SEQ ID NO 17
<211> LENGTH: 247
<212> TYPE: PRT
<213> ORGANISM: Artificial Sequence
<220> FEATURE:
<223> OTHER INFORMATION: AA6-E3 heterodimer

<400> SEQUENCE: 17

```
Gln Leu Gln Leu Val Glu Thr Gly Gly Gly Leu Val Gln Pro Gly Gly
1               5                   10                  15

Ser Leu Arg Leu Ser Cys Ala Ala Ser Gly Phe Thr Phe Ser Asp Tyr
            20                  25                  30

Val Met Thr Trp Val Arg Gln Ala Pro Gly Lys Gly Pro Glu Trp Ile
        35                  40                  45

Ala Thr Ile Asn Thr Asp Gly Ser Thr Met Arg Asp Asp Ser Thr Lys
    50                  55                  60

Gly Arg Phe Thr Ile Ser Arg Asp Asn Ala Lys Asn Thr Leu Tyr Leu
65                  70                  75                  80

Gln Met Thr Ser Leu Lys Pro Glu Asp Thr Ala Leu Tyr Tyr Cys Ala
                85                  90                  95

Arg Gly Arg Val Ile Ser Ala Ser Ala Ile Arg Gly Ala Val Arg Gly
            100                 105                 110

Pro Gly Thr Gln Val Thr Val Ser Ser Gly Gly Gly Ser Gly Gly
        115                 120                 125

Gly Gly Ser Gly Gly Gly Gly Ser Gln Val Gln Leu Val Glu Ser Gly
    130                 135                 140

Gly Gly Leu Val Gln Thr Gly Gly Ser Leu Arg Leu Ser Cys Ala Ser
145                 150                 155                 160
```

```
Ser Gly Ser Ile Ala Gly Phe Glu Thr Val Thr Trp Ser Arg Gln Ala
            165                 170                 175

Pro Gly Lys Ser Leu Gln Trp Val Ala Ser Met Thr Lys Thr Asn Asn
        180                 185                 190

Glu Ile Tyr Ser Asp Ser Val Lys Gly Arg Phe Ile Ile Ser Arg Asp
            195                 200                 205

Asn Ala Lys Asn Thr Val Tyr Leu Gln Met Asn Ser Leu Lys Pro Glu
        210                 215                 220

Asp Thr Gly Val Tyr Phe Cys Lys Gly Pro Glu Leu Arg Gly Gln Gly
225                 230                 235                 240

Ile Gln Val Thr Val Ser Ser
            245
```

```
<210> SEQ ID NO 18
<211> LENGTH: 741
<212> TYPE: DNA
<213> ORGANISM: Artificial Sequence
<220> FEATURE:
<223> OTHER INFORMATION: AA6-E3 heterodimer

<400> SEQUENCE: 18
caactgcagc tggtagagac agggggcggc ttagttcagc tggagggtc tctcagactg      60 tcatgcgctg cctctggctt taccttcagt gactacgtga tgacatgggt ccgccaagct    120
ccagggaagg ggcctgagtg gatcgctact attaatacag atggcagcac aatgcgggac    180
gactccacaa agggcggtt caccatttcc agagacaacg ccaagaatac tctgtacctt    240
cagatgacca gtctgaaacc cgaggacact gctctgtact attgtgcaag aggccgggtg    300
atctctgctt ccgctatcag aggcgcagta aggggccctg aacacaggt aaccgtttca    360 tccggggag gcggttcagg cggtggggga tctggcgggg gtggatccca agttcagctg    420
gtcgaatccg ggggcggact ggtccagaca gggggctccc tgaggctctc ctgtgcatct    480
tccggaagca tcgccggctt cgagaccgtg acctggtctc gccaggctcc cgggaagtct    540
ctgcagtggg tcgcttccat gactaagact aacaacgaga tctactctga ctcagtgaaa    600
ggccgcttca tcatttctag agataacgct aaaaacacag tgtatctgca gatgaatagt    660
ctcaaacctg aagacacagg cgtgtatttc tgtaagggtc ctgagctgag gggccagggc    720
atccaggtaa cagtctcgag t                                              741
```

```
<210> SEQ ID NO 19
<211> LENGTH: 532
<212> TYPE: PRT
<213> ORGANISM: Artificial Sequence
<220> FEATURE:
<223> OTHER INFORMATION: ABAB binding agent

<400> SEQUENCE: 19

Gln Val Gln Leu Val Glu Thr Gly Gly Gly Leu Val Gln Pro Gly Gly
1               5                   10                  15

Ser Leu Arg Leu Ser Cys Ala Ala Ser Gly Phe Thr Leu Asp Tyr Ser
            20                  25                  30

Ser Ile Gly Trp Phe Arg Gln Ala Pro Gly Lys Glu Arg Glu Gly Val
        35                  40                  45

Ser Cys Ile Ser Ser Ser Gly Asp Ser Thr Lys Tyr Ala Asp Ser Val
    50                  55                  60

Lys Gly Arg Phe Thr Thr Ser Arg Asp Asn Ala Lys Asn Thr Val Tyr
65                  70                  75                  80
```

```
Leu Gln Met Asn Ser Leu Lys Pro Asp Asp Thr Ala Val Tyr Tyr Cys
                 85                  90                  95

Ala Ala Phe Arg Ala Thr Met Cys Gly Val Phe Pro Leu Ser Pro Tyr
            100                 105                 110

Gly Lys Asp Asp Trp Gly Lys Gly Thr Leu Val Thr Val Ser Ser Gly
            115                 120                 125

Gly Gly Gly Ser Gly Gly Gly Ser Gly Gly Gly Ser Gln Val
        130                 135             140

Gln Leu Val Glu Ser Gly Gly Leu Val Gln Pro Gly Gly Ser Leu
145                 150                 155                 160

Arg Leu Ser Cys Glu Ala Ser Gly Phe Thr Leu Asp Tyr Tyr Gly Ile
                165                 170                 175

Gly Trp Phe Arg Gln Pro Pro Gly Lys Glu Arg Glu Ala Val Ser Tyr
            180                 185                 190

Ile Ser Ala Ser Ala Arg Thr Ile Leu Tyr Ala Asp Ser Val Lys Gly
            195                 200                 205

Arg Phe Thr Ile Ser Arg Asp Asn Ala Lys Asn Ala Val Tyr Leu Gln
210                 215                 220

Met Asn Ser Leu Lys Arg Glu Asp Thr Ala Val Tyr Tyr Cys Ala Arg
225                 230                 235                 240

Arg Arg Phe Ser Ala Ser Ser Val Asn Arg Trp Leu Ala Asp Asp Tyr
                245                 250                 255

Asp Val Trp Gly Arg Gly Thr Gln Val Ala Val Ser Ser Gly Gly Gly
            260                 265                 270

Ser Gly Gly Gly Ser Gly Gly Gly Ser Gly Gly Gly Ser Gln Leu Gln
        275                 280                 285

Leu Val Glu Thr Gly Gly Gly Leu Val Gln Pro Gly Gly Ser Leu Arg
        290                 295                 300

Leu Ser Cys Ala Ala Ser Gly Phe Thr Phe Ser Asp Tyr Val Met Thr
305                 310                 315                 320

Trp Val Arg Gln Ala Pro Gly Lys Gly Pro Glu Trp Ile Ala Thr Ile
                325                 330                 335

Asn Thr Asp Gly Ser Thr Met Arg Asp Asp Ser Thr Lys Gly Arg Phe
            340                 345                 350

Thr Ile Ser Arg Asp Asn Ala Lys Asn Thr Leu Tyr Leu Gln Met Thr
            355                 360                 365

Ser Leu Lys Pro Glu Asp Thr Ala Leu Tyr Tyr Cys Ala Arg Gly Arg
        370                 375                 380

Val Ile Ser Ala Ser Ala Ile Arg Gly Ala Val Arg Gly Pro Gly Thr
385                 390                 395                 400

Gln Val Thr Val Ser Ser Gly Gly Gly Ser Gly Gly Gly Ser Gly Ser
                405                 410                 415

Gly Gly Gly Gly Ser Gln Val Gln Leu Val Glu Ser Gly Gly Gly Leu
            420                 425                 430

Val Gln Thr Gly Gly Ser Leu Arg Leu Ser Cys Ala Ser Ser Gly Ser
            435                 440                 445

Ile Ala Gly Phe Glu Thr Val Thr Trp Ser Arg Gln Ala Pro Gly Lys
        450                 455                 460

Ser Leu Gln Trp Val Ala Ser Met Thr Lys Thr Asn Asn Glu Ile Tyr
465                 470                 475                 480

Ser Asp Ser Val Lys Gly Arg Phe Ile Ile Ser Arg Asp Asn Ala Lys
                485                 490                 495

Asn Thr Val Tyr Leu Gln Met Asn Ser Leu Lys Pro Glu Asp Thr Gly
```

```
                500              505              510
        Val Tyr Phe Cys Lys Gly Pro Glu Leu Arg Gly Gln Gly Ile Gln Val
                515              520              525

Thr Val Ser Ser
            530

<210> SEQ ID NO 20
<211> LENGTH: 1596
<212> TYPE: DNA
<213> ORGANISM: Artificial Sequence
<220> FEATURE:
<223> OTHER INFORMATION: ABAB binding agent

<400> SEQUENCE: 20
caggtacagc tggtggagac ggggggaggg ctggtacaac caggcgggtc actgaggctt      60
tcctgtgccg catctgggtt cacactggat tattcgtcca tagggtggtt tcggcaggct     120
cctggcaaag agcgtgaggg ggtctcatgt attagtagta gtggtgatag cacaaagtac     180
gccgattccg taaagggccg gtttacaacc tccaggata atgctaagaa caccgtatat      240
ctccagatga actctctgaa gcccgacgat acggccgtat attactgtgc ggctttcagg     300
gcgactatgt gcggcgtgtt ccctctgagc ccttacggca aggacgactg gggcaagggg     360
accctggtga ccgtatcctc aggcggtgga gggtctggtg ggggaggctc aggggggtgga    420 ggcagccagg tgcaactggt tgaatctggg ggaggcttgg tacaacctgg gggatccctg     480
agactctctt gcgaggcctc cggattcacc ttggactact atggcatcgg ctggttccgc     540
cagcccccag ggaaggagcg ggaggccgtt tcatacatta gtgccagtgc ccggaccata     600
ctgtacgcag actctgtgaa gggacgcttt accatctcta gggacaatgc caaaaatgct     660
gtgtacctgc aaatgaacag cctcaagcgg aggataccg cagtgtacta ctgcgcgaga     720
cggcgcttct ccgcttctag cgtgaataga tggctggccg acgactacga cgtgtgggga    780
cggggcacac aggtggctgt gtcttccggt ggcggaagcg gaggggggcag cggggggtggg    840 agcggtgggg gcagccaact gcagctggta gagacagggg gcggcttagt tcagcctgga     900
gggtctctca gactgtcatg cgctgcctct ggctttacct tcagtgacta cgtgatgaca    960
tgggtccgcc aagctccagg gaaggggcct gagtggatcg ctactattaa tacagatggc    1020
agcacaatgc gggacgactc cacaaagggg cggttcacca tttccagaga caacgccaag    1080
aatactctgt accttcagat gaccagtctg aaacccgagg cactgctct gtactattgt    1140 gcaagaggcc gggtgatctc tgcttccgct atcagaggcg cagtaagggg ccctggaaca    1200
caggtaaccg tttcatccgg gggaggcggt tcaggcggtg ggggatctgg cggggggtgga   1260 tcccaagttc agctggtcga atccggggggc ggactggtcc agacagggg ctccctgagg    1320 ctctcctgtg catcttccgg aagcatcgcc ggcttcgaga ccgtgacctg gtctcgccag    1380
gctcccggga gtctctgca gtgggtcgct tccatgacta agactaacaa cgagatctac    1440
tctgactcag tgaaaggccg cttcatcatt tctagagata cgctaaaaa cacagtgtat    1500 ctgcagatga atagtctcaa acctgaagac acaggcgtgt atttctgtaa gggtcctgag    1560 ctgagggggcc agggcatcca ggtaacagtc tcgagt                             1596

<210> SEQ ID NO 21
<211> LENGTH: 12
<212> TYPE: PRT
<213> ORGANISM: Artificial Sequence
<220> FEATURE:
<223> OTHER INFORMATION: Albumin-binding peptide
```

<400> SEQUENCE: 21

Asp Ile Cys Leu Pro Arg Trp Gly Cys Leu Trp Asp
1               5                   10

<210> SEQ ID NO 22
<211> LENGTH: 761
<212> TYPE: PRT
<213> ORGANISM: Artificial Sequence
<220> FEATURE:
<223> OTHER INFORMATION: ABAB-Fc binding agent

<400> SEQUENCE: 22

Gln Val Gln Leu Val Glu Thr Gly Gly Gly Leu Val Gln Pro Gly Gly
1               5                   10                  15

Ser Leu Arg Leu Ser Cys Ala Ala Ser Gly Phe Thr Leu Asp Tyr Ser
            20                  25                  30

Ser Ile Gly Trp Phe Arg Gln Ala Pro Gly Lys Glu Arg Glu Gly Val
        35                  40                  45

Ser Cys Ile Ser Ser Ser Gly Asp Ser Thr Lys Tyr Ala Asp Ser Val
    50                  55                  60

Lys Gly Arg Phe Thr Thr Ser Arg Asp Asn Ala Lys Asn Thr Val Tyr
65                  70                  75                  80

Leu Gln Met Asn Ser Leu Lys Pro Asp Asp Thr Ala Val Tyr Tyr Cys
                85                  90                  95

Ala Ala Phe Arg Ala Thr Met Cys Gly Val Phe Pro Leu Ser Pro Tyr
            100                 105                 110

Gly Lys Asp Asp Trp Gly Lys Gly Thr Leu Val Thr Val Ser Ser Gly
        115                 120                 125

Gly Gly Gly Ser Gly Gly Gly Ser Gly Gly Gly Ser Gln Val
    130                 135                 140

Gln Leu Val Glu Ser Gly Gly Gly Leu Val Gln Pro Gly Gly Ser Leu
145                 150                 155                 160

Arg Leu Ser Cys Glu Ala Ser Gly Phe Thr Leu Asp Tyr Tyr Gly Ile
                165                 170                 175

Gly Trp Phe Arg Gln Pro Pro Gly Lys Glu Arg Glu Ala Val Ser Tyr
            180                 185                 190

Ile Ser Ala Ser Ala Arg Thr Ile Leu Tyr Ala Asp Ser Val Lys Gly
        195                 200                 205

Arg Phe Thr Ile Ser Arg Asp Asn Ala Lys Asn Ala Val Tyr Leu Gln
    210                 215                 220

Met Asn Ser Leu Lys Arg Glu Asp Thr Ala Val Tyr Tyr Cys Ala Arg
225                 230                 235                 240

Arg Arg Phe Ser Ala Ser Ser Val Asn Arg Trp Leu Ala Asp Asp Tyr
                245                 250                 255

Asp Val Trp Gly Arg Gly Thr Gln Val Ala Val Ser Ser Gly Gly Gly
            260                 265                 270

Ser Gly Gly Gly Ser Gly Gly Gly Ser Gly Gly Gly Ser Gln Leu Gln
        275                 280                 285

Leu Val Glu Thr Gly Gly Gly Leu Val Gln Pro Gly Gly Ser Leu Arg
    290                 295                 300

Leu Ser Cys Ala Ala Ser Gly Phe Thr Phe Ser Asp Tyr Val Met Thr
305                 310                 315                 320

Trp Val Arg Gln Ala Pro Gly Lys Gly Pro Glu Trp Ile Ala Thr Ile
                325                 330                 335

```
Asn Thr Asp Gly Ser Thr Met Arg Asp Asp Ser Thr Lys Gly Arg Phe
                340                 345                 350

Thr Ile Ser Arg Asp Asn Ala Lys Asn Thr Leu Tyr Leu Gln Met Thr
            355                 360                 365

Ser Leu Lys Pro Glu Asp Thr Ala Leu Tyr Tyr Cys Ala Arg Gly Arg
        370                 375                 380

Val Ile Ser Ala Ser Ala Ile Arg Gly Ala Val Arg Gly Pro Gly Thr
385                 390                 395                 400

Gln Val Thr Val Ser Gly Gly Gly Ser Gly Gly Gly Gly Ser
                405                 410                 415

Gly Gly Gly Gly Ser Gln Val Gln Leu Val Glu Ser Gly Gly Gly Leu
            420                 425                 430

Val Gln Thr Gly Gly Ser Leu Arg Leu Ser Cys Ala Ser Ser Gly Ser
            435                 440                 445

Ile Ala Gly Phe Glu Thr Val Thr Trp Ser Arg Gln Ala Pro Gly Lys
            450                 455                 460

Ser Leu Gln Trp Val Ala Ser Met Thr Lys Thr Asn Asn Glu Ile Tyr
465                 470                 475                 480

Ser Asp Ser Val Lys Gly Arg Phe Ile Ile Ser Arg Asp Asn Ala Lys
                485                 490                 495

Asn Thr Val Tyr Leu Gln Met Asn Ser Leu Lys Pro Glu Asp Thr Gly
                500                 505                 510

Val Tyr Phe Cys Lys Gly Pro Glu Leu Arg Gly Gln Gly Ile Gln Val
            515                 520                 525

Thr Val Ser Ser Gly Ser Asp Lys Thr His Thr Cys Pro Pro Cys Pro
            530                 535                 540

Ala Pro Glu Leu Leu Gly Gly Pro Ser Val Phe Leu Phe Pro Pro Lys
545                 550                 555                 560

Pro Lys Asp Thr Leu Met Ile Ser Arg Thr Pro Glu Val Thr Cys Val
                565                 570                 575

Val Val Asp Val Ser His Glu Asp Pro Glu Val Lys Phe Asn Trp Tyr
            580                 585                 590

Val Asp Gly Val Glu Val His Asn Ala Lys Thr Lys Pro Arg Glu Glu
            595                 600                 605

Gln Tyr Asn Ser Thr Tyr Arg Val Val Ser Val Leu Thr Val Leu His
            610                 615                 620

Gln Asp Trp Leu Asn Gly Lys Glu Tyr Lys Cys Lys Val Ser Asn Lys
625                 630                 635                 640

Ala Leu Pro Ala Pro Ile Glu Lys Thr Ile Ser Lys Ala Lys Gly Gln
                645                 650                 655

Pro Arg Glu Pro Gln Val Tyr Thr Leu Pro Pro Ser Arg Glu Glu Met
            660                 665                 670

Thr Lys Asn Gln Val Ser Leu Thr Cys Leu Val Lys Gly Phe Tyr Pro
            675                 680                 685

Ser Asp Ile Ala Val Glu Trp Glu Ser Asn Gly Gln Pro Glu Asn Asn
            690                 695                 700

Tyr Lys Thr Thr Pro Pro Val Leu Asp Ser Asp Gly Ser Phe Phe Leu
705                 710                 715                 720

Tyr Ser Lys Leu Thr Val Asp Lys Ser Arg Trp Gln Gln Gly Asn Val
                725                 730                 735

Phe Ser Cys Ser Val Met His Glu Ala Leu His Asn His Tyr Thr Gln
            740                 745                 750

Lys Ser Leu Ser Leu Ser Pro Gly Lys
```

755           760

<210> SEQ ID NO 23
<211> LENGTH: 2286
<212> TYPE: DNA
<213> ORGANISM: Artificial Sequence
<220> FEATURE:
<223> OTHER INFORMATION: ABAB-Fc binding agent

<400> SEQUENCE: 23

| | | |
|---|---|---|
| caggtacagc tggtggagac gggggagggg ctggtacaac caggcgggtc actgaggctt | 60 |
| tcctgtgccg catctgggtt cacactggat tattcgtcca tagggtggtt tcggcaggct | 120 |
| cctggcaaag agcgtgaggg ggtctcatgt attagtagta gtggtgatag cacaaagtac | 180 |
| gccgattccg taaagggccg gtttacaacc tccagggata tgctaagaa caccgtatat | 240 |
| ctccagatga actctctgaa gcccgacgat acggccgtat attactgtgc ggctttcagg | 300 |
| gcgactatgt gcggcgtgtt ccctctgagc ccttacggca aggacgactg gggcaagggg | 360 |
| accctggtga ccgtatcctc aggcggtgga gggtctggtg ggggaggctc aggggggtgga | 420 |
| ggcagccagg tgcaactggt tgaatctggg ggaggcttgg tacaacctgg ggatccctg | 480 |
| agactctctt gcgaggcctc cggattcacc ttgactact atggcatcgg ctggttccgc | 540 |
| cagcccccag ggaaggagcg ggaggccgtt tcatacatta gtgccagtgc ccggaccata | 600 |
| ctgtacgcag actctgtgaa ggacgctttt accatctcta gggacaatgc aaaaatgct | 660 |
| gtgtacctgc aaatgaacag cctcaagcgg aggataccg cagtgtacta ctgcgcgaga | 720 |
| cggcgcttct ccgcttctag cgtgaataga tggctggccg acgactacga cgtgtgggga | 780 |
| cggggcacac aggtggctgt gtcttccggt ggcggaagcg gaggggggcag cgggggtggg | 840 |
| agcggtgggg gcagccaact gcagctggta gagacagggg gcggcttagt tcagcctgga | 900 |
| gggtctctca gactgtcatg cgctgcctct ggctttacct tcagtgacta cgtgatgaca | 960 |
| tgggtccgcc aagctccagg gaaggggcct gagtggatcg ctactattaa tacagatggc | 1020 |
| agcacaatgc gggacgactc cacaaagggg cggttcacca tttccagaga caacgccaag | 1080 |
| aatactctgt accttcagat gaccagtctg aaacccgagg acactgctct gtactattgt | 1140 |
| gcaagaggcc gggtgatctc tgcttccgct atcagaggcg cagtaagggg ccctggaaca | 1200 |
| caggtaaccg tttcatccgg gggaggcggt tcaggcggtg ggggatctgg cggggggtgga | 1260 |
| tcccaagttc agctggtcga atccgggggc ggactggtcc agacagggggg ctccctgagg | 1320 |
| ctctcctgtg catcttccgg aagcatcgcc ggcttcgaga ccgtgacctg gtctcgccag | 1380 |
| gctcccggga agtctctgca gtgggtcgct tccatgacta agactaacaa cgagatctac | 1440 |
| tctgactcag tgaaaggccg cttcatcatt tctagagata cgctaaaaa cacagtgtat | 1500 |
| ctgcagatga atagtctcaa acctgaagac acaggcgtgt atttctgtaa gggtcctgag | 1560 |
| ctgaggggcc agggcatcca ggtaacagtc tcgagcggat ccgacaaaac tcacacatgc | 1620 |
| ccaccgtgcc cagcacctga actcctgggg ggaccgtcag tcttcctctt ccccccaaaa | 1680 |
| cccaaggaca ccctcatgat ctcccggacc cctgaggtca catgcgtggt ggtggacgtg | 1740 |
| agccacgaag accctgaggt caagttcaac tggtacgtgg acggcgtgga ggtgcataat | 1800 |
| gccaagacaa agccgcggga ggagcagtac aacagcacgt accgtgtggt cagcgtcctc | 1860 |
| accgtcctgc accaggactg gctgaatggc aaggagtaca agtgcaaggt ctccaacaaa | 1920 |
| gccctcccag cccccatcga gaaaaccatc tccaaagcca agggcagccc cgagaaccca | 1980 |
| caggtgtaca ccctgccccc atcccgggag gagatgacca agaaccaggt cagcctgacc | 2040 |

```
tgcctggtca aaggcttcta tcccagcgac atcgccgtgg agtgggagag caatgggcag    2100
ccggagaaca actacaagac cacgcctccc gtgctggact ccgacggctc cttcttcctc    2160
tatagcaagc tcaccgtgga caagagcagg tggcagcagg ggaacgtctt ctcatgctcc    2220
gtgatgcatg aggctctgca caaccactac acgcagaaga gcctctccct gtctccgggt    2280
aaatga                                                                2286
```

<210> SEQ ID NO 24
<211> LENGTH: 356
<212> TYPE: PRT
<213> ORGANISM: Artificial Sequence
<220> FEATURE:
<223> OTHER INFORMATION: 5D-Fc binding agent

<400> SEQUENCE: 24

```
Gln Val Gln Leu Val Glu Ser Gly Gly Gly Leu Val Gln Pro Gly Gly
1               5                   10                  15

Ser Leu Arg Leu Ser Cys Glu Ala Ser Gly Phe Thr Leu Asp Tyr Tyr
            20                  25                  30

Gly Ile Gly Trp Phe Arg Gln Pro Pro Gly Lys Glu Arg Glu Ala Val
        35                  40                  45

Ser Tyr Ile Ser Ala Ser Ala Arg Thr Ile Leu Tyr Ala Asp Ser Val
    50                  55                  60

Lys Gly Arg Phe Thr Ile Ser Arg Asp Asn Ala Lys Asn Ala Val Tyr
65                  70                  75                  80

Leu Gln Met Asn Ser Leu Lys Arg Glu Asp Thr Ala Val Tyr Tyr Cys
                85                  90                  95

Ala Arg Arg Arg Phe Ser Ala Ser Ser Val Asn Arg Trp Leu Ala Asp
            100                 105                 110

Asp Tyr Asp Val Trp Gly Arg Gly Thr Gln Val Ala Val Ser Ser Gly
        115                 120                 125

Ser Asp Lys Thr His Thr Cys Pro Pro Cys Pro Ala Pro Glu Leu Leu
    130                 135                 140

Gly Gly Pro Ser Val Phe Leu Phe Pro Pro Lys Pro Lys Asp Thr Leu
145                 150                 155                 160

Met Ile Ser Arg Thr Pro Glu Val Thr Cys Val Val Val Asp Val Ser
                165                 170                 175

His Glu Asp Pro Glu Val Lys Phe Asn Trp Tyr Val Asp Gly Val Glu
            180                 185                 190

Val His Asn Ala Lys Thr Lys Pro Arg Glu Glu Gln Tyr Asn Ser Thr
        195                 200                 205

Tyr Arg Val Val Ser Val Leu Thr Val Leu His Gln Asp Trp Leu Asn
    210                 215                 220

Gly Lys Glu Tyr Lys Cys Lys Val Ser Asn Lys Ala Leu Pro Ala Pro
225                 230                 235                 240

Ile Glu Lys Thr Ile Ser Lys Ala Lys Gly Gln Pro Arg Glu Pro Gln
                245                 250                 255

Val Tyr Thr Leu Pro Pro Ser Arg Glu Glu Met Thr Lys Asn Gln Val
            260                 265                 270

Ser Leu Thr Cys Leu Val Lys Gly Phe Tyr Pro Ser Asp Ile Ala Val
        275                 280                 285

Glu Trp Glu Ser Asn Gly Gln Pro Glu Asn Asn Tyr Lys Thr Thr Pro
    290                 295                 300

Pro Val Leu Asp Ser Asp Gly Ser Phe Phe Leu Tyr Ser Lys Leu Thr
```

```
                305                 310                 315                 320
Val Asp Lys Ser Arg Trp Gln Gln Gly Asn Val Phe Ser Cys Ser Val
                    325                 330                 335

Met His Glu Ala Leu His Asn His Tyr Thr Gln Lys Ser Leu Ser Leu
            340                 345                 350

Ser Pro Gly Lys
        355

<210> SEQ ID NO 25
<211> LENGTH: 1071
<212> TYPE: DNA
<213> ORGANISM: Artificial Sequence
<220> FEATURE:
<223> OTHER INFORMATION: 5D-Fc binding agent

<400> SEQUENCE: 25
caggtgcaac tggttgaatc tggggggaggc ttggtacaac ctgggggatc cctgagactc      60
tcttgcgagg cctccggatt caccttggac tactatggca tcggctggtt ccgccagccc     120
ccagggaagg agcgggaggc cgtttcatac attagtgcca gtgcccggac catactgtac     180
gcagactctg tgaagggacg ctttaccatc tctagggaca tgccaaaaa tgctgtgtac     240 ctgcaaatga acagcctcaa gcgggaggat accgcagtgt actactgcgc gagacggcgc     300
ttctccgctt ctagcgtgaa tagatggctg ccgacgact acgacgtgtg gggacgggc      360 acacaggtgg ctgtctcgag cggatccgac aaaactcaca catgcccacc gtgcccagca     420
cctgaactcc tggggggacc gtcagtcttc ctcttccccc caaaacccaa ggacaccctc     480
atgatctccc ggacccctga ggtcacatgc gtggtggtgg acgtgagcca cgaagaccct     540
gaggtcaagt tcaactggta cgtggacggc gtggaggtgc ataatgccaa gacaaagccg     600
cgggaggagc agtacaacag cacgtaccgt gtggtcagcg tcctcaccgt cctgcaccag     660
gactggctga atggcaagga gtacaagtgc aaggtctcca acaaagccct cccagccccc     720
atcgagaaaa ccatctccaa agccaaaggg cagccccgag aaccacaggt gtacaccctg     780
cccccatccc gggaggagat gaccaagaac caggtcagcc tgacctgcct ggtcaaaggc     840
ttctatccca gcgacatcgc cgtggagtgg gagagcaatg ggcagccgga gaacaactac     900
aagaccacgc ctcccgtgct ggactccgac ggctccttct tcctctatag caagctcacc     960
gtggacaaga gcaggtggca gcaggggaac gtcttctcat gctccgtgat gcatgaggct    1020
ctgcacaacc actacacgca gaagagcctc tccctgtctc cgggtaaatg a             1071

<210> SEQ ID NO 26
<211> LENGTH: 340
<212> TYPE: PRT
<213> ORGANISM: Artificial Sequence
<220> FEATURE:
<223> OTHER INFORMATION: E3-Fc binding agent

<400> SEQUENCE: 26

Gln Val Gln Leu Val Glu Ser Gly Gly Gly Leu Val Gln Thr Gly Gly
1               5                   10                  15

Ser Leu Arg Leu Ser Cys Ala Ser Ser Gly Ser Ile Ala Gly Phe Glu
            20                  25                  30

Thr Val Thr Trp Ser Arg Gln Ala Pro Gly Lys Ser Leu Gln Trp Val
        35                  40                  45

Ala Ser Met Thr Lys Thr Asn Asn Glu Ile Tyr Ser Asp Ser Val Lys
    50                  55                  60
```

Gly Arg Phe Ile Ile Ser Arg Asp Asn Ala Lys Asn Thr Val Tyr Leu
 65                  70                  75                  80

Gln Met Asn Ser Leu Lys Pro Glu Asp Thr Gly Val Tyr Phe Cys Lys
                 85                  90                  95

Gly Pro Glu Leu Arg Gly Gln Gly Ile Gln Val Thr Val Ser Ser Gly
            100                 105                 110

Ser Asp Lys Thr His Thr Cys Pro Pro Cys Pro Ala Pro Glu Leu Leu
        115                 120                 125

Gly Gly Pro Ser Val Phe Leu Phe Pro Pro Lys Pro Lys Asp Thr Leu
    130                 135                 140

Met Ile Ser Arg Thr Pro Glu Val Thr Cys Val Val Val Asp Val Ser
145                 150                 155                 160

His Glu Asp Pro Glu Val Lys Phe Asn Trp Tyr Val Asp Gly Val Glu
                165                 170                 175

Val His Asn Ala Lys Thr Lys Pro Arg Glu Glu Gln Tyr Asn Ser Thr
            180                 185                 190

Tyr Arg Val Val Ser Val Leu Thr Val Leu His Gln Asp Trp Leu Asn
        195                 200                 205

Gly Lys Glu Tyr Lys Cys Lys Val Ser Asn Lys Ala Leu Pro Ala Pro
    210                 215                 220

Ile Glu Lys Thr Ile Ser Lys Ala Lys Gly Gln Pro Arg Glu Pro Gln
225                 230                 235                 240

Val Tyr Thr Leu Pro Pro Ser Arg Glu Glu Met Thr Lys Asn Gln Val
                245                 250                 255

Ser Leu Thr Cys Leu Val Lys Gly Phe Tyr Pro Ser Asp Ile Ala Val
            260                 265                 270

Glu Trp Glu Ser Asn Gly Gln Pro Glu Asn Asn Tyr Lys Thr Thr Pro
        275                 280                 285

Pro Val Leu Asp Ser Asp Gly Ser Phe Phe Leu Tyr Ser Lys Leu Thr
    290                 295                 300

Val Asp Lys Ser Arg Trp Gln Gln Gly Asn Val Phe Ser Cys Ser Val
305                 310                 315                 320

Met His Glu Ala Leu His Asn His Tyr Thr Gln Lys Ser Leu Ser Leu
                325                 330                 335

Ser Pro Gly Lys
            340

<210> SEQ ID NO 27
<211> LENGTH: 1023
<212> TYPE: DNA
<213> ORGANISM: Artificial Sequence
<220> FEATURE:
<223> OTHER INFORMATION: E3-Fc binding agent

<400> SEQUENCE: 27
caagttcagc tggtcgaatc cggggggcgga ctggtccaga caggggggctc cctgaggctc        60 tcctgtgcat cttccggaag catcgccggc ttcgagaccg tgacctggtc tcgccaggct       120
cccgggaagt ctctgcagtg ggtcgcttcc atgactaaga ctaacaacga gatctactct       180
gactcagtga aggccgcttc atcatttctc agagataacg ctaaaaacac agtgtatctg       240
cagatgaata gtctcaaacc tgaagacaca ggcgtgtatt tctgtaaggg tcctgagctg       300 agggggccagg gcatccaggt aacagtctcg agcggatccg acaaaactca cacatgccca       360
ccgtgcccag cacctgaact cctggggggga ccgtcagtct tcctcttccc cccaaaaccc       420
aaggacaccc tcatgatctc ccggacccct gaggtcacat gcgtggtggt ggacgtgagc       480

-continued

```
cacgaagacc ctgaggtcaa gttcaactgg tacgtggacg gcgtggaggt gcataatgcc      540
aagacaaagc cgcgggagga gcagtacaac agcacgtacc gtgtggtcag cgtcctcacc      600
gtcctgcacc aggactggct gaatggcaag gagtacaagt gcaaggtctc caacaaagcc      660
ctcccagccc ccatcgagaa aaccatctcc aaagccaaag gcagccccg agaaccacag       720 gtgtacaccc tgcccccatc ccgggaggag atgaccaaga accaggtcag cctgacctgc      780
ctggtcaaag gcttctatcc agcgacatc gccgtggagt gggagagcaa tgggcagccg       840
gagaacaact acaagaccac gcctcccgtg ctggactccg acggctcctt cttcctctat      900
agcaagctca ccgtggacaa gagcaggtgg cagcagggga acgtcttctc atgctccgtg      960
atgcatgagg ctctgcacaa ccactacacg cagaagagcc tctccctgtc tccgggtaaa     1020
tga                                                                  1023
```

<210> SEQ ID NO 28
<211> LENGTH: 350
<212> TYPE: PRT
<213> ORGANISM: Artificial Sequence
<220> FEATURE:
<223> OTHER INFORMATION: AA6-Fc binding agent

<400> SEQUENCE: 28

```
Gln Leu Gln Leu Val Glu Thr Gly Gly Gly Leu Val Gln Pro Gly Gly
1               5                   10                  15

Ser Leu Arg Leu Ser Cys Ala Ala Ser Gly Phe Thr Phe Ser Asp Tyr
            20                  25                  30

Val Met Thr Trp Val Arg Gln Ala Pro Gly Lys Gly Pro Glu Trp Ile
        35                  40                  45

Ala Thr Ile Asn Thr Asp Gly Ser Thr Met Arg Asp Asp Ser Thr Lys
    50                  55                  60

Gly Arg Phe Thr Ile Ser Arg Asp Asn Ala Lys Asn Thr Leu Tyr Leu
65                  70                  75                  80

Gln Met Thr Ser Leu Lys Pro Glu Asp Thr Ala Leu Tyr Tyr Cys Ala
                85                  90                  95

Arg Gly Arg Val Ile Ser Ala Ser Ala Ile Arg Gly Ala Val Arg Gly
            100                 105                 110

Pro Gly Thr Gln Val Thr Val Ser Ser Gly Ser Asp Lys Thr His Thr
        115                 120                 125

Cys Pro Pro Cys Pro Ala Pro Glu Leu Leu Gly Gly Pro Ser Val Phe
    130                 135                 140

Leu Phe Pro Pro Lys Pro Lys Asp Thr Leu Met Ile Ser Arg Thr Pro
145                 150                 155                 160

Glu Val Thr Cys Val Val Val Asp Val Ser His Glu Asp Pro Glu Val
                165                 170                 175

Lys Phe Asn Trp Tyr Val Asp Gly Val Glu Val His Asn Ala Lys Thr
            180                 185                 190

Lys Pro Arg Glu Glu Gln Tyr Asn Ser Thr Tyr Arg Val Val Ser Val
        195                 200                 205

Leu Thr Val Leu His Gln Asp Trp Leu Asn Gly Lys Glu Tyr Lys Cys
    210                 215                 220

Lys Val Ser Asn Lys Ala Leu Pro Ala Pro Ile Glu Lys Thr Ile Ser
225                 230                 235                 240

Lys Ala Lys Gly Gln Pro Arg Glu Pro Gln Val Tyr Thr Leu Pro Pro
                245                 250                 255
```

Ser Arg Glu Glu Met Thr Lys Asn Gln Val Ser Leu Thr Cys Leu Val
            260                 265                 270

Lys Gly Phe Tyr Pro Ser Asp Ile Ala Val Glu Trp Glu Ser Asn Gly
        275                 280                 285

Gln Pro Glu Asn Asn Tyr Lys Thr Thr Pro Pro Val Leu Asp Ser Asp
    290                 295                 300

Gly Ser Phe Phe Leu Tyr Ser Lys Leu Thr Val Asp Lys Ser Arg Trp
305                 310                 315                 320

Gln Gln Gly Asn Val Phe Ser Cys Ser Val Met His Glu Ala Leu His
                325                 330                 335

Asn His Tyr Thr Gln Lys Ser Leu Ser Leu Ser Pro Gly Lys
            340                 345                 350

<210> SEQ ID NO 29
<211> LENGTH: 1053
<212> TYPE: DNA
<213> ORGANISM: Artificial Sequence
<220> FEATURE:
<223> OTHER INFORMATION: AA6-Fc binding agent

<400> SEQUENCE: 29
caactgcagc tggtagagac aggggcggc ttagttcagc tggagggtc tctcagactg        60 tcatgcgctg cctctggctt taccttcagt gactacgtga tgacatgggt ccgccaagct     120
ccagggaagg ggcctgagtg gatcgctact attaatacag atggcagcac aatgcgggac     180
gactccacaa aggggcggtt caccatttcc agagacaacg ccaagaatac tctgtacctt     240
cagatgacca gtctgaaacc cgaggacact gctctgtact attgtgcaag aggccgggtg     300
atctctgctt ccgctatcag aggcgcagta aggggccctg aacacaagt aactgtctcg     360 agcggatccg acaaaactca cacatgccca ccgtgcccag cacctgaact cctgggggga    420
ccgtcagtct tcctcttccc cccaaaaccc aaggacaccc tcatgatctc ccggacccct    480
gaggtcacat gcgtggtggt ggacgtgagc cacgaagacc ctgaggtcaa gttcaactgg    540
tacgtggacg gcgtggaggt gcataatgcc aagacaaagc cgcgggagga gcagtacaac    600
agcacgtacc gtgtggtcag cgtcctcacc gtcctgcacc aggactggct gaatggcaag    660
gagtacaagt gcaaggtctc caacaaagcc ctcccagccc ccatcgagaa aaccatctcc    720
aaagccaaag gcagccccg agaaccacag gtgtacaccc tgcccccatc ccgggaggag    780
atgaccaaga accaggtcag cctgacctgc ctggtcaaag gcttctatcc cagcgacatc    840
gccgtggagt gggagagcaa tgggcagccg gagaacaact acaagaccac gcctcccgtg    900
ctggactccg acggctcctt cttcctctat agcaagctca ccgtggacaa gagcaggtgg    960
cagcagggga acgtcttctc atgctccgtg atgcatgagg ctctgcacaa ccactacacg   1020
cagaagagcc tctccctgtc tccgggtaaa tga                                 1053

<210> SEQ ID NO 30
<211> LENGTH: 356
<212> TYPE: PRT
<213> ORGANISM: Artificial Sequence
<220> FEATURE:
<223> OTHER INFORMATION: AH3-Fc binding agent

<400> SEQUENCE: 30

Gln Val Gln Leu Val Glu Thr Gly Gly Gly Leu Val Gln Pro Gly Gly
1               5                   10                  15

Ser Leu Arg Leu Ser Cys Ala Ala Ser Gly Phe Thr Leu Asp Tyr Ser
            20                  25                  30

Ser Ile Gly Trp Phe Arg Gln Ala Pro Gly Lys Glu Arg Glu Gly Val
         35                  40                  45

Ser Cys Ile Ser Ser Gly Asp Ser Thr Lys Tyr Ala Asp Ser Val
 50                  55                  60

Lys Gly Arg Phe Thr Thr Ser Arg Asp Asn Ala Lys Asn Thr Val Tyr
 65                  70                  75                  80

Leu Gln Met Asn Ser Leu Lys Pro Asp Asp Thr Ala Val Tyr Tyr Cys
                 85                  90                  95

Ala Ala Phe Arg Ala Thr Met Cys Gly Val Phe Pro Leu Ser Pro Tyr
            100                 105                 110

Gly Lys Asp Asp Trp Gly Lys Gly Thr Leu Val Thr Val Ser Ser Gly
        115                 120                 125

Ser Asp Lys Thr His Thr Cys Pro Pro Cys Pro Ala Pro Glu Leu Leu
    130                 135                 140

Gly Gly Pro Ser Val Phe Leu Phe Pro Pro Lys Pro Lys Asp Thr Leu
145                 150                 155                 160

Met Ile Ser Arg Thr Pro Glu Val Thr Cys Val Val Val Asp Val Ser
                165                 170                 175

His Glu Asp Pro Glu Val Lys Phe Asn Trp Tyr Val Asp Gly Val Glu
            180                 185                 190

Val His Asn Ala Lys Thr Lys Pro Arg Glu Glu Gln Tyr Asn Ser Thr
        195                 200                 205

Tyr Arg Val Val Ser Val Leu Thr Val Leu His Gln Asp Trp Leu Asn
    210                 215                 220

Gly Lys Glu Tyr Lys Cys Lys Val Ser Asn Lys Ala Leu Pro Ala Pro
225                 230                 235                 240

Ile Glu Lys Thr Ile Ser Lys Ala Lys Gly Gln Pro Arg Glu Pro Gln
                245                 250                 255

Val Tyr Thr Leu Pro Pro Ser Arg Glu Glu Met Thr Lys Asn Gln Val
            260                 265                 270

Ser Leu Thr Cys Leu Val Lys Gly Phe Tyr Pro Ser Asp Ile Ala Val
        275                 280                 285

Glu Trp Glu Ser Asn Gly Gln Pro Glu Asn Asn Tyr Lys Thr Thr Pro
    290                 295                 300

Pro Val Leu Asp Ser Asp Gly Ser Phe Phe Leu Tyr Ser Lys Leu Thr
305                 310                 315                 320

Val Asp Lys Ser Arg Trp Gln Gln Gly Asn Val Phe Ser Cys Ser Val
                325                 330                 335

Met His Glu Ala Leu His Asn His Tyr Thr Gln Lys Ser Leu Ser Leu
            340                 345                 350

Ser Pro Gly Lys
        355

<210> SEQ ID NO 31
<211> LENGTH: 1071
<212> TYPE: DNA
<213> ORGANISM: Artificial Sequence
<220> FEATURE:
<223> OTHER INFORMATION: AH3-Fc binding agent

<400> SEQUENCE: 31
caggtacagc tggtggagac ggggggaggg ctggtacaac caggcgggtc actgaggctt     60
tcctgtgccg catctgggtt cacactggat tattcgtcca tagggtggtt tcggcaggct    120
cctggcaaag agcgtgaggg ggtctcatgt attagtagta gtggtgatag cacaaagtac    180

```
gccgattccg taaagggccg gtttacaacc tccagggata atgctaagaa caccgtatat    240
ctccagatga actctctgaa gcccgacgat acggccgtat attactgtgc ggctttcagg    300
gcgactatgt gcggcgtgtt ccctctgagc ccttacggca aggacgactg gggcaagggg    360
accctggtga ccgtctcgag cggatccgac aaaactcaca catgcccacc gtgcccagca    420
cctgaactcc tggggggacc gtcagtcttc ctcttccccc caaaacccaa ggacaccctc    480
atgatctccc ggacccctga ggtcacatgc gtggtggtgg acgtgagcca cgaagaccct    540
gaggtcaagt tcaactggta cgtggacggc gtggaggtgc ataatgccaa gacaaagccg    600
cgggaggagc agtacaacag cacgtaccgt gtggtcagcg tcctcaccgt cctgcaccag    660
gactggctga atggcaagga gtacaagtgc aaggtctcca acaaagccct cccagccccc    720
atcgagaaaa ccatctccaa agccaaaggg cagccccgag aaccacaggt gtacaccctg    780
cccccatccc gggaggagat gaccaagaac caggtcagcc tgacctgcct ggtcaaaggc    840
ttctatccca gcgacatcgc cgtggagtgg gagagcaatg ggcagccgga gaacaactac    900
aagaccacgc ctcccgtgct ggactccgac ggctccttct tcctctatag caagctcacc    960
gtggacaaga gcaggtggca gcaggggaac gtcttctcat gctccgtgat gcatgaggct   1020
ctgcacaacc actacacgca gaagagcctc tccctgtctc cgggtaaatg a            1071
```

<210> SEQ ID NO 32
<211> LENGTH: 498
<212> TYPE: PRT
<213> ORGANISM: Artificial Sequence
<220> FEATURE:
<223> OTHER INFORMATION: AH3-5D-Fc binding agent

<400> SEQUENCE: 32

```
Gln Val Gln Leu Val Glu Thr Gly Gly Gly Leu Val Gln Pro Gly Gly
1               5                   10                  15

Ser Leu Arg Leu Ser Cys Ala Ala Ser Gly Phe Thr Leu Asp Tyr Ser
            20                  25                  30

Ser Ile Gly Trp Phe Arg Gln Ala Pro Gly Lys Glu Arg Glu Gly Val
        35                  40                  45

Ser Cys Ile Ser Ser Ser Gly Asp Ser Thr Lys Tyr Ala Asp Ser Val
    50                  55                  60

Lys Gly Arg Phe Thr Thr Ser Arg Asp Asn Ala Lys Asn Thr Val Tyr
65                  70                  75                  80

Leu Gln Met Asn Ser Leu Lys Pro Asp Asp Thr Ala Val Tyr Tyr Cys
                85                  90                  95

Ala Ala Phe Arg Ala Thr Met Cys Gly Val Phe Pro Leu Ser Pro Tyr
            100                 105                 110

Gly Lys Asp Asp Trp Gly Lys Gly Thr Leu Val Thr Val Ser Ser Gly
        115                 120                 125

Gly Gly Gly Ser Gly Gly Gly Gly Ser Gly Gly Gly Gly Ser Gln Val
    130                 135                 140

Gln Leu Val Glu Ser Gly Gly Gly Leu Val Gln Pro Gly Gly Ser Leu
145                 150                 155                 160

Arg Leu Ser Cys Glu Ala Ser Gly Phe Thr Leu Asp Tyr Tyr Gly Ile
                165                 170                 175

Gly Trp Phe Arg Gln Pro Pro Gly Lys Glu Arg Glu Ala Val Ser Tyr
            180                 185                 190

Ile Ser Ala Ser Ala Arg Thr Ile Leu Tyr Ala Asp Ser Val Lys Gly
        195                 200                 205
```

```
Arg Phe Thr Ile Ser Arg Asp Asn Ala Lys Asn Ala Val Tyr Leu Gln
            210                 215                 220

Met Asn Ser Leu Lys Arg Glu Asp Thr Ala Val Tyr Tyr Cys Ala Arg
225                 230                 235                 240

Arg Arg Phe Ser Ala Ser Ser Val Asn Arg Trp Leu Ala Asp Asp Tyr
                245                 250                 255

Asp Val Trp Gly Arg Gly Thr Gln Val Ala Val Ser Ser Gly Ser Asp
            260                 265                 270

Lys Thr His Thr Cys Pro Pro Cys Pro Ala Pro Glu Leu Leu Gly Gly
        275                 280                 285

Pro Ser Val Phe Leu Phe Pro Pro Lys Pro Lys Asp Thr Leu Met Ile
290                 295                 300

Ser Arg Thr Pro Glu Val Thr Cys Val Val Val Asp Val Ser His Glu
305                 310                 315                 320

Asp Pro Glu Val Lys Phe Asn Trp Tyr Val Asp Gly Val Glu Val His
                325                 330                 335

Asn Ala Lys Thr Lys Pro Arg Glu Glu Gln Tyr Asn Ser Thr Tyr Arg
            340                 345                 350

Val Val Ser Val Leu Thr Val Leu His Gln Asp Trp Leu Asn Gly Lys
        355                 360                 365

Glu Tyr Lys Cys Lys Val Ser Asn Lys Ala Leu Pro Ala Pro Ile Glu
370                 375                 380

Lys Thr Ile Ser Lys Ala Lys Gly Gln Pro Arg Glu Pro Gln Val Tyr
385                 390                 395                 400

Thr Leu Pro Pro Ser Arg Glu Glu Met Thr Lys Asn Gln Val Ser Leu
                405                 410                 415

Thr Cys Leu Val Lys Gly Phe Tyr Pro Ser Asp Ile Ala Val Glu Trp
            420                 425                 430

Glu Ser Asn Gly Gln Pro Glu Asn Asn Tyr Lys Thr Thr Pro Pro Val
        435                 440                 445

Leu Asp Ser Asp Gly Ser Phe Phe Leu Tyr Ser Lys Leu Thr Val Asp
450                 455                 460

Lys Ser Arg Trp Gln Gln Gly Asn Val Phe Ser Cys Ser Val Met His
465                 470                 475                 480

Glu Ala Leu His Asn His Tyr Thr Gln Lys Ser Leu Ser Leu Ser Pro
                485                 490                 495

Gly Lys

<210> SEQ ID NO 33
<211> LENGTH: 1497
<212> TYPE: DNA
<213> ORGANISM: Artificial Sequence
<220> FEATURE:
<223> OTHER INFORMATION: AH3-5D-Fc binding agent

<400> SEQUENCE: 33
caggtacagc tggtggagac ggggggaggg ctggtacaac aggcgggtc actgaggctt      60 tcctgtgccg catctgggtt cacactggat tattcgtcca tagggtggtt tcggcaggct     120
cctggcaaag agcgtgaggg gtctcatgt attagtagta gtggtgatag cacaaagtac     180
gccgattccg taagggccg gtttacaacc tccagggata atgctaagaa caccgtatat     240
ctccagatga actctctgaa gcccgacgat acgccgtat attactgtgc ggctttcagg     300
gcgactatgt gcggcgtgtt ccctctgagc ccttacggca aggacgactg gggcaagggg     360
```

```
acccctggtga ccgtatcctc aggcggtgga gggtctggtg ggggaggctc agggggtgga      420
ggcagccagg tgcaactggt tgaatctggg ggaggcttgg tacaacctgg ggatccctg        480 agactctctt gcgaggcctc cggattcacc ttggactact atggcatcgg ctggttccgc       540
cagcccccag gaaggagcg ggaggccgtt tcatacatta gtgccagtgc ccggaccata         600
ctgtacgcag actctgtgaa gggacgcttt accatctcta gggacaatgc caaaaatgct       660
gtgtacctgc aaatgaacag cctcaagcgg aggataccg cagtgtacta ctgcgcgaga         720
cggcgcttct ccgcttctag cgtgaataga tggctggccg acgactacga cgtgtgggga       780
cggggcacac aggtggctgt ctcgagcgga tccgacaaaa ctcacacatg cccaccgtgc        840
ccagcacctg aactcctggg gggaccgtca gtcttcctct ccccccaaa acccaaggac         900 accctcatga tctcccggac ccctgaggtc acatgcgtgg tggtggacgt gagccacgaa       960
gaccctgagg tcaagttcaa ctggtacgtg gacggcgtgg aggtgcataa tgccaagaca      1020
aagccgcggg aggagcagta caacagcacg taccgtgtgg tcagcgtcct caccgtcctg      1080
caccaggact ggctgaatgg caaggagtac aagtgcaagg tctccaacaa agccctccca      1140
gcccccatcg agaaaaccat ctccaaagcc aaagggcagc cccgagaacc acaggtgtac      1200
accctgcccc catcccggga ggagatgacc aagaaccagg tcagcctgac ctgcctggtc      1260
aaaggcttct atcccagcga catcgccgtg gagtgggaga gcaatgggca gccggagaac      1320
aactacaaga ccacgcctcc cgtgctggac tccgacggct ccttcttcct ctatagcaag      1380
ctcaccgtgg acaagagcag gtggcagcag gggaacgtct tctcatgctc cgtgatgcat      1440
gaggctctgc acaaccacta cacgcagaag agcctctccc tgtctccggg taaatga         1497
```

<210> SEQ ID NO 34
<211> LENGTH: 476
<212> TYPE: PRT
<213> ORGANISM: Artificial Sequence
<220> FEATURE:
<223> OTHER INFORMATION: AA6-E3-Fc binding agent

<400> SEQUENCE: 34

```
Gln Leu Gln Leu Val Glu Thr Gly Gly Gly Leu Val Gln Pro Gly Gly
1               5                   10                  15

Ser Leu Arg Leu Ser Cys Ala Ala Ser Gly Phe Thr Phe Ser Asp Tyr
            20                  25                  30

Val Met Thr Trp Val Arg Gln Ala Pro Gly Lys Gly Pro Glu Trp Ile
        35                  40                  45

Ala Thr Ile Asn Thr Asp Gly Ser Thr Met Arg Asp Asp Ser Thr Lys
    50                  55                  60

Gly Arg Phe Thr Ile Ser Arg Asp Asn Ala Lys Asn Thr Leu Tyr Leu
65                  70                  75                  80

Gln Met Thr Ser Leu Lys Pro Glu Asp Thr Ala Leu Tyr Tyr Cys Ala
                85                  90                  95

Arg Gly Arg Val Ile Ser Ala Ser Ala Ile Arg Gly Ala Val Arg Gly
            100                 105                 110

Pro Gly Thr Gln Val Thr Val Ser Ser Gly Gly Gly Ser Gly Gly
        115                 120                 125

Gly Gly Ser Gly Gly Gly Ser Gln Val Gln Leu Val Glu Ser Gly
    130                 135                 140

Gly Gly Leu Val Gln Thr Gly Gly Ser Leu Arg Leu Ser Cys Ala Ser
145                 150                 155                 160

Ser Gly Ser Ile Ala Gly Phe Glu Thr Val Thr Trp Ser Arg Gln Ala
```

```
            165                 170                 175
Pro Gly Lys Ser Leu Gln Trp Val Ala Ser Met Thr Lys Thr Asn Asn
            180                 185                 190

Glu Ile Tyr Ser Asp Ser Val Lys Gly Arg Phe Ile Ile Ser Arg Asp
            195                 200                 205

Asn Ala Lys Asn Thr Val Tyr Leu Gln Met Asn Ser Leu Lys Pro Glu
        210                 215                 220

Asp Thr Gly Val Tyr Phe Cys Lys Gly Pro Glu Leu Arg Gly Gln Gly
225                 230                 235                 240

Ile Gln Val Thr Val Ser Ser Gly Ser Asp Lys Thr His Thr Cys Pro
            245                 250                 255

Pro Cys Pro Ala Pro Glu Leu Leu Gly Gly Pro Ser Val Phe Leu Phe
            260                 265                 270

Pro Pro Lys Pro Lys Asp Thr Leu Met Ile Ser Arg Thr Pro Glu Val
            275                 280                 285

Thr Cys Val Val Val Asp Val Ser His Glu Asp Pro Glu Val Lys Phe
            290                 295                 300

Asn Trp Tyr Val Asp Gly Val Glu Val His Asn Ala Lys Thr Lys Pro
305                 310                 315                 320

Arg Glu Glu Gln Tyr Asn Ser Thr Tyr Arg Val Val Ser Val Leu Thr
                325                 330                 335

Val Leu His Gln Asp Trp Leu Asn Gly Lys Glu Tyr Lys Cys Lys Val
            340                 345                 350

Ser Asn Lys Ala Leu Pro Ala Pro Ile Glu Lys Thr Ile Ser Lys Ala
        355                 360                 365

Lys Gly Gln Pro Arg Glu Pro Gln Val Tyr Thr Leu Pro Pro Ser Arg
    370                 375                 380

Glu Glu Met Thr Lys Asn Gln Val Ser Leu Thr Cys Leu Val Lys Gly
385                 390                 395                 400

Phe Tyr Pro Ser Asp Ile Ala Val Glu Trp Glu Ser Asn Gly Gln Pro
                405                 410                 415

Glu Asn Asn Tyr Lys Thr Thr Pro Val Leu Asp Ser Asp Gly Ser
            420                 425                 430

Phe Phe Leu Tyr Ser Lys Leu Thr Val Asp Lys Ser Arg Trp Gln Gln
        435                 440                 445

Gly Asn Val Phe Ser Cys Ser Val Met His Glu Ala Leu His Asn His
    450                 455                 460

Tyr Thr Gln Lys Ser Leu Ser Leu Ser Pro Gly Lys
465                 470                 475

<210> SEQ ID NO 35
<211> LENGTH: 1431
<212> TYPE: DNA
<213> ORGANISM: Artificial Sequence
<220> FEATURE:
<223> OTHER INFORMATION: AA6-E3-Fc binding agent

<400> SEQUENCE: 35
caactgcagc tggtagagac agggggcggc ttagttcagc ctggagggtc tctcagactg     60
tcatgcgctg cctctggctt taccttcagt gactacgtga tgacatgggt ccgccaagct    120
ccagggaagg ggcctgagtg gatcgctact attaatacag atggcagcac aatgcgggac    180
gactccacaa aggggcggtt caccatttcc agagacaacg ccaagaatac tctgtacctt    240
cagatgacca gtctgaaacc cgaggacact gctctgtact attgtgcaag aggccgggtg    300
```

```
atctctgctt ccgctatcag aggcgcagta aggggccctg aacacaggt aaccgtttca    360
tccgggggag gcggttcagg cggtgggga tctggcgggg gtggatccca agttcagctg    420
gtcgaatccg ggggcggact ggtccagaca gggggctccc tgaggctctc ctgtgcatct    480
tccggaagca tcgccggctt cgagaccgtg acctggtctc gccaggctcc cgggaagtct    540
ctgcagtggg tcgcttccat gactaagact aacaacgaga tctactctga ctcagtgaaa    600
ggccgcttca tcatttctag agataacgct aaaaacacag tgtatctgca gatgaatagt    660
ctcaaacctg aagacacagg cgtgtatttc tgtaagggtc ctgagctgag gggccagggc    720
atccaggtaa cagtctcgag cggatccgac aaaactcaca catgcccacc gtgcccagca    780
cctgaactcc tgggggggacc gtcagtcttc ctcttccccc caaaacccaa ggacaccctc    840
atgatctccc ggacccctga ggtcacatgc gtggtggtgg acgtgagcca cgaagaccct    900
gaggtcaagt tcaactggta cgtggacggc gtggaggtgc ataatgccaa gacaaagccg    960
cgggaggagc agtacaacag cacgtaccgt gtggtcagcg tcctcaccgt cctgcaccag   1020
gactggctga atggcaagga gtacaagtgc aaggtctcca acaaagccct cccagccccc   1080
atcgagaaaa ccatctccaa agccaaaggg cagccccgag aaccacaggt gtacaccctg   1140
cccccatccc gggaggagat gaccaagaac caggtcagcc tgacctgcct ggtcaaaggc   1200
ttctatccca gcgacatcgc cgtggagtgg gagagcaatg ggcagccgga gaacaactac   1260
aagaccacgc ctcccgtgct ggactccgac ggctccttct cctctatag caagctcacc   1320
gtggacaaga gcaggtggca gcaggggaac gtcttctcat gctccgtgat gcatgaggct   1380
ctgcacaacc actacacgca gaagagcctc tccctgtctc cgggtaaatg a            1431
```

<210> SEQ ID NO 36
<211> LENGTH: 457
<212> TYPE: PRT
<213> ORGANISM: Artificial Sequence
<220> FEATURE:
<223> OTHER INFORMATION: AH3-IgG1-heavy chain

<400> SEQUENCE: 36

```
Gln Val Gln Leu Val Glu Thr Gly Gly Gly Leu Val Gln Pro Gly Gly
1               5                   10                  15

Ser Leu Arg Leu Ser Cys Ala Ala Ser Gly Phe Thr Leu Asp Tyr Ser
            20                  25                  30

Ser Ile Gly Trp Phe Arg Gln Ala Pro Gly Lys Glu Arg Glu Gly Val
        35                  40                  45

Ser Cys Ile Ser Ser Ser Gly Asp Ser Thr Lys Tyr Ala Asp Ser Val
    50                  55                  60

Lys Gly Arg Phe Thr Thr Ser Arg Asp Asn Ala Lys Asn Thr Val Tyr
65                  70                  75                  80

Leu Gln Met Asn Ser Leu Lys Pro Asp Asp Thr Ala Val Tyr Tyr Cys
                85                  90                  95

Ala Ala Phe Arg Ala Thr Met Cys Gly Val Pro Leu Ser Pro Tyr
            100                 105                 110

Gly Lys Asp Asp Trp Gly Lys Gly Thr Leu Val Thr Val Ser Ser Ala
        115                 120                 125

Ser Thr Lys Gly Pro Ser Val Phe Pro Leu Ala Pro Ser Ser Lys Ser
    130                 135                 140

Thr Ser Gly Gly Thr Ala Ala Leu Gly Cys Leu Val Lys Asp Tyr Phe
145                 150                 155                 160

Pro Glu Pro Val Thr Val Ser Trp Asn Ser Gly Ala Leu Thr Ser Gly
```

```
                    165                 170                 175
Val His Thr Phe Pro Ala Val Leu Gln Ser Ser Gly Leu Tyr Ser Leu
                180                 185                 190

Ser Ser Val Val Thr Val Pro Ser Ser Leu Gly Thr Gln Thr Tyr
            195                 200                 205

Ile Cys Asn Val Asn His Lys Pro Ser Asn Thr Lys Val Asp Lys Arg
        210                 215                 220

Val Glu Pro Lys Ser Cys Asp Lys Thr His Thr Cys Pro Pro Cys Pro
225                 230                 235                 240

Ala Pro Glu Leu Leu Gly Gly Pro Ser Val Phe Leu Phe Pro Pro Lys
                245                 250                 255

Pro Lys Asp Thr Leu Met Ile Ser Arg Thr Pro Glu Val Thr Cys Val
            260                 265                 270

Val Val Asp Val Ser His Glu Asp Pro Glu Val Lys Phe Asn Trp Tyr
        275                 280                 285

Val Asp Gly Val Glu Val His Asn Ala Lys Thr Lys Pro Arg Glu Glu
290                 295                 300

Gln Tyr Asn Ser Thr Tyr Arg Val Val Ser Val Leu Thr Val Leu His
305                 310                 315                 320

Gln Asp Trp Leu Asn Gly Lys Glu Tyr Lys Cys Lys Val Ser Asn Lys
                325                 330                 335

Ala Leu Pro Ala Pro Ile Glu Lys Thr Ile Ser Lys Ala Lys Gly Gln
            340                 345                 350

Pro Arg Glu Pro Gln Val Tyr Thr Leu Pro Pro Ser Arg Glu Glu Met
        355                 360                 365

Thr Lys Asn Gln Val Ser Leu Thr Cys Leu Val Lys Gly Phe Tyr Pro
    370                 375                 380

Ser Asp Ile Ala Val Glu Trp Glu Ser Asn Gly Gln Pro Glu Asn Asn
385                 390                 395                 400

Tyr Lys Thr Thr Pro Pro Val Leu Asp Ser Asp Gly Ser Phe Phe Leu
                405                 410                 415

Tyr Ser Lys Leu Thr Val Asp Lys Ser Arg Trp Gln Gln Gly Asn Val
            420                 425                 430

Phe Ser Cys Ser Val Met His Glu Ala Leu His Asn His Tyr Thr Gln
        435                 440                 445

Lys Ser Leu Ser Leu Ser Pro Gly Lys
    450                 455

<210> SEQ ID NO 37
<211> LENGTH: 1374
<212> TYPE: DNA
<213> ORGANISM: Artificial Sequence
<220> FEATURE:
<223> OTHER INFORMATION: AH3-IgG1-heavy chain

<400> SEQUENCE: 37
caggtacagc tggtggagac gggggggaggg ctggtacaac caggcgggtc actgaggctt     60
tcctgtgccg catctgggtt cacactggat tattcgtcca tagggtggtt tcggcaggct    120
cctggcaaag agcgtgaggg gtctcatgt attagtagta gtggtgatag cacaaagtac    180
gccgattccg taaagggccg gtttacaacc tccagggata atgctaagaa caccgtatat    240
ctccagatga actctctgaa gcccgacgat acggccgtat attactgtgc ggctttcagg    300
gcgactatgt gcggcgtgtt ccctctgagc ccttacggca aggacgactg ggcaagggg     360 accctggtga ccgtctcgag tgcgtcgacc aagggcccat cggtcttccc gctagcaccc    420
```

```
tcctccaaga gcacctctgg gggcacagcg gccctgggct gcctggtcaa ggactacttc    480
cccgaacctg tgacggtctc gtggaactca ggcgccctga ccagcggcgt gcacaccttc    540
ccggctgtcc tacagtcctc aggactctac tccctcagca gcgtggtgac cgtgccctcc    600
agcagcttgg gcacccagac ctacatctgc aacgtgaatc acaagcccag caacaccaag    660
gtggacaaga gagttgagcc caaatcttgt gacaaaactc acacatgccc accgtgccca    720
gcacctgaac tcctgggggg accgtcagtc ttcctcttcc ccccaaaacc caaggacacc    780
ctcatgatct cccggacccc tgaggtcaca tgcgtggtgg tggacgtgag ccacgaagac    840
cctgaggtca agttcaactg gtacgtggac ggcgtggagg tgcataatgc caagacaaag    900
ccgcgggagg agcagtacaa cagcacgtac cgtgtggtca gcgtcctcac cgtcctgcac    960
caggactggc tgaatggcaa ggagtacaag tgcaaggtct ccaacaaagc cctcccagcc   1020
cccatcgaga aaaccatctc caaagccaaa gggcagcccc gagaaccaca ggtgtacacc   1080
ctgcccccat cccgggagga gatgaccaag aaccaggtca gcctgacctg cctggtcaaa   1140
ggcttctatc ccagcgacat cgccgtggag tgggagagca atgggcagcc ggagaacaac   1200
tacaagacca cgcctcccgt gctggactcc gacggctcct tcttcctcta tagcaagctc   1260
accgtggaca agagcaggtg gcagcagggg aacgtcttct catgctccgt gatgcatgag   1320
gctctgcaca accactacac gcagaagagc ctctccctgt ccccgggtaa atga         1374

<210> SEQ ID NO 38
<211> LENGTH: 457
<212> TYPE: PRT
<213> ORGANISM: Artificial Sequence
<220> FEATURE:
<223> OTHER INFORMATION: 5D-IgG1-heavy chain

<400> SEQUENCE: 38

Gln Val Gln Leu Val Glu Ser Gly Gly Gly Leu Val Gln Pro Gly Gly
1               5                   10                  15

Ser Leu Arg Leu Ser Cys Glu Ala Ser Gly Phe Thr Leu Asp Tyr Tyr
                20                  25                  30

Gly Ile Gly Trp Phe Arg Gln Pro Pro Gly Lys Glu Arg Glu Ala Val
            35                  40                  45

Ser Tyr Ile Ser Ala Ser Ala Arg Thr Ile Leu Tyr Ala Asp Ser Val
    50                  55                  60

Lys Gly Arg Phe Thr Ile Ser Arg Asp Asn Ala Lys Asn Ala Val Tyr
65                  70                  75                  80

Leu Gln Met Asn Ser Leu Lys Arg Glu Asp Thr Ala Val Tyr Tyr Cys
                85                  90                  95

Ala Arg Arg Arg Phe Ser Ala Ser Ser Val Asn Arg Trp Leu Ala Asp
                100                 105                 110

Asp Tyr Asp Val Trp Gly Arg Gly Thr Gln Val Ala Val Ser Ser Ala
            115                 120                 125

Ser Thr Lys Gly Pro Ser Val Phe Pro Leu Ala Pro Ser Ser Lys Ser
    130                 135                 140

Thr Ser Gly Gly Thr Ala Ala Leu Gly Cys Leu Val Lys Asp Tyr Phe
145                 150                 155                 160

Pro Glu Pro Val Thr Val Ser Trp Asn Ser Gly Ala Leu Thr Ser Gly
                165                 170                 175

Val His Thr Phe Pro Ala Val Leu Gln Ser Ser Gly Leu Tyr Ser Leu
            180                 185                 190
```

Ser Ser Val Val Thr Val Pro Ser Ser Leu Gly Thr Gln Thr Tyr
            195                 200                 205

Ile Cys Asn Val Asn His Lys Pro Ser Asn Thr Lys Val Asp Lys Arg
    210                 215                 220

Val Glu Pro Lys Ser Cys Asp Lys Thr His Thr Cys Pro Pro Cys Pro
225                 230                 235                 240

Ala Pro Glu Leu Leu Gly Gly Pro Ser Val Phe Leu Phe Pro Pro Lys
                245                 250                 255

Pro Lys Asp Thr Leu Met Ile Ser Arg Thr Pro Glu Val Thr Cys Val
            260                 265                 270

Val Val Asp Val Ser His Glu Asp Pro Glu Val Lys Phe Asn Trp Tyr
        275                 280                 285

Val Asp Gly Val Glu Val His Asn Ala Lys Thr Lys Pro Arg Glu Glu
    290                 295                 300

Gln Tyr Asn Ser Thr Tyr Arg Val Val Ser Val Leu Thr Val Leu His
305                 310                 315                 320

Gln Asp Trp Leu Asn Gly Lys Glu Tyr Lys Cys Lys Val Ser Asn Lys
                325                 330                 335

Ala Leu Pro Ala Pro Ile Glu Lys Thr Ile Ser Lys Ala Lys Gly Gln
            340                 345                 350

Pro Arg Glu Pro Gln Val Tyr Thr Leu Pro Pro Ser Arg Glu Glu Met
        355                 360                 365

Thr Lys Asn Gln Val Ser Leu Thr Cys Leu Val Lys Gly Phe Tyr Pro
    370                 375                 380

Ser Asp Ile Ala Val Glu Trp Glu Ser Asn Gly Gln Pro Glu Asn Asn
385                 390                 395                 400

Tyr Lys Thr Thr Pro Pro Val Leu Asp Ser Asp Gly Ser Phe Phe Leu
                405                 410                 415

Tyr Ser Lys Leu Thr Val Asp Lys Ser Arg Trp Gln Gln Gly Asn Val
            420                 425                 430

Phe Ser Cys Ser Val Met His Glu Ala Leu His Asn His Tyr Thr Gln
        435                 440                 445

Lys Ser Leu Ser Leu Ser Pro Gly Lys
    450                 455

<210> SEQ ID NO 39
<211> LENGTH: 1374
<212> TYPE: DNA
<213> ORGANISM: Artificial Sequence
<220> FEATURE:
<223> OTHER INFORMATION: 5D-IgG1-heavy chain

<400> SEQUENCE: 39
caggtgcaac tggttgaatc tgggggaggc ttggtacaac tgggggatc cctgagactc      60 tcttgcgagg cctccggatt caccttggac tactatggca tcggctggtt ccgccagccc     120
ccagggaagg agcgggaggc cgtttcatac attagtgcca gtgcccggac atactgtac     180 gcagactctg tgaagggacg ctttaccatc tctagggaca tgccaaaaa tgctgtgtac     240 ctgcaaatga acagcctcaa gcgggaggat accgcagtgt actactgcgc gagacggcgc     300
ttctccgctt ctagcgtgaa tagatggctg gccgacgact acgacgtgtg ggacgggggc     360
acacaggtgg ctgtctcgag cgcgtcgacc aagggcccat cggtcttccc gctagcaccc     420
tcctccaaga gcacctctgg gggcacagcg ccctgggct gctggtcaa ggactacttc     480 cccgaacctg tgacggtctc gtggaactca ggcgccctga ccagcggcgt gcacaccttc     540

```
ccggctgtcc tacagtcctc aggactctac tccctcagca gcgtggtgac cgtgccctcc    600
agcagcttgg gcacccagac ctacatctgc aacgtgaatc acaagcccag caacaccaag    660
gtggacaaga gagttgagcc caaatcttgt gacaaaactc acacatgccc accgtgccca    720
gcacctgaac tcctgggggg accgtcagtc ttcctcttcc ccccaaaacc caaggacacc    780
ctcatgatct cccggacccc tgaggtcaca tgcgtggtgg tggacgtgag ccacgaagac    840
cctgaggtca agttcaactg gtacgtggac ggcgtggagg tgcataatgc caagacaaag    900
ccgcgggagg agcagtacaa cagcacgtac cgtgtggtca gcgtcctcac cgtcctgcac    960
caggactggc tgaatggcaa ggagtacaag tgcaaggtct ccaacaaagc cctcccagcc   1020
cccatcgaga aaaccatctc caaagccaaa gggcagcccc gagaaccaca ggtgtacacc   1080
ctgcccccat cccgggagga gatgaccaag aaccaggtca gcctgacctg cctggtcaaa   1140
ggcttctatc ccagcgacat cgccgtggag tgggagagca atgggcagcc ggagaacaac   1200
tacaagacca cgcctcccgt gctggactcc gacggctcct tcttcctcta tagcaagctc   1260
accgtggaca agagcaggtg gcagcagggg aacgtcttct catgctccgt gatgcatgag   1320
gctctgcaca accactacac gcagaagagc ctctccctgt ccccgggtaa atga         1374
```

<210> SEQ ID NO 40
<211> LENGTH: 228
<212> TYPE: PRT
<213> ORGANISM: Artificial Sequence
<220> FEATURE:
<223> OTHER INFORMATION: AA6-IgG1-kappa chain

<400> SEQUENCE: 40

```
Gln Leu Gln Leu Val Glu Thr Gly Gly Gly Leu Val Gln Pro Gly Gly
1               5                   10                  15

Ser Leu Arg Leu Ser Cys Ala Ala Ser Gly Phe Thr Phe Ser Asp Tyr
            20                  25                  30

Val Met Thr Trp Val Arg Gln Ala Pro Gly Lys Gly Pro Glu Trp Ile
        35                  40                  45

Ala Thr Ile Asn Thr Asp Gly Ser Thr Met Arg Asp Asp Ser Thr Lys
    50                  55                  60

Gly Arg Phe Thr Ile Ser Arg Asp Asn Ala Lys Asn Thr Leu Tyr Leu
65                  70                  75                  80

Gln Met Thr Ser Leu Lys Pro Glu Asp Thr Ala Leu Tyr Tyr Cys Ala
                85                  90                  95

Arg Gly Arg Val Ile Ser Ala Ser Ala Ile Arg Gly Ala Val Arg Gly
            100                 105                 110

Pro Gly Thr Gln Val Thr Val Ser Ser Arg Thr Val Ala Ala Pro Ser
        115                 120                 125

Val Phe Ile Phe Pro Pro Ser Asp Glu Gln Leu Lys Ser Gly Thr Ala
    130                 135                 140

Ser Val Val Cys Leu Leu Asn Asn Phe Tyr Pro Arg Glu Ala Lys Val
145                 150                 155                 160

Gln Trp Lys Val Asp Asn Ala Leu Gln Ser Gly Asn Ser Gln Glu Ser
                165                 170                 175

Val Thr Glu Gln Asp Ser Lys Asp Ser Thr Tyr Ser Leu Ser Ser Thr
            180                 185                 190

Leu Thr Leu Ser Lys Ala Asp Tyr Glu Lys His Lys Val Tyr Ala Cys
        195                 200                 205

Glu Val Thr His Gln Gly Leu Ser Ser Pro Val Thr Lys Ser Phe Asn
    210                 215                 220
```

Arg Gly Glu Cys
225

<210> SEQ ID NO 41
<211> LENGTH: 687
<212> TYPE: DNA
<213> ORGANISM: Artificial Sequence
<220> FEATURE:
<223> OTHER INFORMATION: AA6-IgG1-kappa chain

<400> SEQUENCE: 41

```
caactgcagc tggtagagac aggggggcggc ttagttcagc ctggagggtc tctcagactg      60
tcatgcgctg cctctggctt taccttcagt gactacgtga tgacatgggt ccgccaagct     120
ccagggaagg ggcctgagtg gatcgctact attaatacag atggcagcac aatgcgggac     180
gactccacaa aggggcggtt caccatttcc agagacaacg ccaagaatac tctgtacctt     240
cagatgacca gtctgaaacc cgaggacact gctctgtact attgtgcaag aggccgggtg     300
atctctgctt ccgctatcag aggcgcagta agggggccctg aacacaagt aactgtctcg     360
agccgtacgg tggctgcacc atctgtcttc atcttcccgc catctgatga gcagttgaaa     420
tctggaactg cctctgttgt gtgcctgctg ataacttct atcccagaga ggccaaagta     480
cagtggaagg tggataacgc cctccaatcg ggtaactccc aggagagtgt cacagagcag     540
gacagcaagg acagcaccta cagcctcagc agcaccctga cgctgagcaa agcagactac     600
gagaaacaca agtctacgc ctgcgaagtc acccatcagg gcctgagctc gcccgtcaca     660
aagagcttca cagggggaga gtgttga                                         687
```

<210> SEQ ID NO 42
<211> LENGTH: 218
<212> TYPE: PRT
<213> ORGANISM: Artificial Sequence
<220> FEATURE:
<223> OTHER INFORMATION: E3-IgG1-kappa chain

<400> SEQUENCE: 42

```
Gln Val Gln Leu Val Glu Ser Gly Gly Gly Leu Val Gln Thr Gly Gly
1               5                   10                  15
Ser Leu Arg Leu Ser Cys Ala Ser Ser Gly Ser Ile Ala Gly Phe Glu
            20                  25                  30
Thr Val Thr Trp Ser Arg Gln Ala Pro Gly Lys Ser Leu Gln Trp Val
        35                  40                  45
Ala Ser Met Thr Lys Thr Asn Asn Glu Ile Tyr Ser Asp Ser Val Lys
    50                  55                  60
Gly Arg Phe Ile Ile Ser Arg Asp Asn Ala Lys Asn Thr Val Tyr Leu
65                  70                  75                  80
Gln Met Asn Ser Leu Lys Pro Glu Asp Thr Gly Val Tyr Phe Cys Lys
                85                  90                  95
Gly Pro Glu Leu Arg Gly Gln Gly Ile Gln Val Thr Val Ser Ser Arg
            100                 105                 110
Thr Val Ala Ala Pro Ser Val Phe Ile Phe Pro Pro Ser Asp Glu Gln
        115                 120                 125
Leu Lys Ser Gly Thr Ala Ser Val Val Cys Leu Leu Asn Asn Phe Tyr
    130                 135                 140
Pro Arg Glu Ala Lys Val Gln Trp Lys Val Asp Asn Ala Leu Gln Ser
145                 150                 155                 160
Gly Asn Ser Gln Glu Ser Val Thr Glu Gln Asp Ser Lys Asp Ser Thr
```

-continued

```
                165                 170                 175
Tyr Ser Leu Ser Ser Thr Leu Thr Leu Ser Lys Ala Asp Tyr Glu Lys
            180                 185                 190

His Lys Val Tyr Ala Cys Glu Val Thr His Gln Gly Leu Ser Ser Pro
        195                 200                 205

Val Thr Lys Ser Phe Asn Arg Gly Glu Cys
        210                 215
```

<210> SEQ ID NO 43
<211> LENGTH: 657
<212> TYPE: DNA
<213> ORGANISM: Artificial Sequence
<220> FEATURE:
<223> OTHER INFORMATION: E3-IgG1-kappa chain

<400> SEQUENCE: 43

```
caagttcagc tggtcgaatc cggggggcgga ctggtccaga caggggggctc cctgaggctc      60
tcctgtgcat cttccggaag catcgccggc ttcgagaccg tgacctggtc tcgccaggct     120
cccgggaagt ctctgcagtg ggtcgcttcc atgactaaga ctaacaacga gatctactct     180
gactcagtga aggccgctt catcatttct agagataacg ctaaaaacac agtgtatctg     240
cagatgaata gtctcaaacc tgaagacaca ggcgtgtatt tctgtaaggg tcctgagctg     300
aggggccagg gcatccaggt aacagtctcg agccgtacgg tggctgcacc atctgtcttc     360
atcttcccgc catctgatga gcagttgaaa tctggaactg cctctgttgt gtgcctgctg     420
aataacttct atcccagaga ggccaaagta cagtggaagg tggataacgc cctccaatcg     480
ggtaactccc aggagagtgt cacagagcag gacagcaagg acagcaccta cagcctcagc     540
agcaccctga cgctgagcaa agcagactac gagaaacaca agtctacgc ctgcgaagtc     600
acccatcagg gcctgagctc gcccgtcaca aagagcttca cagggggaga gtgttga      657
```

<210> SEQ ID NO 44
<211> LENGTH: 599
<212> TYPE: PRT
<213> ORGANISM: Artificial Sequence
<220> FEATURE:
<223> OTHER INFORMATION: AH3-5D-IgG1 heavy chain

<400> SEQUENCE: 44

```
Gln Val Gln Leu Val Glu Thr Gly Gly Gly Leu Val Gln Pro Gly Gly
1               5                   10                  15

Ser Leu Arg Leu Ser Cys Ala Ala Ser Gly Phe Thr Leu Asp Tyr Ser
            20                  25                  30

Ser Ile Gly Trp Phe Arg Gln Ala Pro Gly Lys Glu Arg Glu Gly Val
        35                  40                  45

Ser Cys Ile Ser Ser Gly Asp Ser Thr Lys Tyr Ala Asp Ser Val
    50                  55                  60

Lys Gly Arg Phe Thr Thr Ser Arg Asp Asn Ala Lys Asn Thr Val Tyr
65                  70                  75                  80

Leu Gln Met Asn Ser Leu Lys Pro Asp Asp Thr Ala Val Tyr Tyr Cys
                85                  90                  95

Ala Ala Phe Arg Ala Thr Met Cys Gly Val Phe Pro Leu Ser Pro Tyr
            100                 105                 110

Gly Lys Asp Asp Trp Gly Lys Gly Thr Leu Val Thr Val Ser Ser Gly
        115                 120                 125

Gly Gly Gly Ser Gly Gly Gly Gly Ser Gly Gly Gly Gly Ser Gln Val
    130                 135                 140
```

```
Gln Leu Val Glu Ser Gly Gly Leu Val Gln Pro Gly Gly Ser Leu
145                 150                 155                 160

Arg Leu Ser Cys Glu Ala Ser Gly Phe Thr Leu Asp Tyr Tyr Gly Ile
                165                 170                 175

Gly Trp Phe Arg Gln Pro Pro Gly Lys Glu Arg Glu Ala Val Ser Tyr
                180                 185                 190

Ile Ser Ala Ser Ala Arg Thr Ile Leu Tyr Ala Asp Ser Val Lys Gly
                195                 200                 205

Arg Phe Thr Ile Ser Arg Asp Asn Ala Lys Asn Ala Val Tyr Leu Gln
                210                 215                 220

Met Asn Ser Leu Lys Arg Glu Asp Thr Ala Val Tyr Tyr Cys Ala Arg
225                 230                 235                 240

Arg Arg Phe Ser Ala Ser Ser Val Asn Arg Trp Leu Ala Asp Asp Tyr
                245                 250                 255

Asp Val Trp Gly Arg Gly Thr Gln Val Ala Val Ser Ser Ala Ser Thr
                260                 265                 270

Lys Gly Pro Ser Val Phe Pro Leu Ala Pro Ser Ser Lys Ser Thr Ser
                275                 280                 285

Gly Gly Thr Ala Ala Leu Gly Cys Leu Val Lys Asp Tyr Phe Pro Glu
                290                 295                 300

Pro Val Thr Val Ser Trp Asn Ser Gly Ala Leu Thr Ser Gly Val His
305                 310                 315                 320

Thr Phe Pro Ala Val Leu Gln Ser Ser Gly Leu Tyr Ser Leu Ser Ser
                325                 330                 335

Val Val Thr Val Pro Ser Ser Leu Gly Thr Gln Thr Tyr Ile Cys
                340                 345                 350

Asn Val Asn His Lys Pro Ser Asn Thr Lys Val Asp Lys Arg Val Glu
                355                 360                 365

Pro Lys Ser Cys Asp Lys Thr His Thr Cys Pro Pro Cys Pro Ala Pro
                370                 375                 380

Glu Leu Leu Gly Gly Pro Ser Val Phe Leu Phe Pro Pro Lys Pro Lys
385                 390                 395                 400

Asp Thr Leu Met Ile Ser Arg Thr Pro Glu Val Thr Cys Val Val Val
                405                 410                 415

Asp Val Ser His Glu Asp Pro Glu Val Lys Phe Asn Trp Tyr Val Asp
                420                 425                 430

Gly Val Glu Val His Asn Ala Lys Thr Lys Pro Arg Glu Glu Gln Tyr
                435                 440                 445

Asn Ser Thr Tyr Arg Val Val Ser Val Leu Thr Val Leu His Gln Asp
                450                 455                 460

Trp Leu Asn Gly Lys Glu Tyr Lys Cys Lys Val Ser Asn Lys Ala Leu
465                 470                 475                 480

Pro Ala Pro Ile Glu Lys Thr Ile Ser Lys Ala Lys Gly Gln Pro Arg
                485                 490                 495

Glu Pro Gln Val Tyr Thr Leu Pro Pro Ser Arg Glu Glu Met Thr Lys
                500                 505                 510

Asn Gln Val Ser Leu Thr Cys Leu Val Lys Gly Phe Tyr Pro Ser Asp
                515                 520                 525

Ile Ala Val Glu Trp Glu Ser Asn Gly Gln Pro Glu Asn Asn Tyr Lys
                530                 535                 540

Thr Thr Pro Pro Val Leu Asp Ser Asp Gly Ser Phe Phe Leu Tyr Ser
545                 550                 555                 560
```

```
Lys Leu Thr Val Asp Lys Ser Arg Trp Gln Gln Gly Asn Val Phe Ser
            565                 570                 575
Cys Ser Val Met His Glu Ala Leu His Asn His Tyr Thr Gln Lys Ser
        580                 585                 590
Leu Ser Leu Ser Pro Gly Lys
        595

<210> SEQ ID NO 45
<211> LENGTH: 1800
<212> TYPE: DNA
<213> ORGANISM: Artificial Sequence
<220> FEATURE:
<223> OTHER INFORMATION: AH3-5D-IgG1 heavy chain

<400> SEQUENCE: 45
```

| | | | | | |
|---|---|---|---|---|---|
| caggtacagc | tggtggagac | gggggagggg | ctggtacaac | caggcgggtc | actgaggctt | 60 |
| tcctgtgccg | catctgggtt | cacactggat | tattcgtcca | tagggtggtt | tcggcaggct | 120 |
| cctggcaaag | agcgtgaggg | gtctcatgt | attagtagta | gtggtgatag | cacaaagtac | 180 |
| gccgattccg | taaagggccg | gtttacaacc | tccagggata | atgctaagaa | caccgtatat | 240 |
| ctccagatga | actctctgaa | gcccgacgat | acggccgtat | attactgtgc | ggctttcagg | 300 |
| gcgactatgt | gcggcgtgtt | ccctctgagc | ccttacggca | aggacgactg | ggcaagggg | 360 |
| accctggtga | ccgtatcctc | aggcggtgga | ggtctggtg | ggaggctc | aggggtgga | 420 |
| ggcagccagg | tgcaactggt | tgaatctggg | ggaggcttgg | tacaacctgg | gggatccctg | 480 |
| agactctctt | gcgaggcctc | cggattcacc | ttggactact | atggcatcgg | ctggttccgc | 540 |
| cagcccccag | ggaaggagcg | ggaggccgtt | tcatacatta | gtgccagtgc | ccggaccata | 600 |
| ctgtacgcag | actctgtgaa | gggacgcttt | accatctcta | gggacaatgc | caaaatgct | 660 |
| gtgtacctgc | aaatgaacag | cctcaagcgg | gaggatacg | cagtgtacta | ctgcgcgaga | 720 |
| cggcgcttct | ccgcttctag | cgtgaataga | tggctggccg | acgactacga | cgtgtgggga | 780 |
| cggggcacac | aggtggctgt | ctcgagcgcg | tcgaccaagg | gcccatcggt | cttcccgcta | 840 |
| gcaccctcct | ccaagagcac | ctctgggggc | acagcggccc | tgggctgcct | ggtcaaggac | 900 |
| tacttccccg | aacctgtgac | ggtctcgtgg | aactcaggcg | ccctgaccag | cggcgtgcac | 960 |
| accttcccgg | ctgtcctaca | gtcctcagga | ctctactccc | tcagcagcgt | ggtgaccgtg | 1020 |
| ccctccagca | gcttgggcac | ccagacctac | atctgcaacg | tgaatcacaa | gcccagcaac | 1080 |
| accaaggtgg | acaagagagt | tgagcccaaa | tcttgtgaca | aaactcacac | atgcccaccg | 1140 |
| tgcccagcac | ctgaactcct | gggggaccg | tcagtcttcc | tcttcccccc | aaaacccaag | 1200 |
| gacaccctca | tgatctcccg | gacccctgag | gtcacatgcg | tggtggtgga | cgtgagccac | 1260 |
| gaagaccctg | aggtcaagtt | caactggtac | gtggacggcg | tggaggtgca | taatgccaag | 1320 |
| acaaagccgc | gggaggagca | gtacaacagc | acgtaccgtg | tggtcagcgt | cctcaccgtc | 1380 |
| ctgcaccagg | actggctgaa | tggcaaggag | tacaagtgca | aggtctccaa | caaagccctc | 1440 |
| ccagccccca | tcgagaaaac | catctccaaa | gccaaagggc | agccccgaga | accacaggtg | 1500 |
| tacaccctgc | ccccatcccg | ggaggagatg | accaagaacc | aggtcagcct | gacctgcctg | 1560 |
| gtcaaaggct | tctatcccag | cgacatcgcc | gtggagtggg | agagcaatgg | gcagccggag | 1620 |
| aacaactaca | agaccacgcc | tcccgtgctg | gactccgacg | gctccttctt | cctctatagc | 1680 |
| aagctcaccg | tggacaagag | caggtggcag | caggggaacg | tcttctcatg | ctccgtgatg | 1740 |
| catgaggctc | tgcacaacca | ctacacgcag | aagagcctct | ccctgtcccc | gggtaaatga | 1800 |

```
<210> SEQ ID NO 46
<211> LENGTH: 354
<212> TYPE: PRT
<213> ORGANISM: Artificial Sequence
<220> FEATURE:
<223> OTHER INFORMATION: AA6-E3-IgG1 light chain

<400> SEQUENCE: 46

Gln Leu Gln Leu Val Glu Thr Gly Gly Gly Leu Val Gln Pro Gly Gly
1               5                   10                  15

Ser Leu Arg Leu Ser Cys Ala Ala Ser Gly Phe Thr Phe Ser Asp Tyr
            20                  25                  30

Val Met Thr Trp Val Arg Gln Ala Pro Gly Lys Gly Pro Glu Trp Ile
        35                  40                  45

Ala Thr Ile Asn Thr Asp Gly Ser Thr Met Arg Asp Asp Ser Thr Lys
    50                  55                  60

Gly Arg Phe Thr Ile Ser Arg Asp Asn Ala Lys Asn Thr Leu Tyr Leu
65                  70                  75                  80

Gln Met Thr Ser Leu Lys Pro Glu Asp Thr Ala Leu Tyr Tyr Cys Ala
                85                  90                  95

Arg Gly Arg Val Ile Ser Ala Ser Ala Ile Arg Gly Ala Val Arg Gly
            100                 105                 110

Pro Gly Thr Gln Val Thr Val Ser Ser Gly Gly Gly Ser Gly Gly
        115                 120                 125

Gly Gly Ser Gly Gly Gly Ser Gln Val Gln Leu Val Glu Ser Gly
    130                 135                 140

Gly Gly Leu Val Gln Thr Gly Gly Ser Leu Arg Leu Ser Cys Ala Ser
145                 150                 155                 160

Ser Gly Ser Ile Ala Gly Phe Glu Thr Val Thr Trp Ser Arg Gln Ala
                165                 170                 175

Pro Gly Lys Ser Leu Gln Trp Val Ala Ser Met Thr Lys Thr Asn Asn
            180                 185                 190

Glu Ile Tyr Ser Asp Ser Val Lys Gly Arg Phe Ile Ile Ser Arg Asp
        195                 200                 205

Asn Ala Lys Asn Thr Val Tyr Leu Gln Met Asn Ser Leu Lys Pro Glu
    210                 215                 220

Asp Thr Gly Val Tyr Phe Cys Lys Gly Pro Glu Leu Arg Gly Gln Gly
225                 230                 235                 240

Ile Gln Val Thr Val Ser Ser Arg Thr Val Ala Ala Pro Ser Val Phe
                245                 250                 255

Ile Phe Pro Pro Ser Asp Glu Gln Leu Lys Ser Gly Thr Ala Ser Val
            260                 265                 270

Val Cys Leu Leu Asn Asn Phe Tyr Pro Arg Glu Ala Lys Val Gln Trp
        275                 280                 285

Lys Val Asp Asn Ala Leu Gln Ser Gly Asn Ser Gln Glu Ser Val Thr
    290                 295                 300

Glu Gln Asp Ser Lys Asp Ser Thr Tyr Ser Leu Ser Ser Thr Leu Thr
305                 310                 315                 320

Leu Ser Lys Ala Asp Tyr Glu Lys His Lys Val Tyr Ala Cys Glu Val
                325                 330                 335

Thr His Gln Gly Leu Ser Ser Pro Val Thr Lys Ser Phe Asn Arg Gly
            340                 345                 350

Glu Cys
```

<210> SEQ ID NO 47
<211> LENGTH: 1065
<212> TYPE: DNA
<213> ORGANISM: Artificial Sequence
<220> FEATURE:
<223> OTHER INFORMATION: AA6-E3-IgG1 light chain

<400> SEQUENCE: 47

```
caactgcagc tggtagagac agggggcggc ttagttcagc ctggagggtc tctcagactg      60
tcatgcgctg cctctggctt taccttcagt gactacgtga tgacatgggt ccgccaagct     120
ccagggaagg ggcctgagtg gatcgctact attaatacag atggcagcac aatgcgggac     180
gactccacaa aggggcggtt caccatttcc agagacaacg ccaagaatac tctgtaccct     240
cagatgacca gtctgaaacc cgaggacact gctctgtact attgtgcaag aggccgggtg     300
atctctgctt ccgctatcag aggcgcagta aggggccctg aacacaggt aaccgtttca     360
tccgggggag gcggttcagg cggtggggga tctggcgggg tggatcccaa gttcagctg      420
gtcgaatccg ggggcggact ggtccagaca ggggctccc tgaggctctc ctgtgcatct     480
tccggaagca tcgccggctt cgagaccgtg acctggtctc gccaggctcc cgggaagtct     540
ctgcagtggg tcgcttccat gactaagact aacaacgaga tctactctga ctcagtgaaa     600
ggccgcttca tcatttctag agataacgct aaaaacacag tgtatctgca gatgaatagt     660
ctcaaacctg aagacacagg cgtgtatttc tgtaagggtc tgagctgag gggccagggc     720
atccaggtaa cagtctcgag ccgtacggtg gctgcaccat ctgtcttcat cttcccgcca     780
tctgatgagc agttgaaatc tggaactgcc tctgttgtgt gcctgctgaa taacttctat     840
cccagagagg ccaaagtaca gtggaaggtg ataacgccc tccaatcggg taactcccag     900
gagagtgtca cagagcagga cagcaaggac agcacctaca gcctcagcag caccctgacg     960
ctgagcaaag cagactacga gaacacaaa gtctacgcct gcgaagtcac ccatcagggc    1020
ctgagctcgc ccgtcacaaa gagcttcaac aggggagagt gttga                   1065
```

<210> SEQ ID NO 48
<211> LENGTH: 127
<212> TYPE: PRT
<213> ORGANISM: Artificial Sequence
<220> FEATURE:
<223> OTHER INFORMATION: VHH peptide monomer 5D

<400> SEQUENCE: 48

Gln Val Gln Leu Val Glu Ser Gly Gly Gly Leu Val Gln Pro Gly Gly
1               5                   10                  15

Ser Leu Arg Leu Ser Cys Glu Ala Ser Gly Phe Thr Leu Asp Tyr Tyr
            20                  25                  30

Gly Ile Gly Trp Phe Arg Gln Pro Pro Gly Lys Glu Arg Glu Ala Val
        35                  40                  45

Ser Tyr Ile Ser Ala Ser Ala Arg Thr Ile Leu Tyr Ala Asp Ser Val
    50                  55                  60

Lys Gly Arg Phe Thr Ile Ser Arg Asp Asn Ala Lys Asn Ala Val Tyr
65                  70                  75                  80

Leu Gln Met Asn Ser Leu Lys Arg Glu Asp Thr Ala Val Tyr Tyr Cys
                85                  90                  95

Ala Arg Arg Arg Phe Ser Ala Ser Ser Val Asn Arg Trp Leu Ala Asp
            100                 105                 110

Asp Tyr Asp Val Trp Gly Arg Gly Thr Gln Val Ala Val Ser Ser
        115                 120                 125

<210> SEQ ID NO 49
<211> LENGTH: 381
<212> TYPE: DNA
<213> ORGANISM: Artificial Sequence
<220> FEATURE:
<223> OTHER INFORMATION: VHH peptide monomer 5D

<400> SEQUENCE: 49

```
caggtgcagc tcgtggagtc aggtggaggc ttggtgcagc ctgggggtc tctgagactc      60
tcctgtgaag cctctggatt cactttggat tattatggta taggctggtt ccgccagccc    120
ccagggaagg agcgcgaggc ggtctcatat attagtgcca gtgcccgtac gatattgtat    180
gcagattccg tgaagggccg atttaccatc tccagagaca atgccaagaa cgcggtgtat    240
ctacaaatga acagcctgaa acgtgaggac acggctgtct attactgtgc gaggcggcga    300
ttctccgcgt ctagtgttaa tagatggctt gccgacgact atgacgtctg ggtcggggg    360
acccaggtcg cggtgtcctc a                                              381
```

<210> SEQ ID NO 50
<211> LENGTH: 111
<212> TYPE: PRT
<213> ORGANISM: Artificial Sequence
<220> FEATURE:
<223> OTHER INFORMATION: VHH peptide monomer E3

<400> SEQUENCE: 50

Gln Val Gln Leu Val Glu Ser Gly Gly Gly Leu Val Gln Thr Gly Gly
1               5                   10                  15
Ser Leu Arg Leu Ser Cys Ala Ser Ser Gly Ser Ile Ala Gly Phe Glu
            20                  25                  30
Thr Val Thr Trp Ser Arg Gln Ala Pro Gly Lys Ser Leu Gln Trp Val
        35                  40                  45
Ala Ser Met Thr Lys Thr Asn Asn Glu Ile Tyr Ser Asp Ser Val Lys
    50                  55                  60
Gly Arg Phe Ile Ile Ser Arg Asp Asn Ala Lys Asn Thr Val Tyr Leu
65                  70                  75                  80
Gln Met Asn Ser Leu Lys Pro Glu Asp Thr Gly Val Tyr Phe Cys Lys
                85                  90                  95
Gly Pro Glu Leu Arg Gly Gln Gly Ile Gln Val Thr Val Ser Ser
            100                 105                 110

<210> SEQ ID NO 51
<211> LENGTH: 333
<212> TYPE: DNA
<213> ORGANISM: Artificial Sequence
<220> FEATURE:
<223> OTHER INFORMATION: VHH peptide monomer E3

<400> SEQUENCE: 51

```
caggtgcagc tcgtggagtc gggcggaggc ttggtgcaga ctgggggtc tctgagactc      60
tcctgtgcat cctctggaag tatcgccggt ttcgaaaccg tgacctggtc cgccaggct    120
cctggaaagt cgctccagtg gtcgcatcg atgactaaaa ctaataacga gatctattca    180
gactccgtga aggccgatt catcatctcc agagacaacg ccaagaatac ggtgtatcta    240
caaatgaaca gcctgaaacc tgaggacaca ggcgtctatt tttgtaaagg tcctgagttg    300
aggggccagg ggatccaggt caccgtctcc tcg                                  333
```

<210> SEQ ID NO 52

```
<211> LENGTH: 121
<212> TYPE: PRT
<213> ORGANISM: Artificial Sequence
<220> FEATURE:
<223> OTHER INFORMATION: VHH peptide monomer AA6

<400> SEQUENCE: 52

Gln Leu Gln Leu Val Glu Thr Gly Gly Gly Leu Val Gln Pro Gly Gly
1               5                   10                  15

Ser Leu Arg Leu Ser Cys Ala Ala Ser Gly Phe Thr Phe Ser Asp Tyr
            20                  25                  30

Val Met Thr Trp Val Arg Gln Ala Pro Gly Lys Gly Pro Glu Trp Ile
        35                  40                  45

Ala Thr Ile Asn Thr Asp Gly Ser Thr Met Arg Asp Asp Ser Thr Lys
    50                  55                  60

Gly Arg Phe Thr Ile Ser Arg Asp Asn Ala Lys Asn Thr Leu Tyr Leu
65                  70                  75                  80

Gln Met Thr Ser Leu Lys Pro Glu Asp Thr Ala Leu Tyr Tyr Cys Ala
                85                  90                  95

Arg Gly Arg Val Ile Ser Ala Ser Ala Ile Arg Gly Ala Val Arg Gly
            100                 105                 110

Pro Gly Thr Gln Val Thr Val Ser Ser
        115                 120

<210> SEQ ID NO 53
<211> LENGTH: 363
<212> TYPE: DNA
<213> ORGANISM: Artificial Sequence
<220> FEATURE:
<223> OTHER INFORMATION: VHH peptide monomer AA6

<400> SEQUENCE: 53
cagttgcagc tcgtggagac aggggggaggc ttggtgcagc ctggggggtc tctgagactc       60
tcctgtgcag cctctggatt cacgttcagt gactacgtca tgacctgggt ccgccaggct      120
ccaggaaagg ggcccgaatg gatcgcaact attaatacgg acggtagcac gatgcgtgat      180
gactccacaa aaggccgatt caccatctcc agagacaacg ccaagaacac actgtatctg      240
caaatgacca gcctgaaacc ggaggacacg gccctgtatt actgtgcgag aggccgcgtg      300
atctccgcct ccgcgataag aggggcggtt aggggcccgg ggacccaggt caccgtctcc      360
tca                                                                    363

<210> SEQ ID NO 54
<211> LENGTH: 126
<212> TYPE: PRT
<213> ORGANISM: Artificial Sequence
<220> FEATURE:
<223> OTHER INFORMATION: VHH peptide monomer AH3

<400> SEQUENCE: 54

Gln Val Gln Leu Val Glu Thr Gly Gly Leu Val Gln Pro Gly Gly Ser
1               5                   10                  15

Leu Arg Leu Ser Cys Ala Ala Ser Gly Phe Thr Leu Asp Tyr Ser Ser
            20                  25                  30

Ile Gly Trp Phe Arg Gln Ala Pro Gly Lys Glu Arg Glu Gly Val Ser
        35                  40                  45

Cys Ile Ser Ser Ser Gly Asp Ser Thr Lys Tyr Ala Asp Ser Val Lys
    50                  55                  60

Gly Arg Phe Thr Thr Ser Arg Asp Asn Ala Lys Asn Thr Val Tyr Leu
```

65                  70                  75                  80
Gln Met Asn Ser Leu Lys Pro Asp Asp Thr Ala Val Tyr Tyr Cys Ala
                85                  90                  95

Ala Phe Arg Ala Thr Met Cys Gly Val Phe Pro Leu Ser Pro Tyr Gly
            100                 105                 110

Lys Asp Asp Trp Gly Lys Gly Thr Leu Val Thr Val Ser Ser
        115                 120                 125

<210> SEQ ID NO 55
<211> LENGTH: 378
<212> TYPE: DNA
<213> ORGANISM: Artificial Sequence
<220> FEATURE:
<223> OTHER INFORMATION: VHH peptide monomer AH3

<400> SEQUENCE: 55
caggtgcagc tcgtggagac gggggcttg gtgcagcctg ggggtctct gagactctcc      60 tgtgcagcct ctggattcac tttggattat cgtccatag gctggttccg ccaggcccca   120
gggaaggagc gtgaggggt ctcatgtatt agtagtagtg gtgatagcac aaagtatgca   180
gactccgtga aggccgatt caccacctcc agagacaacg ccaagaacac ggtgtatctg   240
caaatgaaca gcctgaaacc tgacgacaca gccgtttatt actgtgcagc ttttagggcg   300
actatgtgcg gcgtgttccc ccttagcccc tacggcaagg acgactgggg caaagggacc   360
ctggtcaccg tctcctca                                                 378

<210> SEQ ID NO 56
<211> LENGTH: 15
<212> TYPE: PRT
<213> ORGANISM: Artificial Sequence
<220> FEATURE:
<223> OTHER INFORMATION: Flexible linker 1

<400> SEQUENCE: 56

Gly Gly Gly Gly Ser Gly Gly Gly Gly Ser Gly Gly Gly Gly Ser
1               5                   10                  15

<210> SEQ ID NO 57
<211> LENGTH: 45
<212> TYPE: DNA
<213> ORGANISM: Artificial Sequence
<220> FEATURE:
<223> OTHER INFORMATION: Flexible linker 1

<400> SEQUENCE: 57
ggcggtggtg gctctggtgg cggcggttcc ggtggcggtg gcagc                    45

<210> SEQ ID NO 58
<211> LENGTH: 15
<212> TYPE: PRT
<213> ORGANISM: Artificial Sequence
<220> FEATURE:
<223> OTHER INFORMATION: Flexible linker 2

<400> SEQUENCE: 58

Gly Gly Gly Gly Ser Gly Gly Gly Gly Ser Gly Gly Gly Gly Ser
1               5                   10                  15

<210> SEQ ID NO 59
<211> LENGTH: 45
<212> TYPE: DNA
<213> ORGANISM: Artificial Sequence
<220> FEATURE:

<223> OTHER INFORMATION: Flexible linker 2

<400> SEQUENCE: 59
ggtggaggcg gttcaggcgg aggtggctct ggcggtggcg gttcc     45

<210> SEQ ID NO 60
<211> LENGTH: 15
<212> TYPE: PRT
<213> ORGANISM: Artificial Sequence
<220> FEATURE:
<223> OTHER INFORMATION: Flexible linker 3

<400> SEQUENCE: 60

Gly Gly Gly Gly Ser Gly Gly Gly Gly Ser Gly Gly Gly Gly Ser
1               5                   10                  15

<210> SEQ ID NO 61
<211> LENGTH: 45
<212> TYPE: DNA
<213> ORGANISM: Artificial Sequence
<220> FEATURE:
<223> OTHER INFORMATION: Flexible linker 3

<400> SEQUENCE: 61
ggcggtggtg gctctggtgg cggcggttcc ggtggcggtg gcagc     45

<210> SEQ ID NO 62
<211> LENGTH: 259
<212> TYPE: PRT
<213> ORGANISM: Artificial Sequence
<220> FEATURE:
<223> OTHER INFORMATION: 5D-E3 heterodimer

<400> SEQUENCE: 62

Gln Val Gln Leu Val Glu Ser Gly Gly Gly Leu Val Gln Pro Gly Gly
1               5                   10                  15

Ser Leu Arg Leu Ser Cys Glu Ala Ser Gly Phe Thr Leu Asp Tyr Tyr
            20                  25                  30

Gly Ile Gly Trp Phe Arg Gln Pro Pro Gly Lys Glu Arg Glu Ala Val
        35                  40                  45

Ser Tyr Ile Ser Ala Ser Ala Arg Thr Ile Leu Tyr Ala Asp Ser Val
    50                  55                  60

Lys Gly Arg Phe Thr Ile Ser Arg Asp Asn Ala Lys Asn Ala Val Tyr
65                  70                  75                  80

Leu Gln Met Glu Thr Asn Ser Leu Lys Arg Glu Asp Thr Ala Val Tyr
                85                  90                  95

Tyr Cys Ala Arg Arg Arg Phe Ser Ala Ser Ser Val Asn Arg Trp Leu
            100                 105                 110

Ala Asp Asp Tyr Asp Val Trp Gly Arg Gly Thr Gln Val Ala Val Ser
        115                 120                 125

Ser Gly Gly Gly Gly Ser Gly Gly Gly Gly Ser Gly Gly Gly Gly Ser
    130                 135                 140

Gln Val Gln Leu Val Glu Ser Gly Gly Gly Leu Val Gln Thr Gly Gly
145                 150                 155                 160

Ser Leu Arg Leu Ser Cys Ala Ser Ser Gly Ser Ile Ala Gly Phe Glu
                165                 170                 175

Thr Val Thr Trp Ser Arg Gln Ala Pro Gly Lys Ser Leu Gln Trp Val
            180                 185                 190

Ala Ser Met Glu Thr Thr Lys Thr Asn Asn Glu Ile Tyr Ser Asp Ser
        195                 200                 205

```
Val Lys Gly Arg Phe Ile Ile Ser Arg Asp Asn Ala Lys Asn Thr Val
    210                 215                 220

Tyr Leu Gln Met Glu Thr Asn Ser Leu Lys Pro Glu Asp Thr Gly Val
225                 230                 235                 240

Tyr Phe Cys Lys Gly Pro Glu Leu Arg Gly Gln Gly Ile Gln Val Thr
                245                 250                 255

Val Ser Ser
```

<210> SEQ ID NO 63
<211> LENGTH: 759
<212> TYPE: DNA
<213> ORGANISM: Artificial Sequence
<220> FEATURE:
<223> OTHER INFORMATION: 5D-E3 heterodimer

<400> SEQUENCE: 63

```
caggtgcagc tcgtggagtc aggtggaggc ttggtgcagc ctgggggtc  tctgagactc      60
tcctgtgaag cctctggatt cactttggat tattatggta taggctggtt ccgccagccc     120
ccagggaagg agcgcgaggc ggtctcatat attagtgcca gtgcccgtac gatattgtat     180
gcagattccg tgaagggccg atttaccatc tccagagaca tgccaagaa  cgcggtgtat     240
ctacaaatga acagcctgaa acgtgaggac acggctgtct attactgtgc gaggcggcga     300
ttctccgcgt ctagtgttaa tagatggctt gccgacgact atgacgtctg ggtcggggg      360
acccaggtcg cggtgtcctc aggcggtggt ggctctggtg gcggcggttc cggtggcggt     420
ggcagccagg tgcagctcgt ggagtcgggc ggaggcttgg tgcagactgg ggggtctctg     480
agactctcct gtgcatcctc tggaagtatc gccggtttcg aaaccgtgac ctggtcccgc     540
caggctcctg gaaagtcgct ccagtgggtc gcatcgatga ctaaaactaa taacgagatc     600
tattcagact ccgtgaaggg ccgattcatc atctccagag acaacgccaa gaatacggtg     660
tatctacaaa tgaacagcct gaaacctgag gacacaggcg tctatttttg taaaggtcct     720
gagttgaggg gccaggggat ccaggtcacc gtctcctcg                            759
```

<210> SEQ ID NO 64
<211> LENGTH: 272
<212> TYPE: PRT
<213> ORGANISM: Artificial Sequence
<220> FEATURE:
<223> OTHER INFORMATION: AH3-AA6 heterodimer

<400> SEQUENCE: 64

```
Gln Val Gln Leu Val Glu Thr Gly Gly Leu Val Gln Pro Gly Gly Ser
1               5                   10                  15

Leu Arg Leu Ser Cys Ala Ala Ser Gly Phe Thr Leu Asp Tyr Ser Ser
            20                  25                  30

Ile Gly Trp Phe Arg Gln Ala Pro Gly Lys Glu Arg Glu Gly Val Ser
        35                  40                  45

Cys Ile Ser Ser Ser Gly Asp Ser Thr Lys Tyr Ala Asp Ser Val Lys
    50                  55                  60

Gly Arg Phe Thr Thr Ser Arg Asp Asn Ala Lys Asn Thr Val Tyr Leu
65                  70                  75                  80

Gln Met Glu Thr Asn Ser Leu Lys Pro Asp Asp Thr Ala Val Tyr Tyr
                85                  90                  95

Cys Ala Ala Phe Arg Ala Thr Met Glu Thr Cys Gly Val Phe Pro Leu
            100                 105                 110
```

Ser Pro Tyr Gly Lys Asp Asp Trp Gly Lys Gly Thr Leu Val Thr Val
            115                 120                 125

Ser Ser Gly Gly Gly Ser Gly Gly Gly Ser Gly Gly Gly Gly
130                 135                 140

Ser Gln Leu Gln Leu Val Glu Thr Gly Gly Leu Val Gln Pro Gly
145                 150                 155                 160

Gly Ser Leu Arg Leu Ser Cys Ala Ala Ser Gly Phe Thr Phe Ser Asp
                165                 170                 175

Tyr Val Met Glu Thr Thr Trp Val Arg Gln Ala Pro Lys Gly Pro
            180                 185                 190

Glu Trp Ile Ala Thr Ile Asn Thr Asp Gly Ser Thr Met Glu Thr Arg
            195                 200                 205

Asp Asp Ser Thr Lys Gly Arg Phe Thr Ile Ser Arg Asp Asn Ala Lys
210                 215                 220

Asn Thr Leu Tyr Leu Gln Met Glu Thr Thr Ser Leu Lys Pro Glu Asp
225                 230                 235                 240

Thr Ala Leu Tyr Tyr Cys Ala Arg Gly Arg Val Ile Ser Ala Ser Ala
                245                 250                 255

Ile Arg Gly Ala Val Arg Gly Pro Gly Thr Gln Val Thr Val Ser Ser
            260                 265                 270

<210> SEQ ID NO 65
<211> LENGTH: 786
<212> TYPE: DNA
<213> ORGANISM: Artificial Sequence
<220> FEATURE:
<223> OTHER INFORMATION: AH3-AA6 heterodimer

<400> SEQUENCE: 65
caggtgcagc tcgtggagac gggggggcttg gtgcagcctg ggggtctct gagactctcc        60 tgtgcagcct ctggattcac tttggattat cgtccatag gctggttccg ccaggcccca       120
gggaaggagc gtgagggggt ctcatgtatt agtagtagtg gtgatagcac aaagtatgca       180
gactccgtga agggccgatt caccacctcc agagacaacg ccaagaacac ggtgtatctg       240
caaatgaaca gcctgaaacc tgacgacaca gccgtttatt actgtgcagc ttttagggcg       300
actatgtgcg gcgtgttccc ccttagcccc tacggcaagg acgactgggg caaagggacc       360
ctggtcaccg tctcctcagg cggtggtggc tctggtggcg gcggttccgg tggcggtggc       420
agccagttgc agctcgtgga cagggggga ggcttggtgc agcctggggg gtctctgaga       480
ctctcctgtg cagcctctgg attcacgttc agtgactacg tcatgacctg ggtccgccag       540
gctccaggaa agggggcccga atggatcgca actattaata cggacggtag cacgatgcgt       600
gatgactcca caaaggccg attcaccatc tccagadaca cgccaagaa cacactgtat       660 ctgcaaatga ccagcctgaa accggaggac acggccctgt attactgtgc gagaggccgc       720
gtgatctccg cctccgcgat aagaggggcg gttaggggcc cggggaccca ggtcaccgtc       780
tcctca                                                                   786

<210> SEQ ID NO 66
<211> LENGTH: 6
<212> TYPE: PRT
<213> ORGANISM: Artificial Sequence
<220> FEATURE:
<223> OTHER INFORMATION: six-histidine tag

<400> SEQUENCE: 66

His His His His His His

<210> SEQ ID NO 67
<211> LENGTH: 13
<212> TYPE: PRT
<213> ORGANISM: Artificial Sequence
<220> FEATURE:
<223> OTHER INFORMATION: E-tag for protein purification

<400> SEQUENCE: 67

Gly Ala Pro Val Pro Tyr Pro Asp Pro Leu Glu Pro Arg
1               5                   10

<210> SEQ ID NO 68
<211> LENGTH: 6985
<212> TYPE: DNA
<213> ORGANISM: Artificial Sequence
<220> FEATURE:
<223> OTHER INFORMATION: Plasmid pD1214-FAKS-His-hABAB-D7

<400> SEQUENCE: 68

```
tcagaattgg ttaattggtt gtaacactga cccctatttg tttattttc taaatacatt      60 caaatatgta tccgctcatg agacaataac cctgataaat gcttcaataa tattgaaaaa     120
ggaagaatat gagtattcaa catttccgtg tcgcccttat cccttttttt gcggcatttt     180
gccttcctgt ttttgctcac ccagaaacgc tggtgaaagt aaaagatgct gaagatcagt     240
tgggtgcacg agtgggttac atcgaactgg atctcaacag cggtaagatc cttgagagtt     300
ttcgccccga agaacgtttt ccaatgatga gcacttttaa agttctgcta tgtggcgcgg     360
tattatcccg tattgacgcc gggcaagagc aactcggtcg ccgcatacac tattctcaga     420
atgacttggt tgagtactca ccagtcacag aaaagcatct tacgatggc atgacagtaa     480 gagaattatg cagtgctgcc ataaccatga gtgataacac tgcggccaac ttacttctga     540
caacgatcgg aggaccgaag gagctaaccg cttttttgca acatggggg gatcatgtaa     600 ctcgccttga tcgttgggaa ccggagctga atgaagccat accaaacgac gagcgtgaca     660
ccacgatgcc tgtagcgatg gcaacaacgt tgcgcaaact attaactggc gaactactta     720
ctctagcttc ccggcaacaa ttaatagact ggatggaggc ggataaagtt gcaggaccac     780
ttctgcgctc ggcccttccg gctggctggt ttattgctga taaatccgga gccggtgagc     840
gtggttctcg cggtatcatc gcagcgctgg ggccagatgg taagccctcc cgtatcgtag     900
ttatctacac gacggggagt caggcaacta tggatgaacg aaatagacag atcgctgaga     960
taggtgcctc actgattaag cattggtaac tcatgaccaa atcccttaa cgtgagttac    1020 gcgcgcgtcg ttccactgag cgtcagaccc cgtagaaaag atcaaaggat cttcttgaga    1080 tcctttttt ctgcgcgtaa tctgctgctt gcaaacaaaa aaaccaccgc taccagcggt    1140
ggtttgtttg ccggatcaag agctaccaac tcttttttccg aaggtaactg gcttcagcag    1200
agcgcagata ccaaatactg ttcttctagt gtagccgtag ttagcccacc acttcaagaa    1260
ctctgtagca ccgcctacat acctcgctct gctaatcctg ttaccagtgg ctgctgccag    1320
tggcgataag tcgtgtctta ccgggttgga ctcaagacga tagttaccgg ataaggcgca    1380
gcggtcgggc tgaacggggg gttcgtgcac acagcccagc ttggagcgaa cgacctacac    1440
cgaactgaga tacctacagc gtgagctatg agaaagcgcc acgcttcccg aagggagaaa    1500
ggcggacagg tatccggtaa gcggcagggt cggaacagga gagcgcacga gggagcttcc    1560
agggggaaac gcctggtatc tttatagtcc tgtcgggttt cgccacctct gacttgagcg    1620
```

```
tcgattttg tgatgctcgt caggggggcg gagcctatgg aaaaacgcca gcaacgcggc    1680
cttttacgg ttcctggcct tttgctggcc ttttgctcac atgttcttc ctgcgttatc    1740
ccctgattct gtggataacc gtattaccgc ctttgagtga gctgataccg ctcggggtcg   1800
tgcaggtata gcttcaaaat gtttctactc cttttttact cttccagatt ttctcggact   1860
ccgcgcatcg ccgtaccact tcaaaacacc caagcacagc atactaaatt tcccctcttt   1920
cttcctctag ggtgtcgtta attacccgta ctaaaggttt ggaaaagaaa aaagtgaccg   1980
cctcgtttct ttttcttcgt cgaaaaggc aataaaaatt tttatcacgt ttcttttct    2040
tgaaaatttt ttttttgat tttttctct ttcgatgacc tcccattgat atttaagtta    2100
ataaacggac ttcaatttct caagtttcag tttcatttt cttgttctat tacaactttt   2160
tttacttctt gctcattaga aagaaagcat agcaatctaa tctaagttta aatgagattc   2220
ccatctattt tcaccgctgt cttgttcgct gcctcctctg cattggctgc ccctgttaac   2280
actaccactg aagacgagac tgctcaaatt ccagctgaag cagttatcgg ttactctgac   2340
cttgagggtg atttcgacgt cgctgttttg cctttctcta actccactaa caacggtttg   2400
ttgttcatta acaccactat cgcttccatt gctgctaagg aagagggtgt ctctctcgag   2460
aaaagagagg ccgaagctat gcatcatcat catcatcatc aggtacagct ggtggagacg   2520
ggggagggc tggtacaacc aggcgggtca ctgaggcttt cctgtgccgc atctgggttc   2580
acactggatt attcgtccat agggtggttt cggcaggctc ctggcaaaga gcgtgagggg   2640
gtctcatgta ttagtagtag tggtgatagc acaaagtacg ccgattccgt aaagggccgg   2700
tttacaacct ccaggataa tgctaagaac accgtatatc tccagatgaa ctctctgaag   2760
cccgacgata cggccgtata ttactgtgcg gctttcaggg cgactatgtg cggcgtgttc   2820
cctctgagcc cttacggcaa ggacgactgg ggcaagggga ccctggtgac cgtatcctca   2880
ggcggtggag gtctggtgg gggaggctca ggggtggag cagccaggt gcaactggtt    2940
gaatctgggg gaggcttggt acaacctggg ggatccctga actctcttg cgaggcctcc   3000
ggattcacct tggactacta tggcatcggc tggttccgcc agcccccagg gaaggagcgg   3060
gaggccgttt catacattag tgccagtgcc ggaccatac tgtacgcaga ctctgtgaag   3120
ggacgcttta ccatctctag ggacaatgcc aaaaatgctg tgtacctgca aatgaacagc   3180
ctcaagcggg aggataccgc agtgtactac tgcgcgagac ggcgcttctc cgcttctagc   3240
gtgaatagat ggctggccga cgactacgac gtgtggggac ggggcacaca ggtggctgtg   3300
tcttccggtg gcggaagcgg aggggcagc ggggtggga gcggtggggg cagccaactg   3360
cagctggtag agacaggggg cggcttagtt cagcctggag ggtctctcag actgtcatgc   3420
gctgcctctg gctttacctt cagtgactac gtgatgacat gggtccgcca agctccaggg   3480
aagggggcctg agtggatcgc tactattaat acagatggca gcacaatgcg ggacgactcc   3540
acaaaggggc ggttcaccat ttccagagac aacgccaaga atactctgta ccttcagatg   3600
accagtctga aacccgagga cactgctctg tactattgtg caagaggccg ggtgatctct   3660
gcttccgcta tcagaggcgc agtaagggc cctggaacac aggtaaccgt ttcatccggg   3720
ggaggcggtt caggcggtgg gggatctggc ggggtggat cccaagttca gctggtcgaa   3780
tccgggggcg gactggtcca gacaggggc tccctgaggc tctcctgtgc atcttccgga   3840
agcatcgccg gcttcgagac cgtgacctgg tctcgccagg ctcccgggaa gtctctgcag   3900
tgggtcgctt ccatgactaa gactaacaac gagatctact ctgactcagt gaaaggccgc   3960
ttcatcattt ctagagataa cgctaaaaac acagtgtatc tgcagatgaa tagtctcaaa   4020
```

-continued

```
cctgaagaca caggcgtgta tttctgtaag ggtcctgagc tgaggggcca gggcatccag     4080
gtaacagtct cgagtgctcc tacaaaagcc aaacggagag tggtccagag agagaagacc     4140
taataaggtt gaatcatgta attagttatg tcacgcttac attcacgccc tcccccaca      4200 tccgctctaa ccgaaaagga aggagttaga caacctgaag tctaggtccc tatttatttt     4260
tttatagtta tgttagtatt aagaacgtta tttatatttc aaattttct tttttttctg      4320 tacagacgcg tgtacgcatg taacattata ctgaaaacct tgcttgagaa ggttttggga     4380
cgctcgaagg ctttaatttg cggcccctca cctgcacgca aaaagctttt caattcaatt     4440
catcattttt tttttattct tttttttgat ttcggtttct ttgaaatttt tttgattcgg     4500
taatctccga acagaaggaa gaacgaagga aggagcacag acttagattg gtatatatac     4560
gcatatgtag tgttgaagaa acatgaaatt gcccagtatt cttaacccaa ctgcacagaa     4620 caaaaccag caggaaacga agataaatca tgtcgaaagc tacatataag gaacgtgctg      4680
ctactcatcc tagtcctgtt gctgccaagc tatttaatat catgcacgaa aagcaaacaa     4740
acttgtgtgc ttcattggat gttcgtacca ccaaggaatt actggagtta gttgaagcat     4800
taggtcccaa aatttgttta ctaaaaacac atgtggatat cttgactgat ttttccatgg     4860
agggcacagt taagccgcta aaggcattat ccgccaagta caatttttta ctcttcgaag     4920
atagaaaatt tgctgacatt ggtaatacag tcaaattgca gtactctgcg ggtgtataca     4980
gaatagcaga atgggcagac attacgaatg cacacggtgt ggtgggccca ggtattgtta     5040
gcggtttgaa gcaggcggca gaagaagtaa caaaggaacc tagaggcctt ttgatgttag     5100
cagaattgtc atgcaagggc tccctatcta ctggagaata tactaagggt actgttgaca     5160
ttgcgaaaag cgacaaagat tttgttatcg gctttattgc tcaaagagac atgggtggaa     5220
gagatgaagg ttacgattgg ttgattatga cacccggtgt gggtttagat gacaagggag     5280
atgcattggg tcaacagtat agaaccgtgg atgatgttgt ctctacagga tctgacatta     5340
ttattgttgg aagaggacta tttgcaaagg gaagggatgc taaggtagag ggtgaacgtt     5400
acagaaaagc aggctgggaa gcatatttga gaagatgcgg ccagcaaaac taaaaaactg     5460
tattataagt aaatgcatgt atactaaact cacaaattag agcttcaatt taattatatc     5520
agttattacc cacgctatga tccaatatca aaggaaatga tagcattgaa ggatgagact     5580
aatccaattg aggagtggca gcatatagaa cagctaaagg gtagtgctga aggaagcata     5640 cgatacccg catggaatgg gataatatca caggaggtac tagactacct ttcatcctac      5700
ataaatagac gcatataagt acgcatttaa gcataaacac gcactatgcc gttcttctca     5760
tgtatatata tatacaggca acacgcagat ataggtgcga cgtgaacagt gagctgtatg     5820
tgcgcagctc gcgttgcatt ttcggaagcg ctcgttttcg gaaacgcttt gaagttccta     5880
ttccgaagtt cctattctct agaaagtata ggaacttcag agcgcttttg aaaaccaaaa     5940
gcgctctgaa gtcgcacttt caaaaaacca aaaacgcacc ggactgtaac gagctactaa     6000
aatattgcga ataccgcttc cacaaacatt gctcaaaagt atctctttgc tatatatctc     6060
tgtgctatat ccctatataa cctacccatc caccttcgc tccttgaact tgcatctaaa      6120
ctcgacctct acattttta tgtttatctc tagtattact ctttagacaa aaaaattgta     6180
gtaagaacta ttcatagagt gaatcgaaaa caatacgaaa atgtaaacat ttcctatacg     6240
tagtatatag agacaaaata gaagaaaccg ttcataattt tctgaccaat gaagaatcat     6300
caacgctatc actttctgtt cacaaagtat gcgcaatcca catcggtata gaatataatc     6360
```

| | |
|---|---|
| ggggatgcct ttatcttgaa aaaatgcacc cgcagcttcg ctagtaatca gtaaacgcgg | 6420 |
| gaagtggagt caggcttttt ttatggaaga gaaaatagac accaaagtag ccttcttcta | 6480 |
| accttaacgg acctacagtg caaaaagtta tcaagagact gcattataga gcgcacaaag | 6540 |
| gagaaaaaaa gtaatctaag atgctttgtt agaaaaatag cgctctcggg atgcattttt | 6600 |
| gtagaacaaa aagaagtat agattctttg ttggtaaaat agcgctctcg cgttgcattt | 6660 |
| ctgttctgta aaaatgcagc tcagattctt gtttgaaaaa attagcgctc tcgcgttgca | 6720 |
| tttttgtttt acaaaaatga agcacagatt cttcgttggt aaaatagcgc tttcgcgttg | 6780 |
| catttctgtt ctgtaaaaat gcagctcaga ttctttgttt gaaaaattag cgctctcgcg | 6840 |
| ttgcattttt gttctacaaa atgaagcaca gatgcttcgt tcaggtggca cttttcgggg | 6900 |
| aaatgtgcgc ggaacccta tttgtttatt tttctaaata cattcaaata tgtatccgct | 6960 |
| catgagacaa taaccctgat attgg | 6985 |

<210> SEQ ID NO 69
<211> LENGTH: 6916
<212> TYPE: DNA
<213> ORGANISM: Artificial Sequence
<220> FEATURE:
<223> OTHER INFORMATION: Plasmid pD1214-FAKS-hABAB

<400> SEQUENCE: 69

| | |
|---|---|
| tcagaattgg ttaattggtt gtaacactga cccctatttg tttatttttc taaatacatt | 60 |
| caaatatgta tccgctcatg agacaataac cctgataaat gcttcaataa tattgaaaaa | 120 |
| ggaagaatat gagtattcaa catttccgtg tcgcccttat tccctttttt gcggcatttt | 180 |
| gccttcctgt ttttgctcac ccagaaacgc tggtgaaagt aaaagatgct gaagatcagt | 240 |
| tgggtgcacg agtgggttac atcgaactgg atctcaacag cggtaagatc cttgagagtt | 300 |
| ttcgccccga agaacgtttt ccaatgatga gcacttttaa agttctgcta tgtggcgcgg | 360 |
| tattatcccg tattgacgcc gggcaagagc aactcggtcg ccgcatacac tattctcaga | 420 |
| atgacttggt tgagtactca ccagtcacag aaaagcatct tacggatggc atgacagtaa | 480 |
| gagaattatg cagtgctgcc ataaccatga gtgataacac tgcggccaac ttacttctga | 540 |
| caacgatcgg aggaccgaag gagctaaccg cttttttgca acatggggg atcatgtaa | 600 |
| ctcgccttga tcgttgggaa ccggagctga atgaagccat accaaacgac gagcgtgaca | 660 |
| ccacgatgcc tgtagcgatg gcaacaacgt tgcgcaaact attaactggc gaactactta | 720 |
| ctctagcttc ccggcaacaa ttaatagact ggatggaggc ggataaagtt gcaggaccac | 780 |
| ttctgcgctc ggcccttccg gctggctggt ttattgctga taaatccgga gccggtgagc | 840 |
| gtggttctcg cggtatcatc gcagcgctgg ggccagatgg taagccctcc cgtatcgtag | 900 |
| ttatctacac gacggggagt caggcaacta tggatgaacg aaatagacag atcgctgaga | 960 |
| taggtgcctc actgattaag cattggtaac tcatgaccaa atcccttaa cgtgagttac | 1020 |
| gcgcgcgtcg ttccactgag cgtcagaccc cgtagaaaag atcaaaggat cttcttgaga | 1080 |
| tccttttttt ctgcgcgtaa tctgctgctt gcaaacaaaa aaaccaccgc taccagcggt | 1140 |
| ggtttgtttg ccggatcaag agctaccaac tctttttccg aaggtaactg gcttcagcag | 1200 |
| agcgcagata ccaaatactg ttcttctagt gtagccgtag ttagcccacc acttcaagaa | 1260 |
| ctctgtagca ccgcctacat acctcgctct gctaatcctg ttaccagtgg ctgctgccag | 1320 |
| tggcgataag tcgtgtctta ccgggttgga ctcaagacga tagttaccgg ataaggcgca | 1380 |
| gcggtcgggc tgaacggggg gttcgtgcac acagcccagc ttggagcgaa cgacctacac | 1440 |

```
cgaactgaga tacctacagc gtgagctatg agaaagcgcc acgcttcccg aagggagaaa    1500
ggcggacagg tatccggtaa gcggcagggt cggaacagga gagcgcacga gggagcttcc    1560
agggggaaac gcctggtatc tttatagtcc tgtcgggttt cgccacctct gacttgagcg    1620 tcgattttg tgatgctcgt cagggggcg gagcctatgg aaaaacgcca gcaacgcggc      1680
ctttttacgg ttcctggcct tttgctggcc ttttgctcac atgttctttc ctgcgttatc    1740
ccctgattct gtggataacc gtattaccgc ctttgagtga gctgataccg ctcggggtcg    1800
tgcaggtata gcttcaaaat gtttctactc cttttttact cttccagatt ttctcggact    1860
ccgcgcatcg ccgtaccact tcaaaacacc aagcacagc atactaaatt cccctctttt    1920
cttcctctag ggtgtcgtta attcccgta ctaaaggttt ggaaaagaaa aaagtgaccg     1980 cctcgttct ttttcttcgt cgaaaaaggc aataaaaatt tttatcacgt ttcttttct     2040 tgaaaatttt tttttttgat tttttctct ttcgatgacc tcccattgat atttaagtta    2100
ataaacggac ttcaatttct caagtttcag tttcattttt cttgttctat tacaactttt   2160
tttacttctt gctcattaga aagaaagcat agcaatctaa tctaagttta aatgagattc    2220
ccatctattt tcaccgctgt cttgttcgct gcctcctctg cattggctgc ccctgttaac    2280
actaccactg aagacgagac tgctcaaatt ccagctgaag cagttatcgg ttactctgac    2340
cttgagggtg atttcgacgt cgctgttttg cctttctcta actccactaa caacggtttg    2400
ttgttcatta acaccactat cgcttccatt gctgctaagg aagagggtgt ctctctcgag    2460
aaaagagagg ccgaagctat gcaggtacag ctggtggaga cggggggagg gctggtacaa    2520 ccagcgggt cactgaggct ttcctgtgcc gcatctgggt tcacactgga ttattcgtcc    2580
atagggtggt tcggcaggc tcctggcaaa gagcgtgagg gggtctcatg tattagtagt    2640
agtggtgata gcacaaagta cgccgattcc gtaaagggcc ggtttacaac ctccagggat    2700
aatgctaaga acaccgtata tctccagatg aactctctga gcccgacga tacgccgta    2760 tattactgtg cggcttttcag ggcgactatg tgcggcgtgt tccctctgag cccttacggc    2820
aaggacgact ggggcaaggg gaccctggtg accgtatcct caggcggtgg agggtctggt    2880
ggggagggct cagggggtgg aggcagccag gtgcaactgg ttgaatctgg gggaggcttg    2940
gtacaacctg ggggatccct gagactctct tgcgaggcct ccggattcac cttggactac    3000
tatggcatcg gctggttccg ccagccccca gggaaggagc gggaggccgt ttcatacatt    3060
agtgccagtg cccggaccat actgtacgca gactctgtga agggacgctt taccatctct    3120
agggacaatg ccaaaaatgc tgtgtacctg caaatgaaca gcctcaagcg ggaggatacc    3180
gcagtgtact actgcgcgag acggcgcttc tccgcttcta gcgtgaatag atggctggcc    3240
gacgactacg acgtgtgggg acggggcaca caggtggctg tgtcttccgg tggcggaagc    3300 ggaggggggca gcggggggtgg gagcggtggg ggcagccaac tgcagctggt agagacaggg    3360
ggcggcttag ttcagcctgg agggtctctc agactgtcat gcgctgcctc tggctttacc    3420
ttcagtgact acgtgatgac atgggtccgc caagctccag ggaaggggcc tgagtggatc    3480
gctactatta atacagatgg cagcacaatg cgggacgact ccacaaaggg gcggttcacc    3540
atttccagag acaacgccaa gaatactctg taccttcaga tgaccagtct gaaacccgag    3600
gacactgctc tgtactattg tgcaagaggc cgggtgatct ctgcttccgc tatcagaggc    3660
gcagtaaggg gccctggaac acaggtaacc gtttcatccg ggggaggcgg ttcaggcggt    3720
gggggatctg gcggggggtgg atcccaagtt cagctggtcg aatccggggg cggactggtc    3780
```

```
cagacagggg gctccctgag gctctcctgt gcatcttccg gaagcatcgc cggcttcgag    3840
accgtgacct ggtctcgcca ggctcccggg aagtctctgc agtgggtcgc ttccatgact    3900
aagactaaca acgagatcta ctctgactca gtgaaaggcc gcttcatcat ttctagagat    3960
aacgctaaaa acacagtgta tctgcagatg aatagtctca aacctgaaga cacaggcgtg    4020
tatttctgta agggtcctga gctgaggggc cagggcatcc aggtaacagt ctcgagtggt    4080
tgaatcatgt aattagttat gtcacgctta cattcacgcc ctcccccccac atccgctcta    4140 accgaaaagg aaggagttag acaacctgaa gtctaggtcc ctatttattt ttttatagtt    4200
atgttagtat taagaacgtt atttatattt caaattttttc ttttttttttct gtacagacgc    4260 gtgtacgcat gtaacattat actgaaaacc ttgcttgaga aggttttggg acgctcgaag    4320
gctttaattt gcggcccctc acctgcacgc aaaaagcttt tcaattcaat tcatcatttt    4380 tttttttattc tttttttttga tttcggtttc tttgaaattt ttttgattcg gtaatctccg    4440
aacagaagga agaacgaagg aaggagcaca gacttagatt ggtatatata cgcatatgta    4500
gtgttgaaga aacatgaaat tgcccagtat tcttaaccca actgcacaga acaaaaacca    4560
gcaggaaacg aagataaatc atgtcgaaag ctacatataa ggaacgtgct gctactcatc    4620
ctagtcctgt tgctgccaag ctatttaata tcatgcacga aaagcaaaca aacttgtgtg    4680
cttcattgga tgttcgtacc accaaggaat tactggagtt agttgaagca ttaggtccca    4740
aaatttgttt actaaaaaca catgtggata tcttgactga ttttttccatg gagggcacag    4800 ttaagccgct aaaggcatta tccgccaagt acaattttttt actcttcgaa gatagaaaat    4860
ttgctgacat tggtaataca gtcaaattgc agtactctgc gggtgtatac agaatagcag    4920
aatgggcaga cattacgaat gcacacggtg tggtgggccc aggtattgtt agcggtttga    4980
agcaggcggc agaagaagta acaaaggaac ctagaggcct tttgatgtta gcagaattgt    5040
catgcaaggg ctccctatct actggagaat atactaaggg tactgttgac attgcgaaaa    5100
gcgacaaaga ttttgttatc ggcttttattg ctcaaagaga catgggtgga agagatgaag    5160
gttacgattg gttgattatg acacccggtg tgggtttaga tgacaaggga gatgcattgg    5220
gtcaacagta tagaaccgtg gatgatgttg tctctacagg atctgacatt attattgttg    5280
gaagaggact atttgcaaag ggaagggatg ctaaggtaga gggtgaacgt tacagaaaag    5340
caggctggga agcatatttg agaagatgcg gccagcaaaa ctaaaaaact gtattataag    5400
taaatgcatg tatactaaac tcacaaatta gagcttcaat ttaattatat cagttattac    5460
ccacgctatg atccaatatc aaaggaaatg atagcattga aggatgagac taatccaatt    5520
gaggagtggc agcatataga acagctaaag ggtagtgctg aaggaagcat acgataccccc    5580 gcatggaatg ggataatatc acaggaggta ctagactacc tttcatccta cataaataga    5640
cgcatataag tacgcattta agcataaaca cgcactatgc cgttcttctc atgtatatat    5700
atatacaggc aacacgcaga tataggtgcg acgtgaacag tgagctgtat gtgcgcagct    5760
cgcgttgcat tttcggaagc gctcgttttc ggaaacgctt tgaagttcct attccgaagt    5820
tcctattctc tagaaagtat aggaacttca gagcgctttt gaaaaccaaa agcgctctga    5880
agtcgcactt tcaaaaaacc aaaaacgcac cggactgtaa cgagctacta aaatattgcg    5940
ataccgcttt ccacaaacat tgctcaaaag tatctctttg ctatatatct ctgtgctata    6000
tccctatata acctacccat ccaccttttcg ctccttgaac ttgcatctaa actcgacctc    6060
tacatttttt atgtttatct ctagtattac tctttagaca aaaaaattgt agtaagaact    6120
attcatagag tgaatcgaaa acaatacgaa aatgtaaaca tttcctatac gtagtatata    6180
```

```
gagacaaaat agaagaaacc gttcataatt ttctgaccaa tgaagaatca tcaacgctat   6240
cactttctgt tcacaaagta tgcgcaatcc acatcggtat agaatataat cggggatgcc   6300
tttatcttga aaaatgcac ccgcagcttc gctagtaatc agtaaacgcg ggaagtggag   6360
tcaggctttt tttatggaag agaaaataga caccaaagta gccttcttct aaccttaacg   6420
gacctacagt gcaaaagtt atcaagagac tgcattatag agcgcacaaa ggagaaaaaa   6480
agtaatctaa gatgctttgt tagaaaaata gcgctctcgg gatgcatttt tgtagaacaa   6540
aaaagaagta tagattcttt gttggtaaaa tagcgctctc gcgttgcatt tctgttctgt   6600
aaaaatgcag ctcagattct ttgtttgaaa aattagcgct ctcgcgttgc atttttgttt   6660
tacaaaaatg aagcacagat tcttcgttgg taaaatagcg ctttcgcgtt gcatttctgt   6720
tctgtaaaaa tgcagctcag attctttgtt tgaaaaatta gcgctctcgc gttgcatttt   6780
tgttctacaa aatgaagcac agatgcttcg ttcaggtggc acttttcggg gaaatgtgcg   6840
cggaacccct atttgtttat ttttctaaat acattcaaat atgtatccgc tcatgagaca   6900
ataaccctga tattgg                                                     6916
```

<210> SEQ ID NO 70
<211> LENGTH: 6833
<212> TYPE: DNA
<213> ORGANISM: Artificial Sequence
<220> FEATURE:
<223> OTHER INFORMATION: Plasmid pD1214-AKS-hABAB

<400> SEQUENCE: 70

```
ggttaaatca tgtaattagt tatgtcacgc ttacattcac gccctccccc cacatccgct    60
ctaaccgaaa aggaaggagt tagacaacct gaagtctagg tccctatttta ttttttttata  120 gttatgttag tattaagaac gttatttata tttcaaattt ttcttttttt tctgtacaga   180
cgcgtgtacg catgtaacat tatactgaaa accttgcttg agaaggtttt gggacgctcg   240
aaggctttaa tttgcggccc ctcacctgca cgcaaaaagc ttttcaattc aattcatcat   300
ttttttttta ttcttttttt tgatttcggt ttctttgaaa ttttttttgat tcggtaatct   360 ccgaacagaa ggaagaacga aggaaggagc acagacttag attggtatat atacgcatat   420
gtagtgttga agaaacatga aattgcccag tattcttaac ccaactgcac agaacaaaaa   480
ccagcaggaa acgaagataa atcatgtcga agctacata taaggaacgt gctgctactc   540
atcctagtcc tgttgctgcc aagctattta atatcatgca cgaaaagcaa acaaacttgt   600
gtgcttcatt ggatgttcgt accaccaagg aattactgga gttagttgaa gcattaggtc   660
ccaaaatttg tttactaaaa acacatgtgg atatcttgac tgattttttcc atggagggca   720 cagttaagcc gctaaaggca ttatccgcca agtacaattt tttactcttc gaagatagaa   780
aatttgctga cattggtaat acagtcaaat tgcagtactc tgcgggtgta tacagaatag   840
cagaatgggc agacattacg aatgcacacg gtgtggtggg cccaggtatt gttagcggtt   900
tgaagcaggc ggcagaagaa gtaacaaagg aacctagagg ccttttgatg ttagcagaat   960
tgtcatgcaa gggctcccta tctactggag aatatactaa gggtactgtt gacattgcga  1020
aaagcgacaa agattttgtt atcggcttta ttgctcaaag agacatgggt ggaagagatg  1080
aaggttacga ttggttgatt atgacacccg gtgtgggttt agatgacaag ggagatgcat  1140
tgggtcaaca gtatagaacc gtggatgatg ttgtctctac aggatctgac attattattg  1200
ttggaagagg actatttgca aagggaaggg atgctaaggt agagggtgaa cgttacagaa  1260
```

```
aagcaggctg ggaagcatat ttgagaagat gcggccagca aaactaaaaa actgtattat    1320
aagtaaatgc atgtatacta aactcacaaa ttagagcttc aatttaatta tatcagttat    1380
tacccacgct atgatccaat atcaaaggaa atgatagcat tgaaggatga gactaatcca    1440
attgaggagt ggcagcatat agaacagcta aagggtagtg ctgaaggaag catacgatac    1500
cccgcatgga atgggataat atcacaggag gtactagact acctttcatc ctacataaat    1560
agacgcatat aagtacgcat ttaagcataa acacgcacta tgccgttctt ctcatgtata    1620
tatatataca ggcaacacgc agatataggt gcgacgtgaa cagtgagctg tatgtgcgca    1680
gctcgcgttg cattttcgga agcgctcgtt ttcggaaacg cttttgaagtt cctattccga    1740
agttcctatt ctctagaaag tataggaact tcagagcgct tttgaaaacc aaaagcgctc    1800
tgaagtcgca ctttcaaaaa accaaaaacg caccggactg taacgagcta ctaaaatatt    1860
gcgaataccg cttccacaaa cattgctcaa aagtatctct ttgctatata tctctgtgct    1920
atatccctat ataacctacc catccacctt tcgctccttg aacttgcatc taaactcgac    1980
ctctacattt tttatgttta tctctagtat tactcttttag acaaaaaat tgtagtaaga    2040
actattcata gagtgaatcg aaaacaatac gaaaatgtaa acatttccta tacgtagtat    2100
atagagacaa aatagaagaa accgttcata attttctgac caatgaagaa tcatcaacgc    2160
tatcactttc tgttcacaaa gtatgcgcaa tccacatcgg tatagaatat aatcggggat    2220
gcctttatct tgaaaaaatg cacccgcagc ttcgctagta atcagtaaac gcgggaagtg    2280
gagtcaggct tttttatgg aagagaaaat agacaccaaa gtagccttct tctaacctta    2340
acggacctac agtgcaaaaa gttatcaaga gactgcatta tagagcgcac aaaggagaaa    2400
aaaagtaatc taagatgctt tgttagaaaa atagcgctct cgggatgcat ttttgtagaa    2460
caaaaagaa gtatagattc tttgttggta aaatagcgct ctcgcgttgc atttctgttc    2520
tgtaaaaatg cagctcagat tctttgtttg aaaaattagc gctctcgcgt tgcattttg    2580
ttttacaaaa atgaagcaca gattcttcgt tggtaaaata gcgctttcgc gttgcatttc    2640
tgttctgtaa aaatgcagct cagattcttt gtttgaaaaa ttagcgctct cgcgttgcat    2700
ttttgttcta caaatgaag cacagatgct tcgttcaggt ggcacttttc ggggaaatgt    2760
gcgcggaacc cctatttgtt tattttcta aatacattca aatatgtatc cgctcatgag    2820
acaataaccc tgatattggt cagaattggt taattggttg taacactgac ccctatttgt    2880
ttattttct aaatacattc aaatatgtat ccgctcatga caataacc ctgataaatg    2940
cttcaataat attgaaaaag gaagaatatg agtattcaac atttccgtgt cgcccttatt    3000
ccctttttg cggcattttg ccttcctgtt tttgctcacc cagaaacgct ggtgaaagta    3060
aaagatgctg aagatcagtt gggtgcacga gtgggttaca tcgaactgga tctcaacagc    3120
ggtaagatcc ttgagagtttt cgccccgaa gaacgttttc caatgatgag cacttttaaa    3180
gttctgctat gtggcgcggt attatcccgt attgacgccg ggcaagagca actcggtcgc    3240
cgcatacact attctcagaa tgacttggtt gagtactcac cagtcacaga aaagcatctt    3300
acggatggca tgacagtaag agaattatgc agtgctgcca taaccatgag tgataacact    3360
gcggccaact tacttctgac aacgatcgga ggaccgaagg agctaaccgc ttttttgcac    3420
aacatggggg atcatgtaac tcgccttgat cgttgggaac cggagctgaa tgaagccata    3480
ccaaacgacg agcgtgacac cacgatgcct gtagcgatgg caacaacgtt gcgcaaacta    3540
ttaactggcg aactacttac tctagcttcc cggcaacaat taatagactg gatggaggcg    3600
gataaagttg caggaccact tctgcgctcg gcccttccgg ctggctggtt tattgctgat    3660
```

```
aaatccggag ccggtgagcg tggttctcgc ggtatcatcg cagcgctggg gccagatggt    3720
aagccctccc gtatcgtagt tatctacacg acggggagtc aggcaactat ggatgaacga    3780
aatagacaga tcgctgagat aggtgcctca ctgattaagc attggtaact catgaccaaa    3840
atcccttaac gtgagttacg cgcgcgtcgt tccactgagc gtcagacccc gtagaaaaga    3900
tcaaaggatc ttcttgagat ccttttttc tgcgcgtaat ctgctgcttg caaacaaaaa    3960
aaccaccgct accagcggtg gtttgtttgc cggatcaaga ctaccaact cttttccga     4020 aggtaactgg cttcagcaga gcgcagatac caaatactgt tcttctagtg tagccgtagt    4080
tagcccacca cttcaagaac tctgtagcac cgcctacata cctcgctctg ctaatcctgt    4140
taccagtggc tgctgccagt ggcgataagt cgtgtcttac cgggttggac tcaagacgat    4200
agttaccgga taaggcgcag cggtcgggct gaacggggg ttcgtgcaca cagcccagct    4260
tggagcgaac gacctacacc gaactgagat acctacagcg tgagctatga gaaagcgcca    4320
cgcttcccga agggagaaag gcggacaggt atccggtaag cggcagggtc ggaacaggag    4380
agcgcacgag ggagcttcca gggggaaacg cctggtatct ttatagtcct gtcgggtttc    4440
gccacctctg acttgagcgt cgatttttgt gatgctcgtc aggggggcgg agcctatgga    4500
aaaacgccag caacgcggcc ttttacggt tcctggcctt tgctggcct tttgctcaca    4560 tgttctttcc tgcgttatcc cctgattctg tggataaccg tattaccgcc tttgagtgag    4620
ctgataccgc tcgggtcgt gcaggtatag cttcaaaatg tttctactcc tttttactc    4680 ttccagattt tctcggactc cgcgcatcgc cgtaccactt caaaacaccc aagcacagca    4740
tactaaattt ccctcttc ttcctctagg gtgtcgttaa ttacccgtac taaaggtttg    4800
gaaaagaaaa aagtgaccgc ctcgtttctt tttcttcgtc gaaaaaggca ataaaaattt    4860
ttatcacgtt tcttttctt gaaaattttt tttttgatt tttttctctt tcgatgacct    4920
cccattgata tttaagttaa taaacggact tcaatttctc aagtttcagt ttcattttc    4980 ttgttctatt acaacttttt ttacttcttg ctcattagaa agaaagcata gcaatctaat    5040
ctaagtttaa aatgagattt ccttcaattt ttactgctgt tttattcgca gcatcctccg    5100
cattagctgc tccagtcaac actacaacag aagatgaatt agaagggat ttcgatgttg    5160 ctgttttgcc attttccgcc agcattgctg ctaaagaaga aggggtatct ctcgagaaaa    5220
gagaggctga agccatgcag gtacagctgg tggagacggg ggagggctg gtacaaccag    5280 gcgggtcact gaggctttcc tgtgccgcat ctgggttcac actggattat tcgtccatag    5340
ggtggtttcg gcaggctcct ggcaaagagc gtgagggggg ctcatgtatt agtagtagtg    5400
gtgatagcac aaagtacgcc gattccgtaa agggccggtt tacaacctcc agggataatg    5460
ctaagaacac cgtatatctc cagatgaact ctctgaagcc cgacgatacg gccgtatatt    5520
actgtgcggc tttcagggcg actatgtgcg gcgtgttccc tctgagccct acggcaagg    5580 acgactgggg caaggggacc ctggtgaccg tatcctcagg cggtggaggg tctggtgggg    5640
gaggctcagg gggtggaggc agccaggtgc aactggttga atctggggga ggcttggtac    5700
aacctggggg atccctgaga ctctcttgcg aggcctccgg attcaccttg gactactatg    5760
gcatcggctg gttccgccag cccccaggga aggagcggga ggccgtttca tacattagtg    5820
ccagtgcccg gaccatactg tacgcagact ctgtgaaggg acgctttacc atctctaggg    5880
acaatgccaa aaatgctgtg tacctgcaaa tgaacagcct caagcgggag gataccgcag    5940
tgtactactg cgcgagacgg cgcttctccg cttctagcgt gaatagatgg ctggccgacg    6000
```

```
actacgacgt gtggggacgg ggcacacagg tggctgtgtc ttccggtggc ggaagcggag     6060
ggggcagcgg gggtgggagc ggtgggggca gccaactgca gctggtagag acaggggcg     6120
gcttagttca gcctggaggg tctctcagac tgtcatgcgc tgcctctggc tttaccttca     6180
gtgactacgt gatgacatgg gtccgccaag ctccagggaa ggggcctgag tggatcgcta     6240
ctattaatac agatggcagc acaatgcggg acgactccac aaaggggcgg ttcaccattt     6300
ccagagacaa cgccaagaat actctgtacc ttcagatgac cagtctgaaa cccgaggaca     6360
ctgctctgta ctattgtgca agaggccggg tgatctctgc ttccgctatc agaggcgcag     6420
taagggccc tggaacacag gtaaccgttt catccggggg aggcggttca ggcggtgggg       6480
gatctggcgg gggtggatcc caagttcagc tggtcgaatc cggggggcgga ctggtccaga    6540
caggggcctc cctgaggctc tcctgtgcat cttccggaag catcgccggc ttcgagaccg     6600
tgacctggtc tcgccaggct cccgggaagt ctctgcagtg ggtcgcttcc atgactaaga     6660
ctaacaacga gatctactct gactcagtga aggccgctt catcatttct agagataacg      6720
ctaaaaacac agtgtatctg cagatgaata gtctcaaacc tgaagacaca ggcgtgtatt     6780
tctgtaaggg tcctgagctg aggggccagg gcatccaggt aacagtctcg agt            6833

<210> SEQ ID NO 71
<211> LENGTH: 6821
<212> TYPE: DNA
<213> ORGANISM: Artificial Sequence
<220> FEATURE:
<223> OTHER INFORMATION: Plasmid pD1214-AK-hABAB

<400> SEQUENCE: 71
ggttaaatca tgtaattagt tatgtcacgc ttacattcac gccctccccc cacatccgct       60
ctaaccgaaa aggaaggagt tagacaacct gaagtctagg tccctattta ttttttttata    120
gttatgttag tattaagaac gttatttata tttcaaattt ttctttttttt tctgtacaga    180
cgcgtgtacg catgtaacat tatactgaaa accttgcttg agaaggtttt gggacgctcg     240
aaggctttaa tttgcggccc ctcacctgca cgcaaaaagc ttttcaattc aattcatcat     300
ttttttttta ttcttttttt tgatttcggt ttctttgaaa ttttttttgat tcggtaatct    360
ccgaacagaa ggaagaacga aggaaggagc acagacttag attggtatat atacgcatat    420
gtagtgttga agaaacatga aattgcccag tattcttaac ccaactgcac agaacaaaaa    480
ccagcaggaa acgaagataa atcatgtcga aagctacata taaggaacgt gctgctactc    540
atcctagtcc tgttgctgcc aagctatttta atatcatgca cgaaaagcaa acaaacttgt    600
gtgcttcatt ggatgttcgt accaccaagg aattactgga gttagttgaa gcattaggtc     660
ccaaaatttg tttactaaaa acacatgtgg atatcttgac tgattttttcc atggagggca    720
cagttaagcc gctaaaggca ttatccgcca agtacaattt tttactcttc gaagatagaa     780
aatttgctga cattggtaat acagtcaaat gcagtactc tgcgggtgta tacagaatag     840
cagaatgggc agacattacg aatgcacacg gtgtggtggg cccaggtatt gttagcggtt     900
tgaagcaggc ggcagaagaa gtaacaaagg aacctagagg ccttttgatg ttagcagaat     960
tgtcatgcaa gggctcccta tctactggag aatatactaa gggtactgtt gacattgcga    1020
aaagcgacaa agattttgtt atcggcttta ttgctcaaag agacatgggt ggaagagatg    1080
aaggttacga ttggttgatt atgacacccg gtgtgggttt agatgacaag ggagatgcat    1140
tgggtcaaca gtatagaacc gtggatgatg ttgtctctac aggatctgac attattattg    1200
ttggaagagg actatttgca aagggaaggg atgctaaggt agagggtgaa cgttacagaa    1260
```

-continued

```
aagcaggctg ggaagcatat ttgagaagat gcggccagca aaactaaaaa actgtattat    1320
aagtaaatgc atgtatacta aactcacaaa ttagagcttc aatttaatta tatcagttat    1380
tacccacgct atgatccaat atcaaaggaa atgatagcat tgaaggatga gactaatcca    1440
attgaggagt ggcagcatat agaacagcta aagggtagtg ctgaaggaag catacgatac    1500
cccgcatgga atgggataat atcacaggag gtactagact acctttcatc ctacataaat    1560
agacgcatat aagtacgcat ttaagcataa acacgcacta tgccgttctt ctcatgtata    1620
tatatataca ggcaacacgc agatataggt gcgacgtgaa cagtgagctg tatgtgcgca    1680
gctcgcgttg cattttcgga agcgctcgtt ttcggaaacg cttttgaagtt cctattccga    1740 agttcctatt ctctagaaag tataggaact tcagagcgct tttgaaaacc aaaagcgctc    1800
tgaagtcgca ctttcaaaaa accaaaaacg caccggactg taacgagcta ctaaaatatt    1860
gcgaataccg cttccacaaa cattgctcaa aagtatctct ttgctatata tctctgtgct    1920
atatccctat ataacctacc catccaccatt tcgctccttg aacttgcatc taaactcgac    1980
ctctacattt tttatgttta tctctagtat tactctttag acaaaaaaat tgtagtaaga    2040
actattcata gagtgaatcg aaaacaatac gaaaatgtaa acatttccta tacgtagtat    2100
atagagacaa aatagaagaa accgttcata attttctgac caatgaagaa tcatcaacgc    2160
tatcactttc tgttcacaaa gtatgcgcaa tccacatcgg tatagaatat aatcggggat    2220
gcctttatct tgaaaaaatg cacccgcagc ttcgctagta atcagtaaac gcgggaagtg    2280
gagtcaggct ttttttatgg aagagaaaat agacaccaaa gtagccttct tctaaccttta    2340 acggacctac agtgcaaaaa gttatcaaga gactgcatta tagagcgcac aaaggagaaa    2400
aaaagtaatc taagatgctt tgttagaaaa atagcgctct cgggatgcat ttttgtagaa    2460 caaaaagaa gtatagattc tttgttggta aaatagcgct ctcgcgttgc atttctgttc    2520
tgtaaaaatg cagctcagat tctttgtttg aaaaattagc gctctcgcgt tgcatttttg    2580
ttttacaaaa atgaagcaca gattcttcgt tggtaaaata gcgctttcgc gttgcatttc    2640
tgttctgtaa aaatgcagct cagattcttt gtttgaaaaa ttagcgctct cgcgttgcat    2700
ttttgttcta caaaatgaag cacagatgct tcgttcaggt ggcactttc ggggaaatgt    2760 gcgcggaacc cctatttgtt tatttttcta aatacattca aatatgtatc cgctcatgag    2820
acaataaccc tgatattggt cagaattggt taattggttg taacactgac ccctatttgt    2880
ttatttttct aaatacattc aaatatgtat ccgctcatga acaataaccc tgataaatg    2940 cttcaataat attgaaaaag gaagaatatg agtattcaac atttccgtgt cgcccttatt    3000 ccctttttg cggcattttg ccttcctgtt tttgctcacc cagaaacgct ggtgaaagta    3060
aaagatgctg aagatcagtt gggtgcacga gtgggttaca tcgaactgga tctcaacagc    3120
ggtaagatcc ttgagagttt tcgccccgaa gaacgttttc caatgatgag cacttttaaa    3180
gttctgctat gtggcgcggt attatcccgt attgacgccg ggcaagagca actcggtcgc    3240
cgcatacact attctcagaa tgacttggtt gagtactcac cagtcacaga aaagcatctt    3300
acggatggca tgacagtaag agaattatgc agtgctgcca taaccatgag tgataacact    3360
gcggccaact tacttctgac aacgatcgga ggaccgaagg agctaaccgc ttttttgcac    3420
aacatggggg atcatgtaac tcgccttgat cgttgggaac cggagctgaa tgaagccata    3480
ccaaacgacg agcgtgacac cacgatgcct gtagcgatgg caacaacgtt gcgcaaacta    3540
ttaactggcg aactacttac tctagcttcc cggcaacaat taatagactg gatggaggcg    3600
```

```
gataaagttg caggaccact tctgcgctcg gcccttccgg ctggctggtt tattgctgat   3660
aaatccggag ccggtgagcg tggttctcgc ggtatcatcg cagcgctggg gccagatggt   3720
aagccctccc gtatcgtagt tatctacacg acggggagtc aggcaactat ggatgaacga   3780
aatagacaga tcgctgagat aggtgcctca ctgattaagc attggtaact catgaccaaa   3840
atcccttaac gtgagttacg cgcgcgtcgt tccactgagc gtcagacccc gtagaaaaga   3900
tcaaaggatc ttcttgagat ccttttttc tgcgcgtaat ctgctgcttg caaacaaaaa   3960
aaccaccgct accagcggtg gtttgtttgc cggatcaaga gctaccaact cttttccga   4020
aggtaactgg cttcagcaga gcgcagatac caaatactgt tcttctagtg tagccgtagt   4080
tagcccacca cttcaagaac tctgtagcac cgcctacata cctcgctctg ctaatcctgt   4140
taccagtggc tgctgccagt ggcgataagt cgtgtcttac cgggttggac tcaagacgat   4200
agttaccgga taaggcgcag cggtcgggct gaacggggggg ttcgtgcaca cagcccagct   4260
tggagcgaac gacctacacc gaactgagat acctacagcg tgagctatga aaagcgcca   4320
cgcttcccga agggagaaag gcggacaggt atccggtaag cggcagggtc ggaacaggag   4380
agcgcacgag ggagcttcca gggggaaacg cctggtatct ttatagtcct gtcgggtttc   4440
gccacctctg acttgagcgt cgatttttgt gatgctcgtc agggggggcgg agcctatgga   4500
aaaacgccag caacgcggcc ttttacggt tcctggcctt tgctggcct tttgctcaca   4560
tgttctttcc tgcgttatcc cctgattctg tggataaccg tattaccgcc tttgagtgag   4620
ctgataccgc tcggggtcgt gcaggtatag cttcaaaatg tttctactcc tttttactc   4680
ttccagattt tctcggactc cgcgcatcgc cgtaccactt caaaacaccc aagcacagca   4740
tactaaattt cccctctttc ttcctctagg gtgtcgttaa ttacccgtac taaaggtttg   4800
gaaaagaaaa aagtgaccgc ctcgtttctt tttcttcgtc gaaaaaggca ataaaaattt   4860
ttatcacgtt tctttttctt gaaaattttt tttttgatt tttttctctt tcgatgacct   4920
cccattgata tttaagttaa taaacggact tcaatttctc aagtttcagt ttcattttc   4980
ttgttctatt acaactttt ttacttcttg ctcattagaa agaaagcata gcaatctaat   5040
ctaagtttaa aatgagattt ccttcaattt ttactgctgt tttattcgca gcatcctccg   5100
cattagctgc tccagtcaac actacaacag aagatgaatt agaaggggat ttcgatgttg   5160
ctgttttgcc attttccgcc agcattgctg ctaaagaaga aggggtatct ctcgagaaaa   5220
gaatgcaggt acagctggtg gagacggggg gagggctggt acaaccaggc gggtcactga   5280
ggctttcctg tgccgcatct gggttcacac tggattattc gtccataggg tggtttcggc   5340
aggctcctgg caaagagcgt gaggggggtct catgtattag tagtagtggt gatagcacaa   5400
agtacgccga ttccgtaaag gccggttta caacctccag ggataatgct aagaacaccg   5460
tatatctcca gatgaactct ctgaagcccg acgatacggc cgtatattac tgtgcggctt   5520
tcagggcgac tatgtgcggc gtgttccctc tgagccctta cggcaaggac gactggggca   5580
aggggaccct ggtgaccgta tcctcaggcg gtggagggtc tggtggggga ggctcagggg   5640
gtggaggcag ccaggtgcaa ctggttgaat ctggggagg cttggtacaa cctgggggat   5700
ccctgagact ctcttgcgag gcctccggat tcaccttgga ctactatggc atcggctggt   5760
tccgccagcc cccagggaag gagcgggagg ccgtttcata cattagtgcc agtgcccgga   5820
ccatactgta cgcagactct gtgaagggac gctttaccat ctctagggac aatgccaaaa   5880
atgctgtgta cctgcaaatg aacagcctca agcggggagga taccgcagtg tactactgcg   5940
cgagacggcg cttctccgct tctagcgtga atagatggct ggccgacgac tacgacgtgt   6000
```

```
ggggacgggg cacacaggtg gctgtgtctt ccggtggcgg aagcggaggg ggcagcgggg    6060
gtgggagcgg tgggggcagc caactgcagc tggtagagac aggggggcggc ttagttcagc    6120 ctggagggtc tctcagactg tcatgcgctg cctctggctt taccttcagt gactacgtga    6180
tgacatgggt ccgccaagct ccagggaagg ggcctgagtg gatcgctact attaatacag    6240
atggcagcac aatgcgggac gactccacaa aggggcggtt caccatttcc agagacaacg    6300
ccaagaatac tctgtacctt cagatgacca gtctgaaacc cgaggacact gctctgtact    6360
attgtgcaag aggccgggtg atctctgctt ccgctatcag aggcgcagta aggggccctg    6420
gaacacaggt aaccgtttca tccggggggag gcggttcagg cggtgggggga tctggcgggg    6480 gtggatccca agttcagctg gtcgaatccg ggggcggact ggtccagaca ggggggctccc    6540 tgaggctctc ctgtgcatct tccggaagca tcgccggctt cgagaccgtg acctggtctc    6600
gccaggctcc cgggaagtct ctgcagtggg tcgcttccat gactaagact aacaacgaga    6660
tctactctga ctcagtgaaa ggccgcttca tcatttctag agataacgct aaaaacacag    6720
tgtatctgca gatgaatagt ctcaaacctg aagcacagg cgtgtatttc tgtaagggtc    6780
ctgagctgag gggccagggc atccaggtaa cagtctcgag t    6821
```

<210> SEQ ID NO 72
<211> LENGTH: 6707
<212> TYPE: DNA
<213> ORGANISM: Artificial Sequence
<220> FEATURE:
<223> OTHER INFORMATION: Plasmid pD1214-AT-hABAB

<400> SEQUENCE: 72

```
ggttaaatca tgtaattagt tatgtcacgc ttacattcac gccctccccc cacatccgct      60
ctaaccgaaa aggaaggagt tagacaacct gaagtctagg tccctattta tttttttata    120
gttatgttag tattaagaac gttatttata tttcaaattt ttctttttttt tctgtacaga    180 cgcgtgtacg catgtaacat tatactgaaa accttgcttg agaaggtttt gggacgctcg    240
aaggctttaa tttgcggccc ctcacctgca cgcaaaaagc ttttcaattc aattcatcat    300
ttttttttta ttctttttttt tgatttcggt ttctttgaaa ttttttttgat tcggtaatct    360 ccgaacagaa ggaagaacga aggaaggagc acagacttag attggtatat atacgcatat    420
gtagtgttga agaaacatga aattgcccag tattcttaac ccaactgcac agaacaaaaa    480
ccagcaggaa acgaagataa atcatgtcga aagctacata taaggaacgt gctgctactc    540
atcctagtcc tgttgctgcc aagctatta atatcatgca cgaaaagcaa acaaacttgt    600
gtgcttcatt ggatgttcgt accaccaagg aattactgga gttagttgaa gcattaggtc    660
ccaaaatttg tttactaaaa acacatgtgg atatcttgac tgattttttcc atggagggca    720 cagttaagcc gctaaaggca ttatccgcca agtacaattt tttactcttc gaagatagaa    780
aatttgctga cattggtaat acagtcaaat gcagtactc tgcgggtgta tacagaatag    840
cagaatgggc agacattacg aatgcacacg gtgtggtggg cccaggtatt gttagcggtt    900
tgaagcaggc ggcagaagaa gtaacaaagg aacctagagg ccttttgatg ttagcagaat    960
tgtcatgcaa gggctcccta tctactggag aatatactaa gggtactgtt gacattgcga    1020
aaagcgacaa agattttgtt atcggcttta ttgctcaaag agacatgggt ggaagagatg    1080
aaggttacga ttggttgatt atgacacccg gtgtgggttt agatgacaag ggagatgcat    1140
tgggtcaaca gtatagaacc gtggatgatg ttgtctctac aggatctgac attattattg    1200
```

```
ttggaagagg actatttgca aagggaaggg atgctaaggt agagggtgaa cgttacagaa      1260
aagcaggctg ggaagcatat ttgagaagat gcggccagca aaactaaaaa actgtattat      1320
aagtaaatgc atgtatacta aactcacaaa ttagagcttc aatttaatta tatcagttat      1380
tacccacgct atgatccaat atcaaaggaa atgatagcat tgaaggatga gactaatcca      1440
attgaggagt ggcagcatat agaacagcta aagggtagtg ctgaaggaag catacgatac      1500
cccgcatgga atgggataat atcacaggag gtactagact acctttcatc ctacataaat      1560
agacgcatat aagtacgcat ttaagcataa acacgcacta tgccgttctt ctcatgtata      1620
tatatataca ggcaacacgc agatataggt gcgacgtgaa cagtgagctg tatgtgcgca      1680
gctcgcgttg cattttcgga agcgctcgtt ttcggaaacg ctttgaagtt cctattccga      1740
agttcctatt ctctagaaag tataggaact tcagagcgct tttgaaaacc aaaagcgctc      1800
tgaagtcgca ctttcaaaaa accaaaaacg caccggactg taacgagcta ctaaaatatt      1860
gcgaataccg cttccacaaa cattgctcaa aagtatctct ttgctatata tctctgtgct      1920
atatccctat ataacctacc catccacctt tcgctccttg aacttgcatc taaactcgac      1980
ctctacattt tttatgttta tctctagtat tactctttag acaaaaaaat tgtagtaaga      2040
actattcata gagtgaatcg aaaacaatac gaaaatgtaa acatttccta tacgtagtat      2100
atagagacaa aatagaagaa accgttcata atttctgac caatgaagaa tcatcaacgc      2160
tatcactttc tgttcacaaa gtatgcgcaa tccacatcgg tatagaatat aatcggggat      2220
gcctttatct tgaaaaaatg cacccgcagc ttcgctagta atcagtaaac gcgggaagtg      2280
gagtcaggct ttttttatgg aagagaaaat agacaccaaa gtagccttct tctaacctta      2340
acggacctac agtgcaaaaa gttatcaaga gactgcatta tagagcgcac aaaggagaaa      2400
aaaagtaatc taagatgctt tgttagaaaa atagcgctct cgggatgcat ttttgtagaa      2460 caaaaagaa gtatagattc tttgttggta aaatagcgct ctcgcgttgc atttctgttc      2520
tgtaaaaatg cagctcagat tctttgtttg aaaaattagc gctctcgcgt tgcatttttg      2580
ttttacaaaa atgaagcaca gattcttcgt tggtaaaata gcgctttcgc gttgcatttc      2640
tgttctgtaa aaatgcagct cagattcttt gtttgaaaaa ttagcgctct cgcgttgcat      2700
ttttgttcta caaaatgaag cacagatgct tcgttcaggt ggcactttt ggggaaatgt      2760 gcgcggaacc cctatttgtt tatttttcta aatacattca aatatgtatc cgctcatgag      2820
acaataaccc tgatattggt cagaattggt taattggttg taacactgac ccctatttgt      2880
ttatttttct aaatacattc aaatatgtat ccgctcatga caataaacc ctgataaatg      2940 cttcaataat attgaaaaag gaagaatatg agtattcaac atttccgtgt cgcccttatt      3000 ccctttttg cggcattttg ccttcctgtt tttgctcacc cagaaacgct ggtgaaagta      3060
aaagatgctg aagatcagtt gggtgcacga gtgggttaca tcgaactgga tctcaacagc      3120
ggtaagatcc ttgagagttt tcgccccgaa gaacgttttc caatgatgag cacttttaaa      3180
gttctgctat gtggcgcggt attatcccgt attgacgccg ggcaagagca actcggtcgc      3240
cgcatacact attctcagaa tgacttggtt gagtactcac cagtcacaga aaagcatctt      3300
acggatggca tgacagtaag agaattatgc agtgctgcca taaccatgag tgataacact      3360
gcggccaact tacttctgac aacgatcgga ggaccgaagg agctaaccgc ttttttgcac      3420
aacatggggg atcatgtaac tcgccttgat cgttgggaac cggagctgaa tgaagccata      3480
ccaaacgacg agcgtgacac cacgatgcct gtagcgatgg caacaacgtt gcgcaaacta      3540
ttaactggcg aactacttac tctagcttcc cggcaacaat taatagactg gatggaggcg      3600
```

```
gataaagttg caggaccact tctgcgctcg gcccttccgg ctggctggtt tattgctgat    3660
aaatccggag ccggtgagcg tggttctcgc ggtatcatcg cagcgctggg gccagatggt    3720
aagccctccc gtatcgtagt tatctacacg acggggagtc aggcaactat ggatgaacga    3780
aatagacaga tcgctgagat aggtgcctca ctgattaagc attggtaact catgaccaaa    3840
atcccttaac gtgagttacg cgcgcgtcgt tccactgagc gtcagacccc gtagaaaaga    3900
tcaaaggatc ttcttgagat cctttttttc tgcgcgtaat ctgctgcttg caaacaaaaa    3960
aaccaccgct accagcggtg gtttgtttgc cggatcaaga gctaccaact cttttccga    4020 aggtaactgg cttcagcaga gcgcagatac caaatactgt tcttctagtg tagccgtagt    4080
tagcccacca cttcaagaac tctgtagcac cgcctacata cctcgctctg ctaatcctgt    4140
taccagtggc tgctgccagt ggcgataagt cgtgtcttac cgggttggac tcaagacgat    4200
agttaccgga taaggcgcag cggtcgggct gaacggggggt tcgtgcaca cagcccagct    4260 tggagcgaac gacctacacc gaactgagat acctacagcg tgagctatga aaagcgcca    4320 cgcttcccga agggagaaag gcggacaggt atccggtaag cggcagggtc ggaacaggag    4380
agcgcacgag ggagcttcca gggggaaacg cctggtatct ttatagtcct gtcgggtttc    4440
gccacctctg acttgagcgt cgatttttgt gatgctcgtc aggggggcgg agcctatgga    4500
aaaacgccag caacgcggcc ttttacggt tcctggcctt ttgctggcct tttgctcaca    4560
tgttctttcc tgcgttatcc cctgattctg tggataaccg tattaccgcc tttgagtgag    4620
ctgataccgc tcgggggtcgt gcaggtatag cttcaaaatg tttctactcc ttttttactc    4680
ttccagattt tctcggactc cgcgcatcgc cgtaccactt caaaacaccc aagcacagca    4740
tactaaattt cccctctttc ttcctctagg gtgtcgttaa ttacccgtac taaaggtttg    4800
gaaaagaaaa aagtgaccgc ctcgtttctt tttcttcgtc gaaaaaggca ataaaaattt    4860
ttatcacgtt tcttttctt gaaaatttt tttttgatt tttttctctt tcgatgacct    4920
cccattgata tttaagttaa taaacggact tcaatttctc aagtttcagt ttcattttc    4980 ttgttctatt acaactttt ttacttcttg ctcattagaa agaaagcata gcaatctaat    5040
ctaagtttaa aatgagattt ccttcaattt ttactgctgt tttattcgca gcatcctccg    5100
cattagctat gcaggtacag ctggtggaga cgggggggagg gctggtacaa ccaggcgggt    5160
cactgaggct ttcctgtgcc gcatctgggt tcacactgga ttattcgtcc ataggtggt    5220 ttcggcaggc tcctggcaaa gagcgtgagg gggtctcatg tattagtagt agtggtgata    5280
gcacaaagta cgccgattcc gtaaagggcc ggtttacaac ctccagggat aatgctaaga    5340
acaccgtata tctccagatg aactctctga agcccgacga tacggccgta tattactgtg    5400
cggctttcag ggcgactatg tgcggcgtgt ccctctgag cccttacggc aaggacgact    5460
ggggcaaggg gaccctggtg accgtatcct caggcggtgg agggtctggt gggggaggct    5520 caggggggtgg aggcagccag gtgcaactgg ttgaatctgg gggaggcttg gtacaacctg    5580
ggggatccct gagactctct tgcgaggcct ccggattcac cttggactac tatggcatcg    5640
gctggttccg ccagccccca gggaaggagc gggaggccgt ttcatacatt agtgccagtg    5700 cccgaccat actgtacgca gactctgtga agggacgctt taccatctct agggacaatg    5760
ccaaaaatgc tgtgtacctg caaatgaaca gcctcaagcg ggaggatacc gcagtgtact    5820
actgcgcgag acgcgcttc tccgcttcta gcgtgaatag atggctggcc gacgactacg    5880
acgtgtgggg acggggcaca caggtggctg tgtcttccgg tggcggaagc ggaggggggca    5940
```

```
gcggggtgg gagcggtggg ggcagccaac tgcagctggt agagacaggg ggcggcttag    6000
ttcagcctgg agggtctctc agactgtcat gcgctgcctc tggctttacc ttcagtgact    6060
acgtgatgac atgggtccgc caagctccag ggaaggggcc tgagtggatc gctactatta    6120
atacagatgg cagcacaatg cgggacgact ccacaagggg gcggttcacc atttccagag    6180
acaacgccaa gaatactctg taccttcaga tgaccagtct gaaacccgag gacactgctc    6240
tgtactattg tgcaagaggc cgggtgatct ctgcttccgc tatcagaggc gcagtaaggg    6300
gccctggaac acaggtaacc gtttcatccg ggggaggcgg ttcaggcggt gggggatctg    6360
gcggggtgg atcccaagtt cagctggtcg aatccggggg cggactggtc cagacagggg    6420
gctccctgag gctctcctgt gcatcttccg gaagcatcgc cggcttcgag accgtgacct    6480
ggtctcgcca ggctcccggg aagtctctgc agtgggtcgc ttccatgact aagactaaca    6540
acgagatcta ctctgactca gtgaaaggcc gcttcatcat ttctagagat aacgctaaaa    6600
acacagtgta tctgcagatg aatagtctca aacctgaaga cacaggcgtg tatttctgta    6660
agggtcctga gctgaggggc cagggcatcc aggtaacagt ctcgagt             6707

<210> SEQ ID NO 73
<211> LENGTH: 6710
<212> TYPE: DNA
<213> ORGANISM: Artificial Sequence
<220> FEATURE:
<223> OTHER INFORMATION: Plasmid pD1214-AA-hABAB

<400> SEQUENCE: 73
ggttaaatca tgtaattagt tatgtcacgc ttacattcac gccctccccc cacatccgct      60
ctaaccgaaa aggaaggagt tagacaacct gaagtctagg tccctattta tttttttata     120
gttatgttag tattaagaac gttatttata tttcaaattt ttctttttt tctgtacaga     180
cgcgtgtacg catgtaacat tatactgaaa accttgcttg agaaggtttt gggacgctcg     240
aaggctttaa tttgcggccc ctcacctgca cgcaaaaagc ttttcaattc aattcatcat     300
tttttttta ttctttttt tgatttcggt ttctttgaaa tttttttgat tcggtaatct     360
ccgaacagaa ggaagaacga aggaaggagc acagacttag attggtatat atacgcatat     420
gtagtgttga agaaacatga aattgcccag tattcttaac ccaactgcac agaacaaaaa     480
ccagcaggaa acgaagataa atcatgtcga aagctacata taggaacgt gctgctactc     540
atcctagtcc tgttgctgcc aagctatta atatcatgca cgaaaagcaa acaaacttgt     600
gtgcttcatt ggatgttcgt accaccaagg aattactgga gttagttgaa gcattaggtc     660
ccaaaatttg tttactaaaa acacatgtgg atatcttgac tgattttcc atggagggca     720
cagttaagcc gctaaaggca ttatccgcca agtacaattt tttactcttc gaagatagaa     780
aatttgctga cattggtaat acagtcaaat tgcagtactc tgcgggtgta tacagaatag     840
cagaatgggc agacattacg aatgcacacg gtgtggtggg cccaggtatt gttagcggtt     900
tgaagcaggc ggcagaagaa gtaacaaagg aacctagagg cctttttgatg ttagcagaat     960
tgtcatgcaa gggctcccta tctactggag aatatactaa gggtactgtt gacattgcga    1020
aaagcgacaa agattttgtt atcggcttta ttgctcaaag agacatgggt ggaagagatg    1080
aaggttacga ttggttgatt atgacacccg gtgtgggttt agatgacaag ggagatgcat    1140
tgggtcaaca gtatagaacc gtggatgatg ttgtctctac aggatctgac attattattg    1200
ttggaagagg actatttgca aagggaaggg atgctaaggt agagggtgaa cgttacagaa    1260
aagcaggctg ggaagcatat ttgagaagat gcggccagca aaactaaaaa actgtattat    1320
```

```
aagtaaatgc atgtatacta aactcacaaa ttagagcttc aatttaatta tatcagttat    1380
tacccacgct atgatccaat atcaaaggaa atgatagcat tgaaggatga actaatcca     1440 attgaggagt ggcagcatat agaacagcta aagggtagtg ctgaaggaag catacgatac    1500
cccgcatgga atgggataat atcacaggag gtactagact acctttcatc ctacataaat    1560
agacgcatat aagtacgcat ttaagcataa acacgcacta tgccgttctt ctcatgtata    1620
tatatataca ggcaacacgc agatataggt gcgacgtgaa cagtgagctg tatgtgcgca    1680
gctcgcgttg cattttcgga agcgctcgtt ttcggaaacg ctttgaagtt cctattccga    1740
agttcctatt ctctagaaag tataggaact tcagagcgct tttgaaaacc aaaagcgctc    1800
tgaagtcgca ctttcaaaaa accaaaaacg caccggactg taacgagcta ctaaaatatt    1860
gcgaataccg cttccacaaa cattgctcaa aagtatctct ttgctatata tctctgtgct    1920
atatccctat ataacctacc catccacctt tcgctccttg aacttgcatc taaactcgac    1980
ctctacattt tttatgttta tctctagtat tactctttag acaaaaaaat tgtagtaaga    2040
actattcata gagtgaatcg aaaacaatac gaaaatgtaa acatttccta tacgtagtat    2100
atagagacaa aatagaagaa accgttcata attttctgac caatgaagaa tcatcaacgc    2160
tatcactttc tgttcacaaa gtatgcgcaa tccacatcgg tatagaatat aatcggggat    2220
gcctttatct tgaaaaaatg cacccgcagc ttcgctagta atcagtaaac gcgggaagtg    2280
gagtcaggct ttttttatgg aagagaaaat agacaccaaa gtagccttct tctaacctta    2340
acggacctac agtgcaaaaa gttatcaaga gactgcatta tagagcgcac aaaggagaaa    2400
aaaagtaatc taagatgctt tgttagaaaa atagcgctct cgggatgcat ttttgtagaa    2460 caaaaagaa gtatagattc tttgttggta aaatagcgct ctcgcgttgc atttctgttc     2520
tgtaaaaatg cagctcagat tctttgtttg aaaaattagc gctctcgcgt tgcatttttg    2580
ttttacaaaa atgaagcaca gattcttcgt tggtaaaata gcgctttcgc gttgcatttc    2640
tgttctgtaa aaatgcagct cagattcttt gtttgaaaaa ttagcgctct cgcgttgcat    2700
ttttgttcta caaatgaag cacagatgct tcgttcaggt ggcacttttc ggggaaatgt     2760
gcgcggaacc cctatttgtt tattttttcta aatacattca aatatgtatc cgctcatgag    2820
acaataaccc tgatattggt cagaattggt taattggttg taacactgac ccctatttgt    2880
ttattttctt aaatacattc aaatatgtat ccgctcatga caataaacc ctgataaatg      2940 cttcaataat attgaaaaag gaagaatatg agtattcaac atttccgtgt cgcccttatt    3000 ccctttttg cggcattttg ccttcctgtt tttgctcacc cagaaacgct ggtgaaagta      3060
aaagatgctg aagatcagtt gggtgcacga gtgggttaca tcgaactgga tctcaacagc    3120
ggtaagatcc ttgagagttt tcgccccgaa gaacgttttc caatgatgag cacttttaaa    3180
gttctgctat gtggcgcggt attatcccgt attgacgccg ggcaagagca actcggtcgc    3240
cgcatacact attctcagaa tgacttggtt gagtactcac cagtcacaga aaagcatctt    3300
acggatggca tgacagtaag agaattatgc agtgctgcca taaccatgag tgataacact    3360
gcggccaact tacttctgac aacgatcgga ggaccgaagg agctaaccgc ttttttgcac    3420
aacatggggg atcatgtaac tcgccttgat cgttgggaac cggagctgaa tgaagccata    3480
ccaaacgacg agcgtgacac cacgatgcct gtagcgatgg caacaacgtt gcgcaaacta    3540
ttaactggcg aactacttac tctagcttcc cggcaacaat taatagactg gatgaggcg     3600 gataaagttg caggaccact tctgcgctcg gcccttccgg ctggctggtt tattgctgat    3660
```

```
aaatccggag ccggtgagcg tggttctcgc ggtatcatcg cagcgctggg gccagatggt    3720
aagccctccc gtatcgtagt tatctacacg acggggagtc aggcaactat ggatgaacga    3780
aatagacaga tcgctgagat aggtgcctca ctgattaagc attggtaact catgaccaaa    3840
atcccttaac gtgagttacg cgcgcgtcgt tccactgagc gtcagacccc gtagaaaaga    3900
tcaaaggatc ttcttgagat cctttttttc tgcgcgtaat ctgctgcttg caaacaaaaa    3960
aaccaccgct accagcggtg gtttgtttgc cggatcaaga ctaccaact cttttttccga    4020 aggtaactgg cttcagcaga gcgcagatac caaatactgt tcttctagtg tagccgtagt    4080
tagcccacca cttcaagaac tctgtagcac cgcctacata cctcgctctg ctaatcctgt    4140
taccagtggc tgctgccagt ggcgataagt cgtgtcttac cgggttggac tcaagacgat    4200
agttaccgga taaggcgcag cggtcgggct gaacggggg ttcgtgcaca cagcccagct    4260
tggagcgaac gacctacacc gaactgagat acctacagcg tgagctatga aaagcgcca    4320 cgcttcccga agggagaaag gcggacaggt atccggtaag cggcagggtc ggaacaggag    4380
agcgcacgag ggagcttcca gggggaaacg cctggtatct ttatagtcct gtcgggtttc    4440
gccacctctg acttgagcgt cgatttttgt gatgctcgtc aggggggcgg agcctatgga    4500
aaaacgccag caacgcggcc tttttacggt tcctggcctt ttgctggcct tttgctcaca    4560
tgttctttcc tgcgttatcc cctgattctg tggataaccg tattaccgcc tttgagtgag    4620
ctgataccgc tcgggtcgt gcaggtatag cttcaaaatg tttctactcc ttttttactc    4680
ttccagattt tctcggactc cgcgcatcgc cgtaccactt caaaacaccc aagcacagca    4740
tactaaattt cccctctttc ttcctctagg gtgtcgttaa ttacccgtac taaaggtttg    4800
gaaaagaaaa aagtgaccgc ctcgtttctt tttcttcgtc gaaaaaggca ataaaaattt    4860
ttatcacgtt tcttttttctt gaaaattttt tttttttgatt ttttttctctt tcgatgacct    4920 cccattgata tttaagttaa taaacggact tcaatttctc aagtttcagt ttcatttttc    4980
ttgttctatt acaactttt ttacttcttg ctcattagaa agaaagcata gcaatctaat    5040
ctaagtttaa aatggttgcc tggtggtccc ttttcctgta cggtttacaa gtcgctgctc    5100
ctgcattggc aatgcaggta cagctggtgg agacgggggg agggctggta caaccaggcg    5160
ggtcactgag gctttcctgt gccgcatctg ggttcacact ggattattcg tccatagggt    5220
ggtttcggca ggtcctggc aaagagcgtg agggggtctc atgtattagt agtagtggtg    5280
atagcacaaa gtacgccgat tccgtaaagg gccggtttac aacctccagg gataatgcta    5340
agaacaccgt atatctccag atgaactctc tgaagcccga cgatacgcc gtatattact    5400 gtgcggcttt cagggcgact atgtgcggcg tgttccctct gagcccttac ggcaaggacg    5460 actgggggcaa ggggaccctg gtgaccgtat cctcaggcgg tggagggtct ggtgggggag    5520
gctcaggggg tggaggcagc caggtgcaac tggttgaatc tgggggaggc ttggtacaac    5580 ctggggggatc cctgagactc tcttgcgagg cctccggatt cacccttggac tactatggca    5640 tcggctggtt ccgccagccc ccagggaagg agcgggaggc cgtttcatac attagtgcca    5700
gtgcccggac catactgtac gcagactctg tgaagggacg ctttaccatc tctagggaca    5760
atgccaaaaa tgctgtgtac ctgcaaatga acagcctcaa gcgggaggat accgcagtgt    5820
actactgcgc gagacggcgc ttctccgctt ctagcgtgaa tagatggctg ccgacgact    5880 acgacgtgtg gggacgggc acacaggtgg ctgtgtcttc cggtggcgga agcggagggg    5940
gcagcggggg tgggagcggt gggggcagcc aactgcagct ggtagagaca gggggcggct    6000
tagttcagcc tggagggtct ctcagactgt catgcgctgc ctctggcttt accttcagtg    6060
```

| | | |
|---|---|---|
| actacgtgat gacatgggtc cgccaagctc cagggaaggg gcctgagtgg atcgctacta | 6120 |
| ttaatacaga tggcagcaca atgcgggacg actccacaaa ggggcggttc accatttcca | 6180 |
| gagacaacgc caagaatact ctgtaccttc agatgaccag tctgaaaccc gaggacactg | 6240 |
| ctctgtacta ttgtgcaaga ggccgggtga tctctgcttc cgctatcaga ggcgcagtaa | 6300 |
| ggggcccctgg aacacaggta accgtttcat ccggggagg cggttcaggc ggtgggggat | 6360 |
| ctggcggggg tggatcccaa gttcagctgg tcgaatccgg gggcggactg gtccagacag | 6420 |
| ggggctccct gaggctctcc tgtgcatctt ccggaagcat cgccggcttc gagaccgtga | 6480 |
| cctggtctcg ccaggctccc gggaagtctc tgcagtgggt cgcttccatg actaagacta | 6540 |
| acaacgagat ctactctgac tcagtgaaag gccgcttcat catttctaga gataacgcta | 6600 |
| aaaacacagt gtatctgcag atgaatagtc tcaaacctga agacacaggc gtgtatttct | 6660 |
| gtaagggtcc tgagctgagg ggccagggca tccaggtaac agtctcgagt | 6710 |

<210> SEQ ID NO 74
<211> LENGTH: 6704
<212> TYPE: DNA
<213> ORGANISM: Artificial Sequence
<220> FEATURE:
<223> OTHER INFORMATION: Plasmid pD1214-GA-hABAB

<400> SEQUENCE: 74

| | | |
|---|---|---|
| ggttaaatca tgtaattagt tatgtcacgc ttacattcac gccctccccc cacatccgct | 60 |
| ctaaccgaaa aggaaggagt tagacaacct gaagtctagg tccctatttta ttttttttata | 120 |
| gttatgttag tattaagaac gttatttata tttcaaattt ttctttttttt tctgtacaga | 180 |
| cgcgtgtacg catgtaacat tatactgaaa accttgcttg agaaggtttt gggacgctcg | 240 |
| aaggctttaa tttgcggccc ctcacctgca cgcaaaaagc ttttcaattc aattcatcat | 300 |
| tttttttta ttcttttttt tgatttcggt ttctttgaaa ttttttttgat tcggtaatct | 360 |
| ccgaacagaa ggaagaacga aggaaggagc acagacttag attggtatat atacgcatat | 420 |
| gtagtgttga agaaacatga aattgcccag tattcttaac ccaactgcac agaacaaaaa | 480 |
| ccagcaggaa acgaagataa atcatgtcga aagctacata taaggaacgt gctgctactc | 540 |
| atcctagtcc tgttgctgcc aagctatttta atatcatgca cgaaaagcaa acaaacttgt | 600 |
| gtgcttcatt ggatgttcgt accaccaagg aattactgga gttagttgaa gcattaggtc | 660 |
| ccaaaatttg tttactaaaa acacatgtgg atatcttgac tgattttttcc atggagggca | 720 |
| cagttaagcc gctaaaggca ttatccgcca agtacaattt tttactcttc gaagatagaa | 780 |
| aatttgctga cattggtaat acagtcaaat tgcagtactc tgcgggtgta tacagaatag | 840 |
| cagaatgggc agacattacg aatgcacacg gtgtggtggg cccaggtatt gttagcggtt | 900 |
| tgaagcaggc ggcagaagaa gtaacaaagg aacctagagg cctttttgatg ttagcagaat | 960 |
| tgtcatgcaa gggctcccta tctactggag aatatactaa gggtactgtt gacattgcga | 1020 |
| aaagcgacaa agattttgtt atcggcttta ttgctcaaag agacatgggt ggaagagatg | 1080 |
| aaggttacga ttggttgatt atgacacccg gtgtgggttt agatgacaag ggagatgcat | 1140 |
| tgggtcaaca gtatagaacc gtggatgatg ttgtctctac aggatctgac attattattg | 1200 |
| ttggaagagg actatttgca aagggaaggg atgctaaggt agagggtgaa cgttacagaa | 1260 |
| aagcaggctg ggaagcatat ttgagaagat gcggccagca aaactaaaaa actgtattat | 1320 |
| aagtaaatgc atgtatacta aactcacaaa ttagagcttc aatttaatta tatcagttat | 1380 |

```
tacccacgct atgatccaat atcaaaggaa atgatagcat tgaaggatga gactaatcca    1440
attgaggagt ggcagcatat agaacagcta aagggtagtg ctgaaggaag catacgatac    1500
cccgcatgga atgggataat atcacaggag gtactagact acctttcatc ctacataaat    1560
agacgcatat aagtacgcat ttaagcataa acacgcacta tgccgttctt ctcatgtata    1620
tatatataca ggcaacacgc agatataggt gcgacgtgaa cagtgagctg tatgtgcgca    1680
gctcgcgttg cattttcgga agcgctcgtt ttcggaaacg cttttgaagtt cctattccga    1740
agttcctatt ctctagaaag tataggaact tcagagcgct tttgaaaacc aaaagcgctc    1800
tgaagtcgca ctttcaaaaa accaaaaacg caccggactg taacgagcta ctaaaatatt    1860
gcgaataccg cttccacaaa cattgctcaa aagtatctct ttgctatata tctctgtgct    1920
atatccctat ataacctacc catccacctt tcgctccttg aacttgcatc taaactcgac    1980
ctctacattt tttatgttta tctctagtat tactctttag acaaaaaaat tgtagtaaga    2040
actattcata gagtgaatcg aaaacaatac gaaaatgtaa acatttccta tacgtagtat    2100
atagagacaa aatagaagaa accgttcata attttctgac caatgaagaa tcatcaacgc    2160
tatcactttc tgttcacaaa gtatgcgcaa tccacatcgg tatagaatat aatcggggat    2220
gcctttatct tgaaaaaatg cacccgcagc ttcgctagta atcagtaaac gcgggaagtg    2280
gagtcaggct ttttttatgg aagagaaaat agacaccaaa gtagccttct tctaaccttaa   2340
acggacctac agtgcaaaaa gttatcaaga gactgcatta tagagcgcac aaaggagaaa    2400
aaaagtaatc taagatgctt tgttagaaaa atagcgctct cgggatgcat ttttgtagaa    2460
caaaaaagaa gtatagattc tttgttggta aaatagcgct ctcgcgttgc atttctgttc    2520
tgtaaaaatg cagctcagat tctttgtttg aaaaattagc gctctcgcgt tgcatttttg    2580
ttttacaaaa atgaagcaca gattcttcgt tggtaaaata gcgctttcgc gttgcatttc    2640
tgttctgtaa aaatgcagct cagattcttt gtttgaaaaa ttagcgctct cgcgttgcat    2700
ttttgttcta caaatgaag cacagatgct tcgttcaggt ggcactttc ggggaaatgt      2760
gcgcggaacc cctatttgtt tattttttcta aatacattca aatatgtatc cgctcatgag    2820
acaataaccc tgatattggt cagaattggt taattggttg taacactgac ccctatttgt    2880
ttatttttct aaatacattc aaatatgtat ccgctcatga acaataaccc tgataaatg    2940
cttcaataat attgaaaaag gaagaatatg agtattcaac atttccgtgt cgcccttatt    3000
ccctttttg cggcattttg ccttcctgtt tttgctcacc cagaaacgct ggtgaaagta    3060
aaagatgctg aagatcagtt gggtgcacga gtgggttaca tcgaactgga tctcaacagc    3120
ggtaagatcc ttgagagttt tcgccccgaa gaacgttttc caatgatgag cacttttaaa    3180
gttctgctat gtggcgcggt attatcccgt attgacgccg ggcaagagca actcggtcgc    3240
cgcatacact attctcagaa tgacttggtt gagtactcac cagtcacaga aaagcatctt    3300
acggatggca tgacagtaag agaattatgc agtgctgcca taaccatgag tgataacact    3360
gcggccaact tacttctgac aacgatcgga ggaccgaagg agctaaccgc ttttttgcac    3420
aacatggggg atcatgtaac tcgccttgat cgttgggaac cggagctgaa tgaagccata    3480
ccaaacgacg agcgtgacac cacgatgcct gtagcgatgg caacaacgtt gcgcaaacta    3540
ttaactggcg aactacttac tctagcttcc cggcaacaat taatagactg gatggaggcg    3600
gataaagttg caggaccact tctgcgctcg gcccttccgg ctggctggtt tattgctgat    3660
aaatccggag ccggtgagcg tggttctcgc ggtatcatcg cagcgctggg gccagatggt    3720
aagccctccc gtatcgtagt tatctacacg acggggagtc aggcaactat ggatgaacga    3780
```

```
aatagacaga tcgctgagat aggtgcctca ctgattaagc attggtaact catgaccaaa   3840
atcccttaac gtgagttacg cgcgcgtcgt tccactgagc gtcagacccc gtagaaaaga   3900
tcaaaggatc ttcttgagat cctttttttc tgcgcgtaat ctgctgcttg caaacaaaaa   3960
aaccaccgct accagcggtg gtttgtttgc cggatcaaga gctaccaact cttttttccga  4020 aggtaactgg cttcagcaga gcgcagatac caaatactgt tcttctagtg tagccgtagt   4080
tagcccacca cttcaagaac tctgtagcac cgcctacata cctcgctctg ctaatcctgt   4140
taccagtggc tgctgccagt ggcgataagt cgtgtcttac cgggttggac tcaagacgat   4200
agttaccgga taaggcgcag cggtcgggct gaacggggg ttcgtgcaca cagcccagct    4260
tggagcgaac gacctacacc gaactgagat acctacagcg tgagctatga aaagcgcca    4320 cgcttcccga agggagaaag gcggacaggt atccggtaag cggcagggtc ggaacaggag   4380
agcgcacgag ggagcttcca gggggaaacg cctggtatct ttatagtcct gtcgggtttc   4440
gccacctctg acttgagcgt cgatttttgt gatgctcgtc agggggggg agcctatgga    4500 aaaacgccag caacgcggcc ttttacggt tcctggcctt ttgctggcct tttgctcaca    4560
tgttctttcc tgcgttatcc cctgattctg tggataaccg tattaccgcc tttgagtgag   4620
ctgataccgc tcggggtcgt gcaggtatag cttcaaaatg tttctactcc tttttactc    4680 ttccagattt tctcggactc cgcgcatcgc cgtaccactt caaaacaccc aagcacagca   4740
tactaaattt cccctctttc ttcctctagg gtgtcgttaa ttacccgtac taaaggtttg   4800
gaaaagaaaa aagtgaccgc ctcgtttctt tttcttcgtc gaaaaaggca ataaaaattt   4860
ttatcacgtt tcttttcttt gaaaatttt ttttttgatt tttttctctt tcgatgacct    4920
cccattgata tttaagttaa taaacggact tcaatttctc aagtttcagt ttcatttttc   4980
ttgttctatt acaactttt ttacttcttg ctcattagaa agaaagcata gcaatctaat    5040
ctaagtttaa aatgtctttt agatcacttt tagctctgtc cggtttggtt tgtagtggat   5100
tggcaatgca ggtacagctg gtggagacgg ggggagggct ggtacaacca ggcgggtcac   5160
tgaggctttc ctgtgccgca tctgggttca cactggatta ttcgtccata gggtggtttc   5220
ggcaggctcc tggcaaagag cgtgaggggg tctcatgtat tagtagtagt ggtgatagca   5280
caaagtacgc cgattccgta aagggccggt ttacaacctc cagggataat gctaagaaca   5340
ccgtatatct ccagatgaac tctctgaagc ccgacgatac ggccgtatat tactgtgcgg   5400
ctttcagggc gactatgtgc ggcgtgttcc ctctgagccc ttacggcaag gacgactggg   5460 gcaagggac cctggtgacc gtatcctcag gcggtgaggt gtctggtggg ggaggctcag    5520
ggggtggagg cagccaggtg caactggttg aatctggggg aggcttggta caacctgggg   5580
gatccctgag actctcttgc gaggcctccg gattcacctt ggactactat ggcatcggct   5640
ggttccgcca gccccagg aaggagcgg aggccgttc atacattagt gccagtgccc       5700
ggaccatact gtacgcagac tctgtgaagg gacgctttac catctctagg gacaatgcca   5760
aaaatgctgt gtacctgcaa atgaacagcc tcaagcggga ggataccgca gtgtactact   5820
gcgcgagacg gcgcttctcc gcttctagcg tgaatagatg gctggccgac gactacgacg   5880
tgtggggacg gggcacacag gtggctgtgt cttccggtgg cggaagcgga ggggcagcg    5940 ggggtgggag cggtggggc agccaactgc agctggtaga gacaggggc ggcttagttc     6000 agcctggagg gtctctcaga ctgtcatgcg ctgcctctgg ctttaccttc agtgactacg   6060
tgatgacatg ggtccgccaa gctccaggga aggggcctga gtggatcgct actattaata   6120
```

| | | |
|---|---|---|
| cagatggcag cacaatgcgg gacgactcca caaaggggcg gttcaccatt tccagagaca | 6180 | |
| acgccaagaa tactctgtac cttcagatga ccagtctgaa acccgaggac actgctctgt | 6240 | |
| actattgtgc aagaggccgg gtgatctctg cttccgctat cagaggcgca gtaaggggcc | 6300 | |
| ctggaacaca ggtaaccgtt tcatccgggg gaggcggttc aggcggtggg ggatctggcg | 6360 | |
| ggggtggatc ccaagttcag ctggtcgaat ccggggggcgg actggtccag acaggggggct | 6420 | |
| ccctgaggct ctcctgtgca tcttccggaa gcatcgccgg cttcgagacc gtgacctggt | 6480 | |
| ctcgccaggc tcccgggaag tctctgcagt gggtcgcttc catgactaag actaacaacg | 6540 | |
| agatctactc tgactcagtg aaaggccgct tcatcatttc tagagataac gctaaaaaca | 6600 | |
| cagtgtatct gcagatgaat agtctcaaac ctgaagacac aggcgtgtat ttctgtaagg | 6660 | |
| gtcctgagct gaggggccag ggcatccagg taacagtctc gagt | 6704 | |

<210> SEQ ID NO 75
<211> LENGTH: 6698
<212> TYPE: DNA
<213> ORGANISM: Artificial Sequence
<220> FEATURE:
<223> OTHER INFORMATION: Plasmid pD1214-IN-hABAB

<400> SEQUENCE: 75

| | | |
|---|---|---|
| ggttaaatca tgtaattagt tatgtcacgc ttacattcac gccctccccc cacatccgct | 60 | |
| ctaaccgaaa aggaaggagt tagacaacct gaagtctagg tccctattta ttttttttata | 120 | |
| gttatgttag tattaagaac gttatttata tttcaaattt ttctttttttt tctgtacaga | 180 | |
| cgcgtgtacg catgtaacat tatactgaaa accttgcttg agaaggtttt gggacgctcg | 240 | |
| aaggctttaa tttgcggccc ctcacctgca cgcaaaaagc ttttcaattc aattcatcat | 300 | |
| tttttttta ttcttttttt tgatttcggt ttcttttgaaa ttttttttgat tcggtaatct | 360 | |
| ccgaacagaa ggaagaacga aggaaggagc acagacttag attggtatat atacgcatat | 420 | |
| gtagtgttga agaaacatga aattgcccag tattcttaac ccaactgcac agaacaaaaa | 480 | |
| ccagcaggaa acgaagataa atcatgtcga agctacata taaggaacgt gctgctactc | 540 | |
| atcctagtcc tgttgctgcc aagctattta atatcatgca cgaaaagcaa acaaacttgt | 600 | |
| gtgcttcatt ggatgttcgt accaccaagg aattactgga gttagttgaa gcattaggtc | 660 | |
| ccaaaatttg tttactaaaa acacatgtgg atatcttgac tgattttttcc atggagggca | 720 | |
| cagttaagcc gctaaaggca ttatccgcca agtacaattt tttactcttc gaagatagaa | 780 | |
| aatttgctga cattggtaat acagtcaaat tgcagtactc tgcgggtgta tacagaatag | 840 | |
| cagaatgggc agacattacg aatgcacacg gtgtggtggg cccaggtatt gttagcggtt | 900 | |
| tgaagcaggc ggcagaagaa gtaacaaagg aacctagagg ccttttgatg ttagcagaat | 960 | |
| tgtcatgcaa gggctcccta tctactggag aatatactaa gggtactgtt gacattgcga | 1020 | |
| aaagcgacaa agattttgtt atcggcttta ttgctcaaag agacatgggt ggaagagatg | 1080 | |
| aaggttacga ttggttgatt atgacacccg gtgtgggttt agatgacaag ggagatgcat | 1140 | |
| tgggtcaaca gtatagaacc gtggatgatg ttgtctctac aggatctgac attattattg | 1200 | |
| ttggaagagg actatttgca aagggaaggg atgctaaggt agagggtgaa cgttacagaa | 1260 | |
| aagcaggctg ggaagcatat ttgagaagat gcggccagca aaactaaaaa actgtattat | 1320 | |
| aagtaaatgc atgtatacta aactcacaaa ttagagcttc aatttaatta tatcagttat | 1380 | |
| tacccacgct atgatccaat atcaaaggaa atgatagcat tgaaggatga gactaatcca | 1440 | |
| attgaggagt ggcagcatat agaacagcta aagggtagtg ctgaaggaag catacgatac | 1500 | |

```
cccgcatgga atgggataat atcacaggag gtactagact accttctcatc ctacataaat    1560
agacgcatat aagtacgcat ttaagcataa acacgcacta tgccgttctt ctcatgtata    1620
tatatataca ggcaacacgc agatataggt gcgacgtgaa cagtgagctg tatgtgcgca    1680
gctcgcgttg cattttcgga agcgctcgtt ttcggaaacg ctttgaagtt cctattccga    1740
agttcctatt ctctagaaag tataggaact tcagagcgct tttgaaaacc aaaagcgctc    1800
tgaagtcgca ctttcaaaaa accaaaaacg caccggactg taacgagcta ctaaaatatt    1860
gcgaataccg cttccacaaa cattgctcaa aagtatctct ttgctatata tctctgtgct    1920
atatccctat ataacctacc catccacctt tcgctccttg aacttgcatc taaactcgac    1980
ctctacattt tttatgttta tctctagtat tactctttag acaaaaaaat tgtagtaaga    2040
actattcata gagtgaatcg aaaacaatac gaaaatgtaa acatttccta tacgtagtat    2100
atagagacaa aatagaagaa accgttcata attttctgac caatgaagaa tcatcaacgc    2160
tatcactttc tgttcacaaa gtatgcgcaa tccacatcgg tatagaatat aatcggggat    2220
gcctttatct tgaaaaaatg cacccgcagc ttcgctagta atcagtaaac gcgggaagtg    2280
gagtcaggct tttttttatgg aagagaaaat agacaccaaa gtagccttct tctaaccttta    2340
acggacctac agtgcaaaaa gttatcaaga gactgcatta tagagcgcac aaaggagaaa    2400
aaaagtaatc taagatgctt tgttagaaaa atagcgctct cgggatgcat ttttgtagaa    2460
caaaaagaa gtatagattc tttgttggta aaatagcgct ctcgcgttgc atttctgttc    2520
tgtaaaaatg cagctcagat tctttgtttg aaaaattagc gctctcgcgt tgcatttttg    2580
ttttacaaaa atgaagcaca gattcttcgt tggtaaaata gcgctttcgc gttgcatttc    2640
tgttctgtaa aaatgcagct cagattcttt gtttgaaaaa ttagcgctct cgcgttgcat    2700
ttttgttcta caaaatgaag cacagatgct tcgttcaggt ggcacttttc ggggaaatgt    2760
gcgcggaacc cctatttgtt tattttttcta aatacattca aatatgtatc cgctcatgag    2820
acaataaccc tgatattggt cagaattggt taattggttg taacactgac ccctatttgt    2880
ttattttttct aaatacattc aaatatgtat ccgctcatga caataaacc ctgataaatg    2940
cttcaataat attgaaaaag gaagaatatg agtattcaac atttccgtgt cgcccttatt    3000
ccctttttg cggcattttg ccttcctgtt tttgctcacc cagaaacgct ggtgaaagta    3060
aaagatgctg aagatcagtt gggtgcacga gtgggttaca tcgaactgga tctcaacagc    3120
ggtaagatcc ttgagagttt tcgccccgaa gaacgttttc caatgatgag cacttttaaa    3180
gttctgctat gtggcgcggt attatcccgt attgacgccg ggcaagagca actcggtcgc    3240
cgcatacact attctcagaa tgacttggtt gagtactcac cagtcacaga aaagcatctt    3300
acggatggca tgacagtaag agaattatgc agtgctgcca taaccatgag tgataacact    3360
gcggccaact tacttctgac aacgatcgga ggaccgaagg agctaaccgc ttttttgcac    3420
aacatggggg atcatgtaac tcgccttgat cgttgggaac cggagctgaa tgaagccata    3480
ccaaacgacg agcgtgacac cacgatgcct gtagcgatgg caacaacgtt gcgcaaacta    3540
ttaactggcg aactacttac tctagcttcc cggcaacaat taatagactg gatggaggcg    3600
gataaagttg caggaccact tctgcgctcg gcccttccgg ctggctggtt tattgctgat    3660
aaatccggag ccggtgagcg tggttctcgc ggtatcatcg cagcgctggg gccagatggt    3720
aagccctccc gtatcgtagt tatctacacg acggggagtc aggcaactat ggatgaacga    3780
aatagacaga tcgctgagat aggtgcctca ctgattaagc attggtaact catgaccaaa    3840
```

```
atcccttaac gtgagttacg cgcgcgtcgt tccactgagc gtcagacccc gtagaaaaga    3900
tcaaaggatc ttcttgagat cctttttttc tgcgcgtaat ctgctgcttg caaacaaaaa    3960
aaccaccgct accagcggtg gtttgtttgc cggatcaaga gctaccaact cttttccga    4020 aggtaactgg cttcagcaga gcgcagatac caaatactgt tcttctagtg tagccgtagt    4080
tagcccacca cttcaagaac tctgtagcac cgcctacata cctcgctctg ctaatcctgt    4140
taccagtggc tgctgccagt ggcgataagt cgtgtcttac cgggttggac tcaagacgat    4200
agttaccgga taaggcgcag cggtcgggct gaacggggggt tcgtgcaca cagcccagct    4260 tggagcgaac gacctacacc gaactgagat acctacagcg tgagctatga aaagcgcca    4320 cgcttcccga agggagaaag gcggacaggt atccggtaag cggcagggtc ggaacaggag    4380
agcgcacgag ggagcttcca gggggaaacg cctggtatct ttatagtcct gtcgggtttc    4440
gccacctctg acttgagcgt cgatttttgt gatgctcgtc aggggggcgg agcctatgga    4500
aaaacgccag caacgcggcc ttttttacggt tcctggcctt ttgctggcct tttgctcaca    4560
tgttctttcc tgcgttatcc cctgattctg tggataaccg tattaccgcc tttgagtgag    4620
ctgataccgc tcggggtcgt gcaggtatag cttcaaaatg tttctactcc tttttttactc    4680 ttccagattt tctcggactc cgcgcatcgc cgtaccactc aaaacaccc aagcacagca    4740 tactaaattt cccctctttc ttcctctagg gtgtcgttaa ttacccgtac taaaggtttg    4800
gaaaagaaaa aagtgaccgc ctcgtttctt tttcttcgtc gaaaaaggca ataaaaattt    4860
ttatcacgtt tcttttttctt gaaaattttt tttttttgatt tttttctctt tcgatgacct    4920
cccattgata tttaagttaa taaacggact tcaatttctc aagttcagt ttcattttc    4980 ttgttctatt acaactttt ttacttcttg ctcattagaa agaaagcata gcaatctaat    5040
ctaagtttaa aatgaaactt gcttactctc tgttgttacc attggccggt gtttccgcaa    5100
tgcaggtaca gctggtggag acggggggag ggctggtaca accaggcggg tcactgaggc    5160
tttcctgtgc cgcatctggg ttcacactgg attattcgtc catagggtgg tttcggcagg    5220
ctcctggcaa agagcgtgag ggggtctcat gtattagtag tagtggtgat agcacaaagt    5280
acgccgattc cgtaaagggc cggtttacaa cctccaggga taatgctaag aacaccgtat    5340
atctccagat gaactctctg aagcccgacg atacggccgt atattactgt gcggctttca    5400
gggcgactat gtgcggcgtg ttccctctga gcccttacgg caaggacgac tggggcaagg    5460
ggaccctggt gaccgtatcc tcaggcggtg gagggtctgg tggggaggc tcaggggtg    5520 gaggcagcca ggtgcaactg gttgaatctg gggggaggctt ggtacaacct ggggggatccc    5580 tgagactctc ttgcgaggcc tccggattca ccttggacta ctatggcatc ggctggttcc    5640
gccagccccc agggaaggag cgggaggccg tttcatacat tagtgccagt gcccggacca    5700
tactgtacgc agactctgtg aagggacgct ttaccatctc tagggacaat gccaaaaatg    5760
ctgtgtacct gcaaatgaac agcctcaagc gggaggatac cgcagtgtac tactgcgcga    5820
gacggcgctt ctccgcttct agcgtgaata gatggctggc cgacgactac gacgtgtggg    5880
gacggggcac acaggtggct gtgtcttccg gtggcggaag cggagggggc agcggggtg    5940 ggagcggtgg gggcagccaa ctgcagctgg tagagacagg gggcggctta gttcagcctg    6000
gagggtctct cagactgtca tgcgctgcct ctggctttac cttcagtgac tacgtgatga    6060
catgggtccg ccaagctcca gggaaggggc ctgagtggat cgctactatt aatacagatg    6120
gcagcacaat gcgggacgac tccacaaagg ggcggttcac catttccaga gacaacgcca    6180
agaatactct gtaccttcag atgaccagtc tgaaacccga ggacactgct ctgtactatt    6240
```

```
gtgcaagagg ccgggtgatc tctgcttccg ctatcagagg cgcagtaagg ggccctggaa    6300
cacaggtaac cgtttcatcc gggggaggcg gttcaggcgg tggggatct ggcggggtg       6360 gatcccaagt tcagctggtc gaatccgggg gcggactggt ccagacaggg ggctccctga    6420
ggctctcctg tgcatcttcc ggaagcatcg ccggcttcga ccgtgacc tggtctcgcc      6480 aggctcccgg gaagtctctg cagtgggtcg cttccatgac taagactaac aacgagatct    6540
actctgactc agtgaaaggc cgcttcatca tttctagaga taacgctaaa aacacagtgt    6600
atctgcagat gaatagtctc aaacctgaag acacaggcgt gtatttctgt aagggtcctg    6660
agctgagggg ccagggcatc caggtaacag tctcgagt                             6698

<210> SEQ ID NO 76
<211> LENGTH: 6707
<212> TYPE: DNA
<213> ORGANISM: Artificial Sequence
<220> FEATURE:
<223> OTHER INFORMATION: Plasmid pD1214-IVS-hABAB

<400> SEQUENCE: 76
ggttaaatca tgtaattagt tatgtcacgc ttacattcac gccctccccc cacatccgct      60
ctaaccgaaa aggaaggagt tagacaacct gaagtctagg tccctattta tttttttata    120
gttatgttag tattaagaac gttatttata tttcaaattt ttcttttttt tctgtacaga    180
cgcgtgtacg catgtaacat tatactgaaa accttgcttg agaaggtttt gggacgctcg    240
aaggctttaa tttgcggccc ctcacctgca cgcaaaaagc ttttcaattc aattcatcat    300 tttttttta ttcttttttt tgatttcggt ttctttgaaa ttttttgat tcggtaatct      360 ccgaacagaa ggaagaacga aggaaggagc acagacttag attggtatat atacgcatat    420
gtagtgttga agaaacatga aattgcccag tattcttaac ccaactgcac agaacaaaaa    480
ccagcaggaa acgaagataa atcatgtcga aagctacata taggaacgt gctgctactc     540 atcctagtcc tgttgctgcc aagctattta atatcatgca cgaaaagcaa acaaacttgt    600
gtgcttcatt ggatgttcgt accaccaagg aattactgga gttagttgaa gcattaggtc    660
ccaaaatttg tttactaaaa acacatgtgg atatcttgac tgattttttcc atggagggca   720 cagttaagcc gctaaaggca ttatccgcca agtacaattt tttactcttc gaagatagaa    780
aatttgctga cattggtaat acagtcaaat tgcagtactc tgcgggtgta tacagaatag    840
cagaatgggc agacattacg aatgcacacg tgtggtggg cccaggtatt gttagcggtt     900
tgaagcaggc ggcagaagaa gtaacaaagg aacctagagg ccttttgatg ttagcagaat    960
tgtcatgcaa gggctcccta tctactggag aatatactaa gggtactgtt gacattgcga   1020
aaagcgacaa agattttgtt atcggcttta ttgctcaaag agacatgggt ggaagagatg    1080
aaggttacga ttggttgatt atgacacccg gtgtgggttt agatgacaag ggagatgcat    1140
tgggtcaaca gtatagaacc gtggatgatg ttgtctctac aggatctgac attattattg    1200
ttggaagagg actatttgca aagggaaggg atgctaaggt agagggtgaa cgttacagaa    1260
aagcaggctg ggaagcatat ttgagaagat gcggccagca aaactaaaaa actgtattat    1320
aagtaaatgc atgtatacta aactcacaaa ttagagcttc aatttaatta tatcagttat    1380
tacccacgct atgatccaat atcaaaggaa atgatagcat tgaaggatga gactaatcca    1440
attgaggagt ggcagcatat agaacagcta aagggtagtg ctgaaggaag catacgatac    1500
cccgcatgga atgggataat atcacaggag gtactagact acctttcatc ctacataaat    1560
```

-continued

```
agacgcatat aagtacgcat ttaagcataa acacgcacta tgccgttctt ctcatgtata    1620
tatatataca ggcaacacgc agatataggt gcgacgtgaa cagtgagctg tatgtgcgca    1680
gctcgcgttg cattttcgga agcgctcgtt ttcggaaacg ctttgaagtt cctattccga    1740
agttcctatt ctctagaaag tataggaact tcagagcgct tttgaaaacc aaaagcgctc    1800
tgaagtcgca ctttcaaaaa accaaaaacg caccggactg taacgagcta ctaaaatatt    1860
gcgaataccg cttccacaaa cattgctcaa aagtatctct ttgctatata tctctgtgct    1920
atatccctat ataacctacc catccacctt tcgctccttg aacttgcatc taaactcgac    1980
ctctacattt tttatgttta tctctagtat tactctttag acaaaaaaat tgtagtaaga    2040
actattcata gagtgaatcg aaaacaatac gaaaatgtaa acatttccta tacgtagtat    2100
atagagacaa aatagaagaa accgttcata attttctgac caatgaagaa tcatcaacgc    2160
tatcactttc tgttcacaaa gtatgcgcaa tccacatcgg tatagaatat aatcggggat    2220
gcctttatct tgaaaaaatg cacccgcagc ttcgctagta atcagtaaac gcgggaagtg    2280
gagtcaggct ttttttatgg aagagaaaat agacaccaaa gtagccttct tctaacctta    2340
acggacctac agtgcaaaaa gttatcaaga gactgcatta tagagcgcac aaaggagaaa    2400
aaaagtaatc taagatgctt tgttagaaaa atagcgctct cgggatgcat ttttgtagaa    2460
caaaaagaa gtatagattc tttgttggta aaatagcgct ctcgcgttgc atttctgttc    2520
tgtaaaaatg cagctcagat tctttgtttg aaaaattagc gctctcgcgt tgcattttg    2580
ttttacaaaa atgaagcaca gattcttcgt tggtaaaata gcgctttcgc gttgcatttc    2640
tgttctgtaa aaatgcagct cagattcttt gtttgaaaaa ttagcgctct cgcgttgcat    2700
ttttgttcta caaatgaag cacagatgct tcgttcaggt ggcacttttc ggggaaatgt    2760
gcgcggaacc cctatttgtt tatttttcta aatacattca aatatgtatc cgctcatgag    2820
acaataaccc tgatattggt cagaattggt taattggttg taacactgac ccctatttgt    2880
ttatttttct aaatacattc aaatatgtat ccgctcatga caataaacc ctgataaatg    2940
cttcaataat attgaaaaag gaagaatatg agtattcaac atttccgtgt cgcccttatt    3000
ccctttttg cggcattttg ccttcctgtt tttgctcacc cagaaacgct ggtgaaagta    3060
aaagatgctg aagatcagtt gggtgcacga gtgggttaca tcgaactgga tctcaacagc    3120
ggtaagatcc ttgagagttt tcgccccgaa gaacgttttc caatgatgag cacttttaaa    3180
gttctgctat gtggcgcggt attatcccgt attgacgccg ggcaagagca actcggtcgc    3240
cgcatacact attctcagaa tgacttggtt gagtactcac cagtcacaga aaagcatctt    3300
acggatggca tgacagtaag agaattatgc agtgctgcca taaccatgag tgataacact    3360
gcggccaact tacttctgac aacgatcgga ggaccgaagg agctaaccgc ttttttgcac    3420
aacatggggg atcatgtaac tcgccttgat cgttgggaac cggagctgaa tgaagccata    3480
ccaaacgacg agcgtgacac cacgatgcct gtagcgatgg caacaacgtt gcgcaaacta    3540
ttaactggcg aactacttac tctagcttcc cggcaacaat aatagactg gatggaggcg    3600
gataaagttg caggaccact tctgcgctcg gcccttccgg ctggctggtt tattgctgat    3660
aaatccggag ccgtgagcg tggttctcgc ggtatcatcg cagcgctggg gccagatggt    3720
aagccctccc gtatcgtagt tatctacacg acggggagtc aggcaactat ggatgaacga    3780
aatagacaga tcgctgagat aggtgcctca ctgattaagc attggtaact catgaccaaa    3840
atcccttaac gtgagttacg cgcgcgtcgt tccactgagc gtcagacccc gtagaaaaga    3900
tcaaaggatc ttcttgagat cctttttttc tgcgcgtaat ctgctgcttg caaacaaaaa    3960
```

```
aaccaccgct accagcggtg gtttgtttgc cggatcaaga gctaccaact cttttttccga    4020
aggtaactgg cttcagcaga gcgcagatac caaatactgt tcttctagtg tagccgtagt    4080
tagcccacca cttcaagaac tctgtagcac cgcctacata cctcgctctg ctaatcctgt    4140
taccagtggc tgctgccagt ggcgataagt cgtgtcttac cgggttggac tcaagacgat    4200
agttaccgga taaggcgcag cggtcgggct gaacggggggg ttcgtgcaca cagcccagct    4260
tggagcgaac gacctacacc gaactgagat acctacagcg tgagctatga aaagcgcca    4320
cgcttcccga agggagaaag gcggacaggt atccggtaag cggcagggtc ggaacaggag    4380
agcgcacgag ggagcttcca gggggaaacg cctggtatct ttatagtcct gtcgggtttc    4440
gccacctctg acttgagcgt cgattttttgt gatgctcgtc aggggggcgg agcctatgga    4500
aaaacgccag caacgcggcc ttttttacggt tcctggcctt ttgctggcct tttgctcaca    4560
tgttctttcc tgcgttatcc cctgattctg tggataaccg tattaccgcc tttgagtgag    4620
ctgataccgc tcggggtcgt gcaggtatag cttcaaaatg tttctactcc tttttttactc    4680
ttccagattt tctcggactc cgcgcatcgc cgtaccactt caaaacaccc aagcacagca    4740
tactaaattt cccctctttc ttcctctagg gtgtcgttaa ttacccgtac taaaggtttg    4800
gaaagaaaaa aagtgaccgc ctcgtttctt tttcttcgtc gaaaaaggca ataaaaattt    4860
ttatcacgtt tctttttctt gaaaatttt tttttgatt tttttctctt tcgatgacct    4920
cccattgata tttaagttaa taaacggact tcaatttctc aagtttcagt ttcattttc    4980
ttgttctatt acaacttttt ttacttcttg ctcattagaa agaaagcata gcaatctaat    5040
ctaagtttaa aatgttactt caagctttct tgttcctgtt ggctggtttt gccgcaaaaa    5100
tctccgcaat gcaggtacag ctggtggaga cggggggagg gctggtacaa ccaggcgggt    5160
cactgaggct ttcctgtgcc gcatctgggt tcacactgga ttattcgtcc ataggtggt    5220
ttcggcaggc tcctggcaaa gagcgtgagg gggtctcatg tattagtagt agtggtgata    5280
gcacaaagta cgccgattcc gtaaagggcc ggtttacaac ctccagggat aatgctaaga    5340
acaccgtata tctccagatg aactctctga agcccgacga tacggccgta tattactgtg    5400
cggctttcag ggcgactatg tgcggcgtgt tccctctgag cccttacggc aaggacgact    5460
ggggcaaggg gaccctggtg accgtatcct caggcggtgg agggtctggt ggggggaggct    5520
caggggggtgg aggcagccag gtgcaactgg ttgaatctgg gggaggcttg gtacaacctg    5580
ggggatccct gagactctct tgcgaggcct ccggattcac cttggactac tatggcatcg    5640
gctggttccg ccagccccca gggaaggagc gggaggccgt tcatacatt agtgccagtg    5700
cccggaccat actgtacgca gactctgtga agggacgctt taccatctct agggacaatg    5760
ccaaaaatgc tgtgtacctg caaatgaaca gcctcaagcg ggaggatacc gcagtgtact    5820
actgcgcgag acggcgcttc tccgcttcta gcgtgaatag atggctggcc gacgactacg    5880
acgtgtgggg acggggcaca caggtggctg tgtcttccgg tggcggaagc ggaggggggca    5940
gcgggggtgg gagcggtggg ggcagccaac tgcagctggt agagacaggg ggcggcttag    6000
ttcagcctgg agggtctctc agactgtcat gcgctgcctc tggctttacc ttcagtgact    6060
acgtgatgac atgggtccgc caagctccag ggaagggggcc tgagtggatc gctactatta    6120
atacagatgg cagcacaatg cgggacgact ccacaaaggg gcggttcacc atttccagag    6180
acaacgccaa gaatactctg taccttcaga tgaccagtct gaaacccgag gacactgctc    6240
tgtactattg tgcaagaggc cgggtgatct ctgcttccgc tatcagaggc gcagtaaggg    6300
```

```
gccctggaac acaggtaacc gtttcatccg ggggaggcgg ttcaggcggt ggggatctg    6360 gcggggtgg atcccaagtt cagctggtcg aatccggggg cggactggtc cagacagggg    6420
gctccctgag gctctcctgt gcatcttccg gaagcatcgc cggcttcgag accgtgacct   6480
ggtctcgcca ggctcccggg aagtctctgc agtgggtcgc ttccatgact aagactaaca   6540
acgagatcta ctctgactca gtgaaaggcc gcttcatcat ttctagagat aacgctaaaa   6600
acacagtgta tctgcagatg aatagtctca aacctgaaga cacaggcgtg tatttctgta   6660
agggtcctga gctgaggggc cagggcatcc aggtaacagt ctcgagt                 6707

<210> SEQ ID NO 77
<211> LENGTH: 6728
<212> TYPE: DNA
<213> ORGANISM: Artificial Sequence
<220> FEATURE:
<223> OTHER INFORMATION: Plasmid pD1214-KP-hABAB

<400> SEQUENCE: 77
ggttaaatca tgtaattagt tatgtcacgc ttacattcac gccctccccc cacatccgct     60
ctaaccgaaa aggaaggagt tagacaacct gaagtctagg tccctatttta tttttttata   120 gttatgttag tattaagaac gttatttata tttcaaattt ttcttttttt tctgtacaga   180
cgcgtgtacg catgtaacat tatactgaaa accttgcttg agaaggtttt gggacgctcg   240
aaggctttaa tttgcggccc ctcacctgca cgcaaaaagc ttttcaattc aattcatcat   300 tttttttta ttctttttttt tgatttcggt ttctttgaaa ttttttttgat tcggtaatct   360 ccgaacagaa ggaagaacga aggaaggagc acagacttag attggtatat atacgcatat   420
gtagtgttga agaaacatga aattgcccag tattcttaac ccaactgcac agaacaaaaa   480
ccagcaggaa acgaagataa atcatgtcga aagctcacata taaggaacgt gctgctactc   540
atcctagtcc tgttgctgcc aagctattta atatcatgca cgaaaagcaa acaaacttgt    600
gtgcttcatt ggatgttcgt accaccaagg aattactgga gttagttgaa gcattaggtc    660
ccaaaatttg tttactaaaa acacatgtgg atatcttgac tgattttttcc atggagggca   720 cagttaagcc gctaaaggca ttatccgcca agtacaattt tttactcttc gaagatagaa    780
aatttgctga cattggtaat acagtcaaat tgcagtactc tgcgggtgta tacagaatag    840
cagaatgggc agacattacg aatgcacacg gtgtggtggg cccaggtatt gttagcggtt    900
tgaagcaggc ggcagaagaa gtaacaaagg aacctagagg cctttgatg ttagcagaat     960 tgtcatgcaa gggctcccta tctactggag aatatactaa gggtactgtt gacattgcga   1020
aaagcgacaa agattttgtt atcggcttta ttgctcaaag agacatgggt ggaagagatg   1080
aaggttacga ttggttgatt atgacacccg gtgtgggttt agatgacaag ggagatgcat   1140
tgggtcaaca gtatagaacc gtggatgatg ttgtctctac aggatctgac attattattg   1200
ttggaagagg actatttgca aagggaaggg atgctaaggt agagggtgaa cgttacagaa   1260
aagcaggctg ggaagcatat ttgagaagat gcggccagca aaactaaaaa actgtattat   1320
aagtaaatgc atgtatacta aactcacaaa ttagagcttc aatttaatta tatcagttat   1380
tacccacgct atgatccaat atcaaaggaa atgatagcat tgaaggatga gactaatcca   1440
attgaggagt ggcagcatat agaacagcta aagggtagtg ctgaaggaag catacgatac   1500
cccgcatgga atgggataat atcacaggag gtactagact acctttcatc ctacataaat   1560
agacgcatat aagtacgcat ttaagcataa acacgcacta tgccgttctt ctcatgtata   1620
tatatataca ggcaacacgc agatataggt gcgacgtgaa cagtgagctg tatgtgcgca   1680
```

```
gctcgcgttg cattttcgga agcgctcgtt ttcggaaacg ctttgaagtt cctattccga    1740
agttcctatt ctctagaaag tataggaact tcagagcgct tttgaaaacc aaaagcgctc    1800
tgaagtcgca ctttcaaaaa accaaaaacg caccggactg taacgagcta ctaaaatatt    1860
gcgaataccg cttccacaaa cattgctcaa aagtatctct ttgctatata tctctgtgct    1920
atatccctat ataacctacc catccacctt tcgctccttg aacttgcatc taaactcgac    1980
ctctacattt tttatgttta tctctagtat tactctttag acaaaaaaat tgtagtaaga    2040
actattcata gagtgaatcg aaaacaatac gaaaatgtaa acatttccta tacgtagtat    2100
atagagacaa aatagaagaa accgttcata attttctgac caatgaagaa tcatcaacgc    2160
tatcactttc tgttcacaaa gtatgcgcaa tccacatcgg tatagaatat aatcggggat    2220
gcctttatct tgaaaaaatg cacccgcagc ttcgctagta atcagtaaac gcgggaagtg    2280
gagtcaggct ttttttatgg aagagaaaat agacaccaaa gtagccttct tctaacctta    2340
acggacctac agtgcaaaaa gttatcaaga gactgcatta tagagcgcac aaaggagaaa    2400
aaaagtaatc taagatgctt tgttagaaaa atagcgctct cgggatgcat ttttgtagaa    2460
caaaaaagaa gtatagattc tttgttggta aaatagcgct ctcgcgttgc atttctgttc    2520
tgtaaaaatg cagctcagat tctttgtttg aaaaattagc gctctcgcgt tgcatttttg    2580
ttttacaaaa atgaagcaca gattcttcgt tggtaaaata gcgctttcgc gttgcatttc    2640
tgttctgtaa aaatgcagct cagattcttt gtttgaaaaa ttagcgctct cgcgttgcat    2700
ttttgttcta caaatgaag cacagatgct tcgttcaggt ggcactttc ggggaaatgt    2760 gcgcggaacc cctatttgtt tattttctta aatacattca aatatgtatc cgctcatgag    2820
acaataaccc tgatattggt cagaattggt taattggttg taacactgac ccctatttgt    2880
ttatttttct aaatacattc aaatatgtat ccgctcatga caataaacc tgataaatg    2940 cttcaataat attgaaaaag gaagaatatg agtattcaac atttccgtgt cgcccttatt    3000 ccctttttg cggcattttg ccttcctgtt tttgctcacc cagaaacgct ggtgaaagta    3060
aaagatgctg aagatcagtt gggtgcacga gtgggttaca tcgaactgga tctcaacagc    3120
ggtaagatcc ttgagagttt tcgccccgaa gaacgttttc caatgatgag cacttttaaa    3180
gttctgctat gtggcgcggt attatcccgt attgacgccg gcaagagca actcggtcgc    3240 cgcatacact attctcagaa tgacttggtt gagtactcac cagtcacaga aaagcatctt    3300
acggatggca tgacagtaag agaattatgc agtgctgcca taaccatgag tgataacact    3360
gcggccaact tacttctgac aacgatcgga ggaccgaagg agctaaccgc ttttttgcac    3420
aacatggggg atcatgtaac tcgccttgat cgttgggaac cggagctgaa tgaagccata    3480
ccaaacgacg agcgtgacac cacgatgcct gtagcgatgg caacaacgtt gcgcaaacta    3540
ttaactggcg aactacttac tctagcttcc cggcaacaat taatagactg gatggaggcg    3600
gataaagttg caggaccact tctgcgctcg gcccttccgg ctggctggtt tattgctgat    3660
aaatccggag ccggtgagcg tggttctcgc ggtatcatcg cagcgctggg gccagatggt    3720
aagccctccc gtatcgtagt tatctacacg acggggagtc aggcaactat ggatgaacga    3780
aatagacaga tcgctgagat aggtgcctca ctgattaagc attggtaact catgaccaaa    3840
atcccttaac gtgagttacg cgcgcgtcgt tccactgagc gtcagacccc gtagaaaaga    3900
tcaaaggatc ttcttgagat cctttttttc tgcgcgtaat ctgctgcttg caaacaaaaa    3960
aaccaccgct accagcggtg gtttgtttgc cggatcaaga gctaccaact cttttttccga    4020
```

```
aggtaactgg cttcagcaga gcgcagatac caaatactgt tcttctagtg tagccgtagt    4080
tagcccacca cttcaagaac tctgtagcac cgcctacata cctcgctctg ctaatcctgt    4140
taccagtggc tgctgccagt ggcgataagt cgtgtcttac cgggttggac tcaagacgat    4200
agttaccgga taaggcgcag cggtcgggct gaacggggg ttcgtgcaca cagcccagct     4260
tggagcgaac gacctacacc gaactgagat acctacagcg tgagctatga gaaagcgcca    4320
cgcttcccga agggagaaag gcggacaggt atccggtaag cggcagggtc ggaacaggag    4380
agcgcacgag ggagcttcca gggggaaacg cctggtatct ttatagtcct gtcgggtttc    4440
gccacctctg acttgagcgt cgattttgt gatgctcgtc agggggcgg agcctatgga      4500
aaaacgccag caacgcggcc ttttacggt tcctggcctt ttgctggcct tttgctcaca     4560
tgttctttcc tgcgttatcc cctgattctg tggataaccg tattaccgcc tttgagtgag    4620
ctgataccgc tcgggtcgt gcaggtatag cttcaaaatg tttctactcc ttttttactc     4680
ttccagattt tctcggactc cgcgcatcgc cgtaccactt caaaacaccc aagcacagca    4740
tactaaattt cccctctttc ttcctctagg gtgtcgttaa ttacccgtac taaaggtttg    4800
gaaaagaaaa aagtgaccgc ctcgtttctt tttcttcgtc gaaaaaggca ataaaaattt    4860
ttatcacgtt tcttttctt gaaaattttt tttttgatt ttttctctt tcgatgacct       4920
cccattgata tttaagttaa taaacggact tcaatttctc aagtttcagt ttcattttc     4980
ttgttctatt acaactttt ttacttcttg ctcattagaa agaaagcata gcaatctaat     5040
ctaagtttaa aatgacaaaa ccaacccaag tcttggtgag atctgtatcc attcttttct    5100
ttatcacttt attgcatctg gttgttgcta tgcaggtaca gctggtggag acgggggag     5160
ggctggtaca accaggcggg tcactgaggc tttcctgtgc cgcatctggg ttcacactgg    5220
attattcgtc catagggtgg tttcggcagg ctcctggcaa agagcgtgag ggggtctcat    5280
gtattagtag tagtggtgat agcacaaagt acgccgattc cgtaaagggc cggtttacaa    5340
cctccaggga taatgctaag aacaccgtat atctccagat gaactctctg aagcccgacg    5400
atacggccgt atattactgt gcggctttca gggcgactat gtgcggcgtg ttccctctga    5460
gcccttacgg caaggacgac tggggcaagg ggaccctggt gaccgtatcc tcaggcggtg    5520
gagggtctgg tggggaggc tcaggggggtg gaggcagcca ggtgcaactg gttgaatctg    5580
ggggaggctt ggtacaacct gggggatccc tgagactctc ttgcgaggcc tccgattca    5640
ccttggacta ctatggcatc ggctggttcc gccagccccc agggaaggag cgggaggccg    5700
tttcatacat tagtgccagt gcccggacca tactgtacgc agactctgtg aagggacgct    5760
ttaccatctc tagggacaat gccaaaaatg ctgtgtacct gcaaatgaac agcctcaagc    5820
gggaggatac cgcagtgtac tactgcgcga cggcgctt ctccgcttct agcgtgaata     5880
gatggctggc cgacgactac gacgtgtggg gacggggcac acaggtggct gtgtcttccg    5940
gtggcggaag cggagggggc agcggggtg ggagcggtgg gggcagccaa ctgcagctgg     6000
tagagacagg gggcggctta gttcagcctg gagggtctct cagactgtca tgcgctgcct    6060
ctggctttac cttcagtgac tacgtgatga catgggtccg ccaagctcca gggaaggggc    6120
ctgagtggat cgctactatt aatacagatg gcagcacaat gcgggacgac tccacaaagg    6180
ggcggttcac catttccaga gacaacgcca agaatactct gtaccttcag atgaccagtc    6240
tgaaacccga ggacactgct ctgtactatt gtgcaagagg ccgggtgatc tctgcttccg    6300
ctatcagagg cgcagtaagg ggccctggaa cacaggtaac cgtttcatcc ggggaggcg     6360
gttcaggcgg tgggggatct ggcggggtg gatcccaagt tcagctggtc gaatccgggg     6420
```

```
gcggactggt ccagacaggg ggctccctga ggctctcctg tgcatcttcc ggaagcatcg    6480
ccggcttcga gaccgtgacc tggtctcgcc aggctcccgg gaagtctctg cagtgggtcg    6540
cttccatgac taagactaac aacgagatct actctgactc agtgaaaggc cgcttcatca    6600
tttctagaga taacgctaaa aacacagtgt atctgcagat gaatagtctc aaacctgaag    6660
acacaggcgt gtatttctgt aagggtcctg agctgagggg ccagggcatc caggtaacag    6720
tctcgagt                                                             6728

<210> SEQ ID NO 78
<211> LENGTH: 6728
<212> TYPE: DNA
<213> ORGANISM: Artificial Sequence
<220> FEATURE:
<223> OTHER INFORMATION: Plasmid pD1214-LZ-hABAB

<400> SEQUENCE: 78
ggttaaatca tgtaattagt tatgtcacgc ttacattcac gccctccccc cacatccgct      60
ctaaccgaaa aggaaggagt tagacaacct gaagtctagg tccctattta tttttttata    120
gttatgttag tattaagaac gttatttata tttcaaattt ttcttttttt tctgtacaga    180
cgcgtgtacg catgtaacat tatactgaaa accttgcttg agaaggtttt gggacgctcg    240
aaggctttaa tttgcggccc ctcacctgca cgcaaaaagc ttttcaattc aattcatcat    300 tttttttta ttcttttttt tgatttcggt ttctttgaaa ttttttgat tcggtaatct    360 ccgaacagaa ggaagaacga aggaaggagc acagacttag attggtatat atacgcatat    420
gtagtgttga agaaacatga aattgcccag tattcttaac ccaactgcac agaacaaaaa    480
ccagcaggaa acgaagataa atcatgtcga aagctacata taggaacgt gctgctactc    540 atcctagtcc tgttgctgcc aagctatttta atatcatgca cgaaaagcaa acaaacttgt    600
gtgcttcatt ggatgttcgt accaccaagg aattactgga gttagttgaa gcattaggtc    660
ccaaaatttg tttactaaaa acacatgtgg atatcttgac tgattttttcc atggagggca    720 cagttaagcc gctaaaggca ttatccgcca agtacaattt tttactcttc gaagatagaa    780
aatttgctga cattggtaat acagtcaaat tgcagtactc tgcgggtgta tacagaatag    840
cagaatgggc agacattacg aatgcacacg tgtggtggg cccaggtatt gttagcggtt    900
tgaagcaggc ggcagaagaa gtaacaaagg aacctagagg ccttttgatg ttagcagaat    960
tgtcatgcaa gggctcccta tctactggag aatatactaa gggtactgtt gacattgcga    1020
aaagcgacaa agattttgtt atcggcttta ttgctcaaag agacatgggt ggaagagatg    1080
aaggttacga ttggttgatt atgacacccg gtgtgggttt agatgacaag ggagatgcat    1140
tgggtcaaca gtatagaacc gtggatgatg ttgtctctac aggatctgac attattattg    1200
ttggaagagg actatttgca aagggaaggg atgctaaggt agagggtgaa cgttacagaa    1260
aagcaggctg ggaagcatat ttgagaagat gcggccagca aaactaaaaa actgtattat    1320
aagtaaatgc atgtatacta aactcacaaa ttagagcttc aatttaatta tatcagttat    1380
tacccacgct atgatccaat atcaaaggaa atgatagcat tgaaggatga gactaatcca    1440
attgaggagt ggcagcatat agaacagcta aagggtagtg ctgaaggaag catacgatac    1500
cccgcatgga atgggataat atcacaggag gtactagact accttcatc ctacataaat    1560 agacgcatat aagtacgcat ttaagcataa acacgcacta tgccgttctt ctcatgtata    1620
tatatataca ggcaacacgc agatataggt gcgacgtgaa cagtgagctg tatgtgcgca    1680
```

```
gctcgcgttg cattttcgga agcgctcgtt ttcggaaacg ctttgaagtt cctattccga    1740
agttcctatt ctctagaaag tataggaact tcagagcgct tttgaaaacc aaaagcgctc    1800
tgaagtcgca ctttcaaaaa accaaaaacg caccggactg taacgagcta ctaaaatatt    1860
gcgaataccg cttccacaaa cattgctcaa aagtatctct ttgctatata tctctgtgct    1920
atatccctat ataacctacc catccacctt tcgctccttg aacttgcatc taaactcgac    1980
ctctacattt tttatgttta tctctagtat tactctttag acaaaaaaat tgtagtaaga    2040
actattcata gagtgaatcg aaaacaatac gaaaatgtaa acatttccta tacgtagtat    2100
atagagacaa aatagaagaa accgttcata attttctgac caatgaagaa tcatcaacgc    2160
tatcactttc tgttcacaaa gtatgcgcaa tccacatcgg tatagaatat aatcggggat    2220
gcctttatct tgaaaaaatg cacccgcagc ttcgctagta atcagtaaac gcgggaagtg    2280
gagtcaggct ttttttatgg aagagaaaat agacaccaaa gtagccttct tctaacctta    2340
acggacctac agtgcaaaaa gttatcaaga gactgcatta tagagcgcac aaaggagaaa    2400
aaaagtaatc taagatgctt tgttagaaaa atagcgctct cgggatgcat ttttgtagaa    2460 caaaaagaa gtagagattc tttgttggta aaatagcgct ctcgcgttgc atttctgttc    2520
tgtaaaaatg cagctcagat tctttgtttg aaaaattagc gctctcgcgt tgcattttg    2580 ttttacaaaa atgaagcaca gattcttcgt tggtaaaata gcgctttcgc gttgcatttc    2640
tgttctgtaa aaatgcagct cagattcttt gtttgaaaaa ttagcgctct cgcgttgcat    2700
ttttgttcta caaatgaag cacagatgct tcgttcaggt ggcacttttc ggggaaatgt    2760
gcgcggaacc cctatttgtt tatttttcta aatacattca aatatgtatc cgctcatgag    2820
acaataaccc tgatattggt cagaattggt taattggttg taacactgac ccctatttgt    2880
ttatttttct aaatacattc aaatatgtat ccgctcatga caataaccc tgataaatg    2940 cttcaataat attgaaaaag gaagaatatg agtattcaac atttccgtgt cgcccttatt    3000
cccttttttg cggcattttg ccttcctgtt tttgctcacc cagaaacgct ggtgaaagta    3060
aaagatgctg aagatcagtt gggtgcacga gtgggttaca tcgaactgga tctcaacagc    3120
ggtaagatcc ttgagagttt tcgccccgaa gaacgttttc caatgatgag cacttttaaa    3180
gttctgctat gtggcgcggt attatcccgt attgacgccg gcaagagca actcggtcgc    3240 cgcatacact attctcagaa tgacttggtt gagtactcac cagtcacaga aaagcatctt    3300
acggatggca tgacagtaag agaattatgc agtgctgcca taaccatgag tgataacact    3360
gcggccaact tacttctgac aacgatcgga ggaccgaagg agctaaccgc ttttttgcac    3420
aacatggggg atcatgtaac tcgccttgat cgttgggaac cggagctgaa tgaagccata    3480
ccaaacgacg agcgtgacac cacgatgcct gtagcgatgg caacaacgtt gcgcaaacta    3540
ttaactggcg aactacttac tctagcttcc cggcaacaat taatagactg gatggaggcg    3600
gataaagttg caggaccact tctgcgctcg gcccttccgg ctggctggtt tattgctgat    3660
aaatccggag ccggtgagcg tggttctcgc ggtatcatcg cagcgctggg gccagatggt    3720
aagccctccc gtatcgtagt tatctacacg acggggagtc aggcaactat ggatgaacga    3780
aatagacaga tcgctgagat aggtgcctca ctgattaagc attggtaact catgaccaaa    3840

atcccttaac gtgagttacg cgcgcgtcgt tccactgagc gtcagacccc gtagaaaaga    3900

tcaaaggatc ttcttgagat cctttttttc tgcgcgtaat ctgctgcttg caaacaaaaa    3960
aaccaccgct accagcggtg gtttgtttgc cggatcaaga gctaccaact ctttttccga    4020
aggtaactgg cttcagcaga gcgcagatac caaatactgt tcttctagtg tagccgtagt    4080
```

```
tagcccacca cttcaagaac tctgtagcac cgcctacata cctcgctctg ctaatcctgt   4140
taccagtggc tgctgccagt ggcgataagt cgtgtcttac cgggttggac tcaagacgat   4200
agttaccgga taaggcgcag cggtcgggct gaacgggggg ttcgtgcaca cagcccagct   4260
tggagcgaac gacctacacc gaactgagat acctacagcg tgagctatga aaagcgcca    4320 cgcttcccga agggagaaag gcggacaggt atccggtaag cggcagggtc ggaacaggag   4380
agcgcacgag ggagcttcca gggggaaacg cctggtatct ttatagtcct gtcgggtttc   4440
gccacctctg acttgagcgt cgattttgt gatgctcgtc aggggggcgg agcctatgga    4500
aaaacgccag caacgcggcc ttttacggt tcctggcctt ttgctggcct tttgctcaca    4560
tgttctttcc tgcgttatcc cctgattctg tggataaccg tattaccgcc tttgagtgag   4620
ctgataccgc tcgggtcgt gcaggtatag cttcaaaatg tttctactcc ttttttactc    4680
ttccagattt tctcggactc cgcgcatcgc cgtaccactt caaaacaccc aagcacagca   4740
tactaaattt cccctctttc ttcctctagg gtgtcgttaa ttacccgtac taaaggtttg   4800 gaaagaaaa aagtgaccgc ctcgtttctt tttcttcgtc gaaaaaggca ataaaaattt    4860
ttatcacgtt tcttttcttt gaaaattttt tttttgatt tttttctctt tcgatgacct    4920
cccattgata tttaagttaa taaacggact tcaatttctc aagtttcagt ttcattttc    4980 ttgttctatt acaacttttt ttacttcttg ctcattagaa agaaagcata gcaatctaat   5040
ctaagtttaa aatgttaggt aaaaatgatc caatgtgtct ggtgcttgtt ctgttgggtt   5100
tgactgctct attgggtatc tgccaaggaa tgcaggtaca gctggtggag acggggggag   5160
ggctggtaca accaggcggg tcactgaggc tttcctgtgc cgcatctggg ttcacactgg   5220
attattcgtc catagggtgg tttcggcagg ctcctggcaa agagcgtgag ggggtctcat   5280
gtattagtag tagtggtgat agcacaaagt acgccgattc cgtaaagggc cggtttacaa   5340
cctccaggga taatgctaag aacaccgtat atctccagat gaactctctg aagcccgacg   5400
atacggccgt atattactgt gcggctttca gggcgactat gtgcggcgtg ttccctctga   5460
gcccttacgg caaggacgac tggggcaagg ggaccctggt gaccgtatcc tcaggcggtg   5520
gagggtctgg tggggaggc tcaggggtg gaggcagcca ggtgcaactg gttgaatctg     5580
ggggaggctt ggtacaacct gggggatccc tgagactctc ttgcgaggcc tccggattca   5640
ccttggacta ctatggcatc ggctggttcc gccagccccc agggaaggag cgggaggccg   5700
tttcatacat tagtgccagt gcccggacca tactgtacgc agactctgtg aagggacgct   5760
ttaccatctc tagggacaat gccaaaaatg ctgtgtacct gcaaatgaac agcctcaagc   5820
gggaggatac cgcagtgtac tactgcgcga cggcgcttc tccgcttct agcgtgaata    5880 gatggctggc cgacgactac gacgtgtggg gacggggcac acaggtggct gtgtcttccg   5940
gtggcggaag cggagggggc agcggggtg ggagcggtgg gggcagccaa ctgcagctgg    6000
tagagacagg gggcggctta gttcagcctg gagggtctct cagactgtca tgcgctgcct   6060
ctggctttac cttcagtgac tacgtgatga catgggtccg ccaagctcca gggaagggc    6120 ctgagtggat cgctactatt aatacagatg gcagcacaat gcgggacgac tccacaaagg   6180
ggcggttcac catttccaga gacaacgcca agaatactct gtaccttcag atgaccagtc   6240
tgaaacccga ggacactgct ctgtactatt gtgcaagagg ccgggtgatc tctgcttccg   6300
ctatcagagg cgcagtaagg ggccctggaa cacaggtaac cgtttcatcc ggggaggcg    6360 gttcaggcgg tgggggatct ggcggggtg atcccaagt tcagctggtc gaatccggg      6420
```

```
gcggactggt ccagacaggg ggctccctga ggctctcctg tgcatcttcc ggaagcatcg      6480
ccggcttcga gaccgtgacc tggtctcgcc aggctcccgg gaagtctctg cagtgggtcg      6540
cttccatgac taagactaac aacgagatct actctgactc agtgaaaggc cgcttcatca      6600
tttctagaga taacgctaaa aacacagtgt atctgcagat gaatagtctc aaacctgaag      6660
acacaggcgt gtatttctgt aagggtcctg agctgagggg ccagggcatc caggtaacag      6720
tctcgagt                                                              6728

<210> SEQ ID NO 79
<211> LENGTH: 6704
<212> TYPE: DNA
<213> ORGANISM: Artificial Sequence
<220> FEATURE:
<223> OTHER INFORMATION: Plasmid pD1214-SA-hABAB

<400> SEQUENCE: 79
ggttaaatca tgtaattagt tatgtcacgc ttacattcac gccctccccc cacatccgct        60
ctaaccgaaa aggaaggagt tagacaacct gaagtctagg tccctattta tttttttata       120
gttatgttag tattaagaac gttatttata tttcaaattt ttcttttttt tctgtacaga       180
cgcgtgtacg catgtaacat tatactgaaa accttgcttg agaaggtttt gggacgctcg       240
aaggctttaa tttgcggccc ctcacctgca cgcaaaaagc ttttcaattc aattcatcat       300 tttttttta ttctttttt tgatttcggt ttctttgaaa ttttttgat tcggtaatct          360 ccgaacagaa ggaagaacga aggaaggagc acagacttag attggtatat atacgcatat       420
gtagtgttga gaaacatga aattgcccag tattcttaac ccaactgcac agaacaaaaa        480
ccagcaggaa acgaagataa atcatgtcga aagctacata taaggaacgt gctgctactc       540
atcctagtcc tgttgctgcc aagctattta atatcatgca cgaaaagcaa acaaacttgt       600
gtgcttcatt ggatgttcgt accaccaagg aattactgga gttagttgaa gcattaggtc       660
ccaaaatttg tttactaaaa acacatgtgg atatcttgac tgattttttcc atggagggca     720 cagttaagcc gctaaaggca ttatccgcca agtacaattt tttactcttc gaagatagaa      780
aatttgctga cattggtaat acagtcaaat tgcagtactc tgcgggtgta tacagaatag      840
cagaatgggc agacattacg aatgcacacg tgtgtggtggg cccaggtatt gttagcggtt     900
tgaagcaggc ggcagaagaa gtaacaaagg aacctagagg cctttttgatg ttagcagaat    960 tgtcatgcaa gggctcccta tctactggag aatatactaa gggtactgtt gacattgcga    1020
aaagcgacaa agattttgtt atcggcttta ttgctcaaag agacatgggt ggaagagatg    1080
aaggttacga ttggttgatt atgacacccg gtgtgggttt agatgacaag ggagatgcat    1140
tgggtcaaca gtatagaacc gtggatgatg ttgtctctac aggatctgac attattattg    1200
ttggaagagg actatttgca aagggaaggg atgctaaggt agagggtgaa cgttacagaa    1260
aagcaggctg ggaagcatat ttgagaagat gcggccagca aaactaaaaa actgtattat    1320
aagtaaatgc atgtatacta aactcacaaa ttagagcttc aatttaatta tatcagttat    1380
tacccacgct atgatccaat atcaaaggaa atgatagcat tgaaggatga gactaatcca    1440
attgaggagt ggcagcatat agaacagcta aagggtagtg ctgaaggaag catacgatac    1500
cccgcatgga atgggataat atcacaggag gtactagact acctttcatc ctacataaat    1560
agacgcatat aagtacgcat ttaagcataa acacgcacta tgccgttctt ctcatgtata    1620
tatatataca ggcaacacgc agatataggt gcgacgtgaa cagtgagctg tatgtgcgca    1680
gctcgcgttg cattttcgga agcgctcgtt ttcggaaacg ctttgaagtt cctattccga    1740
```

```
agttcctatt ctctagaaag tataggaact tcagagcgct tttgaaaacc aaaagcgctc    1800
tgaagtcgca ctttcaaaaa accaaaaacg caccggactg taacgagcta ctaaaatatt    1860
gcgaataccg cttccacaaa cattgctcaa aagtatctct ttgctatata tctctgtgct    1920
atatccctat ataacctacc catccacctt tcgctccttg aacttgcatc taaactcgac    1980
ctctacattt tttatgttta tctctagtat tactctttag acaaaaaaat tgtagtaaga    2040
actattcata gagtgaatcg aaaacaatac gaaaatgtaa acatttccta tacgtagtat    2100
atagagacaa aatagaagaa accgttcata attttctgac caatgaagaa tcatcaacgc    2160
tatcactttc tgttcacaaa gtatgcgcaa tccacatcgg tatagaatat aatcggggat    2220
gcctttatct tgaaaaaatg cacccgcagc ttcgctagta atcagtaaac gcgggaagtg    2280
gagtcaggct tttttatgg aagagaaaat agacaccaaa gtagccttct tctaacctta    2340
acggacctac agtgcaaaaa gttatcaaga gactgcatta tagagcgcac aaaggagaaa    2400
aaaagtaatc taagatgctt tgttagaaaa atagcgctct cgggatgcat ttttgtagaa    2460 caaaaagaa gtatagattc tttgttggta aaatagcgct ctcgcgttgc atttctgttc    2520
tgtaaaaatg cagctcagat tctttgtttg aaaaattagc gctctcgcgt tgcattttg    2580 ttttacaaaa atgaagcaca gattcttcgt tggtaaaata gcgctttcgc gttgcatttc    2640
tgttctgtaa aaatgcagct cagattcttt gtttgaaaaa ttagcgctct cgcgttgcat    2700
ttttgttcta caaatgaag cacagatgct tcgttcaggt ggcacttttc ggggaaatgt    2760
gcgcggaacc cctatttgtt tatttttcta aatacattca aatatgtatc cgctcatgag    2820
acaataaccc tgatattggt cagaattggt taattggttg taacactgac ccctatttgt    2880
ttatttttct aaatacattc aaatatgtat ccgctcatga acaataaacc ctgataaatg    2940
cttcaataat attgaaaaag gaagaatatg agtattcaac atttccgtgt cgcccttatt    3000 ccctttttg cggcattttg ccttcctgtt tttgctcacc cagaaacgct ggtgaaagta    3060
aaagatgctg aagatcagtt gggtgcacga gtgggttaca tcgaactgga tctcaacagc    3120
ggtaagatcc ttgagagttt tcgccccgaa gaacgttttc caatgatgag cacttttaaa    3180
gttctgctat gtggcgcggt attatcccgt attgacgccg ggcaagagca actcggtcgc    3240
cgcatacact attctcagaa tgacttggtt gagtactcac cagtcacaga aaagcatctt    3300
acggatggca tgacagtaag agaattatgc agtgctgcca taaccatgag tgataacact    3360
gcggccaact tacttctgac aacgatcgga ggaccgaagg agctaaccgc ttttttgcac    3420
aacatggggg atcatgtaac tcgccttgat cgttgggaac cggagctgaa tgaagccata    3480
ccaaacgacg agcgtgacac cacgatgcct gtagcgatgg caacaacgtt gcgcaaacta    3540
ttaactggcg aactacttac tctagcttcc cggcaacaat taatagactg gatggaggcg    3600
gataaagttg caggaccact tctgcgctcg gcccttccgg ctggctggtt tattgctgat    3660
aaatccggag ccggtgagcg tggttctcgc ggtatcatcg cagcgctggg gccagatggt    3720
aagccctccc gtatcgtagt tatctacacg acggggagtc aggcaactat ggatgaacga    3780
aatagacaga tcgctgagat aggtgcctca ctgattaagc attggtaact catgaccaaa    3840
atcccttaac gtgagttacg cgcgcgtcgt tccactgagc gtcagacccc gtagaaaaga    3900
tcaaaggatc ttcttgagat cctttttttc tgcgcgtaat ctgctgcttg caaacaaaaa    3960
aaccaccgct accagcggtg gtttgtttgc cggatcaaga gctaccaact cttttttccga    4020 aggtaactgg cttcagcaga gcgcagatac caaatactgt tcttctagtg tagccgtagt    4080
```

```
tagcccacca cttcaagaac tctgtagcac cgcctacata cctcgctctg ctaatcctgt    4140
taccagtggc tgctgccagt ggcgataagt cgtgtcttac cgggttggac tcaagacgat    4200
agttaccgga taaggcgcag cggtcgggct gaacgggggg ttcgtgcaca cagcccagct    4260
tggagcgaac gacctacacc gaactgagat acctacagcg tgagctatga gaaagcgcca    4320
cgcttcccga agggagaaag gcggacaggt atccggtaag cggcagggtc ggaacaggag    4380
agcgcacgag ggagcttcca gggggaaacg cctggtatct ttatagtcct gtcgggtttc    4440
gccacctctg acttgagcgt cgattttttgt gatgctcgtc agggggggcgg agcctatgga   4500 aaaacgccag caacgcggcc ttttacggtt cctggcctt tgctggcct tttgctcaca      4560 tgttctttcc tgcgttatcc cctgattctg tggataaccg tattaccgcc tttgagtgag    4620
ctgataccgc tcgggtcgt gcaggtatag cttcaaaatg tttctactcc ttttttactc      4680
ttccagattt tctcggactc cgcgcatcgc cgtaccactt caaaacaccc aagcacagca    4740
tactaaattt cccctctttc ttcctctagg gtgtcgttaa ttacccgtac taaaggtttg    4800
gaaaagaaaa aagtgaccgc ctcgtttctt tttcttcgtc gaaaaaggca ataaaaattt    4860
ttatcacgtt tctttttctt gaaaattttt tttttttgatt ttttttctctt tcgatgacct   4920 cccattgata tttaagttaa taaacggact tcaatttctc aagtttcagt ttcatttttc    4980
ttgttctatt acaactttt ttacttcttg ctcattagaa agaaagcata gcaatctaat     5040
ctaagtttaa aatgaaatgg gttactttta tctcactttt gttcctgttc tccagcgctt    5100
actctatgca ggtacagctg gtggagacgg ggggagggct ggtacaacca ggcgggtcac    5160
tgaggctttc ctgtgccgca tctgggttca cactggatta ttcgtccata gggtggtttc    5220
ggcaggctcc tggcaaagag cgtgaggggg tctcatgtat tagtagtagt ggtgatagca    5280
caaagtacgc cgattccgta aagggccggt ttacaacctc cagggataat gctaagaaca    5340
ccgtatatct ccagatgaac tctctgaagc ccgacgatac ggccgtatat tactgtgcgg    5400 cttttcagggc gactatgtgc ggcgtgttcc ctctgagccc ttacggcaag gacgactggg   5460
gcaaggggac cctggtgacc gtatcctcag gcggtggagg gtctggtggg ggaggctcag    5520 gggtggagc cagccaggtg caactggttg aatctggggg aggcttggta caacctgggg    5580
gatccctgag actctcttgc gaggcctccg gattcacctt ggactactat ggcatcggct    5640
ggttccgcca gccccaggg aaggagcggg aggccgtttc atacattagt gccagtgccc     5700
ggaccatact gtacgcagac tctgtgaagg gacgctttac catctctagg gacaatgcca    5760
aaaatgctgt gtacctgcaa atgaacagcc tcaagcggga ggataccgca gtgtactact    5820
gcgcgagacg gcgcttctcc gcttctagcg tgaatagatg gctggccgac gactacgacg    5880
tgtggggacg gggcacacag gtggctgtgt cttccggtgg cggaagcgga ggggcagcg    5940 ggggtgggag cggtggggc agccaactgc agctggtaga gacaggggc ggcttagttc     6000 agcctggagg gtctctcaga ctgtcatgcg ctgcctctgg ctttaccttc agtgactacg    6060
tgatgacatg ggtccgccaa gctccaggga aggggcctga gtggatcgct actattaata   6120
cagatggcag cacaatgcgg gacgactcca caaaggggcg gttcaccatt tccagagaca    6180
acgccaagaa tactctgtac cttcagatga ccagtctgaa acccgaggac actgctctgt    6240
actattgtgc aagaggccgg gtgatctctg cttccgctat cagaggcgca gtaaggggcc    6300
ctggaacaca ggtaaccgtt tcatccgggg gaggcggttc aggcggtggg ggatctggcg    6360
ggggtggatc ccaagttcag ctggtcgaat ccggggggcgg actggtccag acaggggct    6420 ccctgaggct ctcctgtgca tcttccggaa gcatcgccgg cttcgagacc gtgacctggt    6480
```

```
ctcgccaggc tcccgggaag tctctgcagt gggtcgcttc catgactaag actaacaacg      6540
agatctactc tgactcagtg aaaggccgct tcatcatttc tagagataac gctaaaaaca      6600
cagtgtatct gcagatgaat agtctcaaac ctgaagacac aggcgtgtat ttctgtaagg      6660
gtcctgagct gaggggccag ggcatccagg taacagtctc gagt                       6704

<210> SEQ ID NO 80
<211> LENGTH: 6574
<212> TYPE: DNA
<213> ORGANISM: Artificial Sequence
<220> FEATURE:
<223> OTHER INFORMATION: Plasmid pCEV-G4-Km

<400> SEQUENCE: 80
ggagcgacct catgctatac ctgagaaagc aacctgacct acaggaaaga gttactcaag        60
aataagaatt ttcgttttaa aacctaagag tcactttaaa atttgtatac acttattttt       120
tttataactt atttaataat aaaaatcata aatcataaga aattcgctta tttagaagtg       180
tcaacaacgt atctaccaac gatttgaccc ttttccatct tttcgtaaat ttctggcaag       240
gtagacaagc cgacaacctt gattggagac ttgaccaaac ctctggcgaa gaattgttaa       300
ttaagagctc agatcttatc gtcgtcatcc ttgtaatcca tcgatactag ttttttgatt       360
aaaattaaaa aactttttg ttttttgtgtt tattctttgt tcttagaaaa gacaagttga       420
gcttgtttgt tcttgatgtt ttattatttt acaatagctg caaatgaaga atagattcga       480
acattgtgaa gtattggcat atatcgtctc tatttatact ttttttttttt cagttctagt       540 atattttgta ttttcctcct tttcattctt tcagttgcca ataagttaca ggggatctcg       600
aaagatggtg gggatttttc cttgaaagac gacttttttgc catctaattt ttccttgttg       660
cctctgaaaa ttatccagca gaagcaaatg taaaagatga acctcagaag aacacgcagg       720
ggcccgaaat tgttcctacg agaagtagtg ggtcataaaa agtttattcc ctggaaaaaa       780
aattttgcgt tgcctttctg gagaattttt tcgaattagc gtgctgccac tgcatgcatt       840
tctgagaagt gtgggcattc ttccaccagt tgttcctcct aaaaaaaaaa agatttccta       900
ccccgcacaa attcctgcat accctcatt tccacgggc cggccgcaca caccatagct         960
tcaaaatgtt tctactcctt ttttactctt ccagatttttc tcggactccg cgcatcgccg      1020
taccacttca aaacacccaa gcacagcata ctaaatttcc cctctttctt cctctagggt      1080
gtcgttaatt acccgtacta aaggtttgga aaagaaaaaa gagaccgcct cgtttctttt      1140
tcttcgtcga aaaaggcaat aaaaatttt atcacgtttc tttttcttga aaatttttt       1200 ttttgatttt tttctctttc gatgacctcc cattgatatt taagttaata aacggtcttc      1260
aatttctcaa gtttcagttt cattttcttt gttctattac aactttttttt acttcttgct      1320 cattagaaag aaagcatagc aatctaatct aagttttaat tacaaggatc cgtaatacga      1380
ctcactatag ggcccgggcg tcgacatgga acagaagttg atttccgaag aagacctcga      1440
gtaagcttgg taccgcggct agctaagatc cgctctaacc gaaaaggaag gagttagaca      1500
acctgaagtc taggtcccta tttattttt tatagttatg ttagtattaa gaacgttatt      1560
tatatttcaa attttttcttt ttttctgta cagacgcgtg tacgcatgta acattatact      1620
gaaaaccttg cttgagaagg ttttgggacg ctcgaagatc cagctgcatt aatgaatcgg      1680
ccaacgcgcg gggagaggcg gtttgcgtat gggcgctct tccgcttcct cgctcactga      1740
ctcgctgcgc tcggtcgttc ggctgcggcg agcggtatca gctcactcaa aggcggtaat      1800
```

```
acggttatcc acagaatcag gggataacgc aggaaagaac atgtgagcaa aaggccagca    1860
aaaggccagg aaccgtaaaa aggccgcgtt gctggcgttt ttccataggc tccgcccccc    1920
tgacgagcat cacaaaaatc gacgctcaag tcagaggtgg cgaaacccga caggactata    1980
aagataccag gcgtttcccc ctggaagctc cctcgtgcgc tctcctgttc cgaccctgcc    2040
gcttaccgga tacctgtccg cctttctccc ttcgggaagc gtggcgcttt ctcatagctc    2100
acgctgtagg tatctcagtt cggtgtaggt cgttcgctcc aagctgggct gtgtgcacga    2160
accccccgtt cagcccgacc gctgcgcctt atccggtaac tatcgtcttg agtccaaccc    2220
ggtaagacac gacttatcgc cactggcagc agccactggt aacaggatta gcagagcgag    2280
gtatgtaggc ggtgctacag agttcttgaa gtggtggcct aactacggct acactagaag    2340
gacagtattt ggtatctgcg ctctgctgaa gccagttacc ttcggaaaaa gagttggtag    2400
ctcttgatcc ggcaaacaaa ccaccgctgg tagcggtggt ttttttgttt gcaagcagca    2460
gattacgcgc agaaaaaaag gatctcaaga agatcctttg atcttttcta cggggtctga    2520
cgctcagtgg aacgaaaact cacgttaagg gattttggtc atgagattat caaaaaggat    2580
cttcacctag atccttttaa attaaaaatg aagttttaaa tcaatctaaa gtatatatga    2640
gtaaacttgg tctgacagtt accaatgctt aatcagtgag gcacctatct cagcgatctg    2700
tctatttcgt tcatccatag ttgcctgact ccccgtcgtg tagataacta cgatacggga    2760
gggcttacca tctggcccca gtgctgcaat gataccgcga cccacgct caccggctcc     2820 agatttatca gcaataaacc agccagccgg aagggccgag cgcagaagtg gtcctgcaac    2880
tttatccgcc tccatccagt ctattaattg ttgccgggaa gctagagtaa gtagttcgcc    2940
agttaatagt ttgcgcaacg ttgttgccat tgctacaggc atcgtggtgt cacgctcgtc    3000
gtttggtatg gcttcattca gctccggttc ccaacgatca aggcgagtta catgatcccc    3060
catgttgtgc aaaaaagcgg ttagctcctt cggtcctccg atcgttgtca gaagtaagtt    3120
ggccgcagtg ttatcactca tggttatggc agcactgcat aattctctta ctgtcatgcc    3180
atccgtaaga tgcttttctg tgactggtga gtactcaacc aagtcattct gagaatagtg    3240
tatgcggcga ccgagttgct cttgcccggc gtcaatacgg gataataccg cgccacatag    3300
cagaacttta aaagtgctca tcattggaaa acgttcttcg gggcgaaaac tctcaaggat    3360
cttaccgctg ttgagatcca gttcgatgta acccactcgt gcacccaact gatcttcagc    3420
atcttttact ttcaccagcg tttctgggtg agcaaaaaca ggaaggcaaa atgccgcaaa    3480
aaagggaata agggcgacac ggaaatgttg aatactcata ctcttccttt ttcaatatta    3540
ttgaagcatt tatcagggtt attgtctcat gagcggatac atatttgaat gtatttagaa    3600
aaataaacaa ataggggttc cgcgcacatt tccccgaaaa gtgccacctg aacgaagcat    3660
ctgtgcttca ttttgtagaa caaaaatgca acgcgagagc gctaattttt caaacaaaga    3720
atctgagctg catttttaca gaacagaaat gcaacgcgaa agcgctattt taccaacgaa    3780
gaatctgtgc ttcattttg taaaacaaaa atgcaacgcg agagcgctaa ttttcaaac    3840 aaagaatctg agctgcattt ttacagaaca gaaatgcaac gcgagagcgc tattttacca    3900
acaaagaatc tatacttctt ttttgttcta caaaaatgca tcccgagagc gctatttttc    3960
taacaaagca tcttagatta cttttttttct cctttgtgcg ctctataatg cagtctcttg    4020
ataacttttt gcactgtagg tccgttaagg ttagaagaag ctactttgg tgtctatttt     4080 ctcttccata aaaaaagcct gactccactt cccgcgttta ctgattacta gcgaagctgc    4140
gggtgcattt tttcaagata aaggcatccc cgattatatt ctataccgat gtggattgcg    4200
```

```
catactttgt gaacagaaag tgatagcgtt gatgattctt cattggtcag aaaattatga    4260
acggtttctt ctattttgtc tctatatact acgtatagga aatgtttaca ttttcgtatt    4320
gttttcgatt cactctatga atagttctta ctacaatttt tttgtctaaa gagtaatact    4380
agagataaac ataaaaaatg tagaggtcga gtttagatgc aagttcaagg agcgaaaggt    4440
ggatgggtag gttatatagg gatatagcac agagatatat agcaaagaga tacttttgag    4500
caatgtttgt ggaagcggta ttcgcaatat tttagtagct cgttacagtc cggtgcgttt    4560 ttggttttt gaaagtgcgt cttcagagcg cttttggttt tcaaaagcgc tctgaagttc    4620
ctatactttc tagagaatag gaacttcgga ataggaactt caaagcgttt ccgaaaacga    4680
gcgcttccga aaatgcaacg cgagctgcgc acatacagct cactgttcac gtcgcaccta    4740
tatctgcgtg ttgcctgtat atatatatac atgagaagaa cggcatagtg cgtgtttatg    4800
cttaaatgcg tacttatatg cgtctattta tgtaggatga aaggtagtct agtacctcct    4860
gtgatattat cccattccat gcggggtatc gtatgcttcc ttcagcacta cccttttagct   4920 gttctatatg ctgccactcc tcaattggat tagtctcatc cttcaatgct atcatttcct    4980
ttgatattgg atcatggtag acaaccctta atataacttc gtataatgta tgctatacga    5040
agttattagg tctagagatc tgtttagctt gcctcgtccc cgccgggtca cccggccagc    5100
gacatggagg cccagaatac cctccttgac agtcttgacg tgcgcagctc aggggcatga    5160
tgtgactgtc gcccgtacat ttagcccata catccccatg tataatcatt tgcatccata    5220
cattttgatg gccgcacggc gcgaagcaaa aattacggct cctcgctgca gacctgcgag    5280
cagggaaacg ctcccctcac agacgcgttg aattgtcccc acgccgcgcc cctgtagaga    5340
aatataaaag gttaggattt gccactgagg ttcttctttc atatacttcc ttttaaaatc    5400
ttgctaggat acagttctca catcacatcc gaacataaac aaccatgggt aaggaaaaga    5460
ctcacgtttc gaggccgcga ttaaattcca acatggatgc tgatttatat gggtataaat    5520
gggctcgcga taatgtcggg caatcaggtg cgacaatcta tcgattgtat gggaagcccg    5580
atgcgccaga gttgtttctg aaacatggca aaggtagcgt tgccaatgat gttacagatg    5640
agatggtcag actaaactgg ctgacggaat ttatgcctct tccgaccatc aagcatttta    5700
tccgtactcc tgatgatgca tggttactca ccactgcgat ccccggcaaa acagcattcc    5760
aggtattaga agaatatcct gattcaggtg aaaatattgt tgatgcgctg gcagtgttcc    5820
tgcgccggtt gcattcgatt cctgtttgta attgtccttt taacagcgat cgcgtatttc    5880
gtctcgctca ggcgcaatca cgaatgaata cggtttggt tgatgcgagt gattttgatg    5940
acgagcgtaa tggctggcct gttgaacaag tctggaaaga atgcataag cttttgccat    6000 tctcaccgga ttcagtcgtc actcatggtg atttctcact tgataacctt attttttgacg    6060 agggaaatt aataggttgt attgatgttg gacgagtcgg aatcgcagac cgataccagg    6120
atcttgccat cctatggaac tgcctcggtg agttttctcc ttcattacag aaacggcttt    6180
ttcaaaaata tggtattgat aatcctgata tgaataaatt gcagtttcat ttgatgctcg    6240
atgagttttt ctaatcagta ctgacaataa aaagattctt gttttcaaga acttgtcatt    6300
tgtatagttt ttttatattg tagttgttct attttaatca aatgttagcg tgatttatat    6360
tttttttcgc ctcgacatca tctgcccaga tgcgaagtta agtgcgcaga agtaatatc    6420 atgcgtcaat cgtatgtgaa tgctggtcgc tatactgctg tcgattcgat actaacgccg    6480
ccatccagtg tcgaaaacga gctctcgaga acccttaata taacttcgta taatgtatgc    6540
```
tatacgaagt tattaggtga tatcagatcc acta 6574

<210> SEQ ID NO 81
<211> LENGTH: 8211
<212> TYPE: DNA
<213> ORGANISM: Artificial Sequence
<220> FEATURE:
<223> OTHER INFORMATION: Plasmid pCEV-G4-Km-TEF-AT-hABAB*

<400> SEQUENCE: 81

```
gcctaggatg agatttcctt caatttttac tgctgtttta ttcgcagcat cctccgcatt      60
agctggcgcc cacgtgatgc aggtacagct ggtggagacg gggggagggc tggtacaacc     120
aggcgggtca ctgaggcttt cctgtgccgc atctgggttc acactggatt attcgtccat     180
agggtggttt cggcaggctc ctggcaaaga gcgtgagggg gtctcatgta ttagtagtag     240
tggtgatagc acaaagtacg ccgattccgt aaagggccgg tttacaacct ccagggataa     300
tgctaagaac accgtatatc tccagatgaa ctctctgaag cccgacgata cggccgtata     360
ttactgtgcg gctttcaggg cgactatgtg cggcgtgttc cctctgagcc cttacggcaa     420
ggacgactgg ggcaagggga ccctggtgac cgtatcctca ggcggtggag ggtctggtgg     480
gggaggctca gggggtggag gcagccaggt gcaactggtt gaatctgggg gaggcttggt     540
acaacctggg ggatccctga actctcttg cgaggcctcc ggattcaccc tggactacta     600
tggcatcggc tggttccgcc agcccccagg gaaggagcgg gaggccgttt catacattag     660
tgccagtgcc cggaccatac tgtacgcaga ctctgtgaag gacgctttta ccatctctag     720
ggacaatgcc aaaaatgctg tgtacctgca aatgaacagc ctcaagcggg aggataccgc     780
agtgtactac tgcgcgagac ggcgcttctc cgcttctagc gtgaatagat ggctggccga     840
cgactacgac gtgtggggac ggggcacaca ggtggctgtg tcttccggtg gcggaagcgg     900
aggggcagc gggggtggga gcggtggggg cagccaactg cagctggtag agacaggggg     960
cggcttagtt cagcctggag ggtctctcag actgtcatgc gctgcctctg gctttacctt    1020
cagtgactac gtgatgacat gggtccgcca agctccaggg aaggggcctg agtggatcgc    1080
tactattaat acagatggca gcacaatgcg ggacgactcc acaaagggc ggttcaccat    1140
ttccagagac aacgccaaga atactctgta ccttcagatg accagtctga acccgagga    1200
cactgctctg tactattgtg caagaggccg ggtgatctct gcttccgcta tcagaggcgc    1260
agtaaggggc cctggaacac aggtaaccgt tcatccggg ggaggcggtt caggcggtgg    1320
gggatctggc ggggtggat ccaagttca gctggtcgaa tcggggcg gactggtcca    1380
gacaggggc tccctgaggc tctcctgtgc atcttccgga agcatcgccg gcttcgagac    1440
cgtgacctgg tctcgccagg ctcccggaa gtctctgcag tgggtcgctt ccatgactaa    1500
gactaacaac gagatctact ctgactcagt gaaaggccgc ttcatcattt ctagagataa    1560
cgctaaaaac acagtgtatc tgcagatgaa tagtctcaaa cctgaagaca caggcgtgta    1620
tttctgtaag ggtcctgagc tgaggggcca gggcatccag gtaacagtct cgagtgtcga    1680
cggtacctaa gctagctaag atccgctcta accgaaaagg aaggagttag caacctgaa    1740
gtctaggtcc ctatttattt ttttatagtt atgttagtat taagaacgtt atttatattt    1800
caaattttc ttttttttct gtacagacgc gtgtacgcat gtaacattat actgaaaacc    1860
ttgcttgaga aggttttggg acgctcgaag atccagctgc attaatgaat cggccaacgc    1920
gcggggagag gcggtttgcg tattgggcgc tcttccgctt cctcgctcac tgactcgctg    1980
cgctcggtcg ttcggctgcg gcgagcggta tcagctcact caaaggcggt aatacggtta    2040
```

```
tccacagaat caggggataa cgcaggaaag aacatgtgag caaaaggcca gcaaaaggcc   2100
aggaaccgta aaaaggccgc gttgctggcg ttttttccata ggctccgccc ccctgacgag   2160
catcacaaaa atcgacgctc aagtcagagg tggcgaaacc cgacaggact ataaagatac   2220
caggcgtttc ccectggaag ctccctcgtg cgctctcctg ttccgaccct gccgcttacc   2280
ggatacctgt ccgcctttct cccttcggga agcgtggcgc tttctcatag ctcacgctgt   2340
aggtatctca gttcggtgta ggtcgttcgc tccaagctgg gctgtgtgca cgaaccccc    2400 gttcagcccg accgctgcgc cttatccggt aactatcgtc ttgagtccaa cccggtaaga   2460
cacgacttat cgccactggc agcagccact ggtaacagga ttagcagagc gaggtatgta   2520
ggcggtgcta cagagttctt gaagtggtgg cctaactacg gctacactag aaggacagta   2580
tttggtatct gcgctctgct gaagccagtt accttcggaa aaagagttgg tagctcttga   2640
tccggcaaac aaaccaccgc tggtagcggt ggttttttg tttgcaagca gcagattacg   2700
cgcagaaaaa aaggatctca agaagatcct ttgatctttt ctacggggtc tgacgctcag   2760
tggaacgaaa actcacgtta agggattttg gtcatgagat tatcaaaaag gatcttcacc   2820
tagatccttt taaattaaaa atgaagtttt aaatcaatct aaagtatata tgagtaaact   2880
tggtctgaca gttaccaatg cttaatcagt gaggcaccta tctcagcgat ctgtctattt   2940
cgttcatcca tagttgcctg actccccgtc gtgtagataa ctacgatacg ggagggctta   3000
ccatctggcc ccagtgctgc aatgataccg cgagacccac gctcaccggc tccagattta   3060
tcagcaataa accagccagc cggaagggcc gagcgcagaa gtggtcctgc aactttatcc   3120
gcctccatcc agtctattaa ttgttgccgg gaagctagag taagtagttc gccagttaat   3180
agtttgcgca acgttgttgc cattgctaca ggcatcgtgg tgtcacgctc gtcgtttggt   3240
atggcttcat tcagctccgg ttcccaacga tcaaggcgag ttacatgatc ccccatgttg   3300
tgcaaaaaag cggttagctc cttcggtcct ccgatcgttg tcagaagtaa gttggccgca   3360
gtgttatcac tcatggttat ggcagcactg cataattctc ttactgtcat gccatccgta   3420
agatgctttt ctgtgactgg tgagtactca accaagtcat tctgagaata gtgtatgcgg   3480
cgaccgagtt gctcttgccc ggcgtcaata cgggataata ccgcgccaca tagcagaact   3540
ttaaaagtgc tcatcattgg aaaacgttct tcggggcgaa aactctcaag gatcttaccg   3600
ctgttgagat ccagttcgat gtaacccact cgtgcaccca actgatcttc agcatctttt   3660
actttcacca gcgtttctgg gtgagcaaaa acaggaaggc aaaatgccgc aaaaaaggga   3720
ataagggcga cacggaaatg ttgaatactc atactcttcc tttttcaata ttattgaagc   3780
atttatcagg gttattgtct catgagcgga tacatatttg aatgtattta gaaaaataaa   3840
caaatagggg ttccgcgcac atttccccga aaagtgccac ctgaacgaag catctgtgct   3900
tcattttgta gaacaaaaat gcaacgcgag agcgctaatt tttcaaacaa agaatctgag   3960
ctgcattttt acagaacaga atgcaacgc gaaagcgcta ttttaccaac gaagaatctg   4020
tgcttcattt ttgtaaaaca aaaatgcaac gcgagagcgc taattttttca aacaaagaat   4080 ctgagctgca ttttttacaga acagaaatgc aacgcgagag cgctatttta ccaacaaaga   4140
atctatactt cttttttgtt ctacaaaaat gcatcccgag agcgctattt ttctaacaaa   4200
gcatcttaga ttactttttt tctcctttgt gcgctctata atgcagtctc ttgataactt   4260
tttgcactgt aggtccgtta aggttagaag aaggctactt tggtgtctat tttctcttcc   4320
ataaaaaaag cctgactcca cttcccgcgt ttactgatta ctagcgaagc tgcgggtgca   4380
```

```
tttttttcaag ataaaggcat ccccgattat attctatacc gatgtggatt gcgcatactt    4440
tgtgaacaga aagtgatagc gttgatgatt cttcattggt cagaaaatta tgaacggttt    4500
cttctatttt gtctctatat actacgtata ggaaatgttt acattttcgt attgttttcg    4560
attcactcta tgaatagttc ttactacaat ttttttgtct aaagagtaat actagagata    4620
aacataaaaa atgtagaggt cgagtttaga tgcaagttca aggagcgaaa ggtggatggg    4680
taggttatat agggatatag cacagagata tatagcaaag agatactttt gagcaatgtt    4740
tgtggaagcg gtattcgcaa tattttagta gctcgttaca gtccggtgcg ttttggttt     4800 tttgaaagtg cgtcttcaga gcgcttttgg ttttcaaaag cgctctgaag ttcctatact    4860
ttctagagaa taggaacttc ggaataggaa cttcaaagcg tttccgaaaa cgagcgcttc    4920
cgaaaatgca acgcgagctg cgcacataca gctcactgtt cacgtcgcac ctatatctgc    4980
gtgttgcctg tatatatata tacatgagaa gaacggcata gtgcgtgttt atgcttaaat    5040
gcgtacttat atgcgtctat ttatgtagga tgaaaggtag tctagtacct cctgtgatat    5100
tatcccattc catgcggggt atcgtatgct tccttcagca ctacccttta gctgttctat    5160
atgctgccac tcctcaattg gattagtctc atccttcaat gctatcattt cctttgatat    5220
tggatcatgg tagacaaccc ttaatataac ttcgtataat gtatgctata cgaagttatt    5280
aggtctagag atctgtttag cttgcctcgt ccccgccggg tcacccgcc agcgacatgg     5340 aggcccagaa taccctcctt gacagtcttg acgtgcgcag ctcaggggca tgatgtgact    5400
gtcgcccgta catttagccc atacatcccc atgtataatc atttgcatcc atacattttg    5460
atggccgcac ggcgcgaagc aaaaattacg gctcctcgct gcagacctgc gagcagggaa    5520
acgctcccct cacagacgcg ttgaattgtc cccacgccgc gccctgtag agaaatataa     5580 aaggttagga tttgccactg aggttcttct ttcatatact tcctttttaaa atcttgctag   5640 gatacagttc tcacatcaca tccgaacata aacaaccatg ggtaaggaaa agactcacgt    5700
ttcgaggccg cgattaaatt ccaacatgga tgctgattta tatgggtata aatgggctcg    5760
cgataatgtc gggcaatcag gtgcgacaat ctatcgattg tatgggaagc ccgatgcgcc    5820
agagttgttt ctgaaacatg gcaaaggtag cgttgccaat gatgttacag atgagatggt    5880
cagactaaac tggctgacgg aatttatgcc tcttccgacc atcaagcatt ttatccgtac    5940
tcctgatgat gcatggttac tcaccactgc gatccccggc aaaacagcat tccaggtatt    6000
agaagaatat cctgattcag gtgaaaatat tgttgatgcg ctggcagtgt tcctgcgccg    6060
gttgcattcg attcctgttt gtaattgtcc ttttaacagc gatcgcgtat ttcgtctcgc    6120
tcaggcgcaa tcacgaatga ataacggttt ggttgatgcg agtgattttg atgacgagcg    6180
taatggctgg cctgttgaac aagtctggaa agaaatgcat aagcttttgc cattctcacc    6240
ggattcagtc gtcactcatg gtgatttctc acttgataac cttatttttg acgaggggaa    6300
attaataggt tgtattgatg ttggacgagt cggaatcgca gaccgatacc aggatcttgc    6360
catcctatgg aactgcctcg gtgagttttc tccttcatta cagaaacggc ttttttcaaaa   6420 atatggtatt gataatcctg atatgaataa attgcagttt catttgatgc tcgatgagtt    6480
tttctaatca gtactgacaa taaaaagatt cttgttttca gaacttgtc atttgtatag     6540 ttttttttata ttgtagttgt tctatttaa tcaaatgtta gcgtgattta tattttttt    6600 cgcctcgaca tcatctgccc agatgcgaag ttaagtgcgc agaaagtaat atcatgcgtc    6660
aatcgtatgt gaatgctggt cgctatactg ctgtcgattc gatactaacg ccgccatcca    6720
gtgtcgaaaa cgagctctcg agaacccta atataacttc gtataatgta tgctatacga    6780
```

```
agttattagg tgatatcaga tccactagga gcgacctcat gctatacctg agaaagcaac    6840
ctgacctaca ggaaagagtt actcaagaat aagaattttc gttttaaaac ctaagagtca    6900
ctttaaaatt tgtatacact tattttttt ataacttatt taataataaa aatcataaat    6960
cataagaaat tcgcttattt agaagtgtca acaacgtatc taccaacgat ttgacccttt    7020
tccatctttt cgtaaatttc tggcaaggta gacaagccga caaccttgat tggagacttg    7080
accaaacctc tggcgaagaa ttgttaatta agagctcaga tcttatcgtc gtcatccttg    7140
taatccatcg atactagttt tttgattaaa attaaaaaaa cttttgttt ttgtgtttat    7200 tctttgttct tagaaaagac aagttgagct tgtttgttct tgatgtttta ttattttaca    7260
atagctgcaa atgaagaata gattcgaaca ttgtgaagta ttggcatata tcgtctctat    7320
ttatactttt tttttttcag ttctagtata ttttgtattt tcctccttt cattctttca    7380 gttgccaata agttacaggg gatctcgaaa gatggtgggg attttcctt gaaagacgac    7440 ttttgccat ctaatttttc cttgttgcct ctgaaaatta ccagcagaa gcaaatgtaa    7500 aagatgaacc tcagaagaac acgcaggggc ccgaaattgt tcctacgaga agtagtgggt    7560
cataaaaagt ttattccctg gaaaaaaaat tttgcgttgc cttctggag aattttttcg    7620 aattagcgtg ctgccactgc atgcatttct gagaagtgtg ggcattcttc caccagttgt    7680
tcctcctaaa aaaaaaaga tttcctaccc cgcacaaatt cctgcatacc cctcatttcc    7740
acggggccgg ccgcacacac catagcttca aaatgtttct actccttttt tactcttcca    7800
gattttctcg gactccgcgc atcgccgtac cacttcaaaa cacccaagca cagcatacta    7860
aatttcccct ctttcttcct ctagggtgtc gttaattacc cgtactaaag gtttggaaaa    7920
gaaaaaagag accgcctcgt ttcttttct tcgtcgaaaa aggcaataaa aatttttatc    7980
acgtttcttt ttcttgaaaa ttttttttt tgattttttt ctctttcgat gacctcccat    8040
tgatatttaa gttaataaac ggtcttcaat ttctcaagtt tcagtttcat ttttcttgtt    8100
ctattacaac ttttttact tcttgctcat tagaaagaaa gcatagcaat ctaatctaag    8160
ttttaattac aaggatccgt aatacgactc actatagggc ccgggcgtcg a             8211
```

<210> SEQ ID NO 82
<211> LENGTH: 8202
<212> TYPE: DNA
<213> ORGANISM: Artificial Sequence
<220> FEATURE:
<223> OTHER INFORMATION: Plasmid pCEV-G4-Km-TEF-IVS-hABAB*

<400> SEQUENCE: 82

```
catgttactt caagctttct tgttcctgtt ggctggtttt gccgcaaaaa tctccgcagg      60
cgcccacgtg atgcaggtac agctggtgga gacgggggga gggctggtac aaccaggcgg     120
gtcactgagg ctttcctgtg ccgcatctgg gttcacactg gattattcgt ccatagggtg     180
gtttcggcag gctcctggca aagagcgtga gggggtctca tgtattagta gtagtggtga     240
tagcacaaag tacgccgatt ccgtaaaggg ccggtttaca acctccaggg ataatgctaa     300
gaacaccgta tatctccaga tgaactctct gaagcccgac gatacggccg tatattactg     360
tgcggctttc agggcgacta tgtgcggcgt gttccctctg agcccttacg gcaaggacga     420
ctggggcaag gggaccctgg tgaccgtatc ctcaggcggt ggagggtctg gtgggggagg     480
ctcagggggt ggaggcagcc aggtgcaact ggttgaatct ggggaggct tggtacaacc     540 tggggggatcc ctgagactct cttgcgaggc ctccggattc accttggact actatggcat     600
```

```
cggctggttc cgccagcccc cagggaagga gcgggaggcc gtttcataca ttagtgccag      660
tgcccggacc atactgtacg cagactctgt gaagggacgc tttaccatct ctagggacaa      720
tgccaaaaat gctgtgtacc tgcaaatgaa cagcctcaag cgggaggata ccgcagtgta      780
ctactgcgcg agacggcgct tctccgcttc tagcgtgaat agatggctgg ccgacgacta      840
cgacgtgtgg ggacggggca cacaggtggc tgtgtcttcc ggtggcggaa gcggaggggg      900
cagcgggggt gggagcggtg ggggcagcca actgcagctg gtagagacag ggggcggctt      960
agttcagcct ggagggtctc tcagactgtc atgcgctgcc tctggcttta ccttcagtga     1020
ctacgtgatg acatgggtcc gccaagctcc agggaagggg cctgagtgga tcgctactat     1080
taatacagat ggcagcacaa tgcgggacga ctccacaaag gggcggttca ccatttccag     1140
agacaacgcc aagaatactc tgtaccttca gatgaccagt ctgaaacccg aggacactgc     1200
tctgtactat tgtgcaagag gccgggtgat ctctgcttcc gctatcagag gcgcagtaag     1260
gggccctgga acacaggtaa ccgtttcatc cgggggaggc ggttcaggcg gtgggggatc     1320
tggcgggggt ggatcccaag ttcagctggt cgaatccggg ggcggactgg tccagacagg     1380
gggctccctg aggctctcct gtgcatcttc cggaagcatc gccggcttcg agaccgtgac     1440
ctggtctcgc caggctcccg ggaagtctct gcagtgggtc gcttccatga ctaagactaa     1500
caacgagatc tactctgact cagtgaaagg ccgcttcatc atttctagag ataacgctaa     1560
aaacacagtg tatctgcaga tgaatagtct caaacctgaa gacacaggcg tgtatttctg     1620
taagggtcct gagctgaggg gccagggcat ccaggtaaca gtctcgagtt aaggtaccgc     1680
ggctagctaa gatccgctct aaccgaaaag gaaggagtta gacaacctga agtctaggtc     1740
cctatttatt tttttatagt tatgttagta ttaagaacgt tatttatatt tcaaattttt     1800
cttttttttc tgtacagacg cgtgtacgca tgtaacatta tactgaaaac cttgcttgag     1860
aaggttttgg gacgctcgaa gatccagctg cattaatgaa tcggccaacg cgcgggaga     1920 ggcggtttgc gtattgggcg ctcttccgct tcctcgctca ctgactcgct gcgctcggtc     1980
gttcggctgc ggcgagcggt atcagctcac tcaaaggcgg taatacggtt atccacagaa     2040 tcagggata acgcaggaaa gaacatgtga gcaaaaggcc agcaaaaggc caggaaccgt     2100
aaaaaggccg cgttgctggc gtttttccat aggctccgcc cccctgacga gcatcacaaa     2160
aatcgacgct caagtcagag gtggcgaaac ccgacaggac tataaagata ccaggcgttt     2220
ccccctggaa gctccctcgt gcgctctcct gttccgaccc tgccgcttac cggatacctg     2280
tccgcctttc tcccttcggg aagcgtggcg ctttctcata gctcacgctg taggtatctc     2340
agttcggtgt aggtcgttcg ctccaagctg ggctgtgtgc acgaaccccc cgttcagccc     2400
gaccgctgcg ccttatccgg taactatcgt cttgagtcca acccggtaag acacgactta     2460
tcgccactgg cagcagccac tggtaacagg attagcagag cgaggtatgt aggcggtgct     2520
acagagttct tgaagtggtg gcctaactac ggctacacta aggacagt atttggtatc     2580 tgcgctctgc tgaagccagt taccttcgga aaaagagttg gtagctcttg atccggcaaa     2640
caaaccaccg ctggtagcgg tggtttttttt gtttgcaagc agcagattac gcgcagaaaa     2700
aaaggatctc aagaagatcc tttgatcttt tctacgggt ctgacgctca gtggaacgaa     2760
aactcacgtt aagggatttt ggtcatgaga ttatcaaaaa ggatcttcac ctagatcctt     2820
ttaaattaaa aatgaagttt taaatcaatc taaagtatat atgagtaaac ttggtctgac     2880
agttaccaat gcttaatcag tgaggcacct atctcagcga tctgtctatt tcgttcatcc     2940
atagttgcct gactccccgt cgtgtagata actacgatac gggagggctt accatctggc     3000
```

```
cccagtgctg caatgatacc gcgagaccca cgctcaccgg ctccagattt atcagcaata    3060
aaccagccag ccggaagggc cgagcgcaga agtggtcctg caactttatc cgcctccatc    3120
cagtctatta attgttgccg ggaagctaga gtaagtagtt cgccagttaa tagtttgcgc    3180
aacgttgttg ccattgctac aggcatcgtg gtgtcacgct cgtcgtttgg tatggcttca    3240
ttcagctccg gttcccaacg atcaaggcga gttacatgat ccccatgtt gtgcaaaaaa     3300
gcggttagct ccttcggtcc tccgatcgtt gtcagaagta agttggccgc agtgttatca    3360
ctcatggtta tggcagcact gcataattct cttactgtca tgccatccgt aagatgcttt    3420
tctgtgactg gtgagtactc aaccaagtca ttctgagaat agtgtatgcg gcgaccgagt    3480
tgctcttgcc cggcgtcaat acgggataat accgcgccac atagcagaac tttaaaagtg    3540
ctcatcattg gaaaacgttc ttcggggcga aaactctcaa ggatcttacc gctgttgaga    3600
tccagttcga tgtaacccac tcgtgcaccc aactgatctt cagcatcttt tactttcacc    3660
agcgtttctg ggtgagcaaa aacaggaagg caaaatgccg caaaaaaggg aataagggcg    3720
acacggaaat gttgaatact catactcttc ctttttcaat attattgaag catttatcag    3780
ggttattgtc tcatgagcgg atacatattt gaatgtattt agaaaaataa acaaataggg    3840
gttccgcgca catttccccg aaaagtgcca cctgaacgaa gcatctgtgc ttcattttgt    3900
agaacaaaaa tgcaacgcga gagcgctaat ttttcaaaca agaatctga gctgcatttt     3960
tacagaacag aaatgcaacg cgaaagcgct attttaccaa cgaagaatct gtgcttcatt    4020
tttgtaaaac aaaaatgcaa cgcgagagcg ctaattttc aaacaaagaa tctgagctgc     4080
attttacag aacagaaatg caacgcgaga gcgctatttt accaacaaag aatctatact     4140
tctttttgt tctacaaaaa tgcatcccga gagcgctatt tttctaacaa agcatcttag     4200
attactttt ttctcctttg tgcgctctat aatgcagtct cttgataact ttttgcactg     4260
taggtccgtt aaggttagaa gaaggctact ttggtgtcta ttttctcttc cataaaaaaa    4320
gcctgactcc acttcccgcg tttactgatt actagcgaag ctgcgggtgc attttttcaa    4380
gataaaggca tccccgatta tattctatac cgatgtggat tgcgcatact tgtgaacag     4440
aaagtgatag cgttgatgat tcttcattgg tcagaaaatt atgaacggtt tcttctattt    4500
tgtctctata tactacgtat aggaaatgtt tacattttcg tattgtttc gattcactct     4560
atgaatagtt cttactacaa ttttttgtc taaagagtaa tactagagat aaacataaaa     4620
aatgtagagg tcgagtttag atgcaagttc aaggagcgaa aggtggatgg gtaggttata    4680
tagggatata gcacagagat atatagcaaa gagatacttt tgagcaatgt tgtggaagc     4740
ggtattcgca atattttagt agctcgttac agtccggtgc gttttttggtt ttttgaaagt    4800
gcgtcttcag agcgcttttg gttttcaaaa gcgctctgaa gttcctatac tttctagaga    4860
ataggaacttt cggaatagga acttcaaagc gtttccgaaa acgagcgctt ccgaaaatgc    4920
aacgcgagct gcgcacatac agctcactgt tcacgtcgca cctatatctg cgtgttgcct    4980
gtatatatat atacatgaga agaacggcat agtgcgtgtt tatgcttaaa tgcgtactta    5040
tatgcgtcta tttatgtagg atgaaaggta gtctagtacc tcctgtgata ttatcccatt    5100
ccatgcgggg tatcgtatgc ttccttcagc actaccctt agctgttcta tatgctgcca     5160
ctcctcaatt ggattagtct catccttcaa tgctatcatt tcctttgata ttggatcatg    5220
gtagacaacc cttaatataa cttcgtataa tgtatgctat acgaagttat taggtctaga    5280
gatctgttta gcttgcctcg tccccgccgg gtcacccggc cagcgacatg gaggcccaga    5340
```

```
ataccctcct tgacagtctt gacgtgcgca gctcaggggc atgatgtgac tgtcgcccgt    5400
acatttagcc catacatccc catgtataat catttgcatc catacatttt gatggccgca    5460
cggcgcgaag caaaaattac ggctcctcgc tgcagacctg cgagcaggga aacgctcccc    5520
tcacagacgc gttgaattgt ccccacgccg cgcccctgta gagaaatata aaaggttagg    5580
atttgccact gaggttcttc tttcatatac ttccttttaa aatcttgcta ggatacagtt    5640
ctcacatcac atccgaacat aaacaaccat gggtaaggaa aagactcacg tttcgaggcc    5700
gcgattaaat tccaacatgg atgctgattt atatgggtat aaatgggctc gcgataatgt    5760
cgggcaatca ggtgcgacaa tctatcgatt gtatgggaag cccgatgcgc cagagttgtt    5820
tctgaaacat ggcaaaggta gcgttgccaa tgatgttaca gatgagatgg tcagactaaa    5880
ctggctgacg gaatttatgc ctcttccgac catcaagcat tttatccgta ctcctgatga    5940
tgcatggtta ctcaccactg cgatccccgg caaaacagca ttccaggtat tagaagaata    6000
tcctgattca ggtgaaaata ttgttgatgc gctggcagtg ttcctgcgcc ggttgcattc    6060
gattcctgtt tgtaattgtc cttttaacag cgatcgcgta tttcgtctcg ctcaggcgca    6120
atcacgaatg aataacggtt tggttgatgc gagtgatttt gatgacgagc gtaatggctg    6180
gcctgttgaa caagtctgga aagaaatgca taagcttttg ccattctcac cggattcagt    6240
cgtcactcat ggtgatttct cacttgataa ccttattttt gacgagggga aattaatagg    6300
ttgtattgat gttggacgag tcggaatcgc agaccgatac caggatcttg ccatcctatg    6360
gaactgcctc ggtgagtttt ctccttcatt acagaaacgg ctttttcaaa aatatggtat    6420
tgataatcct gatatgaata aattgcagtt tcatttgatg ctcgatgagt ttttctaatc    6480
agtactgaca ataaaaagat tcttgttttc aagaacttgt catttgtata gtttttttat    6540
attgtagttg ttctatttta atcaaatgtt agcgtgattt atatttttt tcgcctcgac    6600 atcatctgcc cagatgcgaa gttaagtgcg cagaaagtaa tatcatgcgt caatcgtatg    6660
tgaatgctgg tcgctatact gctgtcgatt cgatactaac gccgccatcc agtgtcgaaa    6720
acgagctctc gagaacccct taatataactt cgtataatgt atgctatacg aagttattag    6780
gtgatatcag atcccactagg agcgacctca tgctatacct gagaaagcaa cctgacctac    6840
aggaaagagt tactcaagaa taagaatttt cgttttaaaa cctaagagtc actttaaaat    6900
ttgtatacac ttatttttt tataacttat ttaataataa aaatcataaa tcataagaaa    6960
ttcgcttatt tagaagtgtc aacaacgtat ctaccaacga tttgacccct ttccatcttt    7020
tcgtaaattt ctggcaaggt agacaagccg acaaccttga ttggagactt gaccaaacct    7080
ctggcgaaga attgttaatt aagagctcag atcttatcgt cgtcatcctt gtaatccatc    7140
gatactagtt ttttgattaa aattaaaaaa acttttttgtt tttgtgttta ttctttgttc    7200
ttagaaaaga caagttgagc ttgtttgttc ttgatgtttt attattttac aatagctgca    7260
aatgaagaat agattcgaac attgtgaagt attggcatat atcgtctcta tttatacttt    7320
ttttttttca gttctagtat attttgtatt ttcctccttt tcattctttc agttgccaat    7380
aagttacagg ggatctcgaa agatggtggg gattttttcct tgaaagacga ctttttgcca    7440
tctaattttt ccttgttgcc tctgaaaatt atccagcaga agcaaatgta aaagatgaac    7500
ctcagaagaa cacgcagggg cccgaaattg ttcctacgag aagtagtggg tcataaaaag    7560
tttattccct ggaaaaaaaa ttttgcgttg cctttctgga gaattttttc gaattagcgt    7620
gctgccactg catgcatttc tgagaagtgt gggcattctt ccaccagttg ttcctcctaa    7680
aaaaaaaaag atttcctacc ccgcacaaat tcctgcatac ccctcatttc cacggggccg    7740
```

| | | |
|---|---|---|
| gccgcacaca ccatagcttc aaaatgtttc tactccttttt ttactcttcc agattttctc | 7800 | |
| ggactccgcg catcgccgta ccacttcaaa acacccaagc acagcatact aaatttcccc | 7860 | |
| tctttcttcc tctagggtgt cgttaattac ccgtactaaa ggtttggaaa agaaaaaaga | 7920 | |
| gaccgcctcg tttcttttt ttcgtcgaaa aaggcaataa aaattttat cacgtttctt | 7980 | |
| tttcttgaaa attttttttt ttgatttttt tctctttcga tgacctccca ttgatattta | 8040 | |
| agttaataaa cggtcttcaa tttctcaagt ttcagtttca ttttcttgt tctattacaa | 8100 | |
| cttttttac ttcttgctca ttagaaagaa agcatagcaa tctaatctaa gttttaatta | 8160 | |
| caaggatccg taatacgact cactataggg cccgggcgtc ga | 8202 | |

<210> SEQ ID NO 83
<211> LENGTH: 8190
<212> TYPE: DNA
<213> ORGANISM: Artificial Sequence
<220> FEATURE:
<223> OTHER INFORMATION: Plasmid pCEV-G4-Km-TEF-AT-hABAB

<400> SEQUENCE: 83

| | | |
|---|---|---|
| catgagattt ccttcaattt ttactgctgt tttattcgca gcatcctccg cattagctat | 60 | |
| gcaggtacag ctggtggaga cggggggagg gctggtacaa ccaggcgggt cactgaggct | 120 | |
| ttcctgtgcc gcatctgggt tcacactgga ttattcgtcc atagggtggt tcggcaggc | 180 | |
| tcctggcaaa gagcgtgagg gggtctcatg tattagtagt agtggtgata gcacaaagta | 240 | |
| cgccgattcc gtaaagggcc ggtttacaac ctccagggat aatgctaaga acaccgtata | 300 | |
| tctccagatg aactctctga agcccgacga tacgccgta tattactgtg cggctttcag | 360 | |
| ggcgactatg tgcggcgtgt tccctctgag cccttacggc aaggacgact ggggcaaggg | 420 | |
| gaccctggtg accgtatcct caggcggtgg agggtctggt gggggaggct caggggtgg | 480 | |
| aggcagccag gtgcaactgg ttgaatctgg ggaggcttg gtacaacctg ggggatccct | 540 | |
| gagactctct tgcgaggcct ccggattcac cttggactac tatggcatcg ctggttccg | 600 | |
| ccagccccca gggaaggagc gggaggccgt tcatacatt agtgccagtg cccggaccat | 660 | |
| actgtacgca gactctgtga agggacgctt taccatctct agggacaatg ccaaaaatgc | 720 | |
| tgtgtacctg caaatgaaca gcctcaagcg ggaggatacc gcagtgtact actgcgcgag | 780 | |
| acggcgcttc tccgcttcta gcgtgaatag atggctggcc gacgactacg acgtgtgggg | 840 | |
| acggggcaca caggtggctg tgtcttccgg tggcggaagc ggaggggca gcggggtgg | 900 | |
| gagcggtggg ggcagccaac tgcagctggt agagacaggg ggcggcttag ttcagcctgg | 960 | |
| agggtctctc agactgtcat gcgctgcctc tggctttacc ttcagtgact acgtgatgac | 1020 | |
| atgggtccgc caagctccag ggaagggggcc tgagtggatc gctactatta atacagatgg | 1080 | |
| cagcacaatg cgggacgact ccacaaaggg gcggttcacc atttccagag acaacgccaa | 1140 | |
| gaatactctg taccttcaga tgaccagtct gaaacccgag acactgctc tgtactattg | 1200 | |
| tgcaagaggc cgggtgatct ctgcttccgc tatcagaggc gcagtaaggg gccctggaac | 1260 | |
| acaggtaacc gtttcatccg ggggaggcgg ttcaggcggt gggggatctg gcggggtgg | 1320 | |
| atcccaagtt cagctggtcg aatccggggg cggactggtc cagacagggg gctccctgag | 1380 | |
| gctctcctgt gcatcttccg gaagcatcgc cggcttcgag accgtgacct ggtctcgcca | 1440 | |
| ggctcccggg aagtctctgc agtgggtcgc ttccatgact aagactaaca acgagatcta | 1500 | |
| ctctgactca gtgaaaggcc gcttcatcat ttctagagat aacgctaaaa acacagtgta | 1560 | |

```
tctgcagatg aatagtctca aacctgaaga cacaggcgtg tatttctgta agggtcctga      1620
gctgaggggc cagggcatcc aggtaacagt ctcgagttaa ggtaccgcgg ctagctaaga      1680
tccgctctaa ccgaaaagga aggagttaga caacctgaag tctaggtccc tatttatttt     1740
tttatagtta tgttagtatt aagaacgtta tttatatttc aaattttttct tttttttctg    1800 tacagacgcg tgtacgcatg taacattata ctgaaaacct tgcttgagaa ggttttggga     1860
cgctcgaaga tccagctgca ttaatgaatc ggccaacgcg cggggagagg cggtttgcgt     1920
attgggcgct cttccgcttc ctcgctcact gactcgctgc gctcggtcgt tcggctgcgg     1980
cgagcggtat cagctcactc aaaggcggta atacggttat ccacagaatc agggggataac    2040 gcaggaaaga acatgtgagc aaaaggccag caaaaggcca ggaaccgtaa aaaggccgcg     2100
ttgctggcgt ttttccatag gctccgcccc cctgacgagc atcacaaaaa tcgacgctca     2160
agtcagaggt ggcgaaaccc gacaggacta taaagatacc aggcgtttcc ccctggaagc    2220
tccctcgtgc gctctcctgt tccgaccctg ccgcttaccg gatacctgtc cgcctttctc    2280
ccttcgggaa gcgtggcgct ttctcatagc tcacgctgta ggtatctcag ttcggtgtag    2340
gtcgttcgct ccaagctggg ctgtgtgcac gaaccccccg ttcagcccga ccgctgcgcc    2400
ttatccggta actatcgtct tgagtccaac ccggtaagac acgacttatc gccactggca    2460
gcagccactg gtaacaggat tagcagagcg aggtatgtag cggtgctac agagttcttg     2520 aagtggtggc ctaactacgg ctacactaga aggacagtat ttggtatctg cgctctgctg    2580
aagccagtta ccttcggaaa aagagttggt agctcttgat ccggcaaaca accaccgct     2640 ggtagcggtg gttttttgt ttgcaagcag cagattacgc gcagaaaaaa aggatctcaa      2700
gaagatcctt tgatcttttc tacggggtct gacgctcagt ggaacgaaaa ctcacgttaa    2760
gggattttgg tcatgagatt atcaaaaagg atcttcacct agatccttt aaattaaaaa      2820 tgaagtttta aatcaatcta agtatatat gagtaaactt ggtctgacag ttaccaatgc      2880
ttaatcagtg aggcacctat ctcagcgatc tgtctatttc gttcatccat agttgcctga    2940
ctccccgtcg tgtagataac tacgatacgg gagggcttac catctggccc cagtgctgca    3000
atgataccgc gagacccacg ctcaccggct ccagatttat cagcaataaa ccagccagcc    3060
ggaagggccg agcgcagaag tggtcctgca actttatccg cctccatcca gtctattaat    3120
tgttgccggg aagctagagt aagtagttcg ccagttaata gtttgcgcaa cgttgttgcc    3180
attgctacag gcatcgtggt gtcacgctcg tcgtttggta tggcttcatt cagctccggt    3240
tcccaacgat caaggcgagt tacatgatcc cccatgttgt gcaaaaaagc ggttagctcc    3300
ttcggtcctc cgatcgttgt cagaagtaag ttggccgcag tgttatcact catggttatg    3360
gcagcactgc ataattctct tactgtcatg ccatccgtaa gatgctttc tgtgactggt      3420 gagtactcaa ccaagtcatt ctgagaatag tgtatgcggc gaccgagttg ctcttgcccg    3480
gcgtcaatac gggataatac cgcgccacat agcagaactt taaaagtgct catcattgga    3540
aaacgttctt cggggcgaaa actctcaagg atcttaccgc tgttgagatc cagttcgatg    3600
taacccactc gtgcacccaa ctgatcttca gcatctttta ctttcaccag cgtttctggg    3660
tgagcaaaaa caggaaggca aaatgccgca aaaagggaa taaggcgac acggaaatgt      3720 tgaatactca tactcttcct ttttcaatat tattgaagca tttatcaggg ttattgtctc    3780
atgagcggat acatatttga atgtatttag aaaaataaac aaataggggt tccgcgcaca    3840
tttccccgaa aagtgccacc tgaacgaagc atctgtgctt cattttgtag aacaaaaatg    3900
caacgcgaga gcgctaattt ttcaaacaaa gaatctgagc tgcatttta cagaacagaa     3960
```

| | |
|---|---|
| atgcaacgcg aaagcgctat tttaccaacg aagaatctgt gcttcatttt tgtaaaacaa | 4020 |
| aaatgcaacg cgagagcgct aatttttcaa acaaagaatc tgagctgcat ttttacagaa | 4080 |
| cagaaatgca acgcgagagc gctattttac aacaaagaa tctatacttc ttttttgttc | 4140 |
| tacaaaaatg catcccgaga gcgctatttt tctaacaaag catcttagat tactttttt | 4200 |
| ctcctttgtg cgctctataa tgcagtctct gataactttt ttgcactgta ggtccgttaa | 4260 |
| ggttagaaga aggctacttt ggtgtctatt ttctcttcca taaaaaagc ctgactccac | 4320 |
| ttcccgcgtt tactgattac tagcgaagct gcgggtgcat ttttcaaga taaggcatc | 4380 |
| cccgattata ttctataccg atgtggattg cgcatacttt gtgaacagaa agtgatagcg | 4440 |
| ttgatgattc ttcattggtc agaaaattat gaacggtttc ttctattttg tctctatata | 4500 |
| ctacgtatag gaaatgttta cattttcgta ttgttttcga ttcactctat gaatagttct | 4560 |
| tactacaatt ttttgtcta aagagtaata ctagagataa acataaaaaa tgtagaggtc | 4620 |
| gagtttagat gcaagttcaa ggagcgaaag gtggatgggt aggttatata gggatatagc | 4680 |
| acagagatat atagcaaaga gatactttg agcaatgttt gtggaagcgg tattcgcaat | 4740 |
| attttagtag ctcgttacag tccggtgcgt ttttggtttt ttgaaagtgc gtcttcagag | 4800 |
| cgcttttggt tttcaaaagc gctctgaagt tcctatactt tctagagaat aggaacttcg | 4860 |
| gaataggaac ttcaaagcgt ttccgaaaac gagcgcttcc gaaaatgcaa cgcgagctgc | 4920 |
| gcacatacag ctcactgttc acgtcgcacc tatatctgcg tgttgcctgt atatatatat | 4980 |
| acatgagaag aacggcatag tgcgtgttta tgcttaaatg cgtacttata tgcgtctatt | 5040 |
| tatgtaggat gaaaggtagt ctagtacctc ctgtgatatt atcccattcc atgcggggta | 5100 |
| tcgtatgctt ccttcagcac tacccttag ctgttctata tgctgccact cctcaattgg | 5160 |
| attagtctca tccttcaatg ctatcattc ctttgatatt ggatcatggt agacaaccct | 5220 |
| taatataact tcgtataatg tatgctatac gaagttatta ggtctagaga tctgtttagc | 5280 |
| ttgcctcgtc cccgccgggt cacccggcca gcgacatgga ggcccagaat accctccttg | 5340 |
| acagtcttga cgtgcgcagc tcaggggcat gatgtgactg tcgcccgtac atttagccca | 5400 |
| tacatcccca tgtataatca tttgcatcca tacattttga tggccgcacg gcgcgaagca | 5460 |
| aaaattacgg ctcctcgctg cagacctgcg agcagggaaa cgctcccctc acagacgcgt | 5520 |
| tgaattgtcc ccacgccgcg cccctgtaga gaaatataaa aggttaggat ttgccactga | 5580 |
| ggttcttctt tcatatactt cctttaaaa tcttgctagg atacagttct cacatcacat | 5640 |
| ccgaacataa acaaccatgg gtaaggaaaa gactcacgtt tcgaggccgc gattaaattc | 5700 |
| caacatggat gctgatttat atgggtataa atgggctcgc gataatgtcg ggcaatcagg | 5760 |
| tgcgacaatc tatcgattgt atgggaagcc cgatgcgcca gagttgtttc tgaaacatgg | 5820 |
| caaaggtagc gttgccaatg atgttacaga tgagatggtc agactaaact ggctgacgga | 5880 |
| atttatgcct cttccgacca tcaagcattt tatccgtact cctgatgatg catgttact | 5940 |
| caccactgcg atccccggca aaacagcatt ccaggtatta agaatatc ctgattcagg | 6000 |
| tgaaaatatt gttgatgcgc tggcagtgtt cctgcgccgg ttgcattcga ttcctgtttg | 6060 |
| taattgtcct tttaacagcg atcgcgtatt tcgtctcgct caggcgcaat cacgaatgaa | 6120 |
| taacggtttg gttgatgcga gtgattttga tgacgagcgt aatggctggc ctgttgaaca | 6180 |
| agtctggaaa gaaatgcata agcttttgcc attctcaccg gattcagtcg tcactcatgg | 6240 |
| tgatttctca cttgataacc ttattttga cgaggggaaa ttaataggtt gtattgatgt | 6300 |

```
tggacgagtc ggaatcgcag accgatacca ggatcttgcc atcctatgga actgcctcgg    6360
tgagttttct ccttcattac agaaacggct ttttcaaaaa tatggtattg ataatcctga    6420
tatgaataaa ttgcagtttc atttgatgct cgatgagttt ttctaatcag tactgacaat    6480
aaaaagattc ttgttttcaa gaacttgtca tttgtatagt ttttttatat tgtagttgtt    6540 ctatttttaat caaatgttag cgtgatttat atttttttc gcctcgacat catctgccca    6600
gatgcgaagt taagtgcgca gaaagtaata tcatgcgtca atcgtatgtg aatgctggtc    6660
gctatactgc tgtcgattcg atactaacgc cgccatccag tgtcgaaaac gagctctcga    6720
gaacccttaa tataacttcg tataatgtat gctatacgaa gttattaggt gatatcagat    6780
ccactaggag cgacctcatg ctatacctga gaaagcaacc tgacctacag gaaagagtta    6840
ctcaagaata agaattttcg ttttaaaacc taagagtcac tttaaaattt gtatacactt    6900 attttttta taacttattt aataataaaa atcataaatc ataagaaatt cgcttattta    6960
gaagtgtcaa caacgtatct accaacgatt tgacccttt ccatctttc gtaaatttct    7020 ggcaaggtag acaagccgac aaccttgatt ggagacttga ccaaacctct ggcgaagaat    7080
tgttaattaa gagctcagat cttatcgtcg tcatccttgt aatccatcga tactagtttt    7140
ttgattaaaa ttaaaaaaac ttttttgtttt tgtgttatt ctttgttctt agaaaagaca    7200
agttgagctt gtttgttctt gatgttttat tattttacaa tagctgcaaa tgaagaatag    7260
attcgaacat tgtgaagtat tggcatatat cgtctctatt tatactttt ttttttcagt    7320 tctagtatat tttgtatttt cctccttttc attctttcag ttgccaataa gttacagggg    7380
atctcgaaag atggtgggga ttttccttg aaagacgact ttttgccatc taattttcc    7440 ttgttgcctc tgaaaattat ccagcagaag caaatgtaaa agatgaacct cagaagaaca    7500
cgcaggggcc cgaaattgtt cctacgagaa gtagtgggtc ataaaaagtt tattccctgg    7560 aaaaaaatt ttgcgttgcc tttctggaga attttttcga attagcgtgc tgccactgca    7620
tgcatttctg agaagtgtgg gcattcttcc accagttgtt cctcctaaaa aaaaaaagat    7680
ttcctacccc gcacaaattc ctgcataccc ctcatttcca cggggccggc cgcacacacc    7740
atagcttcaa aatgtttcta ctcctttttt actcttccag attttctcgg actccgcgca    7800
tcgccgtacc acttcaaaac acccaagcac agcatactaa atttcccctc tttcttcctc    7860
tagggtgtcg ttaattaccc gtactaaagg tttggaaaag aaaaaagaga ccgcctcgtt    7920 tcttttttctt cgtcgaaaaa ggcaataaaa attttttatca cgtttctttt tcttgaaaat    7980
tttttttttt gatttttttc tctttcgatg acctcccatt gatatttaag ttaataaacg    8040
gtcttcaatt tctcaagttt cagtttcatt tttcttgttc tattacaact ttttttactt    8100
cttgctcatt agaagaaaag catagcaatc taatctaagt tttaattaca aggatccgta    8160
atacgactca ctatagggcc cgggcgtcga                                     8190
```

<210> SEQ ID NO 84
<211> LENGTH: 8190
<212> TYPE: DNA
<213> ORGANISM: Artificial Sequence
<220> FEATURE:
<223> OTHER INFORMATION: Plasmid pCEV-G4-Km-TEF-AT-yABAB

<400> SEQUENCE: 84

```
ggagcgacct catgctatac ctgagaaagc aacctgacct acaggaaaga gttactcaag      60
aataagaatt ttcgttttaa aacctaagag tcactttaaa atttgtatac acttattttt    120
tttataactt atttaataat aaaaatcata atcataaga aattcgctta tttagaagtg    180
```

-continued

| | |
|---|---|
| tcaacaacgt atctaccaac gatttgaccc ttttccatct tttcgtaaat ttctggcaag | 240 |
| gtagacaagc cgacaacctt gattggagac ttgaccaaac ctctggcgaa gaattgttaa | 300 |
| ttaagagctc agatcttatc gtcgtcatcc ttgtaatcca tcgatactag tttttttgatt | 360 |
| aaaattaaaa aaacttttttg ttttttgtgtt tattctttgt tcttagaaaa gacaagttga | 420 |
| gcttgtttgt tcttgatgtt ttattatttt acaatagctg caaatgaaga atagattcga | 480 |
| acattgtgaa gtattggcat atatcgtctc tatttatact ttttttttttt cagttctagt | 540 |
| atattttgta ttttcctcct tttcattctt tcagttgcca ataagttaca ggggatctcg | 600 |
| aaagatggtg gggattttttc cttgaaagac gacttttttgc catctaattt ttccttgttg | 660 |
| cctctgaaaa ttatccagca gaagcaaatg taaaagatga acctcagaag aacacgcagg | 720 |
| ggcccgaaat tgttcctacg agaagtagtg ggtcataaaa agtttattcc ctggaaaaaa | 780 |
| aattttgcgt tgcctttctg gagaattttt tcgaattagc gtgctgccac tgcatgcatt | 840 |
| tctgagaagt gtgggcattc ttccaccagt tgttcctcct aaaaaaaaaa agatttccta | 900 |
| ccccgcacaa attcctgcat acccctcatt tccacggggc cggccgcaca caccatagct | 960 |
| tcaaaatgtt tctactcctt ttttactctt ccagattttc tcggactccg cgcatcgccg | 1020 |
| taccacttca aaacacccaa gcacagcata ctaaatttcc cctctttctt cctctagggt | 1080 |
| gtcgttaatt acccgtacta aaggtttgga aaagaaaaaa gagaccgcct cgtttctttt | 1140 |
| tcttcgtcga aaaaggcaat aaaaattttt atcacgtttc ttttttcttga aaatttttttt | 1200 |
| ttttgatttt tttctctttc gatgacctcc cattgatatt taagttaata aacggtcttc | 1260 |
| aatttctcaa gtttcagttt cattttttctt gttctattac aactttttttt acttcttgct | 1320 |
| cattagaaag aaagcatagc aatctaatct aagtttttaat tacaaggatc cgtaatacga | 1380 |
| ctcactatag ggcccgggcg tcgacatgag atttccttca atttttactg ctgttttatt | 1440 |
| cgcagcatcc tccgcattag ctatgcaagt acaattggtt gaaaccggtg gtggtttagt | 1500 |
| tcaaccaggt ggtagtttga gattatcttg tgctgcatca ggttttacat tggattattc | 1560 |
| ttcaataggt tggttcagac aagctcctgg taaagaaaga gaaggtgttt cttgcatatc | 1620 |
| cagttctggt gactcaacta aatatgctga ctccgttaag ggtagattca ctacttcaag | 1680 |
| agataacgct aaaaatacag tctacttgca aatgaactca ttaaagccag atgcacagc | 1740 |
| agtctattac tgtgccgctt ttagagccac catgtgcggt gtattcccat tgtctcctta | 1800 |
| cggtaaagat gactggggta aaggtacttt agttactgtc tcatccggtg gtggtggttc | 1860 |
| cggtggtggt ggtagtggtg gtggtggttc tcaagttcaa ttagtagaat ccggtggtgg | 1920 |
| tttagtccaa cctggtggta gtttaagatt atcctgcgaa gcaagtggtt ttacattaga | 1980 |
| ttattacggt atcggttggt ttagacaacc acctggtaaa gaaagagaag ctgtctctta | 2040 |
| tatttccgct agtgcaagaa ctatattgta cgcagattct gtaaagggta gattcacaat | 2100 |
| ttcaagagac aatgccaaga acgctgttta tttgcaaatg aactctttga agagagaaga | 2160 |
| caccgcagtt tattactgtg ccagaagaag attttctgct tcttcagtca acagatggtt | 2220 |
| agcagacgat tatgatgttt ggggtagagg tacacaagtc gccgtaagtt ctggtggtgg | 2280 |
| ttccggtggt ggtagtggtg gtggttctgg tggtggttca caattgcaat tagtagaaac | 2340 |
| tggtggtggt ttggttcaac caggtggttc cttgagatta agttgtgctg catctggttt | 2400 |
| tactttctct gattacgtta tgacatggg cagacaagct ccaggtaaag gtcctgaatg | 2460 |
| gatcgctaca attaataccg acggttccac aatgagagat gacagtacca agggtagatt | 2520 |

```
cactatttca agagataacg ctaagaacac attgtactta caaatgacct ctttgaaacc    2580
agaagacacc gcattatatt actgtgccag aggtagagtc atatccgcca gtgctatcag    2640
aggtgcagta agaggtcctg gtactcaagt tacagtctct tcaggtggcg gcggtagtgg    2700
cggcggcggt tctggcggtg gtggttcaca agtccaattg gtagaatctg gtggtggttt    2760
agttcaaact ggtggttcat tgagattatc ctgcgcttcc agtggttcca ttgcaggttt    2820
cgaaactgtt acatggtcaa gacaagctcc aggtaaatct ttgcaatggg tcgcctcaat    2880
gaccaagact aacaacgaaa tctattctga ttcagttaag ggtagattca ttatttcaag    2940
agataatgct aaaaacaccg tttatttgca aatgaactca ttgaagccag aagatactgg    3000
tgtttacttc tgcaagggtc ctgaattaag aggtcaaggt attcaagtaa cagtttcttc    3060
ataaggtacc gcggctagct aagatccgct ctaaccgaaa aggaaggagt tagacaacct    3120
gaagtctagg tccctattta ttttttttata gttatgttag tattaagaac gttatttata    3180
tttcaaattt ttcttttttt tctgtacaga cgcgtgtacg catgtaacat tatactgaaa    3240
accttgcttg agaaggtttt gggacgctcg aagatccagc tgcattaatg aatcggccaa    3300
cgcgcgggga gaggcggttt cgtattggg cgctcttccg cttcctcgct cactgactcg    3360
ctgcgctcgg tcgttcggct gcggcgagcg gtatcagctc actcaaaggc ggtaatacgg    3420
ttatccacag aatcagggga taacgcagga aagaacatgt gagcaaaagg ccagcaaaag    3480
gccaggaacc gtaaaaaggc cgcgttgctg cgttttttcc ataggctccg ccccccctgac   3540
gagcatcaca aaaatcgacg ctcaagtcag aggtggcgaa acccgacagg actataaaga    3600
taccaggcgt ttcccctgg aagctccctc gtgcgctctc ctgttccgac cctgccgctt    3660
accggatacc tgtccgcctt tctcccttcg ggaagcgtgg cgctttctca tagctcacgc    3720
tgtaggtatc tcagttcggt gtaggtcgtt cgctccaagc tgggctgtgt gcacgaaccc    3780
cccgttcagc ccgaccgctg cgccttatcc ggtaactatc gtcttgagtc caacccggta    3840
agacacgact tatcgccact ggcagcagcc actggtaaca ggattagcag agcgaggtat    3900
gtaggcggtg ctacagagtt cttgaagtgg tggcctaact acggctacac tagaaggaca    3960
gtatttggta tctgcgctct gctgaagcca gttaccttcg gaaaaagagt ggtagctct     4020
tgatccggca acaaaccac cgctggtagc ggtggttttt ttgtttgcaa gcagcagatt    4080
acgcgcagaa aaaaggatc tcaagaagat cctttgatct tttctacggg gtctgacgct    4140
cagtggaacg aaaactcacg ttaagggatt ttggtcatga gattatcaaa aaggatcttc   4200
acctagatcc ttttaaatta aaatgaagt tttaaatcaa tctaaagtat atatgagtaa     4260
acttggtctg acagttacca atgcttaatc agtgaggcac ctatctcagc gatctgtcta    4320
tttcgttcat ccatagttgc ctgactcccc gtcgtgtaga taactacgat acgggagggc    4380
ttaccatctg gccccagtgc tgcaatgata ccgcgagacc cacgctcacc ggctccagat    4440
ttatcagcaa taaccagcc agccggaagg gccgagcgca gaagtggtcc tgcaacttta    4500
tccgcctcca tccagtctat taattgttgc cgggaagcta gagtaagtag ttcgccagtt    4560
aatagtttgc gcaacgttgt tgccattgct acaggcatcg tggtgtcacg ctcgtcgttt    4620
ggtatggctt cattcagctc cggttcccaa cgatcaaggc gagttacatg atccccccatg   4680
ttgtgcaaaa aagcggttag ctccttcggt cctccgatcg ttgtcagaag taagttggcc    4740
gcagtgttat cactcatggt tatggcagca ctgcataatt ctcttactgt catgccatcc    4800
gtaagatgct tttctgtgac tggtgagtac tcaaccaagt cattctgaga atagtgtatg    4860
cggcgaccga gttgctcttg cccggcgtca atacgggata ataccgcgcc acatagcaga    4920
```

```
actttaaaag tgctcatcat tggaaaacgt tcttcggggc gaaaactctc aaggatctta    4980
ccgctgttga gatccagttc gatgtaaccc actcgtgcac ccaactgatc ttcagcatct    5040
tttactttca ccagcgtttc tgggtgagca aaaacaggaa ggcaaaatgc cgcaaaaaag    5100
ggaataaggg cgacacggaa atgttgaata ctcatactct tccttttca atattattga    5160 agcatttatc agggttattg tctcatgagc ggatacatat ttgaatgtat ttagaaaaat    5220
aaacaaatag gggttccgcg cacatttccc cgaaaagtgc cacctgaacg aagcatctgt    5280
gcttcatttt gtagaacaaa aatgcaacgc gagagcgcta attttcaaa caagaatct    5340 gagctgcatt tttacagaac agaaatgcaa cgcgaaagcg ctattttacc aacgaagaat    5400
ctgtgcttca tttttgtaaa acaaaaatgc aacgcgagag cgctaatttt tcaaacaaag    5460
aatctgagct gcattttac agaacagaaa tgcaacgcga gagcgctatt ttaccaacaa    5520
agaatctata cttctttttt gttctacaaa aatgcatccc gagagcgcta ttttctaac    5580 aaagcatctt agattacttt ttttctcctt tgtgcgctct ataatgcagt ctcttgataa    5640 cttttttgcac tgtaggtccg ttaaggttag aagaaggcta ctttggtgtc tattttctct    5700
tccataaaaa aagcctgact ccacttcccg cgtttactga ttactagcga agctgcgggt    5760
gcattttttc aagataaagg catccccgat tatattctat accgatgtgg attgcgcata    5820
ctttgtgaac agaaagtgat agcgttgatg attcttcatt ggtcagaaaa ttatgaacgg    5880
tttcttctat tttgtctcta tatactacgt ataggaaatg tttacatttt cgtattgttt    5940
tcgattcact ctatgaatag ttcttactac aatttttttg tctaaagagt aatactagag    6000
ataaacataa aaaatgtaga ggtcgagttt agatgcaagt tcaaggagcg aaaggtggat    6060
gggtaggtta tatagggata tagcacagag atatatagca agagatact tttgagcaat    6120 gtttgtggaa gcggtattcg caatatttta gtagctcgtt acagtccggt gcgtttttgg    6180
ttttttgaaa gtgcgtcttc agagcgcttt tggttttcaa aagcgctctg aagttcctat    6240
actttctaga gaataggaac ttcggaatag gaacttcaaa gcgtttccga aaacgagcgc    6300
ttccgaaaat gcaacgcgag ctgcgcacat acagctcact gttcacgtcg cacctatatc    6360
tgcgtgttgc ctgtatatat atatacatga gaagaacggc atagtgcgtg tttatgctta    6420
aatgcgtact tatatgcgtc tatttatgta ggatgaaagg tagtctagta cctcctgtga    6480
tattatccca ttccatgcgg ggtatcgtat gcttccttca gcactaccct ttagctgttc    6540
tatatgctgc cactcctcaa ttggattagt ctcatccttc aatgctatca tttcctttga    6600
tattggatca tggtagacaa cccttaatat aacttcgtat aatgtatgct atacgaagtt    6660
attaggtcta gagatctgtt tagcttgcct cgtccccgcc gggtcacccg gccagcgaca    6720
tggaggccca gaatacccc cttgacagtc ttgacgtgcg cagctcaggg gcatgatgtg    6780
actgtcgccc gtacatttag cccatacatc cccatgtata atcatttgca tccatacatt    6840
ttgatggccg cacggcgcga agcaaaaatt acggctcctc gctgcagacc tgcgagcagg    6900
gaaacgctcc cctcacagac gcgttgaatt gtccccacgc cgcgcccctg tagagaaata    6960
taaaaggtta ggatttgcca ctgaggttct ctttcatat acttccttt aaaatcttgc    7020 taggatacag ttctcacatc acatccgaac ataacaacc atgggtaagg aaaagactca    7080
cgtttcgagg ccgcgattaa attccaacat ggatgctgat ttatatgggt ataaatgggc    7140
tcgcgataat gtcgggcaat caggtgcgac aatctatcga ttgtatggga agcccgatgc    7200
gccagagttg tttctgaaac atggcaaagg tagcgttgcc aatgatgtta cagatgagat    7260
```

-continued

```
ggtcagacta aactggctga cggaatttat gcctcttccg accatcaagc attttatccg      7320
tactcctgat gatgcatggt tactcaccac tgcgatcccc ggcaaaacag cattccaggt      7380
attagaagaa tatcctgatt caggtgaaaa tattgttgat gcgctggcag tgttcctgcg      7440
ccggttgcat tcgattcctg tttgtaattg tccttttaac agcgatcgcg tatttcgtct      7500
cgctcaggcg caatcacgaa tgaataacgg tttggttgat gcgagtgatt ttgatgacga      7560
gcgtaatggc tggcctgttg aacaagtctg gaaagaaatg cataagcttt tgccattctc      7620
accggattca gtcgtcactc atggtgattt ctcacttgat aaccttattt ttgacgaggg      7680
gaaattaata ggttgtattg atgttggacg agtcggaatc gcagaccgat accaggatct      7740
tgccatccta tggaactgcc tcggtgagtt ttctccttca ttacagaaac ggcttttca      7800
aaaatatggt attgataatc ctgatatgaa taaattgcag tttcatttga tgctcgatga      7860
gttttctaa tcagtactga caataaaaag attcttgttt caagaactt gtcatttgta      7920
tagttttttt atattgtagt tgttctattt taatcaaatg ttagcgtgat ttatattttt      7980
tttcgcctcg acatcatctg cccagatgcg aagttaagtg cgcagaaagt aatatcatgc      8040
gtcaatcgta tgtgaatgct ggtcgctata ctgctgtcga ttcgatacta acgccgccat      8100
ccagtgtcga aaacgagctc tcgagaaccc ttaatataac ttcgtataat gtatgctata      8160
cgaagttatt aggtgatatc agatccacta                                      8190
```

<210> SEQ ID NO 85
<211> LENGTH: 8202
<212> TYPE: DNA
<213> ORGANISM: Artificial Sequence
<220> FEATURE:
<223> OTHER INFORMATION: Plasmid pCEV-G4-Km-TEF-X40-AT-yABAB

<400> SEQUENCE: 85

```
ggagcgacct catgctatac ctgagaaagc aacctgacct acaggaaaga gttactcaag        60
aataagaatt ttcgttttaa aacctaagag tcactttaaa atttgtatac acttattttt       120
tttataactt atttaataat aaaaatcata aatcataaga aattcgctta tttagaagtg       180
tcaacaacgt atctaccaac gatttgaccc ttttccatct tttcgtaaat ttctggcaag       240
gtagacaagc cgacaacctt gattggagac ttgaccaaac ctctggcgaa gaattgttaa       300
ttaagagctc agatcttatc gtcgtcatcc ttgtaatcca tcgatactag ttttttgatt       360
aaaattaaaa aaacttttg tttttgtgtt tattctttgt tcttagaaaa gacaagttga       420
gcttgtttgt tcttgatgtt ttattatttt acaatagctg caaatgaaga atagattcga       480
acattgtgaa gtattggcat atatcgtctc tatttatact tttttttttt cagttctagt       540
atattttgta ttttcctcct tttcattctt tcagttgcca ataagttaca ggggatctcg       600
aaagatggtg gggattttc cttgaaagac gactttttgc catctaattt ttccttgttg       660
cctctgaaaa ttatccagca gaagcaaatg taaaagatga acctcagaag aacacgcagg       720
ggcccgaaat tgttcctacg agaagtagtg ggtcataaaa agtttattcc ctggaaaaaa       780
aattttgcgt tgcctttctg gagaattttt tcgaattagc gtgctgccac tgcatgcatt       840
tctgagaagt gtgggcattc ttccaccagt tgttcctcct aaaaaaaaaa agatttccta       900
ccccgcacaa attcctgcat acccctcatt tccacggggc cggccgcaca caccatagct       960
tcaaaatgtt tctactcctt ttttactctt ccagattttc tcggactccg cgcatcgccg      1020
taccacttca aaacacccaa gcacagcata ctaaatttcc cctctttctt cctctagggt      1080
gtcgttaatt acccgtacta aaggtttgga aaagaaaaaa gagaccgcct cgtttctttt      1140
```

-continued

```
tcttcgtcga aaaaggcaat aaaaatttt atcacgtttc tttttcttga aaattttttt     1200
ttttgatttt tttctctttc gatgacctcc cattgatatt taagttaata aacggtcttc     1260
aatttctcaa gtttcagttt catttttctt gttctattac aactttttt acttcttgct     1320 cattagaaag aaagcatagc aatctaatct aagttttaat tacaaggatc catgagattt     1380
ccttcaattt ttactgctgt tttattcgca gcatcctccg cattagctat gcaagtacaa     1440
ttggttgaaa ccggtggtgg tttagttcaa ccaggtggta gtttgagatt atcttgtgct     1500
gcatcaggtt ttacattgga ttattcttca ataggttggt tcagacaagc tcctggtaaa     1560
gaaagagaag gtgtttcttg catatccagt tctggtgact caactaaata tgctgactcc     1620
gttaagggta gattcactac ttcaagagat aacgctaaaa atacagtcta cttgcaaatg     1680
aactcattaa agccagatga cacagcagtc tattactgtg ccgcttttag agccaccatg     1740
tgcggtgtat tcccattgtc tccttacggt aaagatgact ggggtaaagg tactttagtt     1800
actgtctcat ccggtggtgg tggttccggt ggtggtggta gtggtggtgg tggttctcaa     1860
gttcaattag tagaatccgg tggtggttta gtccaacctg gtggtagttt aagattatcc     1920
tgcgaagcaa gtggttttac attagattat tacggtatcg gttggtttag acaaccacct     1980
ggtaaagaaa gagaagctgt ctcttatatt tccgctagtg caagaactat attgtacgca     2040
gattctgtaa agggtagatt cacaatttca agagacaatg ccaagaacgc tgtttatttg     2100
caaatgaact ctttgaagag agaagacacc gcagtttatt actgtgccag aagaagattt     2160
tctgcttctt cagtcaacag atggttagca gacgattatg atgttgggg tagaggtaca     2220 caagtcgccg taagttctgg tggtggttcc ggtggtggta gtggtggtgg ttctggtggt     2280
ggttcacaat tgcaattagt agaaactggt ggtggtttgg ttcaaccagg tggttccttg     2340
agattaagtt gtgctgcatc tggttttact ttctctgatt acgttatgac atgggtcaga     2400
caagctccag gtaaaggtcc tgaatggatc gctacaatta taccgacgg ttccacaatg     2460 agagatgaca gtaccaaggg tagattcact atttcaagag ataacgctaa gaacacattg     2520
tacttacaaa tgacctcttt gaaaccagaa gacaccgcat tatattactg tgccagaggt     2580
agagtcatat ccgccagtgc tatcagaggt gcagtaagag gtcctggtac tcaagttaca     2640
gtctcttcag gtggcggcgg tagtggcggc ggcggttctg gcggtggtgg ttcacaagtc     2700
caattggtag aatctggtgg tggtttagtt caaactggtg gttcattgag attatcctgc     2760
gcttccagtg gttccattgc aggtttcgaa actgttacat ggtcaagaca agctccaggt     2820
aaatctttgc aatgggtcgc ctcaatgacc aagactaaca acgaaatcta ttctgattca     2880
gttaagggta gattcattat ttcaagagat aatgctaaaa acaccgttta tttgcaaatg     2940
aactcattga agccagaaga tactggtgtt tacttctgca agggtcctga attaagaggt     3000
caaggtattc aagtaacagt ttcttcagtc gacatggaac agaagttgat ttccgaagaa     3060
gacctcgagt aagcttggta ccgcggctag ctaagatccg ctctaaccga aaaggaagga     3120
gttagacaac ctgaagtcta ggtccctatt tatttttta tagttatgtt agtattaaga     3180
acgttattta tatttcaaat ttttcttttt tttctgtaca gacgcgtgta cgcatgtaac     3240
attatactga aaaccttgct tgagaaggtt ttgggacgct cgaagatcca gctgcattaa     3300
tgaatcggcc aacgcgcggg gagaggcggt ttgcgtattg ggcgctcttc cgcttcctcg     3360
ctcactgact cgctgcgctc ggtcgttcgg ctgcggcgag cggtatcagc tcactcaaag     3420
gcggtaatac ggttatccac agaatcaggg gataacgcag gaaagaacat gtgagcaaaa     3480
```

```
ggccagcaaa aggccaggaa ccgtaaaaag gccgcgttgc tggcgttttt ccataggctc    3540
cgccccctg  acgagcatca caaaaatcga cgctcaagtc agaggtggcg aaacccgaca    3600
ggactataaa gataccaggc gtttccccct ggaagctccc tcgtgcgctc tcctgttccg    3660
accctgccgc ttaccggata cctgtccgcc tttctccctt cgggaagcgt ggcgctttct    3720
catagctcac gctgtaggta tctcagttcg gtgtaggtcg ttcgctccaa gctgggctgt    3780
gtgcacgaac cccccgttca gcccgaccgc tgcgccttat ccggtaacta tcgtcttgag    3840
tccaacccgg taagacacga cttatcgcca ctggcagcag ccactggtaa caggattagc    3900
agagcgaggt atgtaggcgg tgctacagag ttcttgaagt ggtggcctaa ctacggctac    3960
actagaagga cagtatttgg tatctgcgct ctgctgaagc cagttacctt cggaaaaaga    4020
gttggtagct cttgatccgg caaacaaacc accgctggta gcggtggttt ttttgtttgc    4080
aagcagcaga ttacgcgcag aaaaaaagga tctcaagaag atcctttgat cttttctacg    4140
gggtctgacg ctcagtggaa cgaaaactca cgttaaggga ttttggtcat gagattatca    4200
aaaaggatct tcacctagat ccttttaaat taaaaatgaa gttttaaatc aatctaaagt    4260
atatatgagt aaacttggtc tgacagttac caatgcttaa tcagtgaggc acctatctca    4320
gcgatctgtc tatttcgttc atccatagtt gcctgactcc ccgtcgtgta gataactacg    4380
atacgggagg gcttaccatc tggccccagt gctgcaatga taccgcgaga cccacgctca    4440
ccggctccag atttatcagc aataaaccag ccagccggaa gggccgagcg cagaagtggt    4500
cctgcaactt tatccgcctc catccagtct attaattgtt gccgggaagc tagagtaagt    4560
agttcgccag ttaatagttt gcgcaacgtt gttgccattg ctacaggcat cgtggtgtca    4620
cgctcgtcgt ttggtatggc ttcattcagc tccggttccc aacgatcaag gcgagttaca    4680
tgatccccca tgttgtgcaa aaaagcggtt agctccttcg gtcctccgat cgttgtcaga    4740
agtaagttgg ccgcagtgtt atcactcatg gttatggcag cactgcataa ttctcttact    4800
gtcatgccat ccgtaagatg cttttctgtg actggtgagt actcaaccaa gtcattctga    4860
gaatagtgta tgcggcgacc gagttgctct tgcccggcgt caatacggga taataccgcg    4920
ccacatagca gaactttaaa agtgctcatc attggaaaac gttcttcggg gcgaaaactc    4980
tcaaggatct taccgctgtt gagatccagt tcgatgtaac ccactcgtgc acccaactga    5040
tcttcagcat cttttacttt caccagcgtt tctgggtgag caaaaacagg aaggcaaaat    5100
gccgcaaaaa agggaataag ggcgacacgg aaatgttgaa tactcatact cttcctttt     5160
caatattatt gaagcattta tcagggttat tgtctcatga gcggatacat atttgaatgt    5220
atttagaaaa ataaacaaat aggggttccg cgcacatttc cccgaaaagt gccacctgaa    5280
cgaagcatct gtgcttcatt ttgtagaaca aaaatgcaac gcgagagcgc taatttttca    5340
aacaaagaat ctgagctgca ttttacaga  acagaaatgc aacgcgaaag cgctatttta    5400
ccaacgaaga atctgtgctt cattttttgta aaacaaaaat gcaacgcgag agcgctaatt    5460
tttcaaacaa agaatctgag ctgcatttt  acagaacaga atgcaacgc  gagagcgcta    5520
ttttaccaac aaagaatcta tacttctttt ttgttctaca aaaatgcatc ccgagagcgc    5580
tattttccta acaaagcatc ttagattact ttttttctcc tttgtgcgct ctataatgca    5640
gtctcttgat aacttttttgc actgtaggtc cgttaaggtt agaagaaggc tactttggtg    5700
tctatttttct cttccataaa aaagcctga  ctccacttcc cgcgtttact gattactagc    5760
gaagctgcgg gtgcattttt tcaagataaa ggcatcccg  attatattct ataccgatgt    5820
ggattgcgca tactttgtga acagaaagtg atagcgttga tgattcttca ttggtcagaa    5880
```

```
aattatgaac ggtttcttct attttgtctc tatatactac gtataggaaa tgtttacatt    5940
ttcgtattgt tttcgattca ctctatgaat agttcttact acaattttt tgtctaaaga     6000 gtaatactag agataaacat aaaaaatgta gaggtcgagt ttagatgcaa gttcaaggag    6060
cgaaaggtgg atgggtaggt tatataggga tatagcacag agatatatag caaagagata   6120
cttttgagca atgtttgtgg aagcggtatt cgcaatattt tagtagctcg ttacagtccg   6180
gtgcgttttt ggttttttga aagtgcgtct tcagagcgct tttggttttc aaaagcgctc   6240
tgaagttcct atactttcta gagaatagga acttcggaat aggaacttca aagcgtttcc   6300
gaaaacgagc gcttccgaaa atgcaacgcg agctgcgcac atacagctca ctgttcacgt   6360
cgcacctata tctgcgtgtt gcctgtatat atatatacat gagaagaacg gcatagtgcg   6420
tgtttatgct taaatgcgta cttatatgcg tctatttatg taggatgaaa ggtagtctag   6480
tacctcctgt gatattatcc cattccatgc ggggtatcgt atgcttcctt cagcactacc   6540
ctttagctgt tctatatgct gccactcctc aattggatta gtctcatcct tcaatgctat   6600
catttccttt gatattggat catggtagac aacccttaat ataacttcgt ataatgtatg   6660
ctatacgaag ttattaggtc tagagatctg tttagcttgc ctcgtcccg ccgggtcacc    6720 cggccagcga catggaggcc cagaataccc tccttgacag tcttgacgtg cgcagctcag   6780
gggcatgatg tgactgtcgc ccgtacattt agcccataca tccccatgta taatcatttg   6840
catccataca ttttgatggc cgcacggcgc gaagcaaaaa ttacggctcc tcgctgcaga   6900
cctgcgagca gggaaacgct cccctcacag acgcgttgaa ttgtcccac gccgcgcccc    6960 tgtagagaaa tataaaaggt taggatttgc cactgaggtt cttctttcat atacttcctt   7020
ttaaaatctt gctaggatac agttctcaca tcacatccga acataaacaa ccatgggtaa   7080
ggaaaagact cacgtttcga ggccgcgatt aaattccaac atggatgctg atttatatgg   7140
gtataaatgg gctcgcgata atgtcgggca atcaggtgcg acaatctatc gattgtatgg   7200
gaagcccgat gcgccagagt tgtttctgaa acatggcaaa ggtagcgttg ccaatgatgt   7260
tacagatgag atggtcagac taaactggct gacggaattt atgcctcttc cgaccatcaa   7320 gcatttatc cgtactcctg atgatgcatg gttactcacc actgcgatcc ccggcaaaac    7380
agcattccag gtattagaag aatatcctga ttcaggtgaa atattgttg atgcgctggc    7440 agtgttcctg cgccggttgc attcgattcc tgtttgtaat tgtccttta acagcgatcg    7500 cgtatttcgt ctcgctcagg cgcaatcacg aatgaataac ggtttggttg atgcgagtga   7560
ttttgatgac gagcgtaatg gctggcctgt gaacaagtc tggaaagaaa tgcataagct    7620
tttgccattc tcaccggatt cagtcgtcac tcatggtgat ttctcacttg ataaccttat   7680
ttttgacgag gggaaattaa taggttgtat tgatgttgga cgagtcggaa tcgcagaccg   7740
ataccaggat cttgccatcc tatggaactg cctcggtgag ttttctcctt cattacagaa   7800
acggcttttt caaaaatatg gtattgataa tcctgatatg aataaattgc agtttcattt   7860
gatgctcgat gagttttct aatcagtact gacaataaaa agattcttgt tttcaagaac    7920
ttgtcatttg tatagttttt ttatattgta gttgttctat tttaatcaaa tgttagcgtg   7980
atttatattt tttttcgcct cgacatcatc tgcccagatg cgaagttaag tgcgcagaaa   8040
gtaatatcat gcgtcaatcg tatgtgaatg ctggtcgcta tactgctgtc gattcgatac   8100
taacgccgcc atccagtgtc gaaaacgagc tctcgagaac ccttaatata acttcgtata   8160
atgtatgcta tacgaagtta ttaggtgata tcagatccac ta                      8202
```

<210> SEQ ID NO 86
<211> LENGTH: 6151
<212> TYPE: DNA
<213> ORGANISM: Artificial Sequence
<220> FEATURE:
<223> OTHER INFORMATION: Plasmid pCEV-G4-Ph

<400> SEQUENCE: 86

```
ggagcgacct catgctatac ctgagaaagc aacctgacct acaggaaaga gttactcaag      60
aataagaatt ttcgttttaa aacctaagag tcactttaaa atttgtatac acttattttt     120
tttataactt atttaataat aaaaatcata aatcataaga aattcgctta tttagaagtg     180
tcaacaacgt atctaccaac gatttgaccc ttttccatct tttcgtaaat ttctggcaag     240
gtagacaagc cgacaacctt gattggagac ttgaccaaac ctctggcgaa gaattgttaa     300
ttaagagctc agatcttatc gtcgtcatcc ttgtaatcca tcgatactag ttttttgatt     360
aaaattaaaa aaactttttg ttttgtgtt tattctttgt tcttagaaaa gacaagttga     420
gcttgtttgt tcttgatgtt ttattatttt acaatagctg caaatgaaga atagattcga     480
acattgtgaa gtattggcat atatcgtctc tatttatact tttttttttt cagttctagt     540
atattttgta ttttcctcct tttcattctt tcagttgcca ataagttaca ggggatctcg     600
aaagatggtg gggattttc cttgaaagac gacttttgc catctaattt ttccttgttg     660
cctctgaaaa ttatccagca gaagcaaatg taaaagatga acctcagaag aacacgcagg     720
ggcccgaaat tgttcctacg agaagtagtg ggtcataaaa agtttattcc ctggaaaaaa     780
aatttgcgt tgcctttctg gagaattttt tcgaattagc gtgctgccac tgcatgcatt     840
tctgagaagt gtgggcattc ttccaccagt tgttcctcct aaaaaaaaaa agatttccta     900
ccccgcacaa attcctgcat accctcatt tccacggggc cggccgcaca caccatagct     960
tcaaaatgtt tctactcctt ttttactctt ccagattttc tcggactccg cgcatcgccg    1020
taccacttca aaacacccaa gcacagcata ctaaatttcc cctctttctt cctctagggt    1080
gtcgttaatt acccgtacta aaggtttgga aaagaaaaaa gagaccgcct cgtttctttt    1140
tcttcgtcga aaaaggcaat aaaaatttt atcacgtttc ttttcttga aaattttttt    1200
ttttgatttt tttctctttc gatgacctcc cattgatatt taagttaata aacggtcttc    1260
aatttctcaa gtttcagttt catttttctt gttctattac actttttttt acttcttgct    1320
cattagaaag aaagcatagc aatctaatct aagttttaat tacaaggatc cgtaatacga    1380
ctcactatag ggcccgggcg tcgacatgga acagaagttg atttccgaag aagacctcga    1440
gtaagcttgg taccgcggct agctaagatc cgctctaacc gaaaaggaag gagttagaca    1500
acctgaagtc taggtcccta tttattttt tatagttatg ttagtattaa gaacgttatt    1560
tatatttcaa attttctttt ttttctgta cagacgcgtg tacgcatgta acattatact    1620
gaaaaccttg cttgagaagg ttttgggacg ctcgaagatc cagctgcatt aatgaatcgg    1680
ccaacgcgcg gggagaggcg gtttgcgtat tgggcgctct tccgcttcct cgctcactga    1740
ctcgctgcgc tcggtcgttc ggctgcggcg agcggtatca gctcactcaa aggcggtaat    1800
acggttatcc acagaatcag gggataacgc aggaaagaac atgtgagcaa aaggccagca    1860
aaaggccagg aaccgtaaaa aggccgcgtt gctggcgttt ttccataggc tccgcccccc    1920
tgacgagcat cacaaaaatc gacgctcaag tcagaggtgg cgaaacccga caggactata    1980
aagataccag gcgtttcccc ctggaagctc cctcgtgcgc tctcctgttc cgaccctgcc    2040
gcttaccgga tacctgtccg cctttctccc ttcgggaagc gtggcgcttt ctcatagctc    2100
```

```
acgctgtagg tatctcagtt cggtgtaggt cgttcgctcc aagctgggct gtgtgcacga    2160
accccccgtt cagcccgacc gctgcgcctt atccggtaac tatcgtcttg agtccaaccc    2220
ggtaagacac gacttatcgc cactggcagc agccactggt aacaggatta gcagagcgag    2280
gtatgtaggc ggtgctacag agttcttgaa gtggtggcct aactacggct acactagaag    2340
gacagtattt ggtatctgcg ctctgctgaa gccagttacc ttcggaaaaa gagttggtag    2400
ctcttgatcc ggcaaacaaa ccaccgctgg tagcggtggt ttttttgttt gcaagcagca    2460
gattacgcgc agaaaaaaag gatctcaaga agatcctttg atcttttcta cggggtctga    2520
cgctcagtgg aacgaaaact cacgttaagg gattttggtc atgagattat caaaaaggat    2580
cttcacctag atccttttaa attaaaaatg aagttttaaa tcaatctaaa gtatatatga    2640
gtaaacttgg tctgacagtt accaatgctt aatcagtgag gcacctatct cagcgatctg    2700
tctatttcgt tcatccatag ttgcctgact ccccgtcgtg tagataacta cgatacggga    2760
gggcttacca tctggcccca gtgctgcaat gataccgcga gacccacgct caccggctcc    2820
agatttatca gcaataaacc agccagccgg aagggccgag cgcagaagtg gtcctgcaac    2880
tttatccgcc tccatccagt ctattaattg ttgccgggaa gctagagtaa gtagttcgcc    2940
agttaatagt ttgcgcaacg ttgttgccat tgctacaggc atcgtggtgt cacgctcgtc    3000
gtttggtatg gcttcattca gctccggttc ccaacgatca aggcgagtta catgatcccc    3060
catgttgtgc aaaaaagcgg ttagctcctt cggtcctccg atcgttgtca gaagtaagtt    3120
ggccgcagtg ttatcactca tggttatggc agcactgcat aattctctta ctgtcatgcc    3180
atccgtaaga tgcttttctg tgactggtga gtactcaacc aagtcattct gagaatagtg    3240
tatgcggcga ccgagttgct cttgcccggc gtcaatacgg gataataccg cgccacatag    3300
cagaacttta aaagtgctca tcattggaaa acgttcttcg gggcgaaaac tctcaaggat    3360
cttaccgctg ttgagatcca gttcgatgta acccactcgt gcacccaact gatcttcagc    3420
atcttttact ttcaccagcg tttctgggtg agcaaaaaca ggaaggcaaa atgccgcaaa    3480
aaagggaata agggcgacac ggaaatgttg aatactcata ctcttccttt ttcaatatta    3540
ttgaagcatt tatcagggtt attgtctcat gagcggatac atatttgaat gtatttagaa    3600
aaataaacaa ataggggttc cgcgcacatt tccccgaaaa gtgccacctg aacgaagcat    3660
ctgtgcttca ttttgtagaa caaaaatgca acgcgagagc gctaattttt caaacaaaga    3720
atctgagctg cattttaca gaacagaaat gcaacgcgaa agcgctattt taccaacgaa    3780
gaatctgtgc ttcattttg taaaacaaaa atgcaacgcg agagcgctaa ttttcaaac    3840 aaagaatctg agctgcattt ttacagaaca gaaatgcaac gcgagagcgc tattttacca    3900
acaaagaatc tatacttctt ttttgttcta caaaaatgca tcccgagagc gctatttttc    3960
taacaaagca tcttagatta cttttttttct cctttgtgcg ctctataatg cagtctcttg    4020 ataactttt gcactgtagg tccgttaagg ttagaagaag gctactttgg tgtctatttt    4080
ctcttccata aaaaaagcct gactccactt cccgcgttta ctgattacta gcgaagctgc    4140
gggtgcattt tttcaagata aaggcatccc cgattatatt ctataccgat gtggattgcg    4200
catactttgt gaacagaaag tgatagcgtt gatgattctt cattggtcag aaaattatga    4260
acggtttctt ctattttgtc tctatatact acgtatagga aatgtttaca ttttcgtatt    4320
gttttcgatt cactctatga atagttctta ctacaatttt tttgtctaaa gagtaatact    4380
agagataaac ataaaaaatg tagaggtcga gtttagatgc aagttcaagg agcgaaaggt    4440
```

| | | | | |
|---|---|---|---|---|
| ggatgggtag | gttatatagg | gatatagcac | agagatatat | agcaaagaga tactttgag | 4500 |
| caatgtttgt | ggaagcggta | ttcgcaatat | tttagtagct | cgttacagtc cggtgcgttt | 4560 |
| ttggttttt | gaaagtgcgt | cttcagagcg | cttttggttt | tcaaaagcgc tctgaagttc | 4620 |
| ctatactttc | tagagaatag | gaacttcgga | ataggaactt | caaagcgttt ccgaaaacga | 4680 |
| gcgcttccga | aaatgcaacg | cgagctgcgc | acatacagct | cactgttcac gtcgcaccta | 4740 |
| tatctgcgtg | ttgcctgtat | atatatatac | atgagaagaa | cggcatagtg cgtgtttatg | 4800 |
| cttaaatgcg | tacttatatg | cgtctatta | tgtaggatga | aaggtagtct agtacctcct | 4860 |
| gtgatattat | cccattccat | gcggggtatc | gtatgcttcc | ttcagcacta cccttagct | 4920 |
| gttctatatg | ctgccactcc | tcaattggat | tagtctcatc | cttcaatgct atcatttcct | 4980 |
| ttgatattgg | atcatggtag | acaaccctta | atataacttc | gtataatgta tgctatacga | 5040 |
| agttattagg | tctagagatc | tgtttagctt | gcctcgtccc | cgccgggtca cccggccagc | 5100 |
| gacatggagg | cccagaatac | cctccttgac | agtcttgacg | tgcgcagctc agggcatga | 5160 |
| tgtgactgtc | gcccgtacat | ttagcccata | catcccatg | tataatcatt tgcatccata | 5220 |
| cattttgatg | gccgcacggc | gcgaagcaaa | aattacggct | cctcgctgca gacctgcgag | 5280 |
| cagggaaacg | ctccctcac | agacgcgttg | aattgtcccc | acgccgcgcc cctgtagaga | 5340 |
| aatataaaag | gttaggattt | gccactgagg | ttcttctttc | atatacttcc tttaaaatc | 5400 |
| ttgctaggat | acagttctca | catcacatcc | gaacataaac | aaccatgggt atgaccgacc | 5460 |
| aagcgacgcc | caacctgcca | tcacgagatt | tcgatcccac | cgccgccttc tatgaaaggt | 5520 |
| tgggcttcgg | aatcgttttc | cgggacgccg | gctggatgat | cctccagcgc ggggatctca | 5580 |
| tgctggagtt | cttcgcccac | cccgggctcg | atccctcgc | gagttggttc agctgctgcc | 5640 |
| tgaggctgga | cgacctcgcg | gagttctacc | ggcagtgcaa | atccgtcggc atccaggaaa | 5700 |
| ccagcagcgg | ctatccgcgc | atccatgccc | ccgaactgca | ggagtgggga ggcacgatgg | 5760 |
| ccgctttggt | cgacccggac | gggacgctcc | tgcgcctgat | acagaacgaa ttgcttgcag | 5820 |
| gcatctcatg | atcagtactg | acaataaaaa | gattcttgtt | ttcaagaact tgtcatttgt | 5880 |
| atagttttt | tatattgtag | ttgttctatt | ttaatcaaat | gttagcgtga tttatatttt | 5940 |
| ttttcgcctc | gacatcatct | gcccagatgc | gaagttaagt | gcgcagaaag taatatcatg | 6000 |
| cgtcaatcgt | atgtgaatgc | tggtcgctat | actgctgtcg | attcgatact aacgccgcca | 6060 |
| tccagtgtcg | aaaacgagct | ctcgagaacc | cttaatataa | cttcgtataa tgtatgctat | 6120 |
| acgaagttat | taggtgatat | cagatccact | a | | 6151 |

<210> SEQ ID NO 87
<211> LENGTH: 6861
<212> TYPE: DNA
<213> ORGANISM: Artificial Sequence
<220> FEATURE:
<223> OTHER INFORMATION: Plasmid pBIS-GALkFLP-URA3

<400> SEQUENCE: 87

| | | | | |
|---|---|---|---|---|
| tcgcgcgttt | cggtgatgac | ggtgaaaacc | tctgacacat | gcagctcccg gagacggtca | 60 |
| cagcttgtct | gtaagcggat | gccggagca | gacaagcccg | tcaggcgcg tcagcgggtg | 120 |
| ttggcgggtg | tcgggctgg | cttaactatg | cggcatcaga | gcagattgta ctgagagtgc | 180 |
| accataccac | agcttttcaa | ttcaattcat | cattttttt | ttattctttt ttttgatttc | 240 |
| ggtttctttg | aaatttttt | gattcggtaa | tctccgaaca | gaaggaagaa cgaaggaagg | 300 |
| agcacagact | tagattggta | tatatacgca | tatgtagtgt | tgaagaaaca tgaaattgcc | 360 |

-continued

```
cagtattctt aacccaactg cacagaacaa aaacctgcag gaaacgaaga taaatcatgt    420
cgaaagctac atataaggaa cgtgctgcta ctcatcctag tcctgttgct gccaagctat    480
ttaatatcat gcacgaaaag caaacaaact tgtgtgcttc attggatgtt cgtaccacca    540
aggaattact ggagttagtt gaagcattag gtcccaaaat ttgtttacta aaacacatg     600 tggatatctt gactgatttt tccatggagg gcacagttaa gccgctaaag gcattatccg    660
ccaagtacaa tttttactc ttcgaagaca gaaaatttgc tgacattggt aatacagtca    720
aattgcagta ctctgcgggt gtatacagaa tagcagaatg ggcagacatt acgaatgcac    780
acggtgtggt gggcccaggt attgttagcg gtttgaagca ggcggcagaa gaagtaacaa    840
aggaacctag aggccttttg atgttagcag aattgtcatg caagggctcc ctatctactg    900
gagaatatac taagggtact gttgacattg cgaagagcga caaagatttt gttatcggct    960
ttattgctca agagacatgg ggtggaagag atgaaggtta cgattggttg attatgacac    1020
ccggtgtggg tttagatgac aagggagacg cattgggtca acagtataga accgtggatg    1080
atgtggtctc tacaggatct gacattatta ttgttggaag aggactatt gcaaagggaa     1140 gggatgctaa ggtagagggt gaacgttaca gaaaagcagg ctgggaagca tatttgagaa    1200
gatgcggcca gcaaaactaa aaaactgtat tataagtaaa tgcatgtata ctaaactcac    1260
aaattagagc ttcaatttaa ttatatcagt tattaccta tgcggtgtga aataccgcac      1320
agatgcgtaa ggagaaaata ccgcatcagg aaattgtaaa cgttaatatt ttgttaaaat    1380
tcgcgttaaa ttttttgttaa atcagctcat tttttaacca ataggccgaa atcggcaaaa   1440
tcccttataa atcaaaagaa tagaccgaga tagggttgag tgttgttcca gtttggaaca    1500
agagtccact attaaagaac gtggactcca acgtcaaagg gcgaaaaacc gtctatcagg    1560
gcgatggccc actacgtgaa ccatcaccct aatcaagttt tttggggtcg aggtgccgta    1620
aagcactaaa tcggaacccct aaagggagcc cccgatttag agcttgacgg ggaaagccgg    1680
cgaacgtggc gagaaaggaa gggaagaaag cgaaaggagc gggcgctagg gcgctggcaa    1740 gtgtagcgt cacgctgcgc gtaaccacca cacccgccgc gcttaatgcg ccgctacagg      1800
gcgcgtcgcg ccattcgcca ttcaggctgc gcaactgttg ggaagggcga tcggtgcggg    1860
cctcttcgct attacgccag ctggcgaaag ggggatgtgc tgcaaggcga ttaagttggg    1920
taacgccagg gttttcccag tcacgacgtt gtaaaacgac ggccagtgag cgcgcgtaat    1980
acgactcact ataggggcgaa ttgggtaccg ggccccccct cgaggtcgac ggtatcgata    2040
agcttgatat cgaattcctg cagcccgggg gatccaaaaa tcatcgcttc gctgattaat    2100
taccccagaa ataaggctaa aaaactaatc gcattatcat cctatggttg ttaatttgat    2160
tcgttcattt gaaggtttgt ggggccaggt tactgccaat ttttcctctt cataaccata    2220
aaagctagta ttgtagaatc tttattgttc ggagcagtgc ggcgcgaggc acatctgcgt    2280
ttcaggaacg cgaccggtga agacgaggac gcacggagga gagtcttcct tcggagggct    2340
gtcacccgct cggcggcttc taatccgtac ttcaatatag caatgagcag ttaagcgtat    2400
tactgaaagt tccaaagaga aggttttttt aggctaagat aatggggctc tttacatttc    2460
cacaacatat aagtaagatt agatatggat atgtatatgg atatgtatat ggtggtaatg    2520
ccatgtaata tgattattaa acttctttgc gtccatccaa aaaaaagta agaattttg      2580 ggtcgacatg ccacaatttg gtatattatg taaaacacca cctaaggtgc ttgttcgtca    2640
gtttgtggaa aggtttgaaa gaccttcagg tgagaaaata gcattatgtg ctgctgaact    2700
```

```
aacctattta tgttggatga ttacacataa cggaacagca atcaagagag ccacattcat    2760
gagctataat actatcataa gcaattcgct gagtttcgat attgtcaata aatcactcca    2820
gtttaaatac aagacgcaaa aagcaacaat tctggaagcc tcattaaaga aattgattcc    2880
tgcttgggaa tttacaatta ttccttacta tggacaaaaa catcaatctg atatcactga    2940
tattgtaagt agtttgcaat tacagttcga atcatcggaa gaagcagata agggaaatag    3000
ccacagtaaa aaaatgctta aagcacttct aagtgagggt gaaagcatct gggagatcac    3060
tgagaaaata ctaaattcgt ttgagtatac ttcgagattt acaaaaacaa aaactttata    3120
ccaattcctc ttcctagcta ctttcatcaa ttgtggaaga ttcagcgata ttaagaacgt    3180
tgatccgaaa tcatttaaat tagtccaaaa taagtatctg ggagtaataa tccagtgttt    3240
agtgacagag acaaagacaa gcgttagtag gcacatatac ttctttagcg caaggggtag    3300
gatcgatcca cttgtatatt tggatgaatt tttgaggaat tctgaaccag tcctaaaacg    3360
agtaaatagg accggcaatt cttcaagcaa taaacaggaa taccaattat taaaagataa    3420
cttagtcaga tcgtacaata aagctttgaa gaaaaatgcg ccttattcaa tctttgctat    3480
aaaaaatggc ccaaaatctc tcattggaag acatttgatg acctcatttc tttcaatgaa    3540
gggcctaacg gagttgacta atgttgtggg aaattggagc gataagcgtg cttctgccgt    3600
ggccaggaca acgtatactc atcagataac agcaatacct gatcactact tcgcactagt    3660
ttctcggtac tatgcatatg atccaatatc aaaggaaatg atagcattga aggatgagac    3720
taatccaatt gaggagtggc agcatataga acagctaaag ggtagtgctg aaggaagcat    3780
acgataccccc gcatggaatg ggataatatc acggaggta ctagactacc tttcatccta    3840
cataaataga cgcatataag tacgcattta agcataaaca cgcactatgc cgttcttctc    3900
atgtatatat atatacaggc aacacgcaga tataggtgcg acgtgaacag tgagctgtat    3960
gtgcgcagct cgcgttgcat tttcggaagc gctcgttttc ggaaacgctt tgaagttcct    4020
attccgaagt tcctattctc tagttctaga gcggccgcca ccgcggtgga gctccagctt    4080
ttgttccctt tagtgagggt taattgcgcg cttggcgtaa tcatggtcat agctgtttcc    4140
tgtgtgaaat tgttatccgc tcacaattcc acacaacata ggagccggaa gcataaagtg    4200
taaagcctgg ggtgcctaat gagtgaggta actcacatta attgcgttgc gctcactgcc    4260
cgctttccag tcgggaaacc tgtcgtgcca gctgcattaa tgaatcggcc aacgcgcggg    4320
gagaggcggt ttgcgtattg ggcgctcttc cgcttcctcg ctcactgact cgctgcgctc    4380
ggtcgttcgg ctgcggcgag cggtatcagc tcactcaaag gcggtaatac ggttatccac    4440
agaatcaggg gataacgcag gaaagaacat gtgagcaaaa ggccagcaaa aggccaggaa    4500
ccgtaaaaag gccgcgttgc tggcgttttt ccataggctc cgcccccctg acgagcatca    4560
caaaaatcga cgctcaagtc agaggtggcg aaacccgaca ggactataaa gataccaggc    4620
gtttccccct ggaagctccc tcgtgcgctc tcctgttccg accctgccgc ttaccggata    4680
cctgtccgcc tttctccctt cgggaagcgt ggcgctttct catagctcac gctgtaggta    4740
tctcagttcg gtgtaggtcg ttcgctccaa gctgggctgt gtgcacgaac cccccgttca    4800
gcccgaccgc tgcgccttat ccggtaacta tcgtcttgag tccaacccgg taagacacga    4860
cttatcgcca ctggcagcag ccactggtaa caggattagc agagcgaggt atgtaggcgg    4920
tgctacagag ttcttgaagt ggtggcctaa ctacggctac actagaagga cagtatttgg    4980
tatctgcgct ctgctgaagc cagttacctt cggaaaaaga gttggtagct cttgatccgg    5040
caaacaaacc accgctggta gcggtggttt ttttgtttgc aagcagcaga ttacgcgcag    5100
```

-continued

```
aaaaaaagga tctcaagaag atcctttgat cttttctacg gggtctgacg ctcagtggaa    5160
cgaaaactca cgttaaggga ttttggtcat gagattatca aaaaggatct tcacctagat    5220
ccttttaaat taaaaatgaa gttttaaatc aatctaaagt atatatgagt aaacttggtc    5280
tgacagttac caatgcttaa tcagtgaggc acctatctca gcgatctgtc tatttcgttc    5340
atccatagtt gcctgactcc ccgtcgtgta gataactacg atacgggagg gcttaccatc    5400
tggccccagt gctgcaatga taccgcgaga cccacgctca ccggctccag atttatcagc    5460
aataaaccag ccagccggaa gggccgagcg cagaagtggt cctgcaactt tatccgcctc    5520
catccagtct attaattgtt gccgggaagc tagagtaagt agttcgccag ttaatagttt    5580
gcgcaacgtt gttgccattg ctacaggcat cgtggtgtca cgctcgtcgt ttggtatggc    5640
ttcattcagc tccggttccc aacgatcaag gcgagttaca tgatccccca tgttgtgcaa    5700
aaaagcggtt agctccttcg gtcctccgat cgttgtcaga agtaagttgg ccgcagtgtt    5760
atcactcatg gttatggcag cactgcataa ttctcttact gtcatgccat ccgtaagatg    5820
cttttctgtg actggtgagt actcaaccaa gtcattctga atagtgta tgcggcgacc    5880
gagttgctct tgcccggcgt caatacggga taataccgcg ccacatagca gaactttaaa    5940
agtgctcatc attggaaaac gttcttcggg gcgaaaactc tcaaggatct taccgctgtt    6000
gagatccagt tcgatgtaac ccactcgtgc acccaactga tcttcagcat cttttacttt    6060
caccagcgtt tctgggtgag caaaaacagg aaggcaaaat gccgcaaaaa agggaataag    6120
ggcgacacgg aaatgttgaa tactcatact cttccttttt caatattatt gaagcattta    6180
tcagggttat tgtctcatga gcggatacat atttgaatgt atttagaaaa ataaacaaat    6240
aggggttccg cgcacatttc cccgaaaagt gccacctggg tccttttcat cacgtgctat    6300
aaaaataatt ataatttaaa ttttttaata taaatatata aattaaaaat agaaagtaaa    6360
aaaagaaatt aaagaaaaaa tagttttttgt tttccgaaga tgtaaaagac tctagggggga    6420
tcgccaacaa atactacctt ttatcttgct cttcctgctc tcaggtatta atgccgaatt    6480
gtttcatctt gtctgtgtag aagaccacac acgaaaatcc tgtgatttta cattttactt    6540
atcgttaatc gaatgtatat ctatttaatc tgcttttctt gtctaataaa tatatatgta    6600
aagtacgctt tttgttgaaa ttttttaaac ctttgtttat ttttttttct tcattccgta    6660
actcttctac cttcttttatt tactttctaa aatccaaata caaaacataa aaataaataa    6720
acacagagta aattcccaaa ttattccatc attaaaagat acgaggcgcg tgtaagttac    6780
aggcaagcga tccgtcctaa gaaaccatta ttatcatgac attaacctat aaaaataggc    6840
gtatcacgag gccctttcgt c                                              6861
```

<210> SEQ ID NO 88
<211> LENGTH: 6857
<212> TYPE: DNA
<213> ORGANISM: Artificial Sequence
<220> FEATURE:
<223> OTHER INFORMATION: Plasmid pCEV-URA3-TEF-AT-yABAB-cMyc

<400> SEQUENCE: 88

```
agcttttcaa ttcaattcat cattttttttt ttattctttt ttttgatttc ggtttctttg      60
aaatttttttt gattcggtaa tctccgaaca gaaggaagaa cgaaggaagg agcacagact     120
tagattggta tatatacgca tatgtagtgt tgaagaaaca tgaaattgcc cagtattctt     180
aacccaactg cacagaacaa aaaccagcag gaaacgaaga taaatcatgt cgaaagctac     240
```

```
atataaggaa cgtgctgcta ctcatcctag tcctgttgct gccaagctat ttaatatcat    300
gcacgaaaag caaacaaact tgtgtgcttc attggatgtt cgtaccacca aggaattact    360
ggagttagtt gaagcattag gtcccaaaat ttgtttacta aaaacacatg tggatatctt    420
gactgatttt tccatggagg gcacagttaa gccgctaaag gcattatccg ccaagtacaa    480
ttttttactc ttcgaagata gaaaatttgc tgacattggt aatacagtca aattgcagta    540
ctctgcgggt gtatacagaa tagcagaatg gcagacatt  acgaatgcac acggtgtggt    600
gggcccaggt attgttagcg gtttgaagca ggcggcagaa gaagtaacaa aggaacctag    660
aggccttttg atgttagcag aattgtcatg caagggctcc ctatctactg gagaatatac    720
taagggtact gttgacattg cgaaaagcga caaagatttt gttatcggct ttattgctca    780
aagagacatg ggtggaagag atgaaggtta cgattggttg attatgacac ccggtgtggg    840
tttagatgac aagggagatg cattgggtca acagtataga accgtggatg atgttgtctc    900
tacaggatct gacattatta ttgttggaag aggactattt gcaagggaa gggatgctaa     960 ggtagagggt gaacgttaca gaaaagcagg ctgggaagca tatttgagaa gatgcggcca   1020
gcaaaactaa aaaactgtat tataagtaaa tgcatgtata ctaaactcac aaattagagc   1080
ttcaatttaa ttatatcagt tattaccccg gccgcacaca ccatagcttc aaaatgtttc   1140
tactcctttt ttactcttcc agattttctc ggactccgcg catcgccgta ccacttcaaa   1200
acacccaagc acagcatact aaattcccc  tctttcttcc tctagggtgt cgttaattac   1260
ccgtactaaa ggtttggaaa agaaaaaaga gaccgcctcg tttctttttc ttcgtcgaaa   1320
aaggcaataa aaattttat  cacgtttctt tttcttgaaa attttttttt ttgattttt    1380 tctctttcga tgacctccca ttgatattta agttaataaa cggtcttcaa tttctcaagt   1440
ttcagtttca ttttctttgt tctattacaa cttttttac  ttcttgctca ttagaaagaa   1500
agcatagcaa tctaatctaa gttttaatta caaggatcca tgagatttcc ttcaattttt   1560
actgctgttt tattcgcagc atcctccgca ttagctatgc aagtacaatt ggttgaaacc   1620
ggtggtggtt tagttcaacc aggtggtagt ttgagattat cttgtgctgc atcaggtttt   1680
acattggatt attcttcaat aggttggttc agacaagctc ctggtaaaga aagagaaggt   1740
gtttcttgca tatccagttc tggtgactca actaaatatg ctgactccgt taagggtaga   1800
ttcactactt caagagataa cgctaaaaat acagtctact tgcaaatgaa ctcattaaag   1860
ccagatgaca cagcagtcta ttactgtgcc gcttttagag ccaccatgtg cggtgtattc   1920
ccattgtctc cttacggtaa agatgactgg ggtaaaggta ctttagttac tgtctcatcc   1980
ggtggtggtg gttccggtgg tggtggtagt ggtggtggtg gttctcaagt tcaattagta   2040
gaatccggtg gtggtttagt ccaacctggt ggtagtttaa gattatcctg cgaagcaagt   2100
ggttttacat tagattatta cggtatcggt tggtttagac aaccacctgg taaagaaaga   2160
gaagctgtct cttatatttc cgctagtgca agaactatat tgtacgcaga ttctgtaaag   2220
ggtagattca caatttcaag agacaatgcc aagaacgctg tttatttgca aatgaactct   2280
ttgaagagag aagacaccgc agtttattac tgtgccagaa aagattttc  tgcttcttca   2340 gtcaacagat ggtagcaga  cgattatgat gtttggggta gaggtacaca agtcgccgta   2400
agttctggtg gtggttccgg tggtggtagt ggtggtggtt ctggtggtgg ttcacaattg   2460
caattagtag aaactggtgg tggttttggtt caaccaggtg gttccttgag attaagttgt   2520
gctgcatctg gttttacttt ctctgattac gttatgacat gggtcagaca agctccaggt   2580
aaaggtcctg aatggatcgc tacaattaat accgacggtt ccacaatgag agatgacagt   2640
```

```
accaagggta gattcactat ttcaagagat aacgctaaga acacattgta cttacaaatg    2700
acctctttga aaccagaaga caccgcatta tattactgtg ccagaggtag agtcatatcc    2760
gccagtgcta tcagaggtgc agtaagaggt cctggtactc aagttacagt ctcttcaggt    2820
ggcggcggta gtggcggcgg cggttctggc ggtggtggtt cacaagtcca attggtagaa    2880
tctggtggtg gtttagttca aactggtggt tcattgagat tatcctgcgc ttccagtggt    2940
tccattgcag gtttcgaaac tgttacatgg tcaagacaag ctccaggtaa atctttgcaa    3000
tgggtcgcct caatgaccaa gactaacaac gaaatctatt ctgattcagt taagggtaga    3060
ttcattattt caagagataa tgctaaaaac accgtttatt tgcaaatgaa ctcattgaag    3120
ccagaagata ctggtgttta cttctgcaag ggtcctgaat taagaggtca aggtattcaa    3180
gtaacagttt cttcagtcga catggaacag aagttgattt ccgaagaaga cctcgagtaa    3240
gcttggtacc gcggctagct aagatccgct ctaaccgaaa aggaaggagt tagacaacct    3300
gaagtctagg tccctatttt atttttttata gttatgttag tattaagaac gttatttata    3360
tttcaaattt ttcttttttt tctgtacaga cgcgtgtacg catgtaacat tatactgaaa    3420
accttgcttg agaaggtttt gggacgctcg aagatccagc tgcattaatg aatcggccaa    3480
cgcgcgggga gaggcggttt gcgtattggg cgctcttccg cttcctcgct cactgactcg    3540
ctgcgctcgg tcgttcggct gcggcgagcg gtatcagctc actcaaaggc ggtaatacgg    3600
ttatccacag aatcagggga taacgcagga aagaacatgt gagcaaaagg ccagcaaaag    3660
gccaggaacc gtaaaaaggc cgcgttgctg gcgtttttcc ataggctccg ccccctgac    3720 gagcatcaca aaaatcgacg ctcaagtcag aggtggcgaa acccgacagg actataaaga    3780
taccaggcgt ttccccctgg aagctccctc gtgcgctctc ctgttccgac cctgccgctt    3840
accggatacc tgtccgcctt tctcccttcg ggaagcgtgg cgctttctca tagctcacgc    3900
tgtaggtatc tcagttcggt gtaggtcgtt cgctccaagc tgggctgtgt gcacgaaccc    3960
cccgttcagc ccgaccgctg cgccttatcc ggtaactatc gtcttgagtc aacccggta    4020 agacacgact tatcgccact ggcagcagcc actggtaaca ggattagcag agcgaggtat    4080
gtaggcggtg ctacagagtt cttgaagtgg tggcctaact acggctacac tagaaggaca    4140
gtatttggta tctgcgctct gctgaagcca gttaccttcg gaaaaagagt tggtagctct    4200
tgatccggca aacaaaccac cgctggtagc ggtggttttt ttgtttgcaa gcagcagatt    4260
acgcgcagaa aaaaggatc tcaagaagat cctttgatct tttctacggg gtctgacgct    4320
cagtggaacg aaaactcacg ttaagggatt ttggtcatga gattatcaaa aaggatcttc    4380
acctagatcc ttttaaatta aaaatgaagt tttaaatcaa tctaaagtat atatgagtaa    4440
acttggtctg acagttacca atgcttaatc agtgaggcac ctatctcagc gatctgtcta    4500
tttcgttcat ccatagttgc ctgactcccc gtcgtgtaga taactacgat acgggagggc    4560
ttaccatctg gccccagtgc tgcaatgata ccgcgagacc cacgctcacc ggctccagat    4620
ttatcagcaa taaaccagcc agccggaagg gccgagcgca gaagtggtcc tgcaacttta    4680
tccgcctcca tccagtctat taattgttgc cgggaagcta gagtaagtag ttcgccagtt    4740
aatagtttgc gcaacgttgt tgccattgct acaggcatcg tggtgtcacg ctcgtcgttt    4800
ggtatggctt cattcagctc cggttcccaa cgatcaaggc gagttacatg atcccccatg    4860
ttgtgcaaaa aagcggttag ctccttcggt cctccgatcg ttgtcagaag taagttggcc    4920
gcagtgttat cactcatggt tatggcagca ctgcataatt ctcttactgt catgccatcc    4980
```

| | |
|---|---|
| gtaagatgct tttctgtgac tggtgagtac tcaaccaagt cattctgaga atagtgtatg | 5040 |
| cggcgaccga gttgctcttg cccggcgtca atacgggata ataccgcgcc acatagcaga | 5100 |
| actttaaaag tgctcatcat tggaaaacgt tcttcggggc gaaaactctc aaggatctta | 5160 |
| ccgctgttga gatccagttc gatgtaaccc actcgtgcac ccaactgatc ttcagcatct | 5220 |
| tttactttca ccagcgtttc tgggtgagca aaaacaggaa ggcaaaatgc cgcaaaaaag | 5280 |
| ggaataaggg cgacacggaa atgttgaata ctcatactct tcctttttca atattattga | 5340 |
| agcatttatc agggttattg tctcatgagc ggatacatat ttgaatgtat ttagaaaaat | 5400 |
| aaacaaatag gggttccgcg cacatttccc cgaaaagtgc cacctgaacg aagcatctgt | 5460 |
| gcttcatttt gtagaacaaa aatgcaacgc gagagcgcta attttttcaaa caagaatct | 5520 |
| gagctgcatt tttacagaac agaaatgcaa cgcgaaagcg ctattttacc aacgaagaat | 5580 |
| ctgtgcttca ttttttgtaaa acaaaaatgc aacgcgagag cgctaatttt tcaaacaaag | 5640 |
| aatctgagct gcattttta c agaacagaaa tgcaacgcga gagcgctatt ttaccaacaa | 5700 |
| agaatctata cttcttttt t gttctacaaa atgcatccc g agagcgcta tttttctaac | 5760 |
| aaagcatctt agattacttt ttttctcctt tgtgcgctct ataatgcagt ctcttgataa | 5820 |
| cttttttgcac tgtaggtccg ttaaggttag aagaaggcta ctttggtgtc tattttctct | 5880 |
| tccataaaaa aagcctgact ccacttcccg cgtttactga ttactagcga agctgcgggt | 5940 |
| gcatttttc aagataaagg catccccgat tatattctat accgatgtgg attgcgcata | 6000 |
| ctttgtgaac agaaagtgat agcgttgatg attcttcatt ggtcagaaaa ttatgaacgg | 6060 |
| tttcttctat tttgtctcta tatactacgt ataggaaatg tttacatttt cgtattgttt | 6120 |
| tcgattcact ctatgaatag ttcttactac aattttttg tctaaagagt aatactagag | 6180 |
| ataaacataa aaaatgtaga ggtcgagttt agatgcaagt tcaaggagcg aaaggtggat | 6240 |
| gggtaggtta tatagggata tagcacagag atatatagca aagagatact tttgagcaat | 6300 |
| gtttgtggaa gcggtattcg caatattta gtagctcgtt acagtccggt gcgtttttgg | 6360 |
| ttttttgaaa gtgcgtcttc agagcgcttt tggttttcaa aagcgctctg aagttcctat | 6420 |
| actttctaga gaataggaac ttcggaatag gaacttcaaa gcgtttccga aaacgagcgc | 6480 |
| ttccgaaaat gcaacgcgag ctgcgcacat acagctcact gttcacgtcg cacctatatc | 6540 |
| tgcgtgttgc ctgtatatat atatacatga gaagaacggc atagtgcgtg tttatgctta | 6600 |
| aatgcgtact tatatgcgtc tatttatgta ggatgaaagg tagtctagta cctcctgtga | 6660 |
| tattatccca ttccatgcgg ggtatcgtat gcttccttca gcactaccct ttagctgttc | 6720 |
| tatatgctgc cactcctcaa ttggattagt ctcatccttc aatgctatca tttcctttga | 6780 |
| tattggatca tggtagacaa cccttaatat aacttcgtat aatgtatgct atacgaagtt | 6840 |
| attaggtcta gagatct | 6857 |

<210> SEQ ID NO 89
<211> LENGTH: 5199
<212> TYPE: DNA
<213> ORGANISM: Artificial Sequence
<220> FEATURE:
<223> OTHER INFORMATION: Plasmid pCEV-URA3-TEF-cMyc
<400> SEQUENCE: 89

| | |
|---|---|
| agcttttcaa ttcaattcat catttttttt ttattctttt ttttgatttc ggtttctttg | 60 |
| aaatttttt gattcggtaa tctccgaaca gaaggaagaa cgaaggaagg agcacagact | 120 |
| tagattggta tatatacgca tatgtagtgt tgaagaaaca tgaaattgcc cagtattctt | 180 |

```
aacccaactg cacagaacaa aaaccagcag gaaacgaaga taaatcatgt cgaaagctac      240
atataaggaa cgtgctgcta ctcatcctag tcctgttgct gccaagctat ttaatatcat      300
gcacgaaaag caaacaaact tgtgtgcttc attggatgtt cgtaccacca aggaattact      360
ggagttagtt gaagcattag gtcccaaaat ttgtttacta aaaacacatg tggatatctt      420
gactgatttt tccatggagg gcacagttaa gccgctaaag gcattatccg ccaagtacaa      480 tttttactc ttcgaagata gaaaatttgc tgacattggt aatacagtca aattgcagta       540
ctctgcgggt gtatacagaa tagcagaatg ggcagacatt acgaatgcac acggtgtggt      600
gggcccaggt attgttagcg gtttgaagca ggcggcagaa gaagtaacaa aggaacctag      660 aggcctttg atgttagcag aattgtcatg caagggctcc ctatctactg gagaatatac       720
taagggtact gttgacattg cgaaaagcga caaagatttt gttatcggct ttattgctca      780
aagagacatg ggtggaagag atgaaggtta cgattggttg attatgacac ccggtgtggg      840
tttagatgac aagggagatg cattgggtca acagtataga accgtggatg atgttgtctc      900
tacaggatct gacattatta ttgttggaag aggactattt gcaaagggaa gggatgctaa      960
ggtagagggt gaacgttaca gaaaagcagg ctgggaagca tatttgagaa gatgcggcca     1020
gcaaaactaa aaaactgtat tataagtaaa tgcatgtata ctaaactcac aaattagagc     1080
ttcaatttaa ttatatcagt tattaccccg gccgcacaca ccatagcttc aaaatgtttc     1140
tactcctttt ttactcttcc agattttctc ggactccgcg catcgccgta ccacttcaaa     1200
acacccaagc acagcatact aaatttcccc tcttctcttcc tctagggtgt cgttaattac     1260
ccgtactaaa ggtttggaaa agaaaaaaga gaccgcctcg tttcttttc ttcgtcgaaa       1320 aaggcaataa aaattttat cacgtttctt tttcttgaaa attttttttt ttgatttttt       1380
tctctttcga tgacctccca ttgatatta agttaataaa cggtcttcaa tttctcaagt      1440
ttcagtttca tttttcttgt tctattacaa cttttttac ttcttgctca ttagaaagaa       1500
agcatagcaa tctaatctaa gttttaatta caaggatctc gacatggaac agaagttgat     1560
ttccgaagaa gacctcgagt aagcttggta ccgcggctag ctaagatccg ctctaaccga     1620
aaaggaagga gttagacaac ctgaagtcta ggtccctatt tattttttta tagttatgtt     1680
agtattaaga acgttattta tatttcaaat ttttctttt tttctgtaca gacgcgtgta      1740
cgcatgtaac attatactga aaaccttgct tgagaaggtt ttgggacgct cgaagatcca     1800
gctgcattaa tgaatcggcc aacgcgcggg gagaggcggt ttgcgtattg ggcgctcttc     1860
cgcttcctcg ctcactgact cgctgcgctc ggtcgttcgg ctgcggcgag cggtatcagc     1920
tcactcaaag gcggtaatac ggttatccac agaatcaggg gataacgcag gaaagaacat     1980
gtgagcaaaa ggccagcaaa aggccaggaa ccgtaaaaag gccgcgttgc tggcgttttt     2040
ccataggctc cgcccccctg acgagcatca caaaaatcga cgctcaagtc agaggtggcg     2100
aaacccgaca ggactataaa gataccaggc gtttccccct ggaagctccc tcgtgcgctc     2160
tcctgttccg accctgccgc ttaccggata cctgtccgcc tttctccctt cgggaagcgt     2220
ggcgctttct catagctcac gctgtaggta tctcagttcg gtgtaggtcg ttcgctccaa     2280
gctgggctgt gtgcacgaac cccccgttca gcccgaccgc tgcgccttat ccggtaacta     2340
tcgtcttgag tccaacccgg taagacacga cttatcgcca ctggcagcag ccactggtaa     2400
caggattagc agagcgaggt atgtaggcgg tgctacagag ttcttgaagt ggtggcctaa     2460
ctacggctac actagaagga cagtatttgg tatctgcgct ctgctgaagc cagttacctt     2520
```

```
cggaaaaaga gttggtagct cttgatccgg caaacaaacc accgctggta gcggtggttt    2580
ttttgtttgc aagcagcaga ttacgcgcag aaaaaaagga tctcaagaag atcctttgat    2640
cttttctacg gggtctgacg ctcagtggaa cgaaaactca cgttaaggga ttttggtcat    2700
gagattatca aaaggatctt caccctagat ccttttaaat taaaaatgaa gttttaaatc    2760
aatctaaagt atatatgagt aaacttggtc tgacagttac caatgcttaa tcagtgaggc    2820
acctatctca gcgatctgtc tatttcgttc atccatagtt gcctgactcc ccgtcgtgta    2880
gataactacg atacgggagg gcttaccatc tggccccagt gctgcaatga taccgcgaga    2940
cccacgctca ccggctccag atttatcagc aataaaccag ccagccggaa gggccgagcg    3000
cagaagtggt cctgcaactt tatccgcctc catccagtct attaattgtt gccgggaagc    3060
tagagtaagt agttcgccag ttaatagttt gcgcaacgtt gttgccattg ctacaggcat    3120
cgtggtgtca cgctcgtcgt ttggtatggc ttcattcagc tccggttccc aacgatcaag    3180
gcgagttaca tgatccccca tgttgtgcaa aaaagcggtt agctccttcg gtcctccgat    3240
cgttgtcaga agtaagttgg ccgcagtgtt atcactcatg gttatggcag cactgcataa    3300
ttctcttact gtcatgccat ccgtaagatg cttttctgtg actggtgagt actcaaccaa    3360
gtcattctga atagtgtata gcggcgacc gagttgctct tgcccggcgt caatacggga    3420
taataccgcg ccacatagca gaactttaaa agtgctcatc attggaaaac gttcttcggg    3480
gcgaaaactc tcaaggatct taccgctgtt gagatccagt tcgatgtaac ccactcgtgc    3540
acccaactga tcttcagcat cttttacttt caccagcgtt tctgggtgag caaaaacagg    3600
aaggcaaaat gccgcaaaaa agggaataag ggcgacacgg aaatgttgaa tactcatact    3660
cttcctttt caatattatt gaagcattta tcagggttat tgtctcatga gcggatacat    3720
atttgaatgt atttagaaaa ataaacaaat aggggttccg cgcacatttc cccgaaaagt    3780
gccacctgaa cgaagcatct gtgcttcatt ttgtagaaca aaaatgcaac gcgagagcgc    3840
taattttca acaaagaat ctgagctgca ttttacaga acagaaatgc aacgcgaaag    3900
cgctatttta ccaacgaaga atctgtgctt cattttgta aaacaaaaat gcaacgcgag    3960
agcgctaatt tttcaaacaa agaatctgag ctgcatttt acagaacaga aatgcaacgc    4020
gagagcgcta ttttaccaac aaagaatcta acttcttttt tgttctaca aaaatgcatc    4080
ccgagagcgc tatttttcta caaagcatc ttagattact ttttttctcc tttgtgcgct    4140
ctataatgca gtctcttgat aacttttgc actgtaggtc cgttaaggtt agaagaaggc    4200
tactttggtg tctatttct cttccataaa aaaagcctga ctccacttcc cgcgtttact    4260
gattactagc gaagctgcgg gtgcatttt tcaagataaa ggcatccccg attatattct    4320
ataccgatgt ggattgcgca ctttgtga acagaaagtg atagcgttga tgattcttca    4380
ttggtcagaa aattatgaac ggtttcttct attttgtctc tatatactac gtataggaaa    4440
tgtttacatt ttcgtattgt tttcgattca ctctatgaat agttcttact acaattttt    4500
tgtctaaaga gtaatactag agataaacat aaaaaatgta gaggtcgagt ttagatgcaa    4560
gttcaaggag cgaaaggtgg atgggtaggt tatataggga tatagcacag agatatatag    4620
caaagagata cttttgagca atgtttgtgg aagcggtatt cgcaatattt tagtagctcg    4680
ttacagtccg gtgcgttttt ggttttttga aagtgcgtct tcagagcgct tttggttttc    4740
aaaagcgctc tgaagttcct atactttcta gagaatagga acttcggaat aggaacttca    4800
aagcgtttcc gaaaacgagc gcttccgaaa atgcaacgcg agctgcgcac atacagctca    4860
ctgttcacgt cgcacctata tctgcgtgtt gcctgtatat atatatacat gagaagaacg    4920
```

```
gcatagtgcg tgtttatgct taaatgcgta cttatatgcg tctatttatg taggatgaaa    4980
ggtagtctag tacctcctgt gatattatcc cattccatgc ggggtatcgt atgcttcctt    5040
cagcactacc ctttagctgt tctatatgct gccactcctc aattggatta gtctcatcct    5100
tcaatgctat catttccttt gatattggat catggtagac aacccttaat ataacttcgt    5160
ataatgtatg ctatacgaag ttattaggtc tagagatct                          5199
```

<210> SEQ ID NO 90
<211> LENGTH: 7208
<212> TYPE: DNA
<213> ORGANISM: Artificial Sequence
<220> FEATURE:
<223> OTHER INFORMATION: Plasmid pCEV-G4-Km-TEF-AT-yABAB hAA6T83N-
tagless

<400> SEQUENCE: 90

```
cacacaccat agcttcaaaa tgtttctact ccttttttac tcttccagat tttctcggac      60
tccgcgcatc gccgtaccac ttcaaaacac ccaagcacag catactaaat ttcccctctt     120
tcttcctcta gggtgtcgtt aattacccgt actaaaggtt tggaaaagaa aaagagacc     180 gcctcgtttc ttttcttcg tcgaaaaagg caataaaaat ttttatcacg tttctttttc     240
ttgaaaattt ttttttttga tttttttctc tttcgatgac ctcccattga tatttaagtt     300
aataaacggt cttcaatttc tcaagtttca gtttcatttt tcttgttcta ttacaacttt     360
ttttacttct tgctcattag aaagaaagca tagcaatcta atctaagttt taattacaag     420
gatccatgag atttccttca attttttactg ctgttttatt cgcagcatcc tccgcattag     480
ctatgcaagt acaattggtt gaaaccggtg gtggtttagt tcaaccaggt ggtagtttga     540
gattatcttg tgctgcatca ggtttttacat tggattattc ttcaataggt tggttcagac     600
aagctcctgg taaagaaaga gaaggtgttt cttgcatatc cagttctggt gactcaacta     660
aatatgctga ctccgttaag ggtagattca ctacttcaag agataacgct aaaaatacag     720
tctacttgca aatgaactca ttaaagccag atgacacagc agtctattac tgtgccgctt     780
ttagagccac catgtgcggt gtattcccat tgtctcctta cggtaaagat gactggggta     840
aaggtacttt agttactgtc tcatccggtg gtggggttc cggtggtggt ggtagtggtg     900
gtggtggttc tcaagttcaa ttagtagaat ccggtggtgg tttagtccaa cctggtggta     960
gtttaagatt atcctgcgaa gcaagtggtt ttacattaga ttattacggt atcggttggt    1020
ttagacaacc acctggtaaa gaaagagaag ctgtctctta tatttccgct agtgcaagaa    1080
ctatattgta cgcagattct gtaaagggta gattcacaat ttcaagagac aatgccaaga    1140
acgctgttta tttgcaaatg aactctttga gagagaagaa caccgcagtt tattactgtg    1200
ccagaagaag attttctgct tcttcagtca acagatggtt agcagacgat tatgatgttt    1260 gggggtagagg tacacaagtc gccgtaagtt ctggtggtgg ttccggtggt ggtagtggtg    1320
gtggttctgg tggtggttca cagctgcagc tggtggagac cggggaggc ttagttcagc    1380 ctgggggtgc cctgagactc tcctgtgcag cctctggatt caccttcagt gactacgtga    1440
tgacctgggt ccgccaagct ccagggaagg ggcctgagtg gatcgcaact attaatactg    1500
atgggagcac aatgcgcgac gactccacaa agggccggtt caccatctcc agagacaacg    1560
ccaagaacac tctgtatctg caaatgaaca gtctgaaacc cgaggacact gctctgtatt    1620
actgtgcaag aggccgggtg atctctgctt ccgctatcag aggcgcagtc agaggccctg    1680
gaacccaggt caccgtctcg agcggtggcg gcggtagtgg cggcggcggt tctggcggtg    1740
```

```
gtggttcaca agtccaattg gtagaatctg gtggtggttt agttcaaact ggtggttcat   1800
tgagattatc ctgcgcttcc agtggttcca ttgcaggttt cgaaactgtt acatggtcaa   1860
gacaagctcc aggtaaatct ttgcaatggg tcgcctcaat gaccaagact aacaacgaaa   1920
tctattctga ttcagttaag ggtagattca ttatttcaag agataatgct aaaaacaccg   1980
tttatttgca aatgaactca ttgaagccag aagatactgg tgtttacttc tgcaagggtc   2040
ctgaattaag aggtcaaggt attcaagtaa cagtttcttc agtcgacgcg gctagctaag   2100
atccgctcta accgaaaagg aaggagttag acaacctgaa gtctaggtcc ctatttattt   2160
ttttatagtt atgttagtat taagaacgtt atttatattt caaattttc ttttttttct    2220
gtacagacgc gtgtacgcat gtaacattat actgaaaacc ttgcttgaga aggttttggg   2280
acgctcgaag atccagctgc attaatgaat cggccaacgc gcggggagag gcggtttgcg   2340
tattgggcgc tcttccgctt cctcgctcac tgactcgctg cgctcggtcg ttcggctgcg   2400
gcgagcggta tcagctcact caaaggcggt aatacggtta ccacagaat caggggataa    2460
cgcaggaaag aacatgtgag caaaaggcca gcaaaaggcc aggaaccgta aaaaggccgc   2520
gttgctggcg ttttccata ggctccgccc ccctgacgag catcacaaaa atcgacgctc     2580
aagtcagagg tggcgaaacc cgacaggact ataaagatac caggcgtttc ccctggaag    2640
ctccctcgtg cgctctcctg ttccgaccct gccgcttacc ggatacctgt ccgcctttct   2700
cccttcggga agcgtggcgc tttctcatag ctcacgctgt aggtatctca gttcggtgta   2760
ggtcgttcgc tccaagctgg gctgtgtgca cgaaccccc gttcagcccg accgctgcgc    2820
cttatccggt aactatcgtc ttgagtccaa cccggtaaga cacgacttat cgccactggc   2880
agcagccact ggtaacagga ttagcagagc gaggtatgta ggcggtgcta cagagttctt   2940
gaagtggtgg cctaactacg gctacactag aaggacagta tttggtatct gcgctctgct   3000
gaagccagtt accttcggaa aaagagttgg tagctcttga tccggcaaac aaaccaccgc   3060
tggtagcggt ggttttttg tttgcaagca gcagattacg cgcagaaaaa aaggatctca    3120
agaagatcct ttgatctttt ctacggggtc tgacgctcag tggaacgaaa actcacgtta   3180
agggattttg gtcatgagat tatcaaaaag gatcttcacc tagatccttt taaattaaaa   3240
atgaagtttt aaatcaatct aaagtatata tgagtaaact tggtctgaca gttaccaatg   3300
cttaatcagt gaggcaccta tctcagcgat ctgtctattt cgttcatcca tagttgcctg   3360
actccccgtc gtgtagataa ctacgatacg ggagggctta ccatctggcc ccagtgctgc   3420
aatgataccg cgagacccac gctcaccggc tccagattta tcagcaataa accagccagc   3480
cggaagggcc gagcgcagaa gtggtcctgc aactttatcc gcctccatcc agtctattaa   3540
ttgttgccgg gaagctagag taagtagttc gccagttaat agtttgcgca acgttgttgc   3600
cattgctaca ggcatcgtgg tgtcacgctc gtcgtttggt atggcttcat tcagctccgg   3660
ttcccaacga tcaaggcgag ttacatgatc ccccatgttg tgcaaaaaag cggttagctc   3720
cttcggtcct ccgatcgttg tcagaagtaa gttggccgca gtgttatcac tcatggttat   3780
ggcagcactg cataattctc ttactgtcat gccatccgta agatgctttt ctgtgactgg   3840
tgagtactca accaagtcat tctgagaata gtgtatgcgg cgaccgagtt gctcttgccc   3900
ggcgtcaata cgggataata ccgcgccaca tagcagaact ttaaaagtgc tcatcattgg   3960
aaaacgttct cggggcgaa aactctcaag gatcttaccg ctgttgagat ccagttcgat    4020
gtaacccact cgtgcaccca actgatcttc agcatctttt actttcacca gcgtttctgg   4080
```

```
gtgagcaaaa acaggaaggc aaaatgccgc aaaaaaggga ataagggcga cacggaaatg   4140
ttgaatactc atactcttcc tttttcaata ttattgaagc atttatcagg gttattgtct   4200
catgagcgga tacatatttg aatgtattta gaaaaataaa caaataggg ttccgcgcac    4260
atttccccga aaagtgccac ctgaacgaag catctgtgct tcattttgta gaacaaaaat   4320
gcaacgcgag agcgctaatt tttcaaacaa agaatctgag ctgcattttt acagaacaga   4380
aatgcaacgc gaaagcgcta ttttaccaac gaagaatctg tgcttcattt ttgtaaaaca   4440
aaaatgcaac gcgagagcgc taattttttca aacaagaat ctgagctgca ttttttacaga  4500
acagaaatgc aacgcgagag cgctatttta ccaacaaaga atctatactt cttttttgtt   4560
ctacaaaaat gcatcccgag agcgctattt ttctaacaaa gcatcttaga ttacttttt    4620
tctcctttgt gcgctctata atgcagtctc ttgataactt tttgcactgt aggtccgtta   4680
aggttagaag aaggctactt tggtgtctat tttctcttcc ataaaaaaag cctgactcca   4740
cttcccgcgt ttactgatta ctagcgaagc tgcgggtgca ttttttcaag ataaaggcat   4800
ccccgattat attctatacc gatgtggatt gcgcatactt tgtgaacaga aagtgatagc   4860
gttgatgatt cttcattggt cagaaaatta tgaacggttt cttctatttt gtctctatat   4920
actacgtata ggaaatgttt acattttcgt attgttttcg attcactcta tgaatagttc   4980
ttactacaat ttttttgtct aaagagtaat actagagata aacataaaaa atgtagaggt   5040
cgagtttaga tgcaagttca aggagcgaaa ggtggatggg taggttatat agggatatag   5100
cacagagata tatagcaaag agatactttt gagcaatgtt tgtggaagcg gtattcgcaa   5160
tattttagta gctcgttaca gtccggtgcg ttttggttt ttgaaagtg cgtcttcaga    5220
gcgcttttgg ttttcaaaag cgctctgaag ttcctatact ttctagagaa taggaacttc   5280
ggaataggaa cttcaaagcg tttccgaaaa cgagcgcttc cgaaaatgca acgcgagctg   5340
cgcacataca gctcactgtt cacgtcgcac ctatatctgc gtgttgcctg tatatatata   5400
tacatgagaa gaacggcata gtgcgtgttt atgcttaaat gcgtacttat atgcgtctat   5460
ttatgtagga tgaaaggtag tctagtacct cctgtgatat tatcccattc catgcgggt    5520
atcgtatgct tccttcagca ctaccctta gctgttctat atgctgccac tcctcaattg    5580
gattagtctc atccttcaat gctatcattt cctttgatat tggatcatgg tagacaaccc   5640
ttaatataac ttcgtataat gtatgctata cgaagttatt aggtctagag atctgtttag   5700
cttgcctcgt ccccgccggg tcacccggcc agcgacatgg aggcccagaa taccctcctt   5760
gacagtcttg acgtgcgcag ctcaggggca tgatgtgact gtcgcccgta catttagccc   5820
atacatcccc atgtataatc atttgcatcc atacattttg atggccgcac ggcgcgaagc   5880
aaaaattacg gctcctcgct gcagacctgc gagcagggaa acgctcccct cacagacgcg   5940
ttgaattgtc cccacgccgc gccctgtag agaaatataa aaggttagga tttgccactg    6000
aggttcttct ttcatatact ccttttaaa atcttgctag gatacagttc tcacatcaca    6060
tccgaacata aacaaccatg ggtaaggaaa agactcacgt ttcgaggccg cgattaaatt   6120
ccaacatgga tgctgattta tatgggtata aatgggctcg cgataatgtc gggcaatcag   6180
gtgcgacaat ctatcgattg tatgggaagc ccgatgcgcc agagttgttt ctgaaacatg   6240
gcaaaggtag cgttgccaat gatgttacag atgagatggt cagactaaac tggctgacgg   6300
aatttatgcc tcttccgacc atcaagcatt ttatccgtac tcctgatgat gcatggttac   6360
tcaccactgc gatccccggc aaaacagcat tccaggtatt agaagaatat cctgattcag   6420
gtgaaaatat tgttgatgcg ctggcagtgt tcctgcgccg gttgcattcg attcctgttt   6480
```

```
gtaattgtcc tttttaacagc gatcgcgtat ttcgtctcgc tcaggcgcaa tcacgaatga    6540
ataacggttt ggttgatgcg agtgattttg atgacgagcg taatggctgg cctgttgaac    6600
aagtctggaa agaaatgcat aagcttttgc cattctcacc ggattcagtc gtcactcatg    6660
gtgatttctc acttgataac cttatttttg acgaggggaa attaataggt tgtattgatg    6720
ttggacgagt cggaatcgca gaccgatacc aggatcttgc catcctatgg aactgcctcg    6780
gtgagttttc tccttcatta cagaaacggc tttttcaaaa atatggtatt gataatcctg    6840
atatgaataa attgcagttt catttgatgc tcgatgagtt tttctaatca gtactgacaa    6900
taaaaagatt cttgttttca agaacttgtc atttgtatag ttttttttata ttgtagttgt    6960 tctattttaa tcaaatgtta gcgtgattta tatttttttt cgcctcgaca tcatctgccc    7020
agatgcgaag ttaagtgcgc agaaagtaat atcatgcgtc aatcgtatgt gaatgctggt    7080
cgctatactg ctgtcgattc gatactaacg ccgccatcca gtgtcgaaaa cgagctctcg    7140 agaacccctta atataacttc gtataatgta tgctatacga agttattagg tgatatcaga    7200
tccactag                                                              7208

<210> SEQ ID NO 91
<211> LENGTH: 10379
<212> TYPE: DNA
<213> ORGANISM: Artificial Sequence
<220> FEATURE:
<223> OTHER INFORMATION: Plasmid pCRI-Sb-delta1

<400> SEQUENCE: 91
tcgcgcgaac ccaactgcac agaacaaaaa cctgcaggaa acgaagataa atcatgtcga      60
aagctacata taaggaacgt gctgctactc atcctagtcc tgttgctgcc aagctattta     120
atatcatgca cgaaaagcaa acaaacttgt gtgcttcatt ggatgttcgt accaccaagg     180
aattactgga gttagttgaa gcattaggtc ccaaaatttg tttactaaaa acacatgtgg     240
atatcttgac tgattttttcc atggagggca cagttaagcc gctaaaggca ttatccgcca     300
agtacaattt tttactcttc gaagacagaa aatttgctga cattggtaat acagtcaaat     360
tgcagtactc tgcgggtgta tacagaatag cagaatgggc agacattacg aatgcacacg     420
gtgtggtggg cccaggtatt gttagcggtt tgaagcaggc ggcagaagaa gtaacaaagg     480
aacctagagg ccttttgatg ttagcagaat tgtcatgcaa gggctcccta tctactggag     540
aatatactaa gggtactgtt gacattgcga gagcgacaa agattttgtt atcggcttta     600
ttgctcaaag agacatgggt ggaagagatg aaggttacga ttggttgatt atgacacccg     660
gtgtgggttt agatgacaag ggagacgcat tgggtcaaca gtatagaacc gtggatgatg     720
tcgtttctac aggatctgac attattattg ttggaagagg actatttgca aagggaaggg     780
atgctaaggt agagggtgaa cgttacagaa aagcaggctg ggaagcatat ttgagaagat     840
gcggccagca aaactaaaaa actgtattat aagtaaatgc atgtatacta aactcacaaa     900
ttagagcttc aatttaatta tatcagttat taccctgtgc tcgagtcttt gaaaagataa     960
tgtatgatta tgctttcact catatttata cagaaacttg atgttttctt tcgagtatat    1020
acaaggtgat tacatgtacg tttgaagtac aactctagat tttgtagtgc cctcttgggc    1080
tagcggtaaa ggtgcgcatt ttttcacacc ctacaatgtt ctgttcaaaa gattttggtc    1140
aaacgctgta gaagtgaaag ttggtgcgca tgtttcggcg ttcgaaactt ctccgcagtg    1200
aaagataaat gatcgggttt tagagctatg ctgtttgaa tggtcccaaa actactagta    1260
```

```
tattatcata tagtttttaga gctatgctgt tttgaatggt cccaaaactt ttttttgtttt     1320
ttatgtctgc atagcttcaa aatgtttcta ctccttttt actcttccag attttctcgg       1380
actccgcgca tcgccgtacc acttcaaaac acccaagcac agcatactaa atttccctc       1440
tttcttcctc tagggtgtcg ttaattaccc gtactaaagg tttggaaaag aaaaaagagg      1500
ccgcctcgtt tcttttcttt cgtcgaaaaa ggcaataaaa atttttatca cgtttctttt     1560
tcttgaaaat tttttttttt gattttttc tctttcgatg acctcccatt gatatttaag      1620
ttaataaacg gtcttcaatt tctcaagttt cagtttcatt tttcttgttc tattacaact     1680
tttttactt cttgctcatt agaaagaaag catagcaatc taatctaagt tttctagatg      1740
gattataaag atgacgatga caaacctcca aaaagaaga gaaggtcga taagaaatac       1800
tcaataggct tagatatcgg cacaaatagc gtcggatggg cggtgatcac tgatgaatat    1860
aaggttccgt ctaaaaagtt caaggttctg ggaaatacag accgccacag tatcaaaaaa   1920
aatcttatag gggctctttt atttgacagt ggagagacag cggaagcgac tcgtctcaaa   1980
cggacagctc gtagaaggta tacacgtcgg aagaatcgta tttgttatct acaggagatt   2040
ttttcaaatg agatggcgaa agtagatgat agtttctttc atcgacttga agagtctttt   2100
ttggtggaag aagacaagaa gcatgaacgt catcctattt ttggaaatat agtagatgaa   2160
gttgcttatc atgagaaata tccaactatc tatcatctgc gaaaaaaatt ggtagattct   2220
acttataaag cggatttgcg cttaatctat ttggccttag cgcatatgat taagtttcgt  2280
ggtcatttttt tgattgaggg agatttaaat cctgataata gtgatgtgga caaactattt   2340
atccagttgg tacaaaccta caatcaatta tttgaagaaa accctattaa cgcaagtgga   2400
gtagatgcta aagcgattct ttctgcacga ttgagtaaat caagacgatt agaaaatctc   2460
attgctcagc tccccggtga agaaaaaat ggcttatttg gaatctcat tgctttgtca     2520
ttgggtttga ccctaatttt aaatcaaat tttgatttgg cagaagatgc taaattacag    2580
cttttcaaaag atacttacga tgatgattta gataattta tggcgcaaat tggagatcaa   2640
tatgctgatt tgttttggc agctaagaat ttatcagatg ctattttact ttcagatatc   2700
ctaagagtaa atactgaaat aactaaggct cccctatcag cttcaatgat taaacgctac   2760
gatgaacatc atcaagactt gactcttta aaagctttag ttcgacaaca acttccagaa    2820
aagtataaag aaatcttttt tgatcaatca aaaaacggat atgcaggtta tattgatggg   2880
ggagctagcc aagaagaatt ttataaattt atcaaaccaa ttttagaaaa aatggatggt  2940
actgaggaat tattggtgaa actaaatcgt gaagatttgc tgcgcaagca acggaccttt    3000
gacaacggct ctattaccca tcaaattcac ttgggtgagc tgcatgctat tttgagaaga  3060
caagaagact tttatccatt tttaaaagac aatcgtgaga agattgaaaa atcttgact    3120
tttcgaattc cttattatgt tggtccattg gcgcgtggca atagtcgttt tgcatggatg  3180
actcggaagt ctgaagaaac aattacccca tggaattttg aagaagttgt cgataaaggt  3240
gcttcagctc aatcatttat tgaacgcatg acaaactttg ataaaaatct tccaaatgaa   3300
aaagtactac caaaacatag tttgctttat gagtatttta cggtttataa cgaattgaca   3360
aaggtcaaat atgttactga aggaatgcga aaaccagcat tctttcagg tgaacagaag   3420
aaagccattg ttgatttact cttcaaaaca aatcgaaaag taaccgttaa gcaattaaaa   3480
gaagattatt tcaaaaaat agaatgtttt gatagtgttg aaattcagg agttgaagat    3540
agatttaatg cttcattagg tacctaccat gatttgctaa aaattattaa agataaagat  3600
ttttggata atgaagaaaa tgaagatatc ttagaggata ttgttttaac attgaccta     3660
```

```
tttgaagata gggagatgat tgaggaaaga cttaaaacat atgctcacct ctttgatgat    3720
aaggtgatga aacagcttaa acgtcgccgt tatactggtt ggggacgttt gtctcgaaaa    3780
ttgattaatg gtattaggga taagcaatct ggcaaaacaa tattagattt tttgaaatca    3840
gatggttttg ccaatcgcaa tttatgcag ctgatccatg atgatagttt gacatttaaa    3900
gaagacattc aaaaagcaca agtgtctgga caaggcgata gtttacatga acatattgca    3960
aatttagctg gtagccctgc tattaaaaaa ggtattttac agactgtaaa agttgttgat    4020
gaattggtca aagtaatggg gcggcataag ccagaaaata tcgttattga aatggcacgt    4080
gaaaatcaga caactcaaaa gggccagaaa aattcgcgag agcgtatgaa acgaatcgaa    4140
gaaggtatca aagaattagg aagtcagatt cttaaagagc atcctgttga aaatactcaa    4200
ttgcaaaatg aaaagctcta tctctattat ctccaaaatg gaagagacat gtatgtggac    4260
caagaattag atattaatcg tttaagtgat tatgatgtcg atcacattgt tccacaaagt    4320
ttccttaaag acgattcaat agacaataag gtcttaacgc gttctgataa aaatcgtggt    4380
aaatcggata acgttccaag tgaagaagta gtcaaaaaga tgaaaaacta ttggagacaa    4440
cttctaaacg ccaagttaat cactcaacgt aagtttgata atttaacgaa agctgaacgt    4500
ggaggtttga gtgaacttga taaagctggt tttatcaaac gccaattggt tgaaactcgc    4560
caaatcacta agcatgtggc acaaattttg gatagtcgca tgaatactaa atacgatgaa    4620
aatgataaac ttattcgaga ggttaaagtg attaccttaa aatctaaatt agtttctgac    4680
ttccgaaaag atttccaatt ctataaagta cgtgagatta caattacca tcatgcccat    4740
gatgcgtatc taaatgccgt cgttggaact gctttgatta agaaatatcc aaaacttgaa    4800
tcggagtttg tctatggtga ttataaagtt tatgatgttc gtaaaatgat tgctaagtct    4860
gagcaagaaa taggcaaagc aaccgcaaaa tatttctttt actctaatat catgaacttc    4920
ttcaaaacag aaattacact tgcaaatgga gagattcgca aacgccctct aatcgaaact    4980
aatggggaaa ctggagaaat tgtctgggat aaagggcgag attttgccac agtgcgcaaa    5040
gtattgtcca tgccccaagt caatattgtc aagaaaacag aagtacagac aggcggattc    5100
tccaaggagt caattttacc aaaaagaaat tcggacaagc ttattgctcg taaaaaagac    5160
tgggatccaa aaaatatgg tggttttgat agtccaacgg tagcttattc agtcctagtg    5220
gttgctaagg tggaaaaagg gaaatcgaag aagttaaaat ccgttaaaga gttactaggg    5280
atcacaatta tggaaagaag ttcctttgaa aaaaatccga ttgactttt agaagctaaa    5340
ggatataagg aagttaaaaa agacttaatc attaaactac ctaaatatag tcttttgag    5400
ttagaaaacg gtcgtaaacg gatgctggct agtgccggag aattacaaaa aggaaatgag    5460
ctggctctgc caagcaaata tgtgaatttt ttatatttag ctagtcatta tgaaaagttg    5520
aagggtagtc cagaagataa cgaacaaaaa caattgtttg tggagcagca taagcattat    5580
ttagatgaga ttattgagca aatcagtgaa ttttctaagc gtgttatttt agcagatgcc    5640
aatttagata aagttcttag tgcatataac aaacatagag acaaaccaat acgtgaacaa    5700
gcagaaaata ttattcattt atttacgttg acgaatcttg gagctcccgc tgcttttaaa    5760
tattttgata caacaattga tcgtaaacga tatacgtcta caaagaagt tttagatgcc    5820
actcttatcc atcaatccat cactggtctt tatgaaacac gcattgattt gagtcagcta    5880
ggaggtgacc ctccaaaaaa gaagagaaag gtctgagcgg atctcttatg tctttacgat    5940
ttatagttt cattatcaag tatgcctata ttagtatata gcatctttag atgacagtgt    6000
```

```
tcgaagtttc acgaataaaa gataatattc tacttttgc tcccaccgcg tttgctagca    6060
cgagtgaaca ccatccctcg cctgtgagtt gtacccattc ctctaaactg tagacatggt    6120
agcttcagca gtgttcgtta tgtacggcat cctccaacaa acagtcggtt atagtttgtc    6180
ctgctcctct gaatcgagtc cctcgatatt tctcatacta gttctagaga tctgccaatt    6240
gaacataaca tggtagttac atatactagt aatatggttc ggcacacatt aaaagtataa    6300
aaactatctg aattacgaat tacatatatt ggtcataaaa atcaatcaat catcgtgtgt    6360
tttatatgtc tcttatctaa gtataagaat atccatagtt aatattcact tacgctacct    6420
tttaacctgt aatcattgtc aacaggatat gttaacgacc cacattgata aacgctagta    6480
tttctttttc ctcttcttat tggccggctg tctctatact cccctatagt ctgtttcttt    6540
tcgtttcgat tgttttacgt ttgaggcctc gtggcgcaca tggtacgctg tggtgctcgc    6600
ggctgggaac gaaactctgg gagctgcgat tggcaggaac cattcaaaac agcatagcaa    6660
gttaaaataa ggctagtccg ttatcaactt gaaaaagtgg caccgagtcg gtgcttttt    6720
tccatatcca acttccaatt taatctttct tttttaattt tcacttattt gcgatacaga    6780
aagaccctgc aggcatgcaa gcttggcgta atcatggtca tagctgtttc ctgtgtgaaa    6840
ttgttatccg ctcacaattc cacacaacat acgagccgga agcataaagt gtaaagcctg    6900
gggtgcctaa tgagtgagct aactcacatt aattgcgttg cgctcactgc ccgctttcca    6960
gtcgggaaac ctgtcgtgcc agctgcatta atgaatcggc caacgcgcgg ggagaggcgg    7020
tttgcgtatt gggcgctctt ccgcttcctc gctcactgac tcgctgcgct cggtcgttcg    7080
gctgcggcga gcggtatcag ctcactcaaa ggcggtaata cggttatcca cagaatcagg    7140
ggataacgca ggaaagaaca tgtgagcaaa aggccagcaa aaggccagga accgtaaaaa    7200
ggccgcgttg ctggcgtttt tccataggct ccgcccccct gacgagcatc acaaaaatcg    7260
acgctcaagt cagaggtggc gaaacccgac aggactataa agataccagg cgtttccccc    7320
tggaagctcc ctcgtgcgct ctcctgttcc gaccctgccg cttaccggat acctgtccgc    7380
ctttctccct tcgggaagcg tggcgctttc tcatagctca cgctgtaggt atctcagttc    7440
ggtgtaggtc gttcgctcca agctgggctg tgtgcacgaa ccccccgttc agcccgaccg    7500
ctgcgcctta tccggtaact atcgtcttga gtccaacccg gtaagacacg acttatcgcc    7560
actggcagca gccactggta acaggattag cagagcgagg tatgtaggcg gtgctacaga    7620
gttcttgaag tggtggccta actacggcta cactagaaga acagtatttg gtatctgcgc    7680
tctgctgaag ccagttacct tcggaaaaag agttggtagc tcttgatccg gcaaacaaac    7740
caccgctggt agcggtggtt tttttgtttg caagcagcag attacgcgca gaaaaaaagg    7800
atctcaagaa gatcctttga tcttttctac ggggtctgac gctcagtgga acgaaaactc    7860
acgttaaggg attttggtca tgagattatc aaaaaggatc ttcacctaga tccttttaaa    7920
ttaaaaatga agttttaaat caatctaaag tatatatgag taaacttggt ctgacagtta    7980
ccaatgctta atcagtgagg cacctatctc agcgatctgt ctatttcgtt catccatagt    8040
tgcctgactc cccgtcgtgt agataactac gatacgggag ggcttaccat ctggccccag    8100
tgctgcaatg ataccgcggc tcccacgctc accggctcca gatttatcag caataaacca    8160
gccagccgga agggccgagc gcagaagtgg tcctgcaact ttatccgcct ccatccagtc    8220
tattaattgt tgccgggaag ctagagtaag tagttcgcca gttaatagtt tgcgcaacgt    8280
tgttgccatt gctacaggca tcgtggtgtc acgctcgtcg tttggtatgg cttcattcag    8340
ctccggttcc caacgatcaa ggcgagttac atgatccccc atgttgtgca aaaaagcggt    8400
```

```
tagctccttc ggtcctccga tcgttgtcag aagtaagttg gccgcagtgt tatcactcat    8460
ggttatggca gcactgcata attctcttac tgtcatgcca tccgtaagat gcttttctgt    8520
gactggtgag tactcaacca agtcattctg agaatagtgt atgcggcgac cgagttgctc    8580
ttgcccggcg tcaatacggg ataataccgc gccacatagc agaactttaa aagtgctcat    8640
cattggaaaa cgttcttcgg ggcgaaaact ctcaaggatc ttaccgctgt tgagatccag    8700
ttcgatgtaa cccactcgtg cacccaactg atcttcagca tcttttactt tcaccagcgt    8760
ttctgggtga gcaaaaacag gaaggcaaaa tgccgcaaaa aagggaataa gggcgacacg    8820
gaaatgttga atactcatac tcttcctttt tcaatattat tgaagcattt atcagggtta    8880
ttgtctcatg agcggataca tatttgaatg tatttagaaa aataaacaaa tagggggttcc    8940 gcgcacattt ccccgaaaag tgccacctga cgaagcatc tgtgcttcat tttgtagaac    9000
aaaaatgcaa cgcgagagcg ctaattttc aaacaaagaa tctgagctgc attttacag     9060 aacagaaatg caacgcgaaa gcgctatttt accaacgaag aatctgtgct tcattttgt    9120 aaaacaaaaa tgcaacgcga gagcgctaat ttttcaaaca agaatctga gctgcatttt   9180 tacagaacag aaatgcaacg cgagagcgct attttaccaa caagaatct atacttcttt    9240 tttgttctac aaaaatgcat cccgagagcg ctattttct aacaaagcat cttagattac    9300 ttttttctc ctttgtgcgc tctataatgc agtctcttga taacttttg cactgtaggt     9360 ccgttaaggt tagaagaagg ctactttggt gtctattttc tcttccataa aaaaagcctg    9420
actccacttc ccgcgtttac tgattactag cgaagctgcg ggtgcatttt ttcaagataa    9480
aggcatcccc gattatattc tataccgatg tggattgcgc atactttgtg aacagaaagt    9540
gatagcgttg atgattcttc attggtcaga aaattatgaa cggtttcttc tatttgtct     9600 ctatatacta cgtataggaa atgtttacat tttcgtattg ttttcgattc actctatgaa    9660
tagttcttac tacaattttt ttgtctaaag agtaatacta gagataaaca taaaaaatgt   9720
agaggtcgag tttagatgca agttcaagga gcgaaaggtg gatgggtagg ttatataggg    9780
atatagcaca gagatatata gcaaagagat acttttgagc aatgtttgtg gaagcggtat    9840
tcgcaatatt ttagtagctc gttacagtcc ggtgcgtttt tggttttttg aaagtgcgtc    9900
ttcagagcgc ttttggtttt caaaagcgct ctgaagttcc tatactttct agagaatagg    9960
aacttcggaa taggaacttc aaagcgtttc cgaaaacgag cgcttccgaa aatgcaacgc   10020
gagctgcgca catacagctc actgttcacg tcgcacctat atctgcgtgt tgcctgtata   10080
tatatacata tgagaagaac ggcatagtgc gtgtttatgc ttaaatgcgt acttatatgc   10140
gtctatttat gtaggatgaa aggtagtcta gtacctcctg tgatattatc ccattccatg   10200
cggggtatcg tatgcttcct tcagcactac cctttagctg ttctatatgc tgccactcct   10260
caattggatt agtctcatcc ttcaatgcta tcatttcctt tgatattgga tcatctaaga   10320
aaccattatt atcatgacat taacctataa aaataggcgt atcacgaggc cctttcgtc    10379
```

<210> SEQ ID NO 92
<211> LENGTH: 10379
<212> TYPE: DNA
<213> ORGANISM: Artificial Sequence
<220> FEATURE:
<223> OTHER INFORMATION: Plasmid pCRI-Sb-delta2

<400> SEQUENCE: 92

```
tcgcgcgaac ccaactgcac agaacaaaaa cctgcaggaa acgaagataa atcatgtcga      60
```

```
aagctacata taaggaacgt gctgctactc atcctagtcc tgttgctgcc aagctattta    120
atatcatgca cgaaaagcaa acaaacttgt gtgcttcatt ggatgttcgt accaccaagg    180
aattactgga gttagttgaa gcattaggtc ccaaaatttg tttactaaaa acacatgtgg    240
atatcttgac tgattttcc atggagggca cagttaagcc gctaaaggca ttatccgcca     300
agtacaattt tttactcttc gaagacagaa aatttgctga cattggtaat acagtcaaat    360
tgcagtactc tgcgggtgta tacagaatag cagaatgggc agacattacg aatgcacacg    420
gtgtggtggg cccaggtatt gttagcggtt tgaagcaggc ggcagaagaa gtaacaaagg    480
aacctagagg cctttgatg ttagcagaat tgtcatgcaa gggctcccta tctactggag      540
aatatactaa gggtactgtt gacattgcga agagcgacaa agattttgtt atcggcttta    600
ttgctcaaag agacatgggt ggaagagatg aaggttacga ttggttgatt atgacacccg    660
gtgtgggttt agatgacaag ggagacgcat tgggtcaaca gtatagaacc gtggatgatg    720
tcgtttctac aggatctgac attattattg ttggaagagg actatttgca aagggaaggg    780
atgctaaggt agagggtgaa cgttacagaa aagcaggctg ggaagcatat ttgagaagat    840
gcggccagca aaactaaaaa actgtattat aagtaaatgc atgtatacta aactcacaaa    900
ttagagcttc aatttaatta tatcagttat taccctgtgc tcgagtcttt gaaaagataa    960
tgtatgatta tgctttcact catatttata cagaaacttg atgttttctt tcgagtatat   1020
acaaggtgat tacatgtacg tttgaagtac aactctagat tttgtagtgc cctcttgggc   1080
tagcggtaaa ggtgcgcatt ttttcacacc ctacaatgtt ctgttcaaaa gatttggtc    1140 aaacgctgta gaagtgaaag ttggtgcgca tgtttcggcg ttcgaaactt ctccgcagtg   1200
aaagataaat gatcgggttt tagagctatg ctgttttgaa tggtcccaaa actatggatt   1260
cctaaatcct cggttttaga gctatgctgt tttgaatggt cccaaaactt ttttgtttt    1320 ttatgtctgc atagcttcaa aatgtttcta ctcctttttt actcttccag attttctcgg    1380
actccgcgca tcgccgtacc acttcaaaac acccaagcac agcatactaa atttcccctc    1440
tttcttcctc tagggtgtcg ttaattaccc gtactaaagg tttggaaaag aaaaaagagg    1500
ccgcctcgtt tctttttctt cgtcgaaaaa ggcaataaaa attttttatca cgtttctttt    1560 tcttgaaaat ttttttttt gatttttttc tctttcgatg acctcccatt gatatttaag     1620
ttaataaacg gtcttcaatt tctcaagttt cagtttcatt tttcttgttc tattacaact    1680 tttttactt cttgctcatt agaaagaaag catagcaatc taatctaagt tttctagatg      1740
gattataaag atgacgatga caaacctcca aaaagaaga gaaaggtcga taagaaatac    1800
tcaataggct tagatatcgg cacaaatagc gtcggatggg cggtgatcac tgatgaatat   1860
aaggttccgt ctaaaagtt caaggttctg ggaaatacag accgccacag tatcaaaaaa     1920
aatcttatag gggctcttt atttgacagt ggagagacag cggaagcgac tcgtctcaaa    1980
cggacagctc gtagaaggta tacacgtcgg aagaatcgta tttgttatct acaggagatt    2040
ttttcaaatg agatggcgaa agtagatgat agtttctttc atcgacttga agagtctttt    2100
ttggtggaag aagacaagaa gcatgaacgt catcctattt ttggaaatat agtagatgaa    2160 gttgctatc atgagaaata tccaactatc tatcatctgc gaaaaaaatt ggtagattct    2220
acttataaag cggatttgcg cttaatctat ttggccttag cgcatatgat taagtttcgt    2280 ggtcatttt tgattgaggg agatttaaat cctgataata gtgatgtgga caaactattt    2340
atccagttgg tacaaaccta caatcaatta tttgaagaaa accctattaa cgcaagtgga    2400
gtagatgcta aagcgattct ttctgcacga ttgagtaaat caagacgatt agaaaatctc    2460
```

```
attgctcagc tccccggtga gaagaaaaat ggcttatttg ggaatctcat tgctttgtca   2520
ttgggtttga cccctaattt taaatcaaat tttgatttgg cagaagatgc taaattacag   2580
ctttcaaaag atacttacga tgatgattta gataatttat tggcgcaaat tggagatcaa   2640
tatgctgatt tgttttggc agctaagaat ttatcagatg ctattttact ttcagatatc   2700
ctaagagtaa atactgaaat aactaaggct ccctatcag cttcaatgat taaacgctac   2760
gatgaacatc atcaagactt gactctttta aaagctttag ttcgacaaca acttccagaa   2820
aagtataaag aaatcttttt tgatcaatca aaaaacggat atgcaggtta tattgatggg   2880
ggagctagcc aagaagaatt ttataaattt atcaaaccaa ttttagaaaa aatggatggt   2940
actgaggaat tattggtgaa actaaatcgt gaagatttgc tgcgcaagca acggaccttt   3000
gacaacggct ctattacca tcaaattcac ttgggtgagc tgcatgctat tttgagaaga   3060
caagaagact tttatccatt tttaaaagac aatcgtgaga agattgaaaa aatcttgact   3120
tttcgaattc cttattatgt tggtccattg gcgcgtggca atagtcgttt tgcatggatg   3180
actcggaagt ctgaagaaac aattacccca tggaattttg aagaagttgt cgataaaggt   3240
gcttcagctc aatcatttat tgaacgcatg acaaactttg ataaaaatct tccaaatgaa   3300
aaagtactac caaaacatag tttgctttat gagtatttta cggtttataa cgaattgaca   3360
aaggtcaaat atgttactga aggaatgcga aaaccagcat ttctttcagg tgaacagaag   3420
aaagccattg ttgatttact cttcaaaaca aatcgaaaag taaccgttaa gcaattaaaa   3480
gaagattatt tcaaaaaaat agaatgtttt gatagtgttg aaatttcagg agttgaagat   3540
agatttaatg cttcattagg tacctaccat gatttgctaa aaattattaa agataaagat   3600 ttttggata atgaagaaaa tgaagatatc ttagaggata ttgtttttaac attgacctta   3660 tttgaagata gggagatgat tgaggaaaga cttaaaacat atgctcacct ctttgatgat   3720
aaggtgatga acagcttaa acgtcgccgt tatactggtt ggggacgttt gtctcgaaaa   3780
ttgattaatg gtattaggga taagcaatct ggcaaaacaa tattagattt tttgaaatca   3840
gatggttttg ccaatcgcaa ttttatgcag ctgatccatg atgatagttt gacatttaaa   3900
gaagacattc aaaaagcaca agtgtctgga caaggcgata gttacatga acatattgca   3960 aatttagctg gtagccctgc tattaaaaaa ggtattttac agactgtaaa agttgttgat   4020
gaattggtca agtaatggg gcggcataag ccagaaaata tcgttattga aatggcacgt   4080
gaaaatcaga caactcaaaa gggccagaaa aattcgcgag agcgtatgaa acgaatcgaa   4140
gaaggtatca agaattagg aagtcagatt cttaaagagc atcctgttga aaatactcaa   4200
ttgcaaaatg aaaagctcta tctctattat ctccaaaatg aagagacat gtatgtggac   4260 caagaattag atattaatcg tttaagtgat tatgatgtcg atcacattgt tccacaaagt   4320
ttccttaaag acgattcaat agacaataag gtcttaacgc gttctgataa aaatcgtggt   4380
aaatcggata cgttccaag tgaagaagta gtcaaaaaga tgaaaaacta ttggagacaa   4440
cttctaaacg ccaagttaat cactcaacgt aagtttgata atttaacgaa agctgaacgt   4500
ggaggtttga gtgaacttga taagctggt tttatcaaac gccaattggt tgaaactcgc   4560
caaatcacta agcatgtggc acaaattttg gatagtcgca tgaatactaa atacgatgaa   4620
aatgataaac ttattcgaga ggttaaagtg attaccttaa aatctaaatt agtttctgac   4680
ttccgaaaag atttccaatt ctataaagta cgtgagatta caattaccca tcatgcccat   4740
gatgcgtatc taaatgccgt cgttggaact gctttgatta agaaatatcc aaaacttgaa   4800
```

| | |
|---|---|
| tcggagtttg tctatggtga ttataaagtt tatgatgttc gtaaaatgat tgctaagtct | 4860 |
| gagcaagaaa taggcaaagc aaccgcaaaa tatttctttt actctaatat catgaacttc | 4920 |
| ttcaaaacag aaattacact tgcaaatgga gagattcgca aacgccctct aatcgaaact | 4980 |
| aatggggaaa ctggagaaat tgtctgggat aaagggcgag attttgccac agtgcgcaaa | 5040 |
| gtattgtcca tgccccaagt caatattgtc aagaaaacag aagtacagac aggcggattc | 5100 |
| tccaaggagt caattttacc aaaaagaaat tcggacaagc ttattgctcg taaaaaagac | 5160 |
| tgggatccaa aaaatatgg tggttttgat agtccaacgg tagcttattc agtcctagtg | 5220 |
| gttgctaagg tggaaaaagg gaaatcgaag aagttaaaat ccgttaaaga gttactaggg | 5280 |
| atcacaatta tggaagaag ttcctttgaa aaaaatccga ttgactttt agaagctaaa | 5340 |
| ggatataagg aagttaaaaa agacttaatc attaaactac ctaaatatag tcttttgag | 5400 |
| ttagaaaacg gtcgtaaacg gatgctggct agtgccggag aattacaaaa aggaaatgag | 5460 |
| ctggctctgc caagcaaata tgtgaatttt ttatatttag ctagtcatta tgaaaagttg | 5520 |
| aagggtagtc cagaagataa cgaacaaaaa caattgtttg tggagcagca taagcattat | 5580 |
| ttagatgaga ttattgagca aatcagtgaa ttttctaagc gtgttatttt agcagatgcc | 5640 |
| aatttagata agttcttag tgcatataac aaacatagac aaaccaat acgtgaacaa | 5700 |
| gcagaaaata ttattcattt atttacgttg acgaatcttg gagctcccgc tgcttttaaa | 5760 |
| tattttgata caacaattga tcgtaaacga tatacgtcta caaagaagt tttagatgcc | 5820 |
| actcttatcc atcaatccat cactggtctt tatgaaacac gcattgattt gagtcagcta | 5880 |
| ggaggtgacc ctccaaaaaa gaagagaaag gtctgagcgg atctcttatg tctttacgat | 5940 |
| ttatagtttt cattatcaag tatgcctata ttagtatata gcatctttag atgacagtgt | 6000 |
| tcgaagtttc acgaataaaa gataatattc tacttttgc tcccaccgcg tttgctagca | 6060 |
| cgagtgaaca ccatccctcg cctgtgagtt gtacccattc ctctaaactg tagacatggt | 6120 |
| agcttcagca gtgttcgtta tgtacggcat cctccaacaa acagtcggtt atagtttgtc | 6180 |
| ctgctcctct gaatcgagtc cctcgatatt tctcatacta gttctagaga tctgccaatt | 6240 |
| gaacataaca tggtagttac atatactagt aatatggttc ggcacacatt aaaagtataa | 6300 |
| aaactatctg aattacgaat tacatatatt ggtcataaaa atcaatcaat catcgtgtgt | 6360 |
| tttatatgtc tcttatctaa gtataagaat atccatagtt aatattcact tacgctacct | 6420 |
| tttaacctgt aatcattgtc aacaggatat gttaacgacc cacattgata aacgctagta | 6480 |
| tttcttttc ctcttcttat tggccggctg tctctatact cccctatagt ctgtttcttt | 6540 |
| tcgtttcgat tgttttacgt ttgaggcctc gtggcgcaca tggtacgctg tggtgctcgc | 6600 |
| ggctgggaac gaaactctgg gagctgcgat tggcaggaac cattcaaaac agcatagcaa | 6660 |
| gttaaaataa ggctagtccg ttatcaactt gaaaaagtgg caccgagtcg gtgctttttt | 6720 |
| tccatatcca acttccaatt taatctttct tttttaattt tcacttattt gcgatacaga | 6780 |
| aagaccctgc aggcatgcaa gcttggcgta atcatggtca tagctgtttc ctgtgtgaaa | 6840 |
| ttgttatccg ctcacaattc cacacaacat acgagccgga agcataaagt gtaaagcctg | 6900 |
| gggtgcctaa tgagtgagct aactcacatt aattgcgttg cgctcactgc ccgctttcca | 6960 |
| gtcgggaaac ctgtcgtgcc agctgcatta atgaatcggc caacgcgcgg ggagaggcgg | 7020 |
| tttgcgtatt gggcgctctt ccgcttcctc gctcactgac tcgctgcgct cggtcgttcg | 7080 |
| gctgcggcga gcggtatcag ctcactcaaa ggcggtaata cggttatcca cagaatcagg | 7140 |
| ggataacgca ggaaagaaca tgtgagcaaa aggccagcaa aaggccagga accgtaaaaa | 7200 |

```
ggccgcgttg ctggcgtttt tccataggct ccgccccct gacgagcatc acaaaaatcg   7260
acgctcaagt cagaggtggc gaaacccgac aggactataa agataccagg cgtttccccc   7320
tggaagctcc ctcgtgcgct ctcctgttcc gaccctgccg cttaccggat acctgtccgc   7380
cttctcccct tcgggaagcg tggcgctttc tcatagctca cgctgtaggt atctcagttc   7440
ggtgtaggtc gttcgctcca agctgggctg tgtgcacgaa ccccccgttc agcccgaccg   7500
ctgcgcctta tccggtaact atcgtcttga gtccaacccg gtaagacacg acttatcgcc   7560
actggcagca gccactggta acaggattag cagagcgagg tatgtaggcg gtgctacaga   7620
gttcttgaag tggtggccta actacggcta cactagaaga acagtatttg gtatctgcgc   7680
tctgctgaag ccagttacct tcggaaaaag agttggtagc tcttgatccg gcaaacaaac   7740
caccgctggt agcggtggtt ttttttgttg caagcagcag attacgcgca gaaaaaaagg   7800
atctcaagaa gatcctttga tcttttctac ggggtctgac gctcagtgga acgaaaactc   7860
acgttaaggg attttggtca tgagattatc aaaaaggatc ttcacctaga tccttttaaa   7920
ttaaaaatga agttttaaat caatctaaag tatatatgag taaacttggt ctgacagtta   7980
ccaatgctta atcagtgagg cacctatctc agcgatctgt ctatttcgtt catccatagt   8040
tgcctgactc cccgtcgtgt agataactac gatacgggag ggcttaccat ctggccccag   8100
tgctgcaatg ataccgcggc tcccacgctc accggctcca gatttatcag caataaacca   8160
gccagccgga agggccgagc gcagaagtgg tcctgcaact ttatccgcct ccatccagtc   8220
tattaattgt tgccgggaag ctagagtaag tagttcgcca gttaatagtt tgcgcaacgt   8280
tgttgccatt gctacaggca tcgtggtgtc acgctcgtcg tttggtatgg cttcattcag   8340
ctccggttcc caacgatcaa ggcgagttac atgatccccc atgttgtgca aaaaagcggt   8400
tagctccttc ggtcctccga tcgttgtcag aagtaagttg gccgcagtgt tatcactcat   8460
ggttatggca gcactgcata attctcttac tgtcatgcca tccgtaagat gcttttctgt   8520
gactggtgag tactcaacca agtcattctg agaatagtgt atgcggcgac cgagttgctc   8580
ttgcccggcg tcaatacggg ataataccgc gccacatagc agaactttaa aagtgctcat   8640
cattggaaaa cgttcttcgg ggcgaaaact ctcaaggatc ttaccgctgt tgagatccag   8700
ttcgatgtaa cccactcgtg cacccaactg atcttcagca tcttttactt tcaccagcgt   8760
ttctgggtga gcaaaaacag gaaggcaaaa tgccgcaaaa aagggaataa gggcgacacg   8820
gaaatgttga atactcatac tcttcctttt tcaatattat tgaagcattt atcagggtta   8880
ttgtctcatg agcggataca tatttgaatg tatttagaaa aataaacaaa taggggttcc   8940
gcgcacattt ccccgaaaag tgccacctga acgaagcatc tgtgcttcat tttgtagaac   9000
aaaaatgcaa cgcgagagcg ctaatttttc aaacaaagaa tctgagctgc attttttacag   9060 aacagaaatg caacgcgaaa gcgctatttt accaacgaag aatctgtgct tcattttttgt   9120 aaaacaaaaa tgcaacgcga gagcgctaat tttcaaaaca aagaatctga gctgcatttt   9180
tacagaacag aaatgcaacg cgagagcgct attttaccaa caagaatct atacttcttt   9240 tttgttctac aaaaatgcat cccgagagcg ctatttttct aacaaagcat cttagattac   9300 ttttttctc cttgtgcgc tctataatgc agtctcttga taacttttg cactgtaggt   9360 ccgttaaggt tagaagaagg ctactttggt gtctattttc tcttccataa aaaaagcctg   9420
actccacttc ccgcgtttac tgattactag cgaagctgcg ggtgcatttt ttcaagataa   9480
aggcatcccc gattatattc tataccgatg tggattgcgc atactttgtg aacagaaagt   9540
```

```
gatagcgttg atgattcttc attggtcaga aaattatgaa cggtttcttc tatttgtct     9600
ctatatacta cgtataggaa atgtttacat tttcgtattg ttttcgattc actctatgaa    9660
tagttcttac tacaattttt ttgtctaaag agtaatacta gagataaaca taaaaaatgt   9720
agaggtcgag tttagatgca agttcaagga gcgaaaggtg gatgggtagg ttatataggg   9780
atatagcaca gagatatata gcaaagagat acttttgagc aatgtttgtg gaagcggtat   9840
tcgcaatatt ttagtagctc gttacagtcc ggtgcgtttt tggtttttg aaagtgcgtc    9900
ttcagagcgc ttttggtttt caaaagcgct ctgaagttcc tatactttct agagaatagg   9960
aacttcggaa taggaacttc aaagcgtttc cgaaaacgag cgcttccgaa aatgcaacgc   10020
gagctgcgca catacagctc actgttcacg tcgcacctat atctgcgtgt tgcctgtata   10080
tatatataca tgagaagaac ggcatagtgc gtgtttatgc ttaaatgcgt acttatatgc   10140
gtctatttat gtaggatgaa aggtagtcta gtacctcctg tgatattatc ccattccatg   10200
cggggtatcg tatgcttcct tcagcactac cctttagctg ttctatatgc tgccactcct   10260
caattggatt agtctcatcc ttcaatgcta tcatttcctt tgatattgga tcatctaaga   10320
aaccattatt atcatgacat taacctataa aaataggcgt atcacgaggc cctttcgtc   10379

<210> SEQ ID NO 93
<211> LENGTH: 126
<212> TYPE: DNA
<213> ORGANISM: Saccharomyces boulardii

<400> SEQUENCE: 93
tgttggaata aaaatcaact atcatctact aactagtatt tacgttacta gtatattatc    60
atatacggtg ttagaagatg acgcaaatga tgagaaatag tcatctaaat tagtggaagc   120
tgaaac                                                              126

<210> SEQ ID NO 94
<211> LENGTH: 105
<212> TYPE: DNA
<213> ORGANISM: Saccharomyces boulardii

<400> SEQUENCE: 94
aatatttata gaattgtgta gaattgcaga ttccctttta tggattccta aatcctcgag    60
gagaacttct agtatatcta catacctaat attatagcct taatc                   105

<210> SEQ ID NO 95
<211> LENGTH: 6919
<212> TYPE: DNA
<213> ORGANISM: Artificial Sequence
<220> FEATURE:
<223> OTHER INFORMATION: Plasmid pPL5071_TEF1-Cre_URA3
<220> FEATURE:
<221> NAME/KEY: misc_feature
<222> LOCATION: (2382)..(2382)
<223> OTHER INFORMATION: n is a, c, g, or t

<400> SEQUENCE: 95
agaaaccatt attatcatga cattaaccta taaaaatagg cgtatcacga ggccctttcg    60
tctcgcgcgt ttcggtgatg acggtgaaaa cctctgacac atgcagctcc cggagacggt   120
cacagcttgt ctgtaagcgg atgccgggag cagacaagcc cgtcagggcg cgtcagcggg   180
tgttggcggg tgtcggggct ggcttaacta tgcggcatca gagcagattg tactgagagt   240
gcaccatacc acagctttc aattcaattc atcatttttt ttttattctt ttttttgatt   300
tcggtttctt tgaaattttt ttgattcggt aatctccgaa cagaaggaag aacgaaggaa   360
```

```
ggagcacaga cttagattgg tatatatacg catatgtagt gttgaagaaa catgaaattg    420
cccagtattc ttaacccaac tgcacagaac aaaaacctgc aggaaacgaa gataaatcat    480
gtcgaaagct acatataagg aacgtgctgc tactcatcct agtcctgttg ctgccaagct    540
atttaatatc atgcacgaaa agcaaacaaa cttgtgtgct tcattggatg ttcgtaccac    600
caaggaatta ctggagttag ttgaagcatt aggtcccaaa atttgtttac taaaaacaca    660
tgtggatatc ttgactgatt tttccatgga gggcacagtt aagccgctaa aggcattatc    720
cgccaagtac aattttttac tcttcgaaga cagaaaattt gctgacattg gtaatacagt    780
caaattgcag tactctgcgg gtgtatacag aatagcagaa tgggcagaca ttacgaatgc    840
acacggtgtg gtgggcccag gtattgttag cggtttgaag caggcggcag aagaagtaac    900
aaaggaacct agaggccttt tgatgttagc agaattgtca tgcaagggct ccctatctac    960
tggagaatat actaagggta ctgttgacat tgcgaagagc gacaaagatt tgttatcgg    1020
ctttattgct caaagagaca tgggtggaag agatgaaggt tacgattggt tgattatgac   1080
acccggtgtg ggtttagatg acaagggaga cgcattgggt caacagtata gaaccgtgga   1140
tgatgtggtc tctacaggat ctgacattat tattgttgga agaggactat ttgcaaaggg   1200
aagggatgct aaggtagagg gtgaacgtta cagaaaagca ggctgggaag catatttgag   1260
aagatgcggc cagcaaaact aaaaaactgt attataagta aatgcatgta tactaaactc   1320
acaaattaga gcttcaattt aattatatca gttattaccc tatgcggtgt gaaataccgc   1380
acagatgcgt aaggagaaaa taccgcatca ggaaattgta aacgttaata ttttgttaaa   1440
attcgcgtta aattttttgtt aaatcagctc attttttaac caataggccg aaatcggcaa   1500
aatcccttat aaatcaaaag aatagaccga gatagggttg agtgttgttc cagtttggaa   1560
caagagtcca ctattaaaga acgtggactc caacgtcaaa gggcgaaaaa ccgtctatca   1620
gggcgatggc ccactacgtg aaccatcacc ctaatcaagt ttttgggggt cgaggtgccg   1680
taaagcacta aatcggaacc ctaaagggag cccccgattt agagcttgac ggggaaagcc   1740
ggcgaacgtg gcgagaaagg aagggaagaa agcgaaagga gcgggcgcta gggcgctggc   1800
aagtgtagcg gtcacgctgc gcgtaaccac cacacccgcc gcgcttaatg cgccgctaca   1860
gggcgcgtcg cgccattcgc cattcaggct gcgcaactgt tgggaagggc gatcggtgcg   1920
ggcctcttcg ctattacgcc agctggcgaa agggggatgt gctgcaaggc gattaagttg   1980
ggtaacgcca gggttttccc agtcacgacg ttgtaaaacg acggccagtg agcgcgcgta   2040
atacgactca ctatagggcg aattgggtac cggccgcaaa ttaaagcctt cgagcgtccc   2100
aaaaccttct caagcaaggt tttcagtata atgttacatg cgtacacgcg tctgtacaga   2160
aaaaaagaa aaatttgaaa tataaataac gttcttaata ctaacataac tataaaaaaa   2220
taaataggga cctagacttc aggttgtcta actccttcct tttcggttag agcggatgtg   2280
gggggagggc gtgaatgtaa gcgtgacata actaattaca tgactcgagg tcgacaattc   2340
caaccttacc caagagttcg ccaaactcag acatcacttt angcaaaacc gcgccgtgct   2400
tcttcctcgg tggcattcat cacgaaatgt tcagcactac gcatactttt gacaggaaac   2460
gcaacggata ttgagtcaat atcaggcatt ctatcgctca gctttacagt gacaatgacg   2520
gctggcgact gaatattagt gcttacagac agcactacat attttccgtc gatgttgaaa   2580
tcctttctca tatgtcacca taaatatcaa ataattatag caatcattta cgcgttaatg   2640
gctaatcgcc atcttccagc aggcgcacca ttgcccctgt ttcactatcc agggtacgga   2700
```

```
tatagttcat gacaatattt acattggtcc agccaccagc ttgcatgatc tccggtattg    2760
aaactccagc gcgggccata tctcgcgcgg ctccgacacg ggcactgtgt ccagaccagg    2820
ccaggtatct ctgaccagag tcatccttag cgccgtaaat caatcgatga gttgcttcaa    2880
aaatcccttc cagggcgcga gttgatagct ggctggtggc agatggcgcg gcaacaccat    2940
tttttctgac ccggcaaaac aggtagttat tcggatcatc agctacacca gagacggaaa    3000
tccatcgctc gaccagttta gttaccccca ggctaagtgc cttctctaca cctgcggtgc    3060
taaccagcgt tttcgttctg ccaatatgga ttaacattct cccaccgtca gtacgtgaga    3120
tatctttaac cctgatcctg gcaatttcgg ctatacgtaa cagggtgtta taagcaatcc    3180
ccagaaatgc cagattacgt atatcctggc agcgatcgct attttccatg agtgaacgaa    3240
cctggtcgaa atcagtgcgt tcgaacgcta gagcctgttt tgcacgttca ccggcatcaa    3300
cgttttcttt tcggatccgc cgcataacca gtgaaacagc attgctgtca cttggtcgtg    3360
gcagcccgga ccgacgatga agcatgttta gctggcccaa atgttgctgg atagttttta    3420
ctgccagacc gcgcgcctga agatatagaa gataatcgcg aacatcttca ggttctgcgg    3480
gaaaccattt ccggttattc aacttgcacc atgccgccca cgaccggcaa acggacagaa    3540
gcattttcca ggtatgctca gaaaacgcct ggcgatccct gaacatgtcc atcaggttct    3600
tgcgaacctc atcactcgtt gcatcgaccg gtaatgcagg caaattttgg tgtacggtca    3660
gtaaattgga catttaacac tcagataatg gttttaagta agtgtacag gatcggctct    3720
gcccctcgac ggtatcgata agcttgatat cgaattcctg cagcccgggg gatccactag    3780
tttttgtaat taaaacttag attagattgc tatgcttttct ttccaatgag caagaagtaa    3840
aaaaagttgt aatagaacag gaaaatgaa gctgaaactt gagaaattga agaccgtttg    3900
ttaactcaaa tatcaatggg aggtcgtcga aagagaacaa aatcgaaaaa aaagttttca    3960
agagaaagaa acgtgataaa aatttttatt gccttctccg acgaagaaaa agggacgagg    4020
cggtctcttt ttccttttcc aaacctttag tacgggtaat taacggcacc ctagaggaag    4080
gaggagggg aatttagtat gctgtgcttg ggtgttttga agtggtacgg cggtgcgcgg    4140
agtccgagaa aatctggaag agtaaaaaag gagtagagac attttgaagc tatccagctt    4200
ttgttccctt tagtgagggt taattgcgcg cttggcgtaa tcatggtcat agctgtttcc    4260
tgtgtgaaat tgttatccgc tcacaattcc acacaacata ggagccggaa gcataaagtg    4320
taaagcctgg ggtgcctaat gagtgaggta actcacatta attgcgttgc gctcactgcc    4380
cgctttccag tcgggaaacc tgtcgtgcca gctgcattaa tgaatcggcc aacgcgcggg    4440
gagaggcggt ttgcgtattg ggcgctcttc cgcttcctcg ctcactgact cgctgcgctc    4500
ggtcgttcgg ctgcggcgag cggtatcagc tcactcaaag gcggtaatac ggttatccac    4560
agaatcaggg gataacgcag gaaagaacat gtgagcaaaa ggccagcaaa aggccaggaa    4620
ccgtaaaaag gccgcgttgc tggcgttttt ccataggctc cgcccccctg acgagcatca    4680
caaaaatcga cgctcaagtc agaggtggcg aaacccgaca ggactataaa gataccaggc    4740
gtttccсccct ggaagctccc tcgtgcgctc tcctgttccg accctgccgc ttaccggata    4800
cctgtccgcc tttctccctt cgggaagcgt ggcgctttct catagctcac gctgtaggta    4860
tctcagttcg gtgtaggtcg ttcgctccaa gctgggctgt gtgcacgaac cccccgttca    4920
gcccgaccgc tgcgccttat ccggtaacta tcgtcttgag tccaacccgg taagacacga    4980
cttatcgcca ctggcagcag ccactggtaa caggattagc agagcgaggt atgtaggcgg    5040
tgctacagag ttcttgaagt ggtggcctaa ctacggctac actagaagga cagtatttgg    5100
```

```
tatctgcgct ctgctgaagc cagttacctt cggaaaaaga gttggtagct cttgatccgg    5160
caaacaaacc accgctggta gcggtggttt ttttgtttgc aagcagcaga ttacgcgcag    5220
aaaaaaagga tctcaagaag atcctttgat cttttctacg gggtctgacg ctcagtggaa    5280
cgaaaactca cgttaaggga ttttggtcat gagattatca aaaaggatct tcacctagat    5340
ccttttaaat taaaaatgaa gttttaaatc aatctaaagt atatatgagt aaacttggtc    5400
tgacagttac caatgcttaa tcagtgaggc acctatctca gcgatctgtc tatttcgttc    5460
atccatagtt gcctgactcc ccgtcgtgta gataactacg atacgggagg gcttaccatc    5520
tggccccagt gctgcaatga taccgcgaga cccacgctca ccggctccag atttatcagc    5580
aataaaccag ccagccggaa gggccgagcg cagaagtggt cctgcaactt tatccgcctc    5640
catccagtct attaattgtt gccgggaagc tagagtaagt agttcgccag ttaatagttt    5700
gcgcaacgtt gttgccattg ctacaggcat cgtggtgtca cgctcgtcgt ttggtatggc    5760
ttcattcagc tccggttccc aacgatcaag gcgagttaca tgatccccca tgttgtgcaa    5820
aaaagcggtt agctccttcg gtcctccgat cgttgtcaga agtaagttgg ccgcagtgtt    5880
atcactcatg gttatggcag cactgcataa ttctcttact gtcatgccat ccgtaagatg    5940
cttttctgtg actggtgagt actcaaccaa gtcattctga atagtgta tgcggcgacc    6000 gagttgctct tgcccggcgt caatacggga taataccgcg ccacatagca gaactttaaa    6060
agtgctcatc attggaaaac gttcttcggg gcgaaaactc tcaaggatct taccgctgtt    6120
gagatccagt tcgatgtaac ccactcgtgc acccaactga tcttcagcat cttttacttt    6180
caccagcgtt tctgggtgag caaaaacagg aaggcaaaat gccgcaaaaa agggaataag    6240
ggcgacacgg aaatgttgaa tactcatact cttcctttt caatattatt gaagcattta    6300
tcagggttat tgtctcatga gcggatacat atttgaatgt atttagaaaa ataaacaaat    6360
aggggttccg cgcacatttc cccgaaaagt gccacctggg tccttttcat cacgtgctat    6420
aaaaataatt ataatttaaa ttttttaata taaatatata aattaaaaat agaaagtaaa    6480
aaaagaaatt aaagaaaaaa tagttttttgt tttccgaaga tgtaaaagac tctagggga    6540 tcgccaacaa atactacctt ttatcttgct cttcctgctc tcaggtatta atgccgaatt    6600
gtttcatctt gtctgtgtag aagaccacac acgaaaatcc tgtgatttta catttcactt    6660
atcgttaatc gaatgtatat ctatttaatc tgcttttctt gtctaataaa tatatatgta    6720
aagtacgctt tttgttgaaa tttttttaaac ctttgtttat ttttttttct tcattccgta    6780
actcttctac cttcttttatt tactttctaa aatccaaata caaaacataa aaataaataa    6840
acacagagta aattcccaaa ttattccatc attaaaagat acgaggcgcg tgtaagttac    6900
aggcaagcga tccgtccta                                                  6919
```

<210> SEQ ID NO 96
<211> LENGTH: 89
<212> TYPE: PRT
<213> ORGANISM: Saccharomyces cerevisiae

<400> SEQUENCE: 96

Met Arg Phe Pro Ser Ile Phe Thr Ala Val Leu Phe Ala Ala Ser Ser
1               5                   10                  15

Ala Leu Ala Ala Pro Val Asn Thr Thr Thr Glu Asp Glu Thr Ala Gln
                20                  25                  30

Ile Pro Ala Glu Ala Val Ile Gly Tyr Ser Asp Leu Glu Gly Asp Phe
        35                  40                  45

Asp Val Ala Val Leu Pro Phe Ser Asn Ser Thr Asn Asn Gly Leu Leu
            50                  55                  60

Phe Ile Asn Thr Thr Ile Ala Ser Ile Ala Ala Lys Glu Glu Gly Val
 65                  70                  75                  80

Ser Leu Glu Lys Arg Glu Ala Glu Ala
                85

<210> SEQ ID NO 97
<211> LENGTH: 61
<212> TYPE: PRT
<213> ORGANISM: Saccharomyces cerevisiae

<400> SEQUENCE: 97

Met Arg Phe Pro Ser Ile Phe Thr Ala Val Leu Phe Ala Ala Ser Ser
 1               5                  10                  15

Ala Leu Ala Ala Pro Val Asn Thr Thr Thr Glu Asp Glu Leu Glu Gly
                20                  25                  30

Asp Phe Asp Val Ala Val Leu Pro Phe Ser Ala Ser Ile Ala Ala Lys
            35                  40                  45

Glu Glu Gly Val Ser Leu Glu Lys Arg Glu Ala Glu Ala
        50                  55                  60

<210> SEQ ID NO 98
<211> LENGTH: 57
<212> TYPE: PRT
<213> ORGANISM: Saccharomyces cerevisiae

<400> SEQUENCE: 98

Met Arg Phe Pro Ser Ile Phe Thr Ala Val Leu Phe Ala Ala Ser Ser
 1               5                  10                  15

Ala Leu Ala Ala Pro Val Asn Thr Thr Thr Glu Asp Glu Leu Glu Gly
                20                  25                  30

Asp Phe Asp Val Ala Val Leu Pro Phe Ser Ala Ser Ile Ala Ala Lys
            35                  40                  45

Glu Glu Gly Val Ser Leu Glu Lys Arg
        50                  55

<210> SEQ ID NO 99
<211> LENGTH: 19
<212> TYPE: PRT
<213> ORGANISM: Saccharomyces cerevisiae

<400> SEQUENCE: 99

Met Arg Phe Pro Ser Ile Phe Thr Ala Val Leu Phe Ala Ala Ser Ser
 1               5                  10                  15

Ala Leu Ala

<210> SEQ ID NO 100
<211> LENGTH: 20
<212> TYPE: PRT
<213> ORGANISM: Aspergillus niger

<400> SEQUENCE: 100

Met Val Ala Trp Trp Ser Leu Phe Leu Tyr Gly Leu Gln Val Ala Ala
 1               5                  10                  15

Pro Ala Leu Ala
            20

<210> SEQ ID NO 101

-continued

```
<211> LENGTH: 18
<212> TYPE: PRT
<213> ORGANISM: Aspergillus awamorii

<400> SEQUENCE: 101

Met Ser Phe Arg Ser Leu Leu Ala Leu Ser Gly Leu Val Cys Ser Gly
1               5                   10                  15

Leu Ala

<210> SEQ ID NO 102
<211> LENGTH: 16
<212> TYPE: PRT
<213> ORGANISM: Kluyveromyces marxianus

<400> SEQUENCE: 102

Met Lys Leu Ala Tyr Ser Leu Leu Pro Leu Ala Gly Val Ser Ala
1               5                   10                  15

<210> SEQ ID NO 103
<211> LENGTH: 19
<212> TYPE: PRT
<213> ORGANISM: Saccharomyces cerevisiae

<400> SEQUENCE: 103

Met Leu Leu Gln Ala Phe Leu Phe Leu Leu Ala Gly Phe Ala Ala Lys
1               5                   10                  15

Ile Ser Ala

<210> SEQ ID NO 104
<211> LENGTH: 26
<212> TYPE: PRT
<213> ORGANISM: Saccharomyces cerevisiae

<400> SEQUENCE: 104

Met Thr Lys Pro Thr Gln Val Leu Val Arg Ser Val Ser Ile Leu Phe
1               5                   10                  15

Phe Ile Thr Leu Leu His Leu Val Val Ala
                20                  25

<210> SEQ ID NO 105
<211> LENGTH: 26
<212> TYPE: PRT
<213> ORGANISM: Gallus gallus

<400> SEQUENCE: 105

Met Leu Gly Lys Asn Asp Pro Met Cys Leu Val Leu Val Leu Leu Gly
1               5                   10                  15

Leu Thr Ala Leu Leu Gly Ile Cys Gln Gly
                20                  25

<210> SEQ ID NO 106
<211> LENGTH: 18
<212> TYPE: PRT
<213> ORGANISM: Homo sapiens

<400> SEQUENCE: 106

Met Lys Trp Val Thr Phe Ile Ser Leu Leu Phe Leu Phe Ser Ser Ala
1               5                   10                  15

Tyr Ser

<210> SEQ ID NO 107
<211> LENGTH: 566
```

```
<212> TYPE: PRT
<213> ORGANISM: Artificial Sequence
<220> FEATURE:
<223> OTHER INFORMATION: ABAB binding protein expressed from plasmid

<400> SEQUENCE: 107
```

| | | | | | | | | | | | | | | |
|---|---|---|---|---|---|---|---|---|---|---|---|---|---|---|
| Met | Arg | Phe | Pro | Ser | Ile | Phe | Thr | Ala | Val | Leu | Phe | Ala | Ser | Ser |
| 1 | | | | 5 | | | | | 10 | | | | | 15 |
| Ala | Leu | Ala | Met | Gln | Val | Gln | Leu | Val | Glu | Thr | Gly | Gly | Gly | Leu | Val |
| | | | 20 | | | | | 25 | | | | | 30 | | |
| Gln | Pro | Gly | Gly | Ser | Leu | Arg | Leu | Ser | Cys | Ala | Ala | Ser | Gly | Phe | Thr |
| | | | 35 | | | | | 40 | | | | | 45 | | |
| Leu | Asp | Tyr | Ser | Ser | Ile | Gly | Trp | Phe | Arg | Gln | Ala | Pro | Gly | Lys | Glu |
| | 50 | | | | | 55 | | | | | 60 | | | | |
| Arg | Glu | Gly | Val | Ser | Cys | Ile | Ser | Ser | Gly | Asp | Ser | Thr | Lys | Tyr |
| 65 | | | | | 70 | | | | | 75 | | | | | 80 |
| Ala | Asp | Ser | Val | Lys | Gly | Arg | Phe | Thr | Thr | Ser | Arg | Asp | Asn | Ala | Lys |
| | | | | 85 | | | | | 90 | | | | | 95 | |
| Asn | Thr | Val | Tyr | Leu | Gln | Met | Asn | Ser | Leu | Lys | Pro | Asp | Asp | Thr | Ala |
| | | | 100 | | | | | 105 | | | | | 110 | | |
| Val | Tyr | Tyr | Cys | Ala | Ala | Phe | Arg | Ala | Thr | Met | Cys | Gly | Val | Phe | Pro |
| | | | 115 | | | | | 120 | | | | | 125 | | |
| Leu | Ser | Pro | Tyr | Gly | Lys | Asp | Asp | Trp | Gly | Lys | Gly | Thr | Leu | Val | Thr |
| | 130 | | | | | 135 | | | | | 140 | | | | |
| Val | Ser | Ser | Gly | Gly | Gly | Gly | Ser | Gly | Gly | Gly | Ser | Gly | Gly | Gly |
| 145 | | | | | 150 | | | | | 155 | | | | | 160 |
| Gly | Ser | Gln | Val | Gln | Leu | Val | Glu | Ser | Gly | Gly | Leu | Val | Gln | Pro |
| | | | | 165 | | | | | 170 | | | | | 175 | |
| Gly | Gly | Ser | Leu | Arg | Leu | Ser | Cys | Glu | Ala | Ser | Gly | Phe | Thr | Leu | Asp |
| | | | 180 | | | | | 185 | | | | | 190 | | |
| Tyr | Tyr | Gly | Ile | Gly | Trp | Phe | Arg | Gln | Pro | Pro | Gly | Lys | Glu | Arg | Glu |
| | | | 195 | | | | | 200 | | | | | 205 | | |
| Ala | Val | Ser | Tyr | Ile | Ser | Ala | Ser | Ala | Arg | Thr | Ile | Leu | Tyr | Ala | Asp |
| | 210 | | | | | 215 | | | | | 220 | | | | |
| Ser | Val | Lys | Gly | Arg | Phe | Thr | Ile | Ser | Arg | Asp | Asn | Ala | Lys | Asn | Ala |
| 225 | | | | | 230 | | | | | 235 | | | | | 240 |
| Val | Tyr | Leu | Gln | Met | Asn | Ser | Leu | Lys | Arg | Glu | Asp | Thr | Ala | Val | Tyr |
| | | | | 245 | | | | | 250 | | | | | 255 | |
| Tyr | Cys | Ala | Arg | Arg | Arg | Phe | Ser | Ala | Ser | Ser | Val | Asn | Arg | Trp | Leu |
| | | | 260 | | | | | 265 | | | | | 270 | | |
| Ala | Asp | Asp | Tyr | Asp | Val | Trp | Gly | Arg | Gly | Thr | Gln | Val | Ala | Val | Ser |
| | | | 275 | | | | | 280 | | | | | 285 | | |
| Ser | Gly | Gly | Gly | Ser | Gly | Gly | Gly | Ser | Gly | Gly | Ser | Gly | Gly | Gly |
| | 290 | | | | | 295 | | | | | 300 | | | | |
| Ser | Gln | Leu | Gln | Leu | Val | Glu | Thr | Gly | Gly | Gly | Leu | Val | Gln | Pro | Gly |
| 305 | | | | | 310 | | | | | 315 | | | | | 320 |
| Gly | Ser | Leu | Arg | Leu | Ser | Cys | Ala | Ala | Ser | Gly | Phe | Thr | Phe | Ser | Asp |
| | | | | 325 | | | | | 330 | | | | | 335 | |
| Tyr | Val | Met | Thr | Trp | Val | Arg | Gln | Ala | Pro | Gly | Lys | Gly | Pro | Glu | Trp |
| | | | 340 | | | | | 345 | | | | | 350 | | |
| Ile | Ala | Thr | Ile | Asn | Thr | Asp | Gly | Ser | Thr | Met | Arg | Asp | Asp | Ser | Thr |
| | | | 355 | | | | | 360 | | | | | 365 | | |
| Lys | Gly | Arg | Phe | Thr | Ile | Ser | Arg | Asp | Asn | Ala | Lys | Asn | Thr | Leu | Tyr |
| | 370 | | | | | 375 | | | | | 380 | | | | |

Leu Gln Met Thr Ser Leu Lys Pro Glu Asp Thr Ala Leu Tyr Tyr Cys
385                 390                 395                 400

Ala Arg Gly Arg Val Ile Ser Ala Ser Ile Arg Gly Ala Val Arg
            405                 410                 415

Gly Pro Gly Thr Gln Val Thr Val Ser Ser Gly Gly Gly Ser Gly
            420                 425                 430

Gly Gly Gly Ser Gly Gly Gly Ser Gln Val Gln Leu Val Glu Ser
        435                 440                 445

Gly Gly Gly Leu Val Gln Thr Gly Gly Ser Leu Arg Leu Ser Cys Ala
        450                 455                 460

Ser Ser Gly Ser Ile Ala Gly Phe Glu Thr Val Thr Trp Ser Arg Gln
465                 470                 475                 480

Ala Pro Gly Lys Ser Leu Gln Trp Val Ala Ser Met Thr Lys Thr Asn
            485                 490                 495

Asn Glu Ile Tyr Ser Asp Ser Val Lys Gly Arg Phe Ile Ile Ser Arg
                500                 505                 510

Asp Asn Ala Lys Asn Thr Val Tyr Leu Gln Met Asn Ser Leu Lys Pro
            515                 520                 525

Glu Asp Thr Gly Val Tyr Phe Cys Lys Gly Pro Glu Leu Arg Gly Gln
            530                 535                 540

Gly Ile Gln Val Thr Val Ser Ser Val Asp Met Glu Gln Lys Leu Ile
545                 550                 555                 560

Ser Glu Glu Asp Leu Glu
                565

<210> SEQ ID NO 108
<211> LENGTH: 1701
<212> TYPE: DNA
<213> ORGANISM: Artificial Sequence
<220> FEATURE:
<223> OTHER INFORMATION: Polynucleotide sequence encoding ABAB binding
      protein expressed from plasmid

<400> SEQUENCE: 108
atgagatttc cttcaatttt tactgctgtt ttattcgcag catcctccgc attagctatg      60
caagtacaat tggttgaaac cggtggtggt ttagttcaac aggtggtag tttgagatta     120 tcttgtgctg catcaggttt tacattggat tattcttcaa taggttggtt cagacaagct     180
cctggtaaag aaagagaagg tgtttcttgc atatccagtt ctggtgactc aactaaatat     240
gctgactccg ttaagggtag attcactact tcaagagata cgctaaaaa tacagtctac     300 ttgcaaatga actcattaaa gccagatgac acagcagtct attactgtgc cgcttttaga     360
gccaccatgt gcggtgtatt cccattgtct ccttacggta agatgactg gggtaaaggt     420 actttagtta ctgtctcatc cggtggtggt ggttccggtg gtggtggtag tggtggtggt     480
ggttctcaag ttcaattagt agaatccggt ggtggtttag tccaacctgg tggtagttta     540
agattatcct gcgaagcaag tggttttaca ttagattatt acggtatcgg ttggtttaga     600
caaccacctg gtaaagaaag agaagctgtc tcttatattt ccgctagtgc aagaactata     660
ttgtacgcag attctgtaaa gggtagatta caatttcaa gagacaatgc caagaacgct     720
gtttatttgc aaatgaactc tttgaagaga agagacaccg cagttattta ctgtgccaga     780
agaagatttt ctgcttcttc agtcaacaga tggttagcag acgattatga tgtttgggt     840 agaggtacac aagtcgccgt aagttctggt ggtggtccg tggtggtag tggtggtggt     900 tctggtggtg gttcacaatt gcaattagta gaaactggtg gtggtttggt tcaaccaggt     960

-continued

```
ggttccttga gattaagttg tgctgcatct ggttttactt tctctgatta cgttatgaca    1020
tgggtcagac aagctccagg taaaggtcct gaatggatcg ctacaattaa taccgacggt    1080
tccacaatga gagatgacag taccaagggt agattcacta tttcaagaga taacgctaag    1140
aacacattgt acttacaaat gacctctttg aaaccagaag acaccgcatt atattactgt    1200
gccagaggta gagtcatatc cgccagtgct atcagaggtg cagtaagagg tcctggtact    1260
caagttacag tctcttcagg tggcggcggt agtggcggcg gcggttctgg cggtggtggt    1320
tcacaagtcc aattggtaga atctggtggt ggtttagttc aaactggtgg ttcattgaga    1380
ttatcctgcg cttccagtgg ttccattgca ggtttcgaaa ctgttacatg gtcaagacaa    1440
gctccaggta aatctttgca atgggtcgcc tcaatgacca agactaacaa cgaaatctat    1500
tctgattcag ttaagggtag attcattatt tcaagagata atgctaaaaa caccgtttat    1560
ttgcaaatga actcattgaa gccagaagat actggtgttt acttctgcaa gggtcctgaa    1620
ttaagaggtc aaggtattca agtaacagtt tcttcagtcg acatggaaca gaagttgatt    1680
tccgaagaag acctcgagta a                                              1701
```

<210> SEQ ID NO 109
<211> LENGTH: 557
<212> TYPE: PRT
<213> ORGANISM: Artificial Sequence
<220> FEATURE:
<223> OTHER INFORMATION: ABAB binding protein expressed from chromosomal
      integration

<400> SEQUENCE: 109

```
Met Arg Phe Pro Ser Ile Phe Thr Ala Val Leu Phe Ala Ala Ser Ser
1               5                   10                  15

Ala Leu Ala Met Gln Val Gln Leu Val Glu Thr Gly Gly Gly Leu Val
            20                  25                  30

Gln Pro Gly Gly Ser Leu Arg Leu Ser Cys Ala Ala Ser Gly Phe Thr
        35                  40                  45

Leu Asp Tyr Ser Ser Ile Gly Trp Phe Arg Gln Ala Pro Gly Lys Glu
    50                  55                  60

Arg Glu Gly Val Ser Cys Ile Ser Ser Gly Asp Ser Thr Lys Tyr
65                  70                  75                  80

Ala Asp Ser Val Lys Gly Arg Phe Thr Thr Ser Arg Asp Asn Ala Lys
                85                  90                  95

Asn Thr Val Tyr Leu Gln Met Asn Ser Leu Lys Pro Asp Asp Thr Ala
            100                 105                 110

Val Tyr Tyr Cys Ala Ala Phe Arg Ala Thr Met Cys Gly Val Phe Pro
        115                 120                 125

Leu Ser Pro Tyr Gly Lys Asp Asp Trp Gly Lys Gly Thr Leu Val Thr
    130                 135                 140

Val Ser Ser Gly Gly Gly Gly Ser Gly Gly Gly Gly Ser Gly Gly Gly
145                 150                 155                 160

Gly Ser Gln Val Gln Leu Val Glu Ser Gly Gly Gly Leu Val Gln Pro
                165                 170                 175

Gly Gly Ser Leu Arg Leu Ser Cys Glu Ala Ser Gly Phe Thr Leu Asp
            180                 185                 190

Tyr Tyr Gly Ile Gly Trp Phe Arg Gln Pro Pro Gly Lys Glu Arg Glu
        195                 200                 205

Ala Val Ser Tyr Ile Ser Ala Ser Ala Arg Thr Ile Leu Tyr Ala Asp
    210                 215                 220
```

Ser Val Lys Gly Arg Phe Thr Ile Ser Arg Asp Asn Ala Lys Asn Ala
225                 230                 235                 240

Val Tyr Leu Gln Met Asn Ser Leu Lys Arg Glu Asp Thr Ala Val Tyr
            245                 250                 255

Tyr Cys Ala Arg Arg Arg Phe Ser Ala Ser Ser Val Asn Arg Trp Leu
        260                 265                 270

Ala Asp Asp Tyr Asp Val Trp Gly Arg Gly Thr Gln Val Ala Val Ser
    275                 280                 285

Ser Gly Gly Gly Ser Gly Gly Ser Gly Gly Gly Ser Gly Gly Gly
290                 295                 300

Ser Gln Leu Gln Leu Val Glu Thr Gly Gly Leu Val Gln Pro Gly
305                 310                 315                 320

Gly Ser Leu Arg Leu Ser Cys Ala Ala Ser Gly Phe Thr Phe Ser Asp
            325                 330                 335

Tyr Val Met Thr Trp Val Arg Gln Ala Pro Gly Lys Gly Pro Glu Trp
        340                 345                 350

Ile Ala Thr Ile Asn Thr Asp Gly Ser Thr Met Arg Asp Asp Ser Thr
    355                 360                 365

Lys Gly Arg Phe Thr Ile Ser Arg Asp Asn Ala Lys Asn Thr Leu Tyr
370                 375                 380

Leu Gln Met Asn Ser Leu Lys Pro Glu Asp Thr Ala Leu Tyr Tyr Cys
385                 390                 395                 400

Ala Arg Gly Arg Val Ile Ser Ala Ser Ala Ile Arg Gly Ala Val Arg
            405                 410                 415

Gly Pro Gly Thr Gln Val Thr Val Ser Ser Gly Gly Gly Ser Gly
        420                 425                 430

Gly Gly Gly Ser Gly Gly Gly Ser Gln Val Gln Leu Val Glu Ser
    435                 440                 445

Gly Gly Gly Leu Val Gln Thr Gly Gly Ser Leu Arg Leu Ser Cys Ala
    450                 455                 460

Ser Ser Gly Ser Ile Ala Gly Phe Glu Thr Val Thr Trp Ser Arg Gln
465                 470                 475                 480

Ala Pro Gly Lys Ser Leu Gln Trp Val Ala Ser Met Thr Lys Thr Asn
            485                 490                 495

Asn Glu Ile Tyr Ser Asp Ser Val Lys Gly Arg Phe Ile Ile Ser Arg
        500                 505                 510

Asp Asn Ala Lys Asn Thr Val Tyr Leu Gln Met Asn Ser Leu Lys Pro
    515                 520                 525

Glu Asp Thr Gly Val Tyr Phe Cys Lys Gly Pro Glu Leu Arg Gly Gln
    530                 535                 540

Gly Ile Gln Val Thr Val Ser Ser Val Asp Ala Ala Ser
545                 550                 555

<210> SEQ ID NO 110
<211> LENGTH: 1674
<212> TYPE: DNA
<213> ORGANISM: Artificial Sequence
<220> FEATURE:
<223> OTHER INFORMATION: Polynucleotide sequence encoding ABAB binding
      protein expressed from chromosomal integration

<400> SEQUENCE: 110
atgagatttc cttcaattt tactgctgtt ttattcgcag catcctccgc attagctatg       60
caagtacaat tggttgaaac cggtggtggt ttagttcaac caggtggtag tttgagatta      120
tcttgtgctg catcaggttt tacattggat tattcttcaa taggttggtt cagacaagct      180

```
cctggtaaag aaagagaagg tgtttcttgc atatccagtt ctggtgactc aactaaatat    240
gctgactccg ttaagggtag attcactact tcaagagata cgctaaaaa tacagtctac    300
ttgcaaatga actcattaaa gccagatgac acagcagtct attactgtgc cgcttttaga    360
gccaccatgt gcggtgtatt cccattgtct ccttacggta agatgactg gggtaaaggt    420
actttagtta ctgtctcatc cggtggtggt ggttccggtg gtggtggtag tggtggtggt    480
ggttctcaag ttcaattagt agaatccggt ggtggtttag tccaacctgg tggtagttta    540
agattatcct gcgaagcaag tggttttaca ttagattatt acggtatcgg ttggtttaga    600
caaccacctg gtaaagaaag agaagctgtc tcttatattt ccgctagtgc aagaactata    660
ttgtacgcag attctgtaaa gggtagattc acaatttcaa gagacaatgc caagaacgct    720
gtttatttgc aaatgaactc tttgaagaga aagacaccg cagtttatta ctgtgccaga    780
agaagatttt ctgcttcttc agtcaacaga tggttagcag acgattatga tgtttgggt    840
agaggtacac aagtcgccgt aagttctggt ggtggttccg gtggtggtag tggtggtggt    900
tctggtggtg gttcacagct gcagctggtg agaccgggg gaggcttagt tcagcctggg    960
gggtccctga ctctcctg tgcagcctct ggattcacct tcagtgacta cgtgatgacc   1020
tgggtccgcc aagctccagg gaaggggcct gagtggatcg caactattaa tactgatggg   1080
agcacaatgc gcgacgactc cacaaagggc cggttcacca tctccagaga caacgccaag   1140
aacactctgt atctgcaaat gaacagtctg aaacccgagg acactgctct gtattactgt   1200
gcaagaggcc gggtgatctc tgcttccgct atcagaggcg cagtcagagg ccctggaacc   1260
caggtcaccg tctcgagcgg tggcggcggt agtggcggcg gcggttctgg cggtggtggt   1320
tcacaagtcc aattggtaga atctggtggt ggtttagttc aaactggtgg ttcattgaga   1380
ttatcctgcg cttccagtgg ttccattgca ggtttcgaaa ctgttacatg gtcaagacaa   1440
gctccaggta atctttgca atgggtcgcc tcaatgacca agactaacaa cgaaatctat   1500
tctgattcag ttaagggtag attcattatt tcaagagata atgctaaaaa caccgtttat   1560
ttgcaaatga actcattgaa gccagaagat actggtgttt acttctgcaa gggtcctgaa   1620
ttaagaggtc aaggtattca agtaacagtt tcttcagtcg acgcggctag ctaa         1674
```

<210> SEQ ID NO 111
<211> LENGTH: 549
<212> TYPE: PRT
<213> ORGANISM: Artificial Sequence
<220> FEATURE:
<223> OTHER INFORMATION: ABA binding agent

<400> SEQUENCE: 111

Gln Val Gln Leu Val Glu Thr Gly Gly Leu Val Gln Pro Gly Gly Ser
1               5                   10                  15

Leu Arg Leu Ser Cys Ala Ala Ser Gly Phe Thr Leu Asp Tyr Ser Ser
            20                  25                  30

Ile Gly Trp Phe Arg Gln Ala Pro Gly Lys Glu Arg Glu Gly Val Ser
        35                  40                  45

Cys Ile Ser Ser Gly Asp Ser Thr Lys Tyr Ala Asp Ser Val Lys
    50                  55                  60

Gly Arg Phe Thr Thr Ser Arg Asp Asn Ala Lys Asn Thr Val Tyr Leu
65                  70                  75                  80

Gln Met Asn Ser Leu Lys Pro Asp Asp Thr Ala Val Tyr Tyr Cys Ala
                85                  90                  95

```
Ala Phe Arg Ala Thr Met Cys Gly Val Phe Pro Leu Ser Pro Tyr Gly
                100                 105                 110

Lys Asp Asp Trp Gly Lys Gly Thr Leu Val Thr Val Ser Ser Glu Pro
            115                 120                 125

Lys Thr Pro Lys Pro Gln Pro Thr Ser Gly Gly Gly Ser Gly Gly
130                 135                 140

Gly Gly Ser Gly Gly Gly Ser Gln Val Gln Leu Val Glu Ser Gly
145                 150                 155                 160

Gly Gly Leu Val Gln Thr Gly Gly Ser Leu Arg Leu Ser Cys Ala Ser
                165                 170                 175

Ser Gly Ser Ile Ala Gly Phe Glu Thr Val Thr Trp Ser Arg Gln Ala
                180                 185                 190

Pro Gly Lys Ser Leu Gln Trp Val Ala Ser Met Thr Lys Thr Asn Asn
                195                 200                 205

Glu Ile Tyr Ser Asp Ser Val Lys Gly Arg Phe Ile Ile Ser Arg Asp
    210                 215                 220

Asn Ala Lys Asn Thr Val Tyr Leu Gln Met Asn Ser Leu Lys Pro Glu
225                 230                 235                 240

Asp Thr Gly Val Tyr Phe Cys Lys Gly Pro Glu Leu Arg Gly Gln Gly
                245                 250                 255

Ile Gln Val Thr Val Ser Ser Glu Pro Lys Thr Pro Lys Pro Gln Thr
                260                 265                 270

Ser Ala Ile Ala Gly Gly Gly Ser Gly Gly Gly Ser Gly Gly
                275                 280                 285

Gly Gly Ser Leu Gln Ala Met Ala Ala Ala Ser Gln Val Gln Leu Val
290                 295                 300

Glu Ser Gly Gly Gly Leu Val Gln Thr Gly Gly Ser Leu Arg Leu Ser
305                 310                 315                 320

Cys Ala Ser Ser Gly Ser Ile Ala Gly Phe Glu Thr Val Thr Trp Ser
                325                 330                 335

Arg Gln Ala Pro Gly Lys Ser Leu Gln Trp Val Ala Ser Met Thr Lys
                340                 345                 350

Thr Asn Asn Glu Ile Tyr Ser Asp Ser Val Lys Gly Arg Phe Ile Ile
                355                 360                 365

Ser Arg Asp Asn Ala Lys Asn Thr Val Tyr Leu Gln Met Asn Ser Leu
370                 375                 380

Lys Pro Glu Asp Thr Gly Val Tyr Phe Cys Lys Gly Pro Glu Leu Arg
385                 390                 395                 400

Gly Gln Gly Ile Gln Val Thr Val Ser Ser Gly Gly Gly Gly Ser Gly
                405                 410                 415

Gly Gly Gly Ser Gly Gly Gly Gly Ser Trp Ala Ala Gln Leu Gln Leu
                420                 425                 430

Val Glu Thr Gly Gly Gly Leu Val Gln Pro Gly Gly Ser Leu Arg Leu
                435                 440                 445

Ser Cys Ala Ala Ser Gly Phe Thr Phe Ser Asp Tyr Val Met Thr Trp
450                 455                 460

Val Arg Gln Ala Pro Gly Lys Gly Pro Glu Trp Ile Ala Thr Ile Asn
465                 470                 475                 480

Thr Asp Gly Ser Thr Met Arg Asp Ser Thr Lys Gly Arg Phe Thr
                485                 490                 495

Ile Ser Arg Asp Asn Ala Lys Asn Thr Leu Tyr Leu Gln Met Thr Ser
                500                 505                 510
```

-continued

```
Leu Lys Pro Glu Asp Thr Ala Leu Tyr Tyr Cys Ala Arg Gly Arg Val
        515                 520                 525

Ile Ser Ala Ser Ala Ile Arg Gly Ala Val Arg Gly Pro Gly Thr Gln
    530                 535                 540

Val Thr Val Ser Ser
545
```

YEAST-BASED IMMUNOTHERAPY AGAINST CLOSTRIDIUM DIFFICILE INFECTION

STATEMENT OF FEDERALLY SPONSORED RESEARCH AND DEVELOPMENT

This invention was made with government support under Grant Numbers DK084509 and AI109776 awarded by the National Institutes of Health. The government has certain rights in the invention.

SEQUENCE LISTING

A sequence listing in electronic (ASCII text file) format is filed with this application and incorporated herein by reference. The name of the ASCII file is "2016_1343A_ST25.txt"; the file was created on Oct. 13, 2016; the size of the file is 407 KB.

BACKGROUND

The bacterium *Clostridium difficile* is the most common cause of nosocomial antibiotic-associated diarrhea as well as the etiologic agent of pseudomembranous colitis [1]. It is estimated that over 500,000 cases of *C. difficile*-associated disease (CDI) occur annually in the United States, with the annual mortality rate ranging from about 3-17%, depending on the strains. With the emergence of hypervirulent and antibiotic-resistant strains, the incidence of mortality in CDI patients is increasing rapidly [2].

CDI is mainly caused by the two *C. difficile* exotoxins TcdA and TcdB (as TcdA-TcdB-strains are avirulent) [21, 22]. The two toxins are structurally similar and exhibit a similar mode of action on host cells. Both toxins target host Rho GTPases, leading to their inactivation as well as cytoskeleton disorganization. The relative roles of the two toxins in the pathogenesis of CDI are not well understood, but it is clear that either toxin individually can cause CDI in animals [22,23].

The options for treating CDI patients are limited and the recurrence rate is high (20-35% of patients). Current standard treatment for CDI using antibiotics causes the disruption of microflora and results in a relapse rate approaching 35% [3,13]. While other interventions have been tried (e.g., probiotics, toxin-absorbing polymers, and toxoid vaccines), neither prevention nor treatment strategies have kept up with the increased incidence and severity of this infection. The risk of further episodes of CDI in recurrent patients can be more than 50% [14] and a subset of patients will have multiple recurrences. Recurrent CDI can be caused by the same strain or newly colonizing strains [15-18].

Newer immune-based therapies have been shown to be somewhat effective in clinical trials, including intravenous immunoglobulin (IVIG) against severe CDI [4-8] and human monoclonal antibodies against recurrent CDI [9]. Fidaxomicin, a narrow spectrum macrocyclic antibiotic, showed an effect similar to oral vancomycin on CDI but was significantly better at lowering the relapse rate [10]. Fecal transplantation is effective against refractory and recurrent CDI, but it is difficult to standardize and it is associated with risks [11,12].

CDI is a frustrating condition that is difficult to treat and may affect patients for months or even years, causing tremendous morbidity and mortality [19]. Accordingly, there is a need for new treatments for CDI, and means for preventing both primary and recurrent CDI in subjects at risk of developing CDI.

BRIEF SUMMARY OF INVENTION

Provided herein are antibody-based fusion protein binding agents that selectively bind *C. difficile* virulence factors TcdA and TcdB, and strains of the probiotic yeast *Saccharomyces* genetically engineered to express and secrete these *C. difficile* toxin binding agents. Both the yeast and the binding agents show utility in treating and preventing primary and recurrent CDI in a subject. Orally administered *Saccharomyces* secreting the binding agents in host intestines can relieve ongoing CDI and prevent recurrence.

The present invention is thus directed to *C. difficile* toxin binding agents, strains of *Saccharomyces* including, but not limited to, *Saccharomyces boulardii* engineered to produce the binding agents, methods of making the engineered strains of yeast, and methods of treating and preventing primary and recurrent CDI using the binding agents and the engineered strains of yeast, among other important features.

Binding Agents

The binding agents of the present invention include simple $V_HH$ peptide monomers and linked groups of $V_HH$ peptide monomers (comprising 2, 3, 4, or more monomers), as well as more complex binding agents that comprise $V_HH$ peptide monomers joined to antibody Fc domains, as well as $V_HH$ peptide monomers joined to partial or full IgG antibodies.

In a first embodiment, the present invention is directed to binding agents comprising $V_HH$ peptide monomers and linked groups of $V_HH$ peptide monomers comprising two, three, four, or more monomers, each of which binds TcdA and/or TcdB, preferably with specificity. Thus, the invention encompasses $V_HH$ peptide binding agents comprising at least one $V_HH$ peptide monomer, wherein each $V_HH$ peptide monomer has binding specificity for an epitope of *C. difficile* toxin A (TcdA) or toxin B (TcdB). In certain aspects, these binding agents comprise two, three, four, or more linked $V_HH$ peptide monomers. The $V_HH$ peptide monomers include, but are not limited to, the $V_HH$ peptide monomers 5D (SEQ ID NO:1), E3 (SEQ ID NO:3), AA6 (SEQ ID NO:5), and AH3 (SEQ ID NO:7).

In aspects of this embodiment where two or more monomer are linked, the monomers may be linked by flexible peptide linkers, generally comprising between 10 and 20 amino acids. Suitable linkers include, but are not limited to, linker-1 (SEQ ID NO:9), linker-2 (SEQ ID NO:11), and linker-3 (SEQ ID NO:13).

In certain aspects of this embodiment, the binding agents bind to TcdA and/or TcdB with specificity. In certain aspects of this embodiment, the binding agents exhibit TcdA and/or TcdB neutralizing activity.

In a specific aspect of this embodiment, the binding agent comprises four linked $V_HH$ peptide monomers where two of the monomers have binding specificity for epitopes of TcdA and two of the monomers have binding specificity for epitopes of TcdB. The epitopes of TcdA may be the same or different. The epitopes of TcdB may be the same or different.

In a specific aspect of this embodiment, the binding agent comprises the amino acid sequence set forth in SEQ ID NO:19 or a sequence variant thereof having at least 95% sequence identity thereto, and wherein the sequence variant retains TcdA and/or TcdB binding specificity, or the sequence variant retains toxin neutralizing activity, or both.

In some instances, variant amino acids of the sequence variant are located in framework regions of the V$_H$H peptide monomers.

In a second embodiment, the invention is directed to binding agents comprising V$_H$H peptide monomers joined to IgG antibodies, where the binding agents bind TcdA and/or TcdB. In these IgG-based binding agents, the variable regions of the light and heavy chains of IgG antibodies are replaced by one, two, three, four or more of the V$_H$H peptide monomers.

In certain aspects of this embodiment, these binding agents comprise two, three, four, or more linked V$_H$H peptide monomers joined to the amino termini of IgG light and heavy chains in place of the variable regions. The V$_H$H peptide monomers include, but are not limited to, the V$_H$H peptide monomers 5D (SEQ ID NO:1), E3 (SEQ ID NO:3), AA6 (SEQ ID NO:5), and AH3 (SEQ ID NO:7).

In aspects of this embodiment where two or more monomer are linked, the monomers may be linked by flexible peptide linkers, generally comprising between 10 and 20 amino acids. Suitable linkers include, but are not limited to, linker-1 (SEQ ID NO:9), linker-2 (SEQ ID NO:11), and linker-3 (SEQ ID NO:13).

In a first sub-embodiment, the invention is directed to tetra-specific, octameric binding agents comprising an IgG antibody, two sets of linked first and second V$_H$H peptide monomers, and two sets of linked third and fourth V$_H$H peptide monomers, wherein the IgG antibody comprises two arms, each arm comprising a heavy chain lacking a variable region and a light chain lacking a variable region, and each chain having an amino terminus, wherein for each arm of the antibody, one set of linked first and second V$_H$H peptide monomers is joined to the amino terminus of the light chain, and one set of linked third and fourth V$_H$H peptide monomers is joined to the amino terminus of the heavy chain, and wherein the V$_H$H peptide monomers have binding specificity for an epitope of *Clostridium difficile* toxin A (TcdA) or toxin B (TcdB). This binding agent is termed "tetra-specific" as it recognizes four different toxin epitopes. It is termed "octameric" as it bears eight V$_H$H peptide monomers (two copies of the first monomer, two copies of the second monomer, two copies of the third monomer, and two copies of the fourth monomer).

In this sub-embodiment, the first, second, third and fourth V$_H$H peptide monomers each has binding specificity for a different epitope.

In certain aspects of this sub-embodiment, two of the V$_H$H peptide monomers have binding specificity for epitopes of TcdA and two of the V$_H$H peptide monomers have binding specificity for epitopes of TcdB.

In certain aspects of this sub-embodiment, the V$_H$H peptide monomers independently have binding specificity for an epitope in the glucosyltransferase domain, cysteine protease domain, translocation domain or receptor binding domain of TcdA or TcdB.

In a specific aspect of this sub-embodiment, the light (kappa) chain of the binding agent comprises the amino acid sequence set forth in SEQ ID NO:46 (AA6/E3 kappa) or a sequence variant having at least 95% sequence identity thereto, and the heavy chain of the binding agent comprises the amino acid sequence set forth in SEQ ID NO:44 (AH3/5D heavy) or a sequence variant having at least 95% sequence identity thereto. As this binding agent is an IgG-based binding agent, it will be clear to the skilled artisan that two heavy chain polypeptides and two light chain polypeptides, having the noted amino acid sequences, will assemble through disulfide bonding to provide the complete binding agent. The sequence variants retain TcdA and/or TcdB binding specificity, or the sequence variants retain toxin-neutralizing activity, or both. The variant amino acids of the sequence variants may be located in framework regions of the V$_H$H peptide monomers.

In a second sub-embodiment, the invention is directed to bi-specific or tetra-specific, tetrameric binding agents comprising an IgG antibody and first, second, third and fourth V$_H$H peptide monomers, wherein the IgG antibody comprises two arms, each arm comprising a heavy chain lacking a variable region and a light chain lacking a variable region, and each chain having an amino terminus, wherein for a first arm of the antibody, the first V$_H$H peptide monomer is joined to the amino terminus of the light chain, and the second V$_H$H peptide monomer is joined to the amino terminus of the heavy chain, wherein for a second arm of the antibody, the third V$_H$H peptide monomer is joined to the amino terminus of the light chain, and the fourth V$_H$H peptide monomer is joined to the amino terminus of the heavy chain, and wherein the V$_H$H peptide monomers have binding specificity for an epitope of *Clostridium difficile* toxin A (TcdA) or toxin B (TcdB). When the binding agent is "tetra-specific", it recognizes four different toxin epitopes; when "bi-specific" it recognizes two different toxin epitopes. The binding agents are "tetrameric" as they bear four V$_H$H peptide monomers (when bi-specific, the first and third monomer have the same sequence and bind the same epitope, and the second and fourth monomers have the same sequence and bind the same epitope; when tetra-specific, each of the monomers has a different sequence and binds a different epitope).

When the binding agent is bi-specific, the first and second monomers have binding specificity for different epitopes, the first and third monomers have identical amino acid sequences, and the second and fourth monomers have identical amino acid sequences. One of the V$_H$H peptide monomers may have binding specificity for an epitope of TcdA and one of the V$_H$H peptide monomers may have binding specificity for an epitope of TcdB.

When the binding agent is tetra-specific, each of the V$_H$H peptide monomers has binding specificity for a different epitope. Two of the V$_H$H peptide monomers may have binding specificity for epitopes of TcdA and two of the V$_H$H peptide monomers may have binding specificity for epitopes of TcdB.

In certain aspects of this sub-embodiment, each of the V$_H$H peptide monomers has binding specificity for epitopes of TcdA.

In certain aspects of this sub-embodiment, each of the V$_H$H peptide monomers has binding specificity for epitopes of TcdB.

In certain aspects of this sub-embodiment, the V$_H$H peptide monomers independently have binding specificity for an epitope in the glucosyltransferase domain, cysteine protease domain, translocation domain or receptor binding domain of TcdA or TcdB.

In a specific aspect of this sub-embodiment, the light (kappa) chain of the binding agent comprises the amino acid sequence set forth in SEQ ID NO:40 (AA6 kappa) or a sequence variant having at least 95% sequence identity thereto, and the heavy chain of the binding agent comprises the amino acid sequence set forth in SEQ ID NO:36 (AH3 heavy) or a sequence variant having at least 95% sequence identity thereto. As this binding agent is an IgG-based binding agent, it will be clear to the skilled artisan that two heavy chain polypeptides and two light chain polypeptides, having the noted amino acid sequences, will assemble through disulfide bonding to provide the complete binding agent. The sequence variants retain TcdA and/or TcdB binding specificity, or the sequence variants retain toxin neutralizing activity, or both. The variant amino acids of the sequence variant may be located in framework regions of the $V_HH$ peptide monomers.

In another specific aspect of this sub-embodiment, the light (kappa) chain of the binding agent comprises the amino acid sequence set forth in SEQ ID NO:42 (E3 kappa) or a sequence variant having at least 95% sequence identity thereto, and the heavy chain of the binding agent comprises the amino acid sequence set forth in SEQ ID NO:38 (5D heavy) or a sequence variant having at least 95% sequence identity thereto. As this binding agent is an IgG-based binding agent, it will be clear to the skilled artisan that two heavy chain polypeptides and two light chain polypeptides, having the noted amino acid sequences, will assemble through disulfide bonding to provide the complete binding agent. The sequence variants retain TcdA and/or TcdB binding specificity, or the sequence variants retain toxin neutralizing activity, or both. The variant amino acids of the sequence variants may be located in framework regions of the $V_HH$ peptide monomers.

In certain aspects of this embodiment and the sub-embodiments, the binding agents bind to TcdA and/or TcdB with specificity. In certain aspects of this embodiment, the binding agents exhibit TcdA and/or TcdB neutralizing activity.

In a third embodiment, the invention is directed to binding agents comprising $V_HH$ peptide monomers joined to antibody Fc domains, where the binding agents bind TcdA and/or TcdB. In these Fc domain-based binding agents, one, two, three, four or more of the $V_HH$ peptide monomers are joined to the hinge, $C_H2$ and $C_H3$ regions of each arm of Fc domain of an antibody heavy chain. Thus, the peptide monomers replace the Fab regions of an antibody.

In certain aspects of this embodiment, these binding agents comprise two, three, four, or more linked $V_HH$ peptide monomers joined to the amino termini of the arms of the Fc domains. The $V_HH$ peptide monomers include, but are not limited to, the $V_HH$ peptide monomers 5D (SEQ ID NO:1), E3 (SEQ ID NO:3), AA6 (SEQ ID NO:5) and AH3 (SEQ ID NO:7).

In aspects of this embodiment where two or more monomer are linked, the monomers may be linked by flexible peptide linkers, generally comprising between 10 and 20 amino acids. Suitable linkers include, but are not limited to, linker-1 (SEQ ID NO:9), linker-2 (SEQ ID NO:11), and linker-3 (SEQ ID NO:13).

In a first sub-embodiment, the invention is directed to tetra-specific, octameric binding agents comprising an antibody Fc domain and two sets of linked first, second, third and fourth $V_HH$ peptide monomers, wherein the antibody Fc domain comprises two arms, each arm comprising hinge, $C_H2$ and $C_H3$ regions of an antibody heavy chain, and each arm having an amino terminus, wherein for each arm of the Fc domain, one set of linked first, second, third and fourth $V_HH$ peptide monomers is joined to the amino terminus of the arm, and where the $V_HH$ peptide monomers have binding specificity for an epitope of *Clostridium difficile* toxin A (TcdA) or toxin B (TcdB). This binding agent is termed "tetra-specific" as it recognizes four different toxin epitopes. It is termed "octameric" as it bears eight $V_HH$ peptide monomers (two copies of the first monomer, two copies of the second monomer, two copies of the third monomer, and two copies of the fourth monomer).

In certain aspects of this sub-embodiment, the first, second, third and fourth $V_HH$ peptide monomers each has binding specificity for a different epitope.

In certain aspects of this sub-embodiment, two of the $V_HH$ peptide monomers have binding specificity for epitopes of TcdA and two of the $V_HH$ peptide monomers have binding specificity for epitopes of TcdB.

In certain aspects of this sub-embodiment, the $V_HH$ peptide monomers independently have binding specificity for an epitope in the glucosyltransferase domain, cysteine protease domain, translocation domain or receptor binding domain of TcdA or TcdB.

In a specific aspect of this sub-embodiment, the binding agent comprises the amino acid sequence set forth in SEQ ID NO:22 (ABAB-Fc) or a sequence variant having at least 95% sequence identity thereto, where the sequence variant retains TcdA and/or TcdB binding specificity, or the sequence variant retains toxin neutralizing activity, or both. As this binding agent is an Fc domain-based binding agent, it will be clear to the skilled artisan that two identical polypeptides, having the noted amino acid sequence, serve as the arms of the binding agent and that the arms will assemble through disulfide bonding to provide the complete binding agent. The variant amino acids of the sequence variant may be located in framework regions of the $V_HH$ peptide monomers.

In a second sub-embodiment, the invention is directed to bi-specific, tetrameric binding agents comprising an antibody Fc domain and two sets of linked first and second $V_HH$ peptide monomers, wherein the antibody Fc domain comprises two arms, each arm comprising hinge, $C_H2$ and $C_H3$ regions of an antibody heavy chain, and each arm having an amino terminus, wherein for each arm of the Fc domain, one set of linked first and second $V_HH$ peptide monomers is joined to the amino terminus of the arm, and where the $V_HH$ peptide monomers have binding specificity for an epitope of *Clostridium difficile* toxin A (TcdA) or toxin B (TcdB). This binding agent is termed "bi-specific" as it recognizes two different toxin epitopes. It is termed "tetrameric" as it bears four $V_HH$ peptide monomers (two copies of the first monomer, and two copies of the second monomer).

In certain aspects of this sub-embodiment, the first and second $V_HH$ peptide monomers have binding specificity for the same or different epitopes.

In certain aspects of this sub-embodiment, the $V_HH$ peptide monomers independently have binding specificity for an epitope in the glucosyltransferase domain, cysteine protease domain, translocation domain or receptor binding domain of TcdA or TcdB.

In a specific aspect of this sub-embodiment, the binding agent comprises the amino acid sequence set forth in SEQ ID NO:32 (AH3/5D-Fc) or a sequence variant having at least 95% sequence identity thereto, where the sequence variant retains TcdA and/or TcdB binding specificity, or the sequence variant retains toxin neutralizing activity, or both. As this binding agent is an Fc domain-based binding agent, it will be clear to the skilled artisan that two identical polypeptides, having the noted amino acid sequence, serve as the arms of the binding agent and that the arms will assemble through disulfide bonding to provide the complete binding agent. The variant amino acids of the sequence variant may be located in framework regions of the $V_HH$ peptide monomers.

In another specific aspect of this sub-embodiment, the binding agent comprises the amino acid sequence set forth in SEQ ID NO:34 (AA6/E3-Fc) or a sequence variant having at least 95% sequence identity thereto, where the sequence variant retains TcdA and/or TcdB binding specificity, or the sequence variant retains toxin neutralizing activity, or both. As this binding agent is an Fc domain-based binding agent, it will be clear to the skilled artisan that two identical polypeptides, having the noted amino acid sequence, serve as the arms of the binding agent and that the arms will assemble through disulfide bonding to provide the complete binding agent. The variant amino acids of the sequence variant may be located in framework regions of the $V_HH$ peptide monomers.

In certain aspects of this embodiment and the sub-embodiments, the binding agents bind to TcdA and/or TcdB with specificity. In certain aspects of this embodiment, the binding agents exhibit TcdA and/or TcdB neutralizing activity.

The invention includes humanized variants of each the binding agents provided in the various embodiments and aspects defined herein. Likewise, the invention includes epitope binding fragments of each the binding agents provided in the various embodiments and aspects defined herein.

Polynucleotides, Expression Vectors, and Host Cells

The invention includes polynucleotides comprising nucleotide sequences encoding each the binding agents provided in the various embodiments and aspects defined herein, as well as complementary strands thereof. The invention also includes expression vectors (e.g., bacterial and yeast) comprising the polynucleotides, and host cells (e.g., bacterial, yeast, mammalian, insect) comprising the expression vectors. The invention further includes methods of producing the binding agents define herein, comprising culturing the host cells under conditions promoting expression of the binding agents encoded by the expression vectors, and recovering the binding agents from the cell cultures.

Engineered Strains of S. boulardii

In a fourth embodiment, the invention is directed to strains of Saccharomyces yeast, such as S. cerevisiae and S. boulardii, engineered to produce one or more of the binding agents defined herein. In preferred aspects, the engineered strains of Saccharomyces yeast secrete the binding agents.

The identity of the Saccharomyces yeast strain is only limited in that it can be engineered to produce, and preferably secrete, one or more of the binding agents of the invention. In preferred aspects of the invention, the strain of Saccharomyces yeast engineered to produce one or more of the binding agents is S. cerevisiae or S. boulardii. The invention thus encompasses an engineered strain of S. cerevisiae that produces one or more of the binding agents defined herein, as well as an engineered strain of S. cerevisiae that secretes one or more of the binding agents defined herein. The invention also encompasses an engineered strain of S. boulardii that produces one or more of the binding agents defined herein, as well as an engineered strain of S. boulardii that secretes one or more of the binding agents defined herein.

In an example of this embodiment, the invention is directed to engineered strains of Saccharomyces yeast that produce a binding agent comprising a $V_HH$ peptide monomer or linked groups of $V_HH$ peptide monomers comprising two, three, four, or more monomers, each of which binds TcdA and/or TcdB, preferably with specificity. Thus, the invention encompasses engineered strains of Saccharomyces yeast that produces $V_HH$ peptide binding agents comprising at least one $V_HH$ peptide monomer, wherein each $V_HH$ peptide monomer has binding specificity for an epitope of C. difficile toxin A (TcdA) or toxin B (TcdB). In certain aspects, these binding agents comprise two, three, four, or more linked $V_HH$ peptide monomers. The $V_HH$ peptide monomers include, but are not limited to, the $V_HH$ peptide monomers 5D (SEQ ID NO:1), E3 (SEQ ID NO:3), AA6 (SEQ ID NO:5), and AH3 (SEQ ID NO:7).

In another example of this embodiment, the invention is directed to engineered strains of Saccharomyces yeast that produce binding agents comprising $V_HH$ peptide monomers joined to IgG antibodies, where the binding agents bind TcdA and/or TcdB, as defined herein. In these IgG-based binding agents, the variable regions of the light and heavy chains of IgG antibodies are replaced by one, two, three, four or more of the $V_HH$ peptide monomers.

In further example of this embodiment, the invention is directed to engineered strains of Saccharomyces yeast that produce binding agents comprising $V_HH$ peptide monomers joined to antibody Fc domains, where the binding agents bind TcdA and/or TcdB, as defined herein. In these Fc domain-based binding agents, one, two, three, four or more of the $V_HH$ peptide monomers are joined to the hinge, $C_H2$ and $C_H3$ regions of each arm of Fc domain of an antibody heavy chain. Thus, the peptide monomers replace the Fab regions of an antibody.

In yet another example of this embodiment, the invention is directed to an engineered strain of Saccharomyces yeast that produces a tetra-specific, tetrameric binding agent, wherein the binding agent comprises linked first, second, third and fourth $V_HH$ peptide monomers, and wherein the $V_HH$ peptide monomers independently have binding specificity for an epitope of Clostridium difficile toxin A (TcdA) or toxin B (TcdB). In certain aspects, the first, second, third and fourth $V_HH$ peptide monomers each has binding specificity for a different epitope. In certain aspects, the two of the $V_HH$ peptide monomers have binding specificity for epitopes of TcdA and two of the $V_HH$ peptide monomers have binding specificity for epitopes of TcdB. In certain aspects, the $V_HH$ peptide monomers independently have binding specificity for an epitope in the glucosyltransferase domain, cysteine protease domain, translocation domain or receptor binding domain of TcdA or TcdB.

In a preferred example of this embodiment, the invention is directed to an engineered strain of yeast, wherein the binding agent is ABAB, wherein the first and third monomers have binding specificity for epitopes of TcdA and the first and third monomers are $V_HH$ peptide monomers AH3 (SEQ ID NO:7) and AA6 (SEQ ID NO:5), respectively, and wherein the second and forth monomers have binding specificity for epitopes of TcdB and the second and forth monomers are $V_HH$ peptide monomers 5D (SEQ ID NO:1) and E3 (SEQ ID NO:3), respectively. In certain aspects, the ABAB binding agent comprises the amino acid sequence set forth in SEQ ID NO:19, or a sequence variant having at least 95% sequence identity thereto, wherein the sequence variant retains TcdA and/or TcdB binding specificity, or the sequence variant retains toxin neutralizing activity, or both. In certain aspects, the ABAB binding agent further comprises an N-terminal secretion signal selected from the AT secretion signal (MRFPSIFTAVLFAASSALA (SEQ ID NO:99)) and the IVS secretion signal (MLLQAFLFL-LAGFAAKISA (SEQ ID NO:103)).

In certain aspects, the ABAB binding agent is expressed from a plasmid within the yeast, wherein the ABAB binding agent comprises the amino acid sequence set forth in SEQ ID NO:107, or a sequence variant having at least 95% sequence identity thereto, and wherein the sequence variant retains TcdA and/or TcdB binding specificity, or the sequence variant retains toxin neutralizing activity, or both.

The plasmid may be, but is not limited to, pCEV-URA3-TEF-AT-yABAB-cMyc (SEQ ID NO:88).

In certain aspects, the ABAB binding agent coding sequence is integrated into a chromosome of the strain of yeast, wherein the ABAB binding agent comprises the amino acid sequence set forth in SEQ ID NO:109, or a sequence variant having at least 95% sequence identity thereto, and wherein the sequence variant retains TcdA and/or TcdB binding specificity, or the sequence variant retains toxin neutralizing activity, or both.

Aspects of this embodiment include engineered strains of *Saccharomyces* yeast that produce a therapeutic protein having binding specificity for a unique epitope of *Clostridium difficile* toxin A (TcdA) or toxin B (TcdB), or both. Preferably, the engineered strain of *Saccharomyces* yeast is *S. cerevisiae* or *S. boulardii*. A therapeutic protein is any protein that can bring about an improvement or cure in a medical condition in a subject, or that can inhibit or prevent a medical condition from developing in a subject. Suitable therapeutic protein include, but are not limited to, proteins that (a) replace a protein that is deficient or abnormal; (b) augment an existing pathway; (c) provide a novel function or activity; (d) interfere with a molecule or organism; and (e) deliver other compounds or proteins, such as a radionuclide, cytotoxic drug, or effector proteins. Therapeutic proteins also include antibodies and antibody-based drugs, Fc fusion proteins, anticoagulants, blood factors, bone morphogenetic proteins, engineered protein scaffolds, enzymes, growth factors, hormones, interferons, interleukins, and thrombolytics. Therapeutic proteins further include bispecific monoclonal antibodies (mAbs) and multispecific fusion proteins, mAbs conjugated with small molecule drugs, and proteins with optimized pharmacokinetics.

Methods of Making Engineered Strains of *S. boulardii*

The invention is also directed to methods of making strains of *Saccharomyces* yeast engineered to produce one or more of the binding agents defined herein.

The invention thus encompasses a method of preparing a strain of *Saccharomyces* yeast engineered to produce one or more of the binding agents defined herein comprising (a) transforming a strain of *Saccharomyces* yeast with an expression vector encoding the binding agent, and (b) screening the yeast of (a) for production of the binding agent. In a certain aspect, the expression vector is plasmid pCEV-URA3-TEF-AT-yABAB-cMyc (SEQ ID NO:88).

The invention thus encompasses a method of preparing a strain of *Saccharomyces* yeast engineered to produce one or more of the binding agents defined herein comprising (a) chromosomally integrating a polynucleotide sequence encoding the binding agent into the genome of the strain of *Saccharomyces* yeast, and (b) screening the yeast of (a) for production of the binding agent. In certain aspects, the chromosomal integration is performed via:

(a) amplifying a polynucleotide sequence encoding the ABAB binding agent from plasmid pCEV-G4-Km-TEF-AT-yABAB hAA6T83N-tagless (SEQ ID NO:90) using primers containing (i) nucleic acid sequence homologous to a selected yeast chromosomal integration site and (ii) nucleic acid sequence homologous to regions 5' and 3' of ABAB binding agent coding sequence of the plasmid, to produce an integration cassette, (b) transforming yeast with the integration cassette produced in (a) with pCRI-Sb-δ1 (SEQ ID NO:91) or pCRI-Sb-δ2 (SEQ ID NO:92) to induce a double stranded break within the corresponding yeast chromosomal delta sites under conditions promoting spontaneous integration of the integration cassette into the site of the double stranded break, (c) screening the transformed yeast of (b) for production of the ABAB binding agent.

In certain aspects of these methods, the strain of *Saccharomyces* yeast engineered to produce the binding agents is an auxotrophic strain of *Saccharomyces* yeast, such as a ura3-strain of yeast. A ura3-strain of yeast can be utilized under ura3 selection.

In certain aspects of these methods, the strain of *Saccharomyces* yeast engineered to produce the binding agents is *S. cerevisiae* or *S. boulardii*.

In certain aspects of these methods, the screening is performed using an immunoassay, such as an ELISA.

Pharmaceutical Formulations

The invention includes pharmaceutical formulations comprising one or more of the binding agents defined herein and a pharmaceutically acceptable carrier or diluent. The invention also includes pharmaceutical formulations comprising one or more of the engineered strains of *Saccharomyces* yeast defined herein and a pharmaceutically acceptable carrier or diluent. In certain aspects, the *Saccharomyces* yeast is *S. cerevisiae* or *S. boulardii*.

Methods of Treating and Preventing

In a sixth embodiment, the invention is directed to methods of treating or preventing a disease symptom induced by *C. difficile* in a subject comprising administering a therapeutically-effective amount of one or more binding agents and/or one or more engineered strains of *Saccharomyces* yeast as defined herein to a subject having *C. difficile* infection or a risk of developing *C. difficile* infection. In preferred aspects, the *Saccharomyces* yeast is *S. cerevisiae* or *S. boulardii*.

In certain aspects of this embodiment, the disease symptom induced by *C. difficile* is diarrhea.

In a seventh embodiment, the invention is directed to methods of neutralizing *C. difficile* toxin TcdA and/or TcdB in a subject infected by *C. difficile* comprising administering a therapeutically-effective amount of one or more binding agents and/or one or more engineered strains of *Saccharomyces* yeast as defined herein to a subject having *C. difficile* infection. In preferred aspects, the *Saccharomyces* yeast is *S. cerevisiae* or *S. boulardii*.

In an eighth embodiment, the invention is directed to methods of treating or preventing *C. difficile* infection in a subject comprising administering a therapeutically-effective amount of one or more of the binding agents and/or one or more engineered strains of *Saccharomyces* yeast as defined herein to a subject having *C. difficile* infection or a risk of developing *C. difficile* infection. In preferred aspects, the *Saccharomyces* yeast is *S. cerevisiae* or *S. boulardii*. In certain aspects of the eighth embodiment, the method further comprises administering a therapeutically-effective amount of an antibiotic to the subject.

In a ninth embodiment, the invention is directed to methods of maintaining normal bowel function in a subject having a *C. difficile* infection comprising administering a therapeutically-effective amount of one or more of the binding agents and/or one or more engineered strains of *Saccharomyces* yeast as defined herein to a subject having *C. difficile* infection or a risk of developing *C. difficile* infection. In preferred aspects, the *Saccharomyces* yeast is *S. cerevisiae* or *S. boulardii*. In certain aspects of the ninth embodiment, the method further comprises administering a therapeutically-effective amount of an antibiotic to the subject.

In certain aspects of the methods, the binding agent is in a pharmaceutical formulation comprising the binding agent and a pharmaceutically acceptable carrier or diluent.

In certain aspects of the methods, the therapeutically-effective amount of the binding agent is between 10 ug/kg and 100 mg/kg of the agent per body weight of the subject.

In certain aspects of the methods, the agent is administered to the subject orally, parenterally or rectally.

In certain aspects of the methods, the engineered strain of *Saccharomyces* yeast is in a pharmaceutical formulation comprising the engineered strain and a pharmaceutically acceptable carrier or diluent. In preferred aspects, the *Saccharomyces* yeast is *S. cerevisiae* or *S. boulardii*.

In certain aspects of the methods, the therapeutically-effective amount of the engineered strain of *Saccharomyces* yeast is between 10 ug/kg and 100 mg/kg of the engineered strain per body weight of the subject. In preferred aspects, the *Saccharomyces* yeast is *S. cerevisiae* or *S. boulardii*.

In certain aspects of the methods, the engineered strain of *Saccharomyces* yeast is administered to the subject orally, nasally or rectally. In preferred aspects, the *Saccharomyces* yeast is *S. cerevisiae* or *S. boulardii*.

The foregoing has outlined rather broadly the features and technical advantages of the present invention in order that the detailed description of the invention that follows may be better understood. Additional features and advantages of the invention will be described herein, which form the subject of the claims of the invention. It should be appreciated by those skilled in the art that any conception and specific embodiment disclosed herein may be readily utilized as a basis for modifying or designing other structures for carrying out the same purposes of the present invention. It should also be realized by those skilled in the art that such equivalent constructions do not depart from the spirit and scope of the invention as set forth in the appended claims. The novel features which are believed to be characteristic of the invention, both as to its organization and method of operation, together with further objects and advantages will be better understood from the following description when considered in connection with the accompanying figures. It is to be expressly understood, however, that any description, figure, example, etc. is provided for the purpose of illustration and description only and is by no means intended to define the limits of the invention.

BRIEF DESCRIPTION OF DRAWINGS

(FIG. 3C) Diagram of two heterodimers against TcdA or TcdB. $His_{(6)}$ tag on N-terminus facilitates purification; a flexible spacer (FS) separate the two $V_HH$s. (FIG. 3D) Dimer 5D/E3 increases its neutralizing activity at least 10-fold over a simple mix of the two $V_HH$s. Heterodimers fully protected mice from lethal ip challenge with TcdB (FIG. 3E) or TcdA (FIG. 3F).

FIGS. 9A-9B. Sandwich ELISA analysis of simultaneous binding of the tetraspecific antibody IgG-ABAB to both TcdA and TcdB. FIG. 9A shows serially diluted ABAB-IgG added to ELISA plates coated with TcdA (TxA), followed by TcdB (TxB). FIG. 9B shows serially diluted ABAB-IgG added to ELISA plates coated with TcdB (TxB), followed by TcdA (TxA).

(FIG. 13A) A diagram of toxins and antibodies setup in ELISA. (FIG. 13B) O.D. reading of various TcdA concentrations; 125 ng/ml of TcdA was chosen for subsequence ELISA.

(FIG. 14A) Neutralizing effect of secreted ABAB in *S. cerevisiae* culture supernatant. Sc: *S. cerevisiae* (BY4741); Sc-ABAB: *S. cerevisiae* (BY4741)—pD1214-FAKS-ABAB; r-ABAB: recombinant ABAB. ABAB in the supernatant of Sc-ABAB is able to fully protect cells from intoxication. ELISA O.D. readings of supernatants from individual Sc-ABAB clones (FIG. 14B).

(FIG. 15A) ABAB secretion measured by ELISA and normalized against cell density based on O.D. 600 in *S. cerevisiae*. Statistical significance was determined by Kruskal-Walls test followed by Dunn's Multiple comparison test. *p<0.05 **p<0.01 (FIG. 15B) ABAB secretion measured by ELISA and normalized against cell density based on O.D. 600 in *S. boulardii*. Statistical significance was determined by Mann Whitney test. ****p<0.0001.

(FIG. 17A) Growth comparison in YPD containing vancomycin (1 mg/ml) versus without. (FIG. 17B) ABAB stability in *S. boulardii* culture supernatant after 2 hours of incubation determined by ELISA. (FIG. 17C) Neutralizing activity of ABAB from the culture supernatant of *S. bou-*

*lardii* URA3Δ/Δ expressing ABAB. (FIG. 17D) ABAB detection in *S. boulardii* URA3Δ/Δ expressing ABAB culture supernatant by western blot. Enriched: ABAB contains c-Myc tag at the end of C-terminus and was further concentrated using α-c-Myc tag antibodies.

(FIG. 18A) Survival rate, (FIG. 18B) Weight loss, (FIG. 18C) Diarrhea incident, throughout the course of infection were recorded and presented. * significance as determined by Fisher's exact test with two tailed and 95% confidence interval; p value is 0.0108 for FIG. 18A and regular two-way ANOVA (not repeated measures) followed by Dunnett's multiple comparison test was used for FIG. 18B and FIG. 18C, *P≤0.05. "Sb: EP" is *S. boulardii* with the empty plasmid; "Sb: ABAB" is *S. boulardii* expressing ABAB.

(FIG. 19A) Survival rate, (FIG. 19B) Weight loss, (FIG. 19C) Diarrhea incident, throughout the course of infection were recorded and presented. * significance as determined by Fisher's exact test with two tailed and 95% confidence interval; p value is 0.0256 for FIG. 19A; regular two-way ANOVA (not repeated measures) followed by Dunnett's multiple comparison test for FIG. 19B and FIG. 19C. *P<0.05 P<0.01 **P<0.0001 for FIG. 19B and FIG. 19C. "Sb: EP" is *S. boulardii* with the empty plasmid; "Sb: ABAB" is *S. boulardii* expressing ABAB.

(FIG. 20A) Survival rate, (FIG. 20B) Weight loss, (FIG. 20C) Diarrhea incident, throughout the course of infection were recorded and presented. * significance as determined by Fisher's exact test with two tailed and 95% confidence interval; p value is 0.017 for FIG. 20A; regular two-way ANOVA (not repeated measures) followed by Dunnett's multiple comparison test for FIG. 20B and FIG. 20C. *P≤0.05 *P≤0.001 **P≤0.0001 for FIG. 20B and FIG. 20C. "Sb:EP" is *S. boulardii* with the empty plasmid; "Sb: ABAB" is *S. boulardii* expressing ABAB.

(FIG. 22A) ABAB secretion measured by ELISA. ITG: ABAB integration cassette. Low: CRISPR plasmid to ITG ratio at 2; High:CRISPR plasmid to ITG ratio at 0.25. (FIG. 22B) ABAB secretion amount comparison. M−/−$^{Cir0}$:pKC, M−/−$^{Cir+}$:ABAB, M−/−$^{Cir0}$:ABAB are plasmid based. Ch$^{Ins}$: single site target chromosomal integration of ABAB cassette through conventional homologous recombination. C$^{RISPR}$1-2:ABAB cassette integration at site I. C$^{RISPR}$3-4: ABAB cassette integration at site II.

(FIG. 23A) Survival rate, (FIG. 23B) Weight loss, (FIG. 23C) Diarrhea incident, throughout the course of infection were recorded and presented. * significance as determined by Fisher's exact test with two tailed and 95% confidence interval; p value is 0.0325 for (FIG. 23A); regular two-way ANOVA (not repeated measures) followed by Dunnett's multiple comparison test for FIG. 23B and FIG. 23C. *P<0.05 **P<0.01 for FIG. 23B and FIG. 23C.

DETAILED DESCRIPTION OF THE INVENTION

I. Definitions

Figure 1:
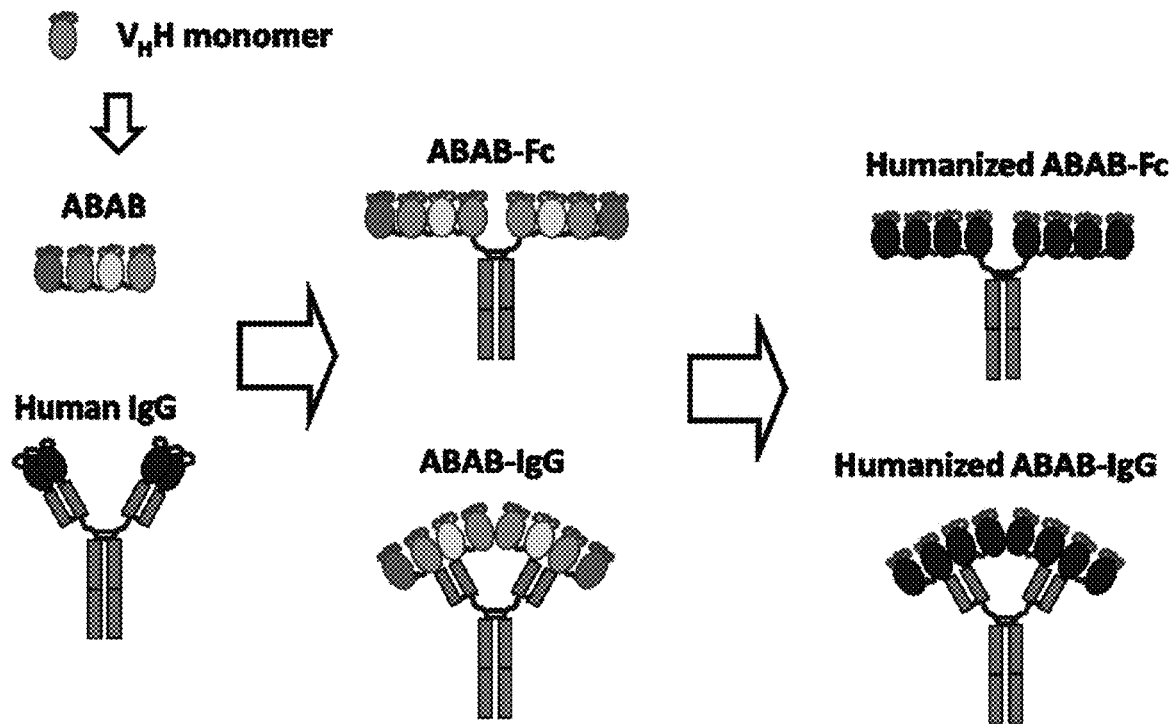
FIG. 1. Illustration of strategies for making binding agents of the invention.

Unless otherwise noted, technical terms are used according to conventional usage. Definitions of common terms in molecular biology may be found, for example, in Benjamin Lewin, Genes VII, published by Oxford University Press, 2000 (ISBN 019879276X); Kendrew et al. (eds.); The Encyclopedia of Molecular Biology, published by Blackwell Publishers, 1994 (ISBN 0632021829); and Robert A. Meyers (ed.), Molecular Biology and Biotechnology: a Comprehensive Desk Reference, published by Wiley, John & Sons, Inc., 1995 (ISBN 0471186341); and other similar technical references.

As used herein, "a" or "an" may mean one or more. As used herein when used in conjunction with the word "comprising," the words "a" or "an" may mean one or more than one. As used herein "another" may mean at least a second or more. Furthermore, unless otherwise required by context, singular terms include pluralities and plural terms include the singular.

As used herein, "about" refers to a numeric value, including, for example, whole numbers, fractions, and percentages, whether or not explicitly indicated. The term "about" generally refers to a range of numerical values (e.g., +/−5-10% of the recited value) that one of ordinary skill in the art would consider equivalent to the recited value (e.g., having the same function or result). In some instances, the term "about" may include numerical values that are rounded to the nearest significant figure.

II. The Present Invention

*C. difficile*-associated disease (CDI) is mainly caused by two large exotoxins, namely toxin A (TcdA) and toxin B (TcdB), produced by the bacteria. These toxins are structurally similar, large, single-chain proteins (TcdA is about 300 kD; TcdB is about 270 kD) that exhibit similar modes of action on host cells. Both toxins target host Rho GTPases, leading to enzyme inactivation, followed by cytoskeleton disorganization and apoptosis. In intestinal epithelial cells, TcdA catalyzes glucosylation of the Rho GTPases, leading to reorganization of the actin cytoskeleton with accompanying morphological changes such as complete rounding of cells and destruction of the intestinal barrier function. The toxins can individually cause CDI in animals, and TcdA$^-$TcdB$^-$ strains of the bacteria are avirulent.

Numerous independent studies have demonstrated that neutralizing antibodies against the toxins confer protection against CDI [24-33]. Because TcdA and TcdB are essential virulence factors for *C. difficile*, neutralizing antibodies produced against both toxins protect against toxigenic *C. difficile* infection in animal models [30-33]. In humans, high serum levels of antitoxin antibodies are associated with reduced disease severity and incidence of relapse [9,25,29].

Therefore, a preventative rationale for systemically and orally administered antitoxin antibodies exists. However, monoclonal antibodies targeting a single epitope are typically low affinity, and use of such antibodies runs the risk of inducing mutations within the epitopes of the toxins thereby creating additional strains. Thus, neutralizing antitoxins targeting multiple, key, and conserved toxin epitopes are highly desirable.

The present invention builds on existing knowledge regarding anti-TcdA and anti-TcdB antibodies for the treatment and prevention of CDI, and the symptoms of CDI. Provided herein are antibody-based, fusion protein binding agents derived from human and camelid immunoglobulins, optionally expressed by the probiotic yeast *Saccharomyces* strain in a subject. These binding agents recognize and bind with specificity to *C. difficile* TcdA and/or TcdB. Some of these binding agents exhibit toxin-neutralizing activity. These yeast-based immunotherapeutic can be used to treat or prevent primary and recurrent CDI, as well as the symptoms of primary and recurrent CDI. In preferred aspects, the *Saccharomyces* yeast is *S. cerevisiae* or *S. boulardii*.

As discussed in detail below, camelid animals (dromedary camels, Bactrian camels, wild Bactrian camels, llamas, alpacas, vicuñas, and guanacos) produce a class of functional immunoglobulins that lack light chains and are thus heavy chain-only antibodies (HCAbs) [34] with binding properties equivalent to those achieved by conventional IgG [35]. The $V_H$ domain of HCAbs, called $V_HH$, is similar to the conventional human $V_H$ domain but has unique sequence and structural characteristics [36]. DNA encoding this domain can be readily cloned and expressed in microbes to yield soluble protein monomers that retain the antigen-binding properties of the parent HCAb. These $V_HH$ peptide monomer binding agents are small (~15 kDa), easy to produce, and generally more stable than conventional antibody fragments [37-39]. $V_HH$s have being explored to treat intestinal diseases since they are relatively resistant to proteases and can be further engineered to enhance such properties [40]. They can also be produced as fusion proteins with human antibodies, such as IgG, and fragments of human antibodies, such as Fc domains.

The present invention utilizes the advantageous characteristics of HCAbs in the production of binding agents that can be used in the treatment and prevention of CDI. As disclosed herein, $V_HH$ peptide monomers were screened for TcdA and TcdB epitope recognition and binding. Those monomers that exhibited epitope binding and had toxin-neutralizing activity were linked to produce the binding agents of the invention. The binding agents include simple $V_HH$ peptide monomers and linked groups of $V_HH$ peptide monomers (comprising 2, 3, 4, or more monomers), as well as more complex binding agents that comprise $V_HH$ peptide monomers joined to antibody Fc domains, as well as $V_HH$ peptide monomers joined to IgG antibodies (see FIG. 1).

Further, *Saccharomyces boulardii*, a Generally Regarded as Safe (GRAS) organism by the FDA, is commonly available over-the-counter for use in promoting intestinal health and amelioration of gastrointestinal illness due to diarrheal diseases. This yeast strain has been studied in multiple randomized double-blinded placebo-controlled clinical trials for both safety and efficacy against intestinal diseases including CDI [42-46]. *S. boulardii* treatment significantly reduced CDI recurrence [44-46], and those recurrent patients had significantly less *S. boulardii* in stools than non-recurring patients [43]. The immune modulatory effects of *S. boulardii* that provide protection against *C. difficile* toxin-induced inflammation have been described [47-49]. In addition, *S. boulardii* may help in maintaining normal microbiota [50]; a recent clinical trial (NCT01473368) found that *S. boulardii* treatment can prevent some antibiotic-induced microbiome changes and, in parallel, can reduce antibiotic-associated diarrhea.

*S. cerevisiae* (commonly known as "brewer's yeast"), which is genetically related to *S. boulardii*, has been used successfully to express $V_HH$s with high yield [51]. *S. boulardii* is physiologically distinct from *S. cerevisiae*, although genome analysis has revealed that both genomes are remarkably similar at the nucleotide level [52,53]. Therefore, molecular genetic tools previously developed for use in *S. cerevisiae* are now being used with *S. boulardii* [54-56], making this probiotic a candidate for engineering as a therapeutic agent against CDI.

There are several additional metabolic characteristics which make *S. boulardii* ideal for use as an oral therapeutic agent. In contrast to *S. cerevisiae*, *S. boulardii* grows well at 37° C. and it is more resistant to acidic environmental conditions [57], making this strain particularly well suited for better surviving and persisting in the human intestinal tract after oral administration. In addition, an experimental murine oral colonization model with *Saccharomyces* is well characterized [58]; using this model, protection has been reported against oral challenge with enteric pathogens such as *Salmonella Typhimurium* [58,59] and *Enteritidis* [60] in conventional mice orally treated with *S. boulardii*, as well as protection against CDI challenge in pretreated gnotobiotic animals [58,61]. The probiotic *S. boulardii*, genetically engineered to secrete $V_HH$ binding agents capable of neutralizing both TcdA and TcdB of *C. difficile*, could significantly improve the therapeutic capacity of this probiotic to disrupt both ongoing and recurrent CDI.

In view of the exceptional characteristics of *S. boulardii*, strains of *S. boulardii* expressing the binding agents defined herein where produced and tested. As described in the Examples, these yeast-based immunotherapeutics can be used to treat or prevent primary and recurrent CDI, as well as the symptoms of primary and recurrent CDI.

$V_HH$ Monomers & $V_HH$ Heterodimers

Figure 2:
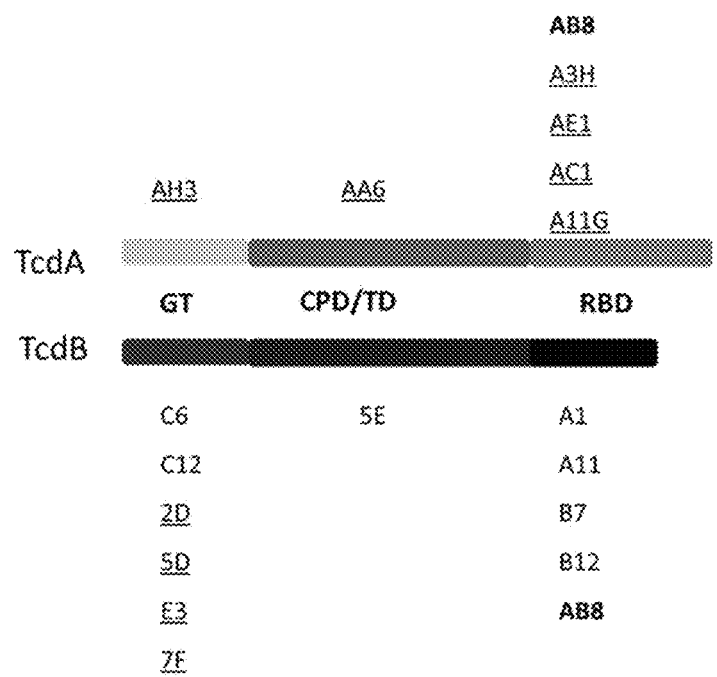
FIG. 2. A diagram of *C. difficile* toxins TcdA and TcdB, showing the glucosyltransferase domains (GT), cysteine protease domains (CPD), translocation domains (TD) and receptor binding domains (RBD) of each toxin. $V_HH$s that recognize and bind the different toxin domains are shown. Those that are underlined are those that have toxin-neutralizing activity.

As initially reported in WO 16/127104, the inventors established an efficient platform to screen $V_HH$ monomers against specific domains of both *C. difficile* toxins. Using highly immunogenic atoxic holotoxins for immunization, and bioactive chimeric toxins (with normal domain functions) for screening, panels of $V_HH$ monomers binding to different domains of TcdA or TcdB were prepared. A majority of these $V_HH$ monomers possessed potent neutralizing activity and their binding to specific domains of TcdA and TcdB was determined (FIG. 2).

Several of the $V_HH$ monomers bind to highly conserved TcdA/TcdB epitopes. For example, the E3 $V_HH$ monomer binds to the Rho GTPase binding site and blocks glucosylation; the AH3 $V_HH$ monomer binds to the GT domain of the toxin; the 7F $V_HH$ monomer binds to cysteine protease cleavage sites and blocks GT domain cleavage and release. Some $V_HH$ monomers have potent toxin neutralizing activity, capable of blocking toxin cytotoxic activity at nM concentrations (monomers underlined in FIG. 2; see also FIGS. 3A and 3B). Table 1 references amino and nucleic acid sequences in the Sequence Listing for some of these $V_HH$ peptide monomers, both wild-type and codon-optimized versions. While both the optimized and non-optimized versions can be used in the production of the various binding agents of the present invention, the codon-optimized versions are preferred for expression in mammalian cells.

The present invention includes each of the $V_HH$ peptide monomers referenced in Table 1 as well as sequence variants thereof having at least 85%, 86%, 87%, 88%, 89%, 90%, 91%, 92%, 93%, 94%, 95%, 96%, 97%, 98%, or 99% sequence identity over the entire length of the peptide sequence and retaining the toxin binding and/or neutralizing activity of the wild-type peptide. The present invention also includes polynucleotide sequences encoding each of the $V_HH$ peptide monomers of Table 1 and the sequence variants thereof, as well as complementary strands thereof.

TABLE 1

| Name | Codon Optimized? | Location of epitope | SEQ ID NO for Amino Acid Seq. | SEQ ID NO for Nucleic Acid Seq. |
|---|---|---|---|---|
| 5D | Yes | TcdB glucosyltransferase domain | 1 | 2 |
| E3 | Yes | TcdB glucosyltransferase domain | 3 | 4 |
| AA6 | Yes | TcdA cysteine protease domain | 5 | 6 |
| AH3 | Yes | TcdA glucosyltransferase domain | 7 | 8 |
| 5D | No | TcdB glucosyltransferase domain | 48 | 49 |
| E3 | No | TcdB glucosyltransferase domain | 50 | 51 |
| AA6 | No | TcdA cysteine protease domain | 52 | 53 |
| AH3 | No | TcdA glucosyltransferase domain | 54 | 55 |

To enhance the binding activity of the peptide monomers, $V_HH$ peptide homo- and hetero-dimer binding agents were created, where two $V_HH$ peptide monomers are linked (FIG. 3C). Homodimer binding agents comprise two identical monomers that bind identical epitopes on two different toxins. Heterodimer binding agents comprise two different monomers that bind two distinct epitopes of the same toxin or distinct epitopes on two different toxins. The $V_HH$ heterodimers were found to possess substantially enhanced neutralizing activities compared with equimolar mixtures of the individual $V_HH$ peptide monomers comprising the heterodimers (FIG. 3D). Indeed, heterodimers 5D/E3 and AH3/AA6 were found to fully protect mice from lethal systemic TcdB or TcdA challenge respectively, whereas mixed 5D and E3, or AA6 alone were only partially protective (FIGS. 3E and 3F).

The $V_HH$ monomers in the homo- and hetero-dimers are linked using a short, flexible linker of between 10 and 20 amino acids. Suitable linkers include those provided in Table 2. Table 2 also includes codon-optimized versions of the three linkers. While both the optimized and non-optimized versions can be used in the production of the various binding agents of the present invention, the codon-optimized versions are preferred for expression in mammalian cells.

TABLE 2

| Name | Codon Optimized? | SEQ ID NO for Amino Acid Seq. | SEQ ID NO for Nucleic Acid Seq. |
|---|---|---|---|
| Linker-1 | Yes | 9 | 10 |
| Linker-2 | Yes | 11 | 12 |
| Linker-3 | Yes | 13 | 14 |
| Linker-1 | No | 56 | 57 |
| Linker-2 | No | 58 | 59 |
| Linker-3 | No | 60 | 61 |

It will be understood by the skilled artisan that minor changes can be made to the sequence of the flexible linker without departing from the properties of the peptide. Sequence variants of the flexible linker having at least 85%, 86%, 87%, 88%, 89%, 90%, 91%, 92%, 93%, 94%, 95%, 96%, 97%, 98%, or 99% sequence identity over the entire length of the peptide sequence and retaining properties of the linker upon which they are based may thus be used.

The present invention includes $V_HH$ peptide homodimer binding agents comprising pairs of any of the monomers listed in Table 1, linked by a flexible linker as defined above. The present invention also includes $V_HH$ peptide heterodimer binding agents comprising any combination of two of the monomers listed in Table 1, linked by a flexible linker as defined above. Exemplary heterodimers are provided in Table 3.

TABLE 3

| Name | SEQ ID NO for Amino Acid Seq. | SEQ ID NO for Nucleic Acid Seq. |
|---|---|---|
| AH3-5D | 15 | 16 |
| AA6-E3 | 17 | 18 |
| 5D-E3 | 62 | 63 |
| AH3-AA6 | 64 | 65 |

The present invention also includes sequence variants of the $V_HH$ peptide homo- and hetero-dimers having at least 85%, 86%, 87%, 88%, 89%, 90%, 91%, 92%, 93%, 94%, 95%, 96%, 97%, 98%, or 99% sequence identity over the entire length of the protein sequence and retaining the toxin binding and/or neutralizing activity of the wild-type protein. The present invention further includes polynucleotide sequences encoding each the $V_HH$ peptide homo-heterodimers and the sequence variants thereof, as well as complementary strands thereof.

The invention also includes $V_HH$ peptide homo- and hetero-trimer binding agents where three monomers are linked using the flexible linkers defined above in Table 2. Any combination of the monomers of Table 1 may be used, including trimers comprising three copies of the same monomer, trimers comprising two copies of one monomer and a single copy of another, and trimers comprising three different monomers. Sequence variants of the $V_HH$ peptide homo- and hetero-trimers are included in the invention, having at least 85%, 86%, 87%, 88%, 89%, 90%, 91%, 92%, 93%, 94%, 95%, 96%, 97%, 98%, or 99% sequence identity over the entire length of the protein sequence and retaining the toxin binding and/or neutralizing activity of the wild-type protein. The present invention further includes polynucleotide sequences encoding each the $V_HH$ peptide homo- and hetero-trimers and the sequence variants thereof, as well as complementary strands thereof.

ABAB

The success of the peptide monomers and heterodimers allowed the inventors to develop binding agents comprising four linked $V_HH$ peptide monomers. This was a goal of the research as earlier work had shown that the most useful agents in the treatment and prevention of CDI would be single antibodies that can simultaneously neutralize both TcdA and TcdB as this would be necessary in order to convey full protection against most pathogenic *C. difficile* strains. By creating tetra-specific binding agents that recognize and bind two epitopes on each of the toxins, the binding and neutralizing activity of the proteins might be strengthened. Therefore, four domain (tetra-specific) $V_HH$ binding agents were generated.

The tetra-specific, tetrameric binding agents can be prepared from any combination of the monomers of Table 1, where the monomers are linked using the flexible linkers of Table 2. These binding agents include those having four copies of the same monomer, those having three copies of the same monomer, those having two copies of the same monomer, those having four unique monomers, and variations therein. Sequence variants of the tetramers are included in the invention, having at least 85%, 86%, 87%, 88%, 89%, 90%, 91%, 92%, 93%, 94%, 95%, 96%, 97%, 98%, or 99% sequence identity over the entire length of the protein sequence and retaining the toxin binding and/or neutralizing activity of the wild-type protein. The present invention further includes polynucleotide sequences encoding each tetramer and the sequence variants thereof, as well as complementary strands thereof.

ABBA is a particular binding agent of the invention that comprises four linked $V_HH$ monomers, AH3-E3-E3-AA6. ABBA thus has two identical monomers (E3) and two additional different monomers (AH3 and AA6) (See Table 1).

ABAB is another particular binding agent of the invention that comprises four linked $V_HH$ monomers, each of which has binding specificity for a different epitope of TcdA or TcdB. ABAB is thus a tetra-specific, tetrameric binding agent that consists of four distinct neutralizing $V_HH$ monomers, two against TcdA and two against TcdB. This structural feature allows ABAB to bind simultaneously to two distinct neutralizing epitopes on each toxin. As described below, affinity/avidity and neutralizing activity of ABAB is more than 3-logs higher than human monoclonal antibodies (HuMabs) currently undergoing clinical trials for treatment of CDI.

ABAB binding agent was prepared by linking $V_HH$ monomers AH3, 5D, AA6, and E3 (Table 1) using flexible linkers (Table 2). This binding agent targets conserved, non-overlapping epitopes and has excellent toxin neutralizing activity. In the design of ABAB (FIG. 4), $V_HH$ peptide monomers AH3 and AA6 were separated by placing the 5D between them because AH3 and AA6 bind to GT and TD respectively (FIG. 2), which are spatially distant to each other. This design allowed AH3 and AA6 to bind to TcdA simultaneously.

The complete amino acid sequence comprising ABAB is provided in SEQ ID NO:19; the nucleic acid sequence encoding the protein is provided in SEQ ID NO:20. The present invention thus includes the ABAB binding agent provided in SEQ ID NO:19, as well as sequence variants of the ABAB binding agent having at least 85%, 86%, 87%, 88%, 89%, 90%, 91%, 92%, 93%, 94%, 95%, 96%, 97%, 98%, or 99% sequence identity over the entire length of the protein sequence and retaining the toxin binding and/or neutralizing activity of the wild-type protein. The sequence variants include variants wherein the variant is humanized and/or wherein the amino acids are optimized for production and secretion by yeast.

The present invention further includes polynucleotide sequences encoding the ABAB binding agent (e.g., SEQ ID NO:20) and the sequence variants thereof, as well as complementary strands thereof.

Modified versions of the ABAB binding agent encompassed by the invention includes those having one or more of (i) a $His_{(6)}$-tag (HHHHHH; SEQ ID NO:66) at the amino terminus of the protein to aid in purification, (ii) an E-tag (GAPVPYPDPLEPR; SEQ ID NO:67) at the carboxy terminus of the protein to aid in detection; (iii) an albumin-binding peptide (ABP) (DICLPRWGCLWD; SEQ ID NO:21) at the carboxyl end of the construct to increase serum half-life of the protein as $V_HH$ monomers have a half-life of 2-3 hr and inclusion of ABP can increase the serum half-life to 10 hr (see FIG. 4); and a D7 tag (SSAPTKAKRRVVQREKT; SEQ ID NO:112) at the carboxy terminus of the protein. The invention includes versions of the ABAB binding agent having one, two, three or four of these tags and peptides. An exemplary modified ABAB binding agent that includes the His tag and the D7 tag comprises the amino acid sequence set forth in SEQ ID NO:113 (the coding sequence is set forth in SEQ ID NO:114).

When yeast strains are engineered to produce ABAB, the protein can be also modified to include a secretion signal at the amino terminus of the protein. The secretion signal may be, but is not limited to, one of the sequences shown in Table 4.

TABLE 4

Secretion sequences for protein secretion in yeast

| Secretion signal | Amino acid sequence | Abbr. |
|---|---|---|
| α-factor_full (*S. cerevisiae*) | MRFPSIFTAVLFAASSALAAPVNTTTEDETAQIPAEAVIGY SDLEGDFDVAVLPFSNSTNNGLLFINTTIASIAAKEEGVSL EKREAKA (SEQ ID NO: 96) | FAKS |
| α-factor_T_kex_ste (*S. cerevisiae*) | MRFPSIFTAVLFAASSALAAPVNTTTEDELEGDFDVAVLP FSASIAAKEEGVSLEKREAEA (SEQ ID NO: 97) | AKS |
| α-factor_T_kex (*S. cerevisiae*) | MRFPSIFTAVLFAASSALAAPVNTTTEDELEGDFDVAVLP FSASIAAKEEGVSLEKR (SEQ ID NO: 98) | AK |
| α-factor_T (*S. cerevisiae*) | MRFPSIFTAVLFAASSALA (SEQ ID NO: 99) | AT |
| Alpha-amylase (*Aspergillus niger*) | MVAWWSLFLYGLQVAAPALA (SEQ ID NO: 100) | AA |

TABLE 4-continued

Secretion sequences for protein secretion in yeast

| Secretion signal | Amino acid sequence | Abbr. |
|---|---|---|
| Glucoamylase (*Aspergillus awamori*) | MSFRSLLALSGLVCSGLA (SEQ ID NO: 101) | GA |
| Inulinase (*Kluyveromyces maxianus*) | MKLAYSLLLPLAGVSA (SEQ ID NO: 102) | IN |
| Invertase (*S. cerevisiae*) | MLLQAFLFLLAGFAAKISA (SEQ ID NO: 103) | IVS |
| Killer protein (*S. cerevisiae*) | MTKPTQVLVRSVSILFFITLLHLVVA (SEQ ID NO: 104) | KP |
| Lysozome (*Gallus gallus*) | MLGKNDPMCLVLVLLGLTALLGICQG (SEQ ID NO: 105) | LZ |
| Serum albumin (*Homo sapiens*) | MKWVTFISLLFLFSSAYS (SEQ ID NO: 106) | SA |

Exemplary modified ABAB binding agents that include an amino-terminal secretion signal include AT-ABAB and IVS-ABAB.

An exemplary modified ABAB binding agent that is expressed from a plasmid in yeast or bacteria includes the ABAB binding agent set forth in SEQ ID NO:107, which is encoded by the polynucleotide sequence set forth in SEQ ID NO:108.

An exemplary modified ABAB binding agent that is expressed in yeast after chromosomal integration includes the ABAB binding agent set forth in SEQ ID NO:109, which is encoded by the polynucleotide sequence set forth in SEQ ID NO:110.

Each of the binding agents of the invention binds to TcdA and/or TcdB with specificity. In certain aspects of the invention, the binding agents exhibit TcdA and/or TcdB neutralizing activity.

For the sake of clarity it can be noted that as used herein, "mono-specific", "bi-specific", "tri-specific", "tetra-specific", etc., mean the particular binding agent binds to 1, 2, 3, 4, etc., different epitopes, respectively. As used herein, "monomeric", "dimeric", "trimeric", "tetrameric", etc., mean the particular binding agent has 1, 2, 3, 4, etc., separate $V_HH$ peptide monomers that bind to the epitopes, respectively. Thus, a mono-specific, dimeric binding agent would display two $V_HH$ peptide monomers that bind to the same epitope (e.g., a homodimer), and a bi-specific, dimeric binding agent would have two $V_HH$ peptide monomers that bind to two different epitopes (e.g., a heterodimer). A tetra-specific, octameric binding agent has eight $V_HH$ peptide monomers that recognize four different epitopes.

$V_HH$-Fc

It is well known that chimeric Fc-fusion proteins have the potential of increasing the half-life of a protein in vivo. This strategy has been applied in several FDA approved drugs, such as Etanercept. A proof-of principle study has shown that single-chain antibodies can be correctly assembled and expressed by B cells of transgenic mice carrying a mini-Ig construct encoding a dromedary $V_HH$ and the Fc domain of human IgG. Also EG2-Fc, a chimeric anti-EGFR/EGFRvIII $V_HH$, exhibited excellent tumor accumulation in vivo and has pharmacokinetic properties that could improve glioblastoma targeting.

The present invention includes binding agents comprising $V_HH$ peptide monomers joined to antibody Fc domains ($V_HH$-Fc), where the binding agents bind TcdA and/or TcdB. In these Fc domain-based binding agents, one, two, three, four or more of the $V_HH$ peptide monomers are joined to the hinge, $C_H2$ and $C_H3$ regions of the Fc domain of an antibody heavy chain. Thus, the peptide monomers replace the Fab regions of the antibody.

The $V_HH$ peptide monomers may be any of those provided in Table 1 above and include 5D (SEQ ID NO:1), E3 (SEQ ID NO:3), AA6 (SEQ ID NO:5) and AH3 (SEQ ID NO:7) $V_HH$ peptide monomers. Where two or more monomers are linked, the monomers may be linked by flexible peptide linkers, generally comprising between 10 and 20 amino acids. Suitable linkers include those linkers provided in Table 2, such as linker-1 (SEQ ID NO:9), linker-2 (SEQ ID NO:11), and linker-3 (SEQ ID NO:13).

While the $V_HH$-Fc will typically be composed of two identical chains that self-assemble intracellularly after production, the invention also includes $V_HH$-Fc binding agents comprising two different Fc chains. In such circumstances, the sequence of the $V_HH$ monomer(s) alone may differ between the two Fc chains, or the Fc chains themselves may differ in sequence, or both the $V_HH$ monomer(s) and the Fc chains may differ in sequence.

One type of $V_HH$-Fc binding agent is an octameric binding agent comprising an antibody Fc domain and first, second, third and fourth $V_HH$ peptide monomers, where the $V_HH$ peptide monomers have binding specificity for an epitope of TcdA or toxin B TcdB, where the first, second, third and fourth $V_HH$ peptide monomers are linked together and joined to amino termini of both antibody Fc domains, and where the antibody Fc domain comprises the hinge, $C_H2$ and $C_H3$ regions of an antibody heavy chain. Because this binding agent has four $V_HH$ peptide monomers, it can be mono-specific (where all of the monomers bind the same epitope), bi-specific (where the monomers bind two different epitopes), tri-specific (where the monomers bind three different epitopes), or tetra-specific (where the monomers bind four different epitopes).

A specific example of a tetra-specific $V_HH$-Fc binding agent is the ABAB-Fc binding agent, a tetra-specific, octameric binding agent comprising an antibody Fc domain and two sets of linked first, second, third and fourth $V_HH$ peptide monomers, wherein the antibody Fc domain comprises two arms, each arm comprising hinge, $C_H2$ and $C_H3$ regions of an antibody heavy chain, and each arm having an amino terminus, wherein for each arm of the Fc domain, one set of linked first, second, third and fourth V$_H$H peptide monomers is joined to the amino terminus of the arm, and where the V$_H$H peptide monomers have binding specificity for an epitope of TcdA or TcdB (see FIG. 1). This binding agent is termed "tetra-specific" as it recognizes four different toxin epitopes. It is termed "octameric" as it bears eight V$_H$H peptide monomers (two copies of the first monomer, two copies of the second monomer, two copies of the third monomer, and two copies of the fourth monomer). ABAB-Fc was found to exhibit specific binding and neutralizing activity.

The ABAB-Fc binding agent was prepared by generating an expression vector encoding the V$_H$H peptide monomers AH3/5D/AA6/E3 (linked in the noted order) joined to a human IgG1 Fc domain. The V$_H$H peptide monomers were separated by flexible linkers of Table 2. The nucleic acid sequence encoding each chain is provided in SEQ ID NO:23. The amino acid sequence of each chain is provided in SEQ ID NO:22. Upon self-assembly of pairs of the chains after expression, the tetra-specific, octameric binding agent resulted. The invention includes the ABAB-Fc binding agent of SEQ ID NO:22, modified versions of ABAB binding agents as defined above, and sequence variants thereof having at least 85%, 86%, 87%, 88%, 89%, 90%, 91%, 92%, 93%, 94%, 95%, 96%, 97%, 98%, or 99% sequence identity over the entire length of the protein sequence and retaining the toxin binding and/or neutralizing activity of the wild-type protein. The present invention further includes polynucleotide sequences encoding these sequence variants and complementary strands thereof.

Mono-specific V$_H$H-Fc binding agents (AH3-Fc, 5D-Fc, E3-Fc, AA6-Fc) and bi-specific V$_H$H-Fc binding agents (e.g., AH3/5D-Fc and AA6/E3-Fc) were also made using this Fc-fusion system. With respect to mono-specific binding agents, single V$_H$H peptide monomers were joined to human IgG1 Fc domains. Upon expression and assembly, pairs of the chains resulted in mono-specific, dimeric binding agents (when the chains were identical) or bi-specific, dimeric binding agents (when the chains were different). With respect to bi-specific binding agents, two linked V$_H$H peptide monomers (V$_H$H homo- or hetero-dimers) were joined to human IgG1 Fc domains. Upon expression and assembly, pairs of the chains resulted in bi-specific, tetrameric binding agents (when the chains were identical) or tetra-specific, tetrameric binding agents (when the chains were different). Table 5 provides the sequences for some these binding agents.

TABLE 5

| Name | SEQ ID NO for Amino Acid Seq. | SEQ ID NO for Nucleic Acid Seq. |
|---|---|---|
| 5D-Fc | 24 | 25 |
| E3-Fc | 26 | 27 |
| AA6-Fc | 28 | 29 |
| AH3-Fc | 30 | 31 |
| AH3-5D-Fc | 32 | 33 |
| AA6-E3-Fc | 34 | 35 |

Specific pairings with one monomer include: 5D-Fc+5D-Fc; E3-Fc+E3-Fc; AA6-Fc+AA6-Fc; AH3-Fc+AH3-Fc; 5D-Fc+E3-Fc; 5D-Fc+AA6-Fc; 5D-Fc+AH3-Fc; E3-Fc+AA6-Fc; E3-Fc+AH3-Fc; and AA6-Fc+AH3-Fc. Specific pairings with two monomers include: AH3-5D-Fc+AH3-5D-Fc; AA6-E3-Fc+AA6-E3-Fc; and AH3-5D-Fc+AA6-E3-Fc.

Bi-specific, tetrameric V$_H$H-Fc binding agents were produced comprising an antibody Fc domain and two sets of linked first and second V$_H$H peptide monomers, wherein the antibody Fc domain comprises two arms, each arm comprising hinge, C$_H$2 and C$_H$3 regions of an antibody heavy chain, and each arm having an amino terminus, wherein for each arm of the Fc domain, one set of linked first and second V$_H$H peptide monomers is joined to the amino terminus of the arm, and where the V$_H$H peptide monomers have binding specificity for an epitope of TcdA or TcdB. This binding agent is termed "bi-specific" as it recognizes two different toxin epitopes. It is termed "tetrameric" as it bears four V$_H$H peptide monomers (two copies of the first monomer, and two copies of the second monomer). The first and second V$_H$H peptide monomers may have binding specificity for the same or different epitopes. The V$_H$H peptide monomers may independently have binding specificity for an epitope in the glucosyltransferase domain, cysteine protease domain, translocation domain or receptor binding domain of TcdA or TcdB.

A specific example of a bi-specific, tetrameric V$_H$H-Fc binding agent comprises the amino acid sequence set forth in SEQ ID NO:32 (AH3/5D-Fc). The invention also includes sequence variants thereof having at least 95% sequence identity, where the sequence variant retains toxin-neutralizing activity. The variant amino acids of the sequence variant may be located in framework regions of the V$_H$H peptide monomers.

A specific example of a bi-specific, tetrameric V$_H$H-Fc binding agent comprises the amino acid sequence set forth in SEQ ID NO:34 (AA6/E3-Fc). The invention also includes sequence variants thereof having at least 95% sequence identity, where the sequence variant retains toxin-neutralizing activity. The variant amino acids of the sequence variant may be located in framework regions of the V$_H$H peptide monomers.

The V$_H$H-Fc binding agents bind to TcdA and/or TcdB with specificity. In certain aspects of the invention, the binding agents exhibit TcdA and/or TcdB neutralizing activity.

V$_H$H-IgG

The present invention also includes binding agents comprising V$_H$H peptide monomers joined to more of an antibody that the Fc domain alone. V$_H$H-IgG binding agents comprise one, two, three, four or more of the V$_H$H peptide monomers are joined to the light (kappa or lambda) and heavy chains of an IgG antibody lacking the variable regions of the antibody. Thus, the peptide monomers replace the variable regions of the antibody.

The V$_H$H peptide monomers may be any of those provided in Table 1 above and include 5D (SEQ ID NO:1), E3 (SEQ ID NO:3), AA6 (SEQ ID NO:5) and AH3 (SEQ ID NO:7) V$_H$H peptide monomers. Where two or more monomers are linked, the monomers may be linked by flexible peptide linkers, generally comprising between 10 and 20 amino acids. Suitable linkers include those linkers provided in Table 2, such as linker-1 (SEQ ID NO:9), linker-2 (SEQ ID NO:11), and linker-3 (SEQ ID NO:13).

V$_H$H-IgG binding agents include octameric binding agents comprising an IgG antibody and first, second, third and fourth V$_H$H peptide monomers, wherein the V$_H$H peptide monomers have binding specificity for an epitope of TcdA or TcdB, wherein first and second V$_H$H peptide monomers are linked together and joined to amino termini of both light chains of the antibody, wherein the light chains lack the antibody variable regions, and wherein third and fourth V$_H$H peptide monomers are linked together and joined to amino termini of both heavy chains of the antibody, wherein the heavy chains lack the antibody variable regions. Because this binding agent has four $V_HH$ peptide monomers, it can be mono-specific (where all of the monomers bind the same epitope), bi-specific (where the monomers bind two different epitopes), tri-specific (where the monomers bind three different epitopes), or tetra-specific (where the monomers bind four different epitopes).

A specific example of a tetra-specific $V_HH$-IgG binding agent is the ABAB-IgG binding agent, a tetra-specific, octameric binding agent comprising an IgG antibody, two sets of linked first and second $V_HH$ peptide monomers, and two sets of linked third and fourth $V_HH$ peptide monomers, wherein the IgG antibody comprises two arms, each arm comprising a heavy chain lacking a variable region and a light chain lacking a variable region, and each chain having an amino terminus, wherein for each arm of the antibody, one set of linked first and second $V_HH$ peptide monomers is joined to the amino terminus of the light chain, and one set of linked third and fourth $V_HH$ peptide monomers is joined to the amino terminus of the heavy chain, and wherein the $V_HH$ peptide monomers have binding specificity for an epitope of TcdA or TcdB (see FIG. 1). This binding agent is termed "tetra-specific" as it recognizes four different toxin epitopes. It is termed "octameric" as it bears eight $V_HH$ peptide monomers (two copies of the first monomer, two copies of the second monomer, two copies of the third monomer, and two copies of the fourth monomer). In certain aspects, the first, second, third and fourth $V_HH$ peptide monomers may each have binding specificity for a different epitope. In certain aspects, two of the $V_HH$ peptide monomers may have binding specificity for epitopes of TcdA and two of the $V_HH$ peptide monomers may have binding specificity for epitopes of TcdB. In certain aspects, the $V_HH$ peptide monomers independently have binding specificity for an epitope in the glucosyltransferase domain, cysteine protease domain, translocation domain or receptor binding domain of TcdA or TcdB.

A specific example of a tetra-specific, octameric ABAB-IgG binding agent comprises a light (kappa) chain having the amino acid sequence set forth in SEQ ID NO:46 (AA6/E3 kappa) or a sequence variant having at least 95% sequence identity thereto, and a heavy chain having the amino acid sequence set forth in SEQ ID NO:44 (AH3/5D heavy) or a sequence variant having at least 95% sequence identity thereto. In this aspect, the sequence variants retain toxin-neutralizing activity. The variant amino acids of the sequence variant may be located in framework regions of the $V_HH$ peptide monomers. This binding agent was produced by preparing two separate expression vectors, the first encoding the $V_HH$ peptide monomers AH3/5D (linked in the noted order) joined to the human IgG1 antibody heavy chain lacking the variable region and the second encoding the $V_HH$ peptide monomers AA6/E3 (linked in the noted order) joined to the human IgG1 antibody light (kappa) chain lacking the variable region. The nucleotide sequence encoding the AA6/E3-IgG1 light (kappa) chain is provided in SEQ ID NO:47. The nucleotide sequence encoding the AH3/5D-IgG1 heavy chain is provided in SEQ ID NO:45. The invention includes sequence variants of ABAB-IgG having at least 85%, 86%, 87%, 88%, 89%, 90%, 91%, 92%, 93%, 94%, 95%, 96%, 97%, 98%, or 99% sequence identity over the entire length of the protein sequence and retaining the toxin binding and/or neutralizing activity of the wild-type protein. The present invention further includes polynucleotide sequences encoding these sequence variants and complementary strands thereof.

Bi-specific or tetra-specific, tetrameric IgG binding agents are included in the invention. Such binding agents comprise an IgG antibody and first, second, third and fourth $V_HH$ peptide monomers, wherein the IgG antibody comprises two arms, each arm comprising a heavy chain lacking a variable region and a light chain lacking a variable region, and each chain having an amino terminus, wherein for a first arm of the antibody, the first $V_HH$ peptide monomer is joined to the amino terminus of the light chain, and the second $V_HH$ peptide monomer is joined to the amino terminus of the heavy chain, wherein for a second arm of the antibody, the third $V_HH$ peptide monomer is joined to the amino terminus of the light chain, and the fourth $V_HH$ peptide monomer is joined to the amino terminus of the heavy chain, and where the $V_HH$ peptide monomers have binding specificity for an epitope of TcdA or TcdB. When the binding agent is "tetra-specific", it recognizes four different toxin epitopes; when "bi-specific" it recognizes two different toxin epitopes. The binding agents "tetrameric" as they bear four $V_HH$ peptide monomers (when bi-specific, the first and second monomer have the same sequence and bind the same epitope, and the third and fourth monomers have the same sequence and bind the same epitope; when tetra-specific, each of the monomers has a different sequence and binds a different epitope).

When the binding agent is bi-specific, the first and third monomers have binding specificity for different epitopes, the first and second monomers have identical amino acid sequences, and the third and fourth monomers have identical amino acid sequences. In certain aspects, one of the $V_HH$ peptide monomers has binding specificity for an epitope of TcdA and one of the $V_HH$ peptide monomers has binding specificity for an epitope of TcdB.

When the binding agent is tetra-specific, each of the $V_HH$ peptide monomers has binding specificity for a different epitope. In certain aspects, two of the $V_HH$ peptide monomers have binding specificity for epitopes of TcdA and two of the $V_HH$ peptide monomers have binding specificity for epitopes of TcdB.

In certain aspects, each of the $V_HH$ peptide monomers has binding specificity for epitopes of TcdA. In other aspects, each of the $V_HH$ peptide monomers has binding specificity for epitopes of TcdB.

In certain aspects, the $V_HH$ peptide monomers independently have binding specificity for an epitope in the glucosyltransferase domain, cysteine protease domain, translocation domain or receptor binding domain of TcdA or TcdB.

A specific example of a bi-specific, tetrameric IgG binding agent comprises a light (kappa) chain having the amino acid sequence set forth in SEQ ID NO:40 (AA6 kappa) and a heavy chain having the amino acid sequence set forth in SEQ ID NO:36 (AH3 heavy). The invention also includes sequence variants thereof having at least 95% sequence identity, where the sequence variant retains toxin neutralizing activity. The variant amino acids of the sequence variant may be located in framework regions of the $V_HH$ peptide monomers.

Another specific example of a bi-specific, tetrameric IgG binding agent comprises a light (kappa) chain having the amino acid sequence set forth in SEQ ID NO:42 (E3 kappa) and a heavy chain having the amino acid sequence set forth in SEQ ID NO:38 (5D heavy). The invention also includes sequence variants thereof having at least 95% sequence identity, where the sequence variant retains toxin neutralizing activity. The variant amino acids of the sequence variant may be located in framework regions of the $V_HH$ peptide monomers.

Table 6 provides the sequences used to generate bi- and tetra-specific V$_H$H-IgG binding agents. Other suitable pairings include (i) 5D-IgG1-heavy chain+AA6-light (kappa or lambda) chain, and (ii) AH3-IgG1-heavy chain+E3-light (kappa or lambda) chain.

TABLE 6

| Name | SEQ ID NO for Amino Acid Seq. | SEQ ID NO for Nucleic Acid Seq. |
| --- | --- | --- |
| AH3-IgG1 heavy chain | 36 | 37 |
| 5D-IgG1 heavy chain | 38 | 39 |
| AA6-IgG1 light (kappa) chain | 40 | 41 |
| E3-IgG1 light (kappa) chain | 42 | 43 |
| AH3/5D-IgG1 heavy chain | 44 | 45 |
| AA6/E3-IgG light (kappa) chain | 46 | 47 |

However, the present invention includes IgG1 heavy chains joined to any of AH3, 5D, AA6 and E3, and IgG1 light (kappa or lambda) chains joined to any of AH3, 5D, AA6 and E3. Further, all possible combinations of the heavy and light (kappa or lambda) chains are encompassed herein.

Humanized Binding Agents

Due to their small size and the high degree of identity of their framework to the human V$_H$ framework of family III, V$_H$H peptide monomers are expected to exhibit low immunogenicity when administered to humans. While the systemic application of small monovalent V$_H$H monomers seems to induce little, if any, neutralizing antibody responses, protein immunogenicity generally increases with size and complexity. Two major hurdles for repeated and/or long-term in vivo use of V$_H$H monomers are their likely short half-life and potential immunogenicity. To increase the valence and circulating half-life, V$_H$H monomers can be fused with human IgG and Fc domains as discussed herein. To address possible immunogenicity, the V$_H$H monomers can be humanized as needed without compromising their expression level, affinity, solubility, and stability. These strategies should result in good expression, stability, and solubility of humanized V$_H$H monomers (hV$_H$H monomers), while retaining the antigen specificity and affinity of the loop donor V$_H$H.

hV$_H$H monomers that gain highest identity to human V$_H$ gene(s) and possess the highest binding/neutralizing activity are selected, after which they are transferred into the V$_H$H-multimers (e.g., ABAB), V$_H$H-Fc and V$_H$H-IgG constructs to generate fully humanized binding agents, such as fully humanized ABAB, ABAB-IgG and ABAB-Fc binding agents. The protein sequences of these humanized binding agents can be essentially identical to that of a human antibody variant, despite the non-human origin of some of its CDR segments that are responsible for the ability of the antibody to bind to its target antigen. Therefore, this strategy decreases the chance for potential immunogenicity in vivo and thus increase their safety and half-life in vivo.

The binding agents of the present invention thus encompasses humanized versions of each of the binding agents defined herein, comprising hV$_H$H peptide monomers.

Epitope Binding Fragments

The binding agents of the invention include epitope binding fragments of each of the V$_H$H-Fc and V$_H$H-IgG binding agents defined herein. Because the V$_H$H-Fc and V$_H$H-IgG binding agents are comparable in structure to human IgG antibodies, where the variable regions are replace by the V$_H$H monomers, terms for human antibody fragments are also applicable to the such binding agents. The fragments include, but are not limited to, Fab fragments, F(ab)$_2$ fragments, single chain Fv (scFv) antibodies, and fragments produced by an Fab expression library, as well as bi-specific antibody and triple-specific antibodies.

The V$_H$H-Fc and V$_H$H-IgG binding agents of the invention include fully human, humanized, and chimeric binding agents. The binding agents may be monoclonal or polyclonal. Further, the binding agents may be recombinant binding agents.

The binding agents may be produced in any species of animal, though preferably from a mammal such as a human, simian, mouse, rat, rabbit, guinea pig, horse, cow, sheep, goat, pig, dog or cat. For example, the binding agents can be human or humanized, or any binding agent preparation suitable for administration to a human.

Polynucleotide, Expression Vectors, Host Cells and Method of Making

The invention includes polynucleotides comprising nucleotide sequences encoding each the binding agents provided herein, as well as complementary strands thereof.

The invention also includes expression vectors comprising the polynucleotides, and host cells comprising the expression vectors. Suitable expression vectors include, e.g., pcDNA3.1 and pSec-His, as well as plasmids used to transform yeast cells into producers and secretors of the binding agents of the invention. Suitable host cells include, e.g., Chinese hamster ovary cells (CHO cells), human embryonic kidney cells 293 (HEK 293 cells), yeast cells, and insect cells.

The invention further includes methods of producing the binding agents defined herein, comprising culturing the host cells under conditions promoting expression of the binding agents encoded by the expression vectors, and recovering the binding agents from the cell cultures.

Engineered Strains of Yeast

Each of the binding agents of the invention may also be produced by engineered strains of Saccharomyces yeast. Accordingly, the invention is also directed to strains of Saccharomyces yeast, such as S. cerevisiae and S. boulardii, engineered to produce one or more of the binding agents defined herein including, but not limited to, V$_H$H monomer binding agents (see Table 1), V$_H$H homodimer binding agents, V$_H$H heterodimer binding agents (see Table 3), ABAB binding agents, V$_H$H-Fc binding agents (see Table 5), V$_H$H-IgG binding agents (see Table 6), and epitope biding fragments thereof. In preferred aspects, the engineered strains of Saccharomyces yeast secrete the binding agents.

The identity of the Saccharomyces yeast strain is only limited in that it can be engineered to produce, and preferably secrete, one or more of the binding agents of the invention. In preferred aspects of the invention, the strain of Saccharomyces yeast engineered to produce one or more of the binding agents is S. cerevisiae or S. boulardii. The invention thus encompasses an engineered strain of S. cerevisiae that produces one or more of the binding agents defined herein, as well as an engineered strain of S. cerevisiae that secretes one or more of the binding agents defined herein. The invention also encompasses an engineered strain of S. boulardii that produces one or more of the binding agents defined herein, as well as an engineered strain of S. boulardii that secretes one or more of the binding agents defined herein. Suitable stains of yeast also include Schizosaccharomyces pombe, Saccharomyces paradoxus, and Saccharomyces unisporus.

S. boulardii is an FDA-designated Generally Regarded as Safe (GRAS) organism and it is commonly available overthe-counter for use in promoting intestinal health and amelioration of gastrointestinal illness due to diarrheal diseases. This species of yeast has been studied in multiple randomized double-blinded placebo-controlled clinical trials for both safety and efficacy against intestinal diseases including CDI [42-46]. A suitable strain of *S. boulardii* is the *S. boulardii* strain MYA796 (ATCC, Manassas, Va.).

A particular example of the engineered strains of *Saccharomyces* yeast of the invention is an engineered strain of *Saccharomyces* yeast that produces a binding agent comprising a $V_HH$ peptide monomer or linked groups of $V_HH$ peptide monomers comprising two, three, four, or more monomers, each of which binds TcdA and/or TcdB, preferably with specificity. Thus, the invention encompasses engineered strains of *Saccharomyces* yeast that produces $V_HH$ peptide binding agents comprising at least one $V_HH$ peptide monomer, wherein each $V_HH$ peptide monomer has binding specificity for an epitope of *C. difficile* toxin A (TcdA) or toxin B (TcdB). In certain aspects, these binding agents comprise two, three, four, or more linked $V_HH$ peptide monomers. The $V_HH$ peptide monomers include, but are not limited to, the $V_HH$ peptide monomers 5D (SEQ ID NO:1), E3 (SEQ ID NO:3), AA6 (SEQ ID NO:5), and AH3 (SEQ ID NO:7).

Another particular example of the engineered strains of *Saccharomyces* yeast of the invention is an engineered strain of *Saccharomyces* yeast that produces binding agents comprising $V_HH$ peptide monomers joined to IgG antibodies, where the binding agents bind TcdA and/or TcdB, as defined herein. In these IgG-based binding agents, the variable regions of the light and heavy chains of IgG antibodies are replaced by one, two, three, four or more of the $V_HH$ peptide monomers.

A further particular example of the engineered strains of *Saccharomyces* yeast of the invention is an engineered strain of *Saccharomyces* yeast that produces binding agents comprising $V_HH$ peptide monomers joined to antibody Fc domains, where the binding agents bind TcdA and/or TcdB, as defined herein. In these Fc domain-based binding agents, one, two, three, four or more of the $V_HH$ peptide monomers are joined to the hinge, $C_H2$ and $C_H3$ regions of each arm of Fc domain of an antibody heavy chain. Thus, the peptide monomers replace the Fab regions of an antibody.

An additional particular example of the engineered strains of *Saccharomyces* yeast of the invention is an engineered strain of *Saccharomyces* yeast that produces a tetra-specific, tetrameric binding agent, wherein the binding agent comprises linked first, second, third and fourth $V_HH$ peptide monomers, and wherein the $V_HH$ peptide monomers independently have binding specificity for an epitope of *Clostridium difficile* toxin A (TcdA) or toxin B (TcdB). In certain aspects, the first, second, third and fourth $V_HH$ peptide monomers each has binding specificity for a different epitope. In certain aspects, the two of the $V_HH$ peptide monomers have binding specificity for epitopes of TcdA and two of the $V_HH$ peptide monomers have binding specificity for epitopes of TcdB. In certain aspects, the $V_HH$ peptide monomers independently have binding specificity for an epitope in the glucosyltransferase domain, cysteine protease domain, translocation domain or receptor binding domain of TcdA or TcdB. Suitable $V_HH$ peptide monomers include the AH3 monomer (SEQ ID NO:7), the AA6 monomer (SEQ ID NO:5), the 5D monomer (SEQ ID NO:1), and the E3 monomer (SEQ ID NO:3). Other monomers include, but are not limited to, those provided in Table 1.

In a preferred example, the invention is directed to an engineered strain of yeast, wherein the binding agent is ABAB, wherein the first and third monomers have binding specificity for epitopes of TcdA and the first and third monomers are $V_HH$ peptide monomers AH3 (SEQ ID NO:7) and AA6 (SEQ ID NO:5), respectively, and wherein the second and forth monomers have binding specificity for epitopes of TcdB and the second and forth monomers are $V_HH$ peptide monomers 5D (SEQ ID NO:1) and E3 (SEQ ID NO:3), respectively.

The ABAB binding agent may comprise the amino acid sequence set forth in SEQ ID NO:19, or a sequence variant having at least 95% sequence identity thereto, wherein the sequence variant retains TcdA and/or TcdB binding specificity, or the sequence variant retains toxin neutralizing activity, or both.

The ABAB binding agent may also comprises an N-terminal secretion signal selected from the secretion signals provided in Table 4. In preferred aspects, the N-terminal secretion signal is the AT secretion signal (MRFPSIFTAVL-FAASSALA (SEQ ID NO:99)) or the IVS secretion signal (MLLQAFLFLLAGFAAKISA (SEQ ID NO:103)).

The ABAB binding agent may be expressed from a plasmid within the yeast. The plasmid may be, but is not limited to, pCEV-URA3-TEF-AT-yABAB-cMyc (SEQ ID NO:88). The ABAB binding agent encoded by the plasmid may comprises the amino acid sequence set forth in SEQ ID NO:107, or a sequence variant having at least 95% sequence identity thereto, and wherein the sequence variant retains TcdA and/or TcdB binding specificity, or the sequence variant retains toxin neutralizing activity, or both.

The ABAB binding agent may also be expressed from coding sequence integrated into a chromosome of yeast. The ABAB binding agent expressed from coding sequence integrated into a yeast chromosome may comprises the amino acid sequence set forth in SEQ ID NO:109, or a sequence variant having at least 95% sequence identity thereto, and wherein the sequence variant retains TcdA and/or TcdB binding specificity, or the sequence variant retains toxin neutralizing activity, or both.

The invention is also directed to engineered strains of *Saccharomyces* yeast that produce a therapeutic protein having binding specificity for a unique epitope of *Clostridium difficile* toxin A (TcdA) or toxin B (TcdB), or both. Preferably, the engineered strain of *Saccharomyces* yeast is *S. cerevisiae* or *S. boulardii*. A therapeutic protein is any protein that can bring about an improvement or cure in a medical condition in a subject, or that can inhibit or prevent a medical condition from developing in a subject. Suitable therapeutic protein include, but are not limited to, proteins that (a) replace a protein that is deficient or abnormal; (b) augment an existing pathway; (c) provide a novel function or activity; (d) interfere with a molecule or organism; and (e) deliver other compounds or proteins, such as a radionuclide, cytotoxic drug, or effector proteins. Therapeutic proteins also include antibodies and antibody-based drugs, Fc fusion proteins, anticoagulants, blood factors, bone morphogenetic proteins, engineered protein scaffolds, enzymes, growth factors, hormones, interferons, interleukins, and thrombolytics. Therapeutic proteins further include bispecific monoclonal antibodies (mAbs) and multispecific fusion proteins, mAbs conjugated with small molecule drugs, and proteins with optimized pharmacokinetics.

Methods of Making Engineered Yeast Strains

The invention is also directed to methods of engineering strains of *Saccharomyces* yeast to produce one or more of the binding agents defined herein. The means used to produce the engineered strains of yeast are not particularly limited and there are a number of well-established techniques available for engineering yeast to produce homologous and heterologous proteins that will be known to the skilled artisan. In certain aspects of these methods, S. cerevisiae or S. boulardii is engineered to produce the binding agents.

As an example, Saccharomyces yeast may be engineered to produce one or more of the binding agents defined herein by (a) transforming a strain of Saccharomyces yeast with an expression vector encoding the binding agent, and (b) screening the resulting yeast for production of the binding agent. In a certain aspect, the expression vector is plasmid pCEV-URA3-TEF-AT-yABAB-cMyc (SEQ ID NO:88). While this plasmid encodes a particular ABAB binding agent, the coding region for this binding agent can be replaced by the coding region of any of the binding agents defined herein.

As a further example, Saccharomyces yeast may be engineered to produce one or more of the binding agents defined herein by (a) chromosomally integrating a polynucleotide sequence encoding the binding agent into the genome of the strain of Saccharomyces yeast, and (b) screening the yeast of (a) for production of the binding agent. In certain aspects, the chromosomal integration is performed using a CRISPR technique [85-88]. As an example, such a method may include the steps of: (a) amplifying a polynucleotide sequence encoding the ABAB binding agent from plasmid pCEV-G4-Km-TEF-AT-yABAB hAA6T83N-tagless (SEQ ID NO:90) using primers containing (i) nucleic acid sequence homologous to a selected yeast chromosomal integration site and (ii) nucleic acid sequence homologous to regions 5' and 3' of ABAB binding agent coding sequence of the plasmid, to produce an integration cassette, (b) transforming yeast with the integration cassette produced in (a) with pCRI-Sb-δ1 (SEQ ID NO:91) or pCRI-Sb-δ2 (SEQ ID NO:92) to induce a double stranded break within the corresponding yeast chromosomal delta sites under conditions promoting spontaneous integration of the integration cassette into the site of the double stranded break, (c) screening the transformed yeast of (b) for production of the ABAB binding agent.

While the plasmid pCEV-G4-Km-TEF-AT-yABAB hAA6T83N-tagless encodes a particular ABAB binding agent, the coding region for this binding agent can be replaced by the coding region of any of the binding agents defined herein.

Suitable means used to screen the yeast for production of the binding agents will be readily apparent to the skilled artisan and include, but are not limited to immunoassays, such as an ELISA or a western blot.

Methods of Treatment and Prevention

The binding agents and engineered strains of Saccharomyces yeast of the invention can be used in methods of treating or preventing a disease symptom induced by C. difficile in a subject. These methods generally comprise administering a therapeutically-effective amount of one or more binding agents and/or one or more engineered strains of Saccharomyces yeast as defined herein to a subject having C. difficile infection or a risk of developing C. difficile infection. In certain aspects of this embodiment, the disease symptom induced by C. difficile is diarrhea The binding agents and engineered strains of Saccharomyces yeast of the invention can also be used in of neutralizing C. difficile toxin TcdA and/or TcdB in a subject infected by C. difficile. These methods generally comprise administering a therapeutically-effective amount of one or more binding agents and/or one or more engineered strains of Saccharomyces yeast as defined herein to a subject having C. difficile infection.

The binding agents and engineered strains of Saccharomyces yeast of the invention can further be used in methods of treating C. difficile infection in a subject. These methods generally comprise administering a therapeutically-effective amount of one or more of the binding agents and/or one or more engineered strains of Saccharomyces yeast as defined herein to a subject having C. difficile infection. These same methods can be used to treat CDI, as defined herein.

The binding agents and engineered strains of Saccharomyces yeast of the invention can also be used in methods of maintaining normal bowel function in a subject having a C. difficile infection. These methods generally comprise administering a therapeutically-effective amount of one or more of the binding agents and/or one or more engineered strains of Saccharomyces yeast as defined herein to a subject having C. difficile infection or a risk of developing C. difficile infection.

The binding agents and engineered strains of Saccharomyces yeast can also be used in immunoprophylaxis in order to prevent immediate CDI threats. In addition, passive immunoprophylaxis can be used to prevent both immediate and longer-term CDI threats. Each approach has its own particular advantages and is suitable to target a particular high-risk population. These methods generally comprises administering a therapeutically-effective amount of one or more of the binding agent and/or one or more engineered strains of Saccharomyces yeast as defined herein to a subject a risk of developing C. difficile infection.

In preferred aspects of the methods of the invention, the Saccharomyces yeast is S. cerevisiae or S. boulardii.

Each of the methods of the invention may include administration of the one or more binding agents and/or the one or more engineered strains of Saccharomyces yeast in one or more pharmaceutical formulations comprising the binding agents and/or the engineered strains of Saccharomyces yeast and a pharmaceutically acceptable carrier or diluent. In preferred aspects, the Saccharomyces yeast is S. cerevisiae or S. boulardii.

As used herein, the terms "treat", "treating", and "treatment" have their ordinary and customary meanings, and include one or more of: blocking, ameliorating, or decreasing in severity and/or frequency a symptom of a C. difficile infection or a C. difficile-related disease (CDI) in a subject; and/or partly or fully inhibiting the biological activity and/or promoting the immunologic clearance of C. difficile TcdA and/or TcdB in a subject infected with C. difficile; and/or growth, division, spread, or proliferation of C. difficile cells or a C. difficile infection in a subject. Treatment means blocking, ameliorating, decreasing, or inhibiting by about 1% to about 100% versus a subject in which the methods of the present invention have not been practiced. Preferably, the blocking, ameliorating, decreasing, or inhibiting is about 100%, 99%, 98%, 97%, 96%, 95%, 90%, 80%, 70%, 60%, 50%, 40%, 30%, 20%, 10%, 5% or 1% versus a subject in which the methods of the present invention have not been practiced.

As used herein, the terms "prevent", "preventing" and "prevention" have their ordinary and customary meanings, and include one or more of, stopping, averting, avoiding, alleviating or blocking C. difficile from colonizing, developing or progressing in a subject; and/or partly or fully inhibiting the biological activity and/or toxic effects of TcdA and/or TcdB in a subject infected with C. difficile; and/or stopping, averting, avoiding, alleviating or blocking the growth, division, spread, or proliferation of bacterial cells or bacterial infection in a subject. Prevention means stopping by at least about 95% versus a subject to which the prevention has not been administered. Preferably, the stopping is about 100%, about 99%, about 98%, about 97%, about 96% or about 95%. The results of the prevention may continue for a period of days (such as 1, 2, 3, 4, 5, 6 or 7 days), weeks (such as 1, 2, 3 or 4 weeks) or months (such as 1, 2, 3, 4, 5, 6 or more months).

The method of treating and preventing provided herein can be supplemented by also administering a therapeutically-effective amount of an antibiotic to the subject. Preferably, the antibiotic will have antibacterial activity against *C. difficile*.

Pharmaceutical Formulations

While the binding agents and engineered strains of *Saccharomyces* yeast may be administered directly to a subject, the methods of the present invention are preferably based on the administration of a pharmaceutical formulation comprising one or more binding agents and/or one or more engineered strains of *Saccharomyces* yeast, and a pharmaceutically acceptable carrier or diluent. Thus, the invention includes pharmaceutical formulations comprising one or more of the binding agents and/or one or more engineered strains of *Saccharomyces* yeast defined herein and a pharmaceutically acceptable carrier or diluent.

Pharmaceutically acceptable carriers and diluents are commonly known and will vary depending on the particular binding agent or engineered strains of *Saccharomyces* yeast being administered and the mode of administration. Examples of generally used carriers and diluents include, without limitation: saline, buffered saline, dextrose, water-for-injection, glycerol, ethanol, and combinations thereof, stabilizing agents, solubilizing agents and surfactants, buffers and preservatives, tonicity agents, bulking agents, and lubricating agents. The formulations comprising binding agents and/or engineered strains of *Saccharomyces* yeast will typically have been prepared and cultured in the absence of any non-human components, such as animal serum (e.g., bovine serum albumin).

Pharmaceutical formulations comprising one or more binding agents and/or one or more engineered strains of *Saccharomyces* yeast may be administered to a subject using modes and techniques known to the skilled artisan. Characteristic of CDI disease may make it more amenable to treatment and prevention using colonic delivery of therapeutic agents, i.e., targeted delivery of binding agents to the lower GI tract, e.g., the large intestine or colon. Other modes of delivery include, but are not limited to, oral, nasal, anal, and via intravenous injection or aerosol administration. Other modes include, without limitation, intradermal, subcutaneous (s.c., s.q., sub-Q, Hypo), intramuscular (i.m.), intraperitoneal (i.p.), intra-arterial, intramedulary, intracardiac, intra-articular (joint), intrasynovial (joint fluid area), intracranial, intraspinal, and intrathecal (spinal fluids).

Depending on the means of administration, the dosage may be administered all at once, such as with an oral formulation in a capsule or liquid, or slowly over a period of time, such as with an intramuscular or intravenous administration.

The amount of binding agents, alone or in a pharmaceutical formulation, administered to a subject is an amount effective for the treatment or prevention of infection. Thus, therapeutically effective amounts are administered to subjects when the methods of the present invention are practiced. In general, between about 1 ug/kg and about 1000 mg/kg of the binding agent per body weight of the subject is administered. Suitable ranges also include between about 50 ug/kg and about 500 mg/kg, and between about 10 ug/kg and about 100 mg/kg. However, the amount of binding agent administered to a subject will vary between wide limits, depending upon the location, source, extent and severity of the infection, the age and condition of the subject to be treated, the means of administration, etc. A physician will ultimately determine appropriate dosages to be used.

The amount of the engineered strains of *Saccharomyces* yeast, alone or in a pharmaceutical formulation, administered to a subject is an amount effective for the treatment or prevention of infection. Thus, therapeutically effective amounts are administered to subjects when the methods of the present invention are practiced. In general, between about 1 ug/kg and about 1000 mg/kg of the engineered strains of *Saccharomyces* yeast per body weight of the subject is administered. Suitable ranges also include between about 50 ug/kg and about 500 mg/kg, and between about 10 ug/kg and about 100 mg/kg. However, the amount of the engineered strains of *Saccharomyces* yeast administered to a subject will vary between wide limits, depending upon the location, source, extent and severity of the infection, the age and condition of the subject to be treated, the means of administration, etc. A physician will ultimately determine appropriate dosages to be used.

Administration frequencies of the binding agents, the engineered strains of *Saccharomyces* yeast, and pharmaceutical formulations comprising the binding agents and/or engineered strains of *Saccharomyces* yeast will vary depending on factors that include the location of the bacterial infection, the particulars of the infection to be treated or prevented, and the mode of administration. Each formulation may be independently administered 4, 3, 2 or once daily, every other day, every third day, every fourth day, every fifth day, every sixth day, once weekly, every eight days, every nine days, every ten days, bi-weekly, monthly and bi-monthly.

The duration of treatment or prevention will be based on location and severity of the infection being treated or the relative risk of contracting the infection, and will be best determined by the attending physician. However, continuation of treatment is contemplated to last for a number of days, weeks, or months.

In each embodiment and aspect of the invention, the subject is a human, a non-human primate, bird, horse, cow, goat, sheep, a companion animal, such as a dog, cat or rodent, or other mammal. The subjects to which the methods of the present invention can be applied include subjects having an underlying disease or condition that makes them more susceptible to *C. difficile* infections.

The invention also provides a kit comprising one or more containers filled with one or more of the binding agents, one or more of the engineered strains of *Saccharomyces* yeast, or one or more pharmaceutical formulations comprising binding agents and/or the engineered strains of *Saccharomyces* yeast. The kit may also include instructions for use. Associated with the kit may further be a notice in the form prescribed by a governmental agency regulating the manufacture, use or sale of pharmaceuticals or biological products, which notice reflects approval by the agency of manufacture, use or sale for human administration.

III. Examples $V_HH$ Monomer and Heterodimer Binding Agents

An efficient platform to screen single domain (monomeric), mono-specific $V_HH$ peptide monomers against specific domains of toxins TcdA and TcdB was established. Using highly immunogenic atoxic holotoxins for immunization, and bioactive chimeric toxins (with normal domain functions) for screening, panels of $V_HH$ monomers binding to different domains of TcdA or TcdB were prepared. A majority of these $V_HH$ monomers possessed potent neutralizing activity and their binding to specific domains was determined (FIG. 2). The atoxic holotoxins have point mutations at their enzymatic glucosyltransferase domains as described previously [33]. The bioactive chimeric toxins were created by switching the functional domains between TcdA and TcdB, which was also described previously [33].

Several of the $V_HH$ monomers bind to highly conserved TcdA/TcdB epitopes. For example, $V_HH$ E3 binds to the Rho GTPase binding site and blocks glucosylation; $V_HH$ AH3 binds to the GT domain of the toxin; $V_HH$ 7F binds to cysteine protease cleavage sites and blocks GT domain cleavage and release. Some $V_HH$ monomers have potent neutralizing activity capable of blocking toxin cytotoxic activity at nM concentrations (See Table 1; FIGS. 3A and 3B).

To enhance the binding activity, two domain (dimeric), bi-specific $V_HH$ heterodimers were created (Table 3; FIG. 3C), allowing a single protein to target two distinctive epitopes of the toxins. These bi-specific $V_HH$ heterodimers possessed substantially enhanced neutralizing activities compared with equimolar mixtures of the same two $V_HH$ monomers (FIG. 3D). Heterodimers 5D/E3 and AH3/AA6 were found to fully protect mice from lethal systemic TcdB or TcdA challenge respectively, whereas mixed 5D and E3, or AA6 alone were only partially protective (FIGS. 3E and 3F).

A tetra-valent, tri-specific $V_HH$ binding agent (ABA) was generated by genetically fusing $V_HH$s with the highest neutralizing activities targeting conserved, non-overlapping epitopes (AH3/E3/E3/AA6) [41]. This rationally designed toxin binder achieved a substantially enhancing binding affinity and neutralizing activity over the individual monomers and potent therapeutic efficacy against fulminant CDI. ABA was able to broadly neutralize toxins from 11 different TcdA⁺TcdB⁺ *C. difficile* clinical isolates but failed to neutralize TcdB derived from two TcdA⁻TcdB⁺ strains. The amino acid sequence of ABA is set forth in SEQ ID NO:111.

The $V_HH$ monomers comprising the heterodimers were linked using a flexible linker selected from SEQ ID NOs: 9-13 (Table 2).

ABAB Binding Agent

Four domain (tetrameric), tetra-specific $V_HH$ binding agents were generated by linking $V_HH$ monomers AH3, 5D, E3, and AA6, namely ABBA (AH3/5D/E3/AA6) and ABAB (AH3/5D/AA6/E3). These tetra-specific, tetrameric binding agent targets conserved, non-overlapping epitopes and had excellent toxin neutralizing activity. In the design of ABAB (FIG. 4), $V_HH$ peptide monomers AH3 and AA6 were separated by placing the 5D monomers between them because AH3 and AA6 bind to GT and TD respectively (FIG. 2), which are spatially distant to each other. This design allowed AH3 and AA6 to bind to TcdA simultaneously.

Figure 4:
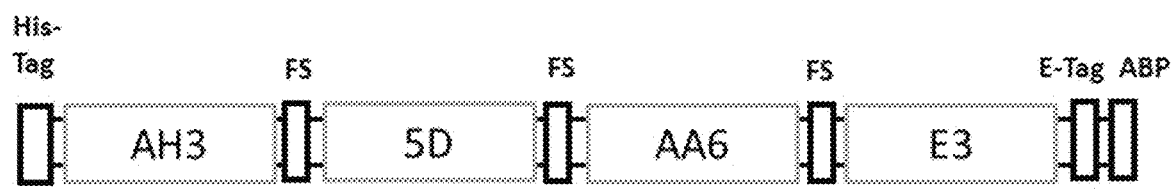
FIG. 4. Diagram of ABAB. His-tag and E-tag are epitope tags for purification and detection, respectively. FS: flexible linker; ABP: albumin binding peptide.

In the construction of the ABAB binding agent, flexible linkers were placed between the $V_HH$ monomers (see FIG. 4). The complete nucleic acid sequence encoding ABAB is provided in SEQ ID NO:20; the amino acid sequence of the protein is provided in SEQ ID NO:19.

In certain variants, a $His_{(6)}$-tag was provided at the amino terminus of the protein to aid in purification, an E-tag was provided at the carboxy terminus of the protein to aid in detection, and/or an albumin-binding peptide (ABP, DICLPRWGCLWD; SEQ ID NO:21) was placed at the carboxyl end of the construct to increase serum half-life of the protein (See FIG. 4).

ABAB was found to exhibit substantial enhanced binding affinity (Table 7) and neutralizing activity (Table 8) over the individual monomers and ABA. In Table 8, Vero cells were exposed to 5 ng/ml of TcdA in the presence of serially diluted AA6, AH3, ABAB or Merck anti-TcdA HuMab [9]. The minimal doses of antibodies protecting cells from TcdA-induced cell rounding are shown.

TABLE 7

| | $V_HH$s | $K_{on}$ (Ms⁻¹) | $K_{off}$ (s⁻¹) | $K_D$ (nM) |
|---|---|---|---|---|
| TcdA | AH3 | $2.20 \times 10^4$ | $7.10 \times 10^{-4}$ | 32.0 |
| | AA6 | $3.52 \times 10^4$ | $6.92 \times 10^{-4}$ | 19.7 |
| | ABAB | $6.96 \times 10^5$ | $1.21 \times 10^{-6}$ | 0.002 |
| TcdB | 5D | $1.52 \times 10^6$ | $9.94 \times 10^{-4}$ | 0.65 |
| | E3 | $2.95 \times 10^6$ | $9.4 \times 10^{-5}$ | 0.03 |
| | ABAB | $1.79 \times 10^6$ | $3.57 \times 10^{-6}$ | 0.002 |

TABLE 8

| AA6 | AH3 | ABAB | Merck Anti-TcdA HuMab |
|---|---|---|---|
| 8 nM | 8 nM | 0.25 nM | >10 nM |

ABAB was also found to compete with all four individual $V_HH$ peptide monomers in a competition ELISA and can simultaneously bind to both TcdA and TcdB as determined by sandwich ELISA. Furthermore, ABAB is broadly reactive, capable of neutralizing toxins from the 13 different *C. difficile* strains that represent most of the current epidemic strains (Table 9).

TABLE 9

| Strains | Ribotype | REA type | PFGE type | Toxins | Place/date of isolation | ABAB neutralization |
|---|---|---|---|---|---|---|
| R20291 | 27 | B1 | NAP1 | TcdA/TcdB | London/2006 | Yes |
| CD196 | 27 | B1 | NAP1 | TcdA/TcdB | France/1985 | Yes |
| 630 | 12 | R | | TcdA/TcdB | Zurich/1982 | Yes |
| M120 | 78 | BK | NAP7, 8, 9 | TcdA/TcdB | UK/2007 | Yes |
| BI-9 | 1 | J | NAP2 | TcdA/TcdB | Gerding Collection | Yes |
| Liv024 | 1 | J | NAP2 | TcdA/TcdB | Liverpool/2009 | Yes |
| Liv022 | 106 | DH | NAP11 | TcdA/TcdB | Liverpool/2009 | Yes |
| TL178 | 2 | G | NAP6 | TcdA/TcdB | Belfast/2009 | Yes |
| TL176 | 14 | Y | NAP4 | TcdA/TcdB | Cambridge, UK/2009 | Yes |
| TL174 | 15 | | | TcdA/TcdB | Cambridge, UK/2009 | Yes |

TABLE 9-continued

| Strains | Ribotype | REA type | PFGE type | Toxins | Place/date of isolation | ABAB neutralization |
|---|---|---|---|---|---|---|
| CD305 | 23 | | | TcdA/TcdB | London/2008 | Yes |
| CFS | 17 | | | TcdB | Belgium/1995/human | Yes |
| M68 | 17 | | | TcdB | Dublin/2006/human | Yes |

Figure 5A:
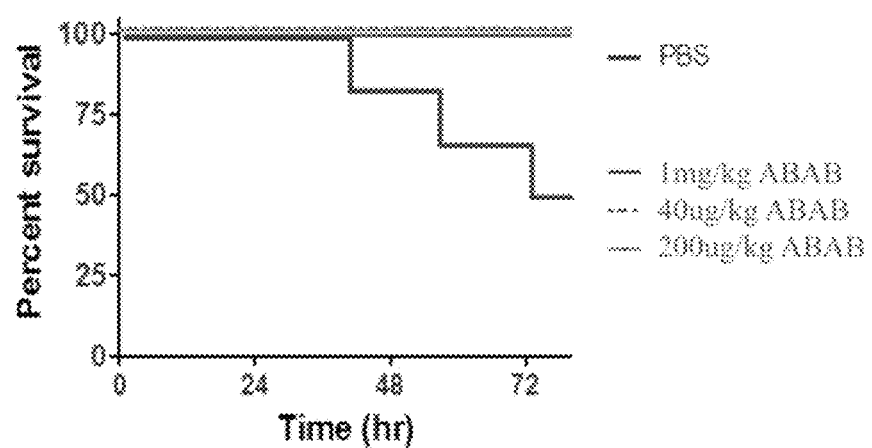
FIGS. 5A-5B. ABAB is highly potent in protecting mice from *C. difficile* spore (FIG. 5A) and toxin (FIG. 5B) challenge. MK HuMabs: a mixture of Merck anti-TcdA (actoxumab) and anti-TcdB (bezlotoxumab) human monoclonal antibodies that are undergoing clinical trials.
Figure 5B:
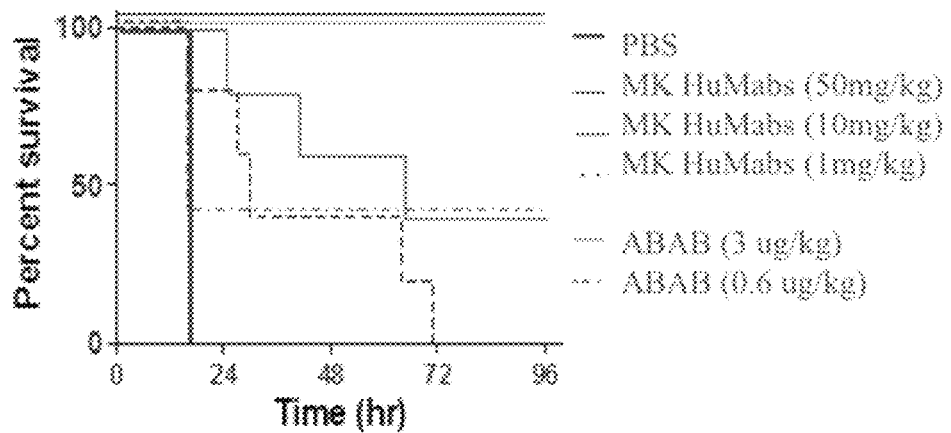

Since ABAB shows high potency in binding to and neutralizing both toxins, its efficacy in treating fulminant CDI was evaluated. A single injection with as low as 40 µg/kg of ABAB one-day post *C. difficile* spore challenge reversed fulminant CDI in mice. None of the ABAB-treated mice died whereas 50% of control mice became moribund by 3 days post-infection (FIG. 5A). ABAB is 4-log more potent in preventing mortality after systemic challenge with TcdA and TcdB than the Merck HuMabs (FIG. 5B) [9]. Thus, ABAB possesses extraordinary in vivo efficacy against *C. difficile* toxins and spore challenge.

Figure 6:
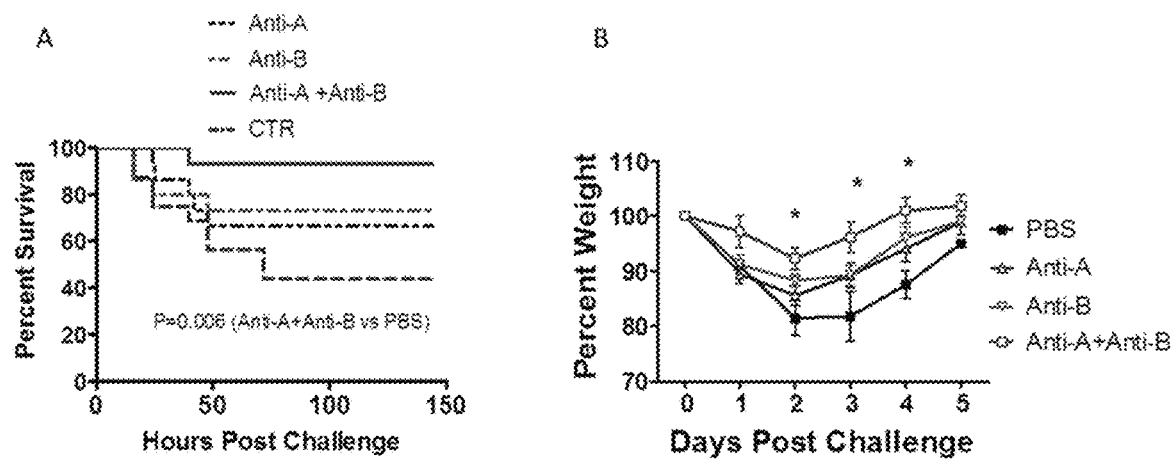
FIGS. 6A-6B. Anti-toxin sera against both toxins protect mice from CDI. Mice were i.p. injected with 50 ul alpaca anti-sera against TcdA ("Anti-A"), TcdB ("Anti-B"), TcdA+TcdB ("Anti-A+Anti-B") or with 100 ul presera or PBS ("CTR") for 4 hours before *C. difficile* spore (UK1 strain, $10^6$ spores/mouse) inoculation. Mouse survival (FIG. 6A; Anti-A+Anti-B vs. PBS, p=0.006) and weight loss (FIG. 6B) are illustrated (*, p<0.05 between Anti-A+Anti-B vs. control).

Animal and human studies demonstrated that passively administered antitoxin antibodies provide protection against CDI. The initial studies here also showed that antitoxin polysera protected mice from primary CDI (FIGS. 6A and 6B) and recurrent/relapse CDI. These findings and results from FIGS. 5A and 5B supported the hypothesis and provided the rationale for development of a parenteral ABAB immunization strategy for preventing CDI. To achieve the goal of optimizing ABAB for systemic delivery, chimeric and humanized ABAB were generated as illustrated in FIG. 1, i.e., $V_HH$-Fc and $V_HH$-IgG binding agents as well as the humanized proteins $hV_HH$-Fc and $hV_HH$-IgG, after which leading proteins were evaluated for in vivo neutralizing activity and protection in animal models. Details regarding the preparation and testing of the additional binding agents are provided in the following paragraphs.

ABAB-Fc

ABAB-Fc binding agent was prepared by generating an expression vector encoding the $V_HH$ peptide monomers AH3/5D/AA6/E3 (linked in the noted order) joined to a human IgG1 Fc domain. The $V_HH$ peptide monomers were separated by flexible linkers of Table 2. The nucleic acid sequence encoding the protein is provided in SEQ ID NO:23. ABAB-Fc was expressed and purified from stable transfected HEK293 cell line culture supernatant using protein A beads under conditions permitting disulfide bond formation and bi-valent molecule production. The expression levels were about 20 mg/L of culture supernatant. ABAB-Fc is fully functional in binding and neutralizing both TcdA and TcdB (data not shown). The amino acid sequence of ABAB-Fc is provided in SEQ ID NO:22.

Mono-specific $V_HH$-Fc binding agents (AH3-Fc, 5D-Fc, E3-Fc, AA6-Fc) and bi-specific $V_HH$-Fc binding agents (AH3/5D-Fc) and AA6/E3-Fc) were also made using this Fc-fusion system. Table 5 above provides the sequences for these additional binding agents.

ABAB-IgG

As illustrated in FIG. 1, bi-specific $V_HH$-IgG (AH3/5D-IgG and E3/AA6-IgG) can be generated by fusing monomers with human IgG heavy and light (kappa or lambda) chains separately. Tetra-specific $V_HH$-IgG (ABAB-IgG) binding agents can be generated by fusing dimers with human IgG heavy and light chains separately. Co-transfecting the heavy and light chain constructs generates the AH3/5D-IgG, E3/AA6-IgG and ABAB-IgG chimeric proteins. The separation of two $V_HH$s into heavy and light chains likely improves the yield and stability of bi-specific and tetra-specific $V_HH$ chimeric proteins. This allows determination of whether $V_HH$-human IgG chimeric antibody helps the stability and efficacy of ABAB in vivo. Similarly, further improvement of in vivo half-life of ABAB-IgG can also be tested in ABAB-IgG variants with enhanced binding affinity to FcRn receptor.

Bi-specific (AH3/5D-IgG1 and E3/AA6-IgG1) and tetra-specific (ABAB-IgG1) IgG1 binding agents were prepared by co-transfecting expression vectors encoding the heavy and light (kappa) chain of each binding agent. The $V_HH$ peptide monomers were separated by flexible linkers of Table 2.

Bi-specific, tetrameric $V_HH$-IgG1 binding agents were produced by preparing two separate expression vectors, the first encoding a $V_HH$ peptide monomer joined to the human IgG1 antibody heavy chain (CH1-Hinge-CH2-CH3) lacking the heavy chain variable region and the second encoding a $V_HH$ peptide monomer joined to the human IgG1 antibody light (kappa) chain (CK) lacking the light chain variable region. These binding agents are bi-specific and tetrameric in that each light chain of the resulting binding agent is linked to a first $V_HH$ monomer and each heavy chain of the resulting binding agent is linked to a second $V_HH$ monomer. Table 6 above provides the sequences for these additional binding agents. Suitable pairings include (i) AH3-IgG1-heavy chain+AA6-light (kappa or lambda) chain, (ii) 5D-IgG1-heavy chain+E3-light (kappa or lambda) chain, (iii) 5D-IgG1-heavy chain+AA6-light (kappa or lambda) chain, and (iv) AH3-IgG1-heavy chain+E3-light (kappa or lambda) chain.

Tetra-specific, octameric ABAB-IgG binding agents were prepared. These binding agents are tetra-specific and octameric in that each light (kappa or lambda) chain of the resulting binding agent is joined to two (a first and second) linked $V_HH$ monomers and each heavy chain of the resulting binding agent is joined to a two (a third and fourth) linked $V_HH$ monomer, where the first, second, third and fourth monomers binds to a different epitope.

Figure 7:
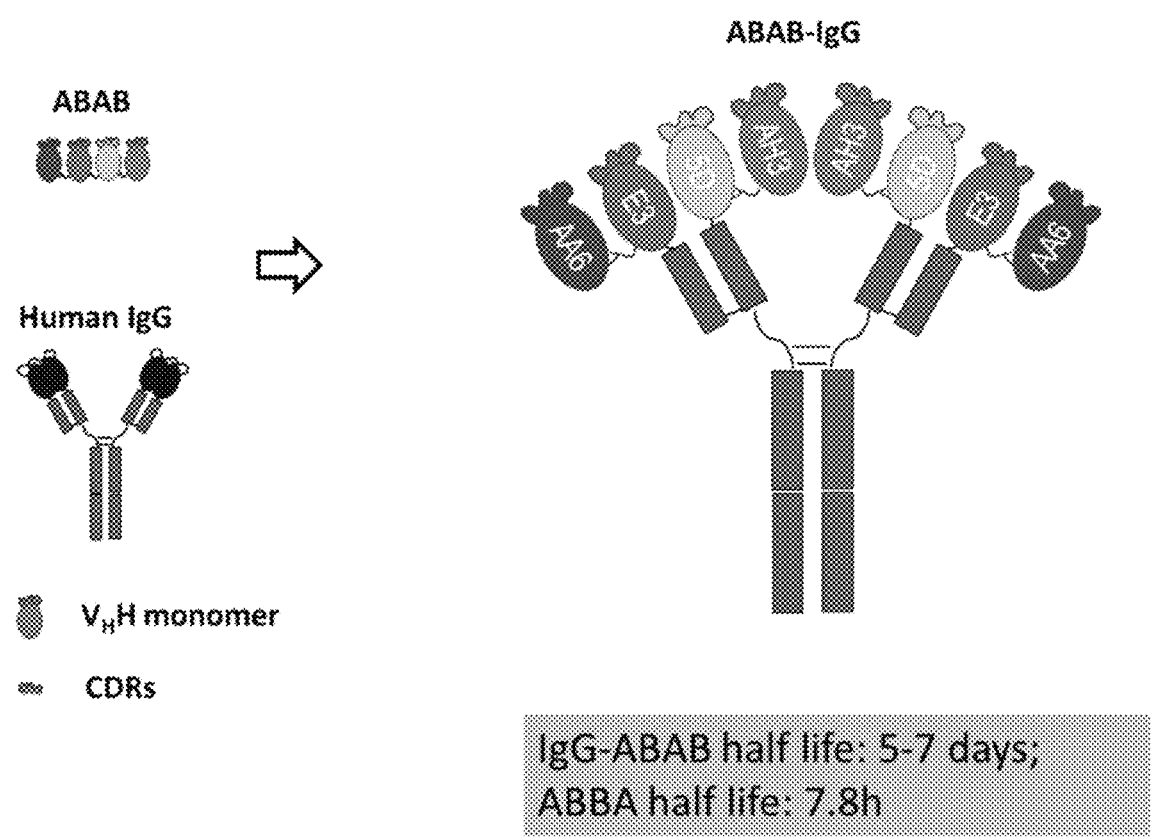
FIG. 7. The diagram of the ABAB and ABAB-IgG molecules.

A particular tetra-specific, octameric ABAB-IgG (FIG. 7) binding agent was produced by preparing two separate expression vectors, the first encoding the $V_HH$ peptide monomers AH3/5D (linked in the noted order) joined to the human IgG1 antibody heavy chain (CH1-Hinge-CH2-CH3) lacking the heavy chain variable region and the second encoding the $V_HH$ peptide monomers AA6/E3 (linked in the noted order) joined to the human IgG1 antibody light (kappa) chain (CK) lacking the light chain variable region. The nucleotide sequence encoding the AH3/5D-IgG1 heavy chain is provided in SEQ ID NO:45; the amino acid sequence is provided in SEQ ID NO:44. The nucleotide sequence encoding the AA6/E3-IgG1 kappa chain is provided in SEQ ID NO:47; the amino acid sequence is provided in SEQ ID NO:46.

The bi-specific (AH3/5D-IgG1 and E3/AA6-IgG1) and tetra-specific (ABAB-IgG1) IgG1 binding agents were expressed and purified from stable transfected HEK293 cell line culture supernatant using protein A beads under conditions permitting disulfide bond formation and bi-valent molecule production. SDS-PAGE shows more than 90% purity of the purified ABAB-IgG1 with total molecular weight (light and heavy chains together) around 218 KDa on non-reduced gel (data not shown). The molecular weight of heavy chain is 68 KDa and light chain is 41 KDa showed on reduced gel.

Figure 8A:
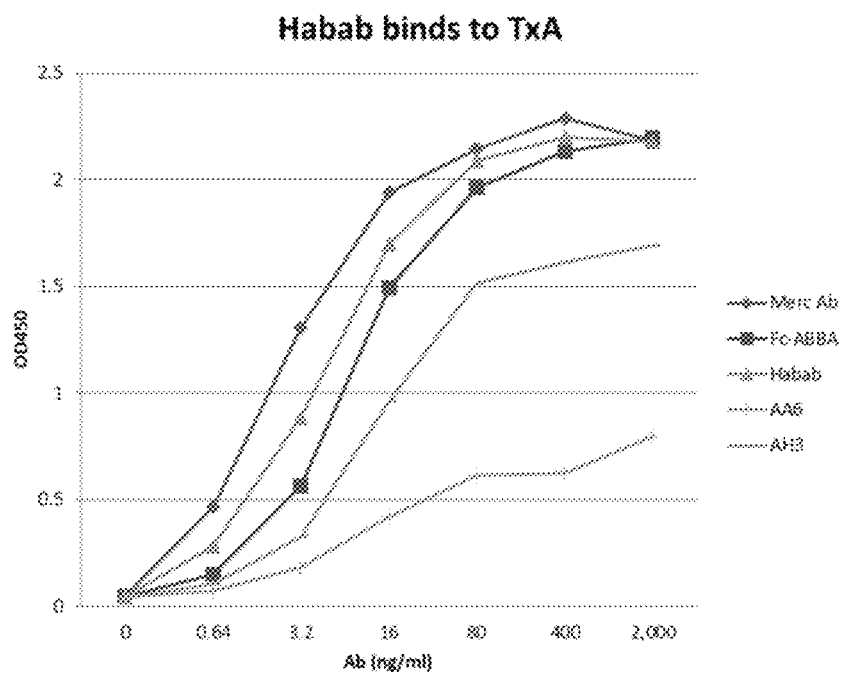
FIGS. 8A-8B. ELISA analysis of binding of ABAB-IgG to TcdA (FIG. 8A) and TcdB (FIG. 8B) as compared with the binding of the individual VHHs to the respective toxins.
Figure 8B:
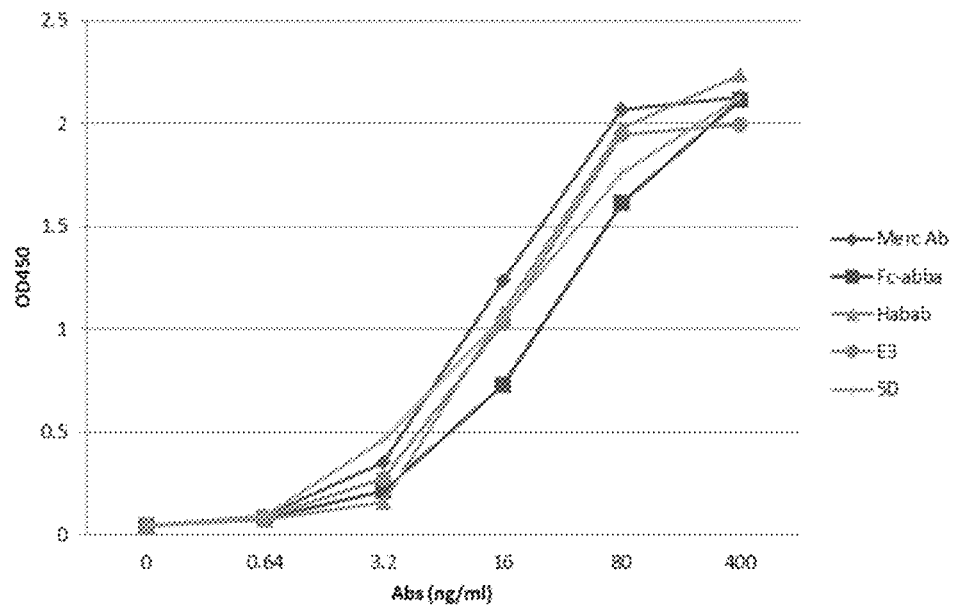

The binding of ABAB-IgG1 to TcdA and TcdB was determined. FIGS. 8A-8B illustrate the comparison of binding ABAB-IgG1 to both toxins with the individual components (AH3, AA6, E3, and 5D). FIG. 8A shows the results of experiments where plates were coated with 1 ug/ml TcdA (TxA). Serially diluted ABAB-IgG was added in concentrations of 0, 0.64, 3.2, 16, 80, 400 and 2,000 ng/ml. The plates were washed and Merck Ab (anti-TcdA), Fc-ABBA (ABAB-Fc), Habab (ABAB-IgG), and $V_HH$ anti-TcdB monomers AA6 and AH3 were added in the indicated amounts (ng/ml). Appropriate labeled antibodies were used for detection. FIG. 8B shows the results of experiments where plates were coated with 1 ug/ml TcdB (TxB). Serially diluted ABAB-IgG was added in concentrations of 0, 0.64, 3.2, 16, 80 and 400 ng/ml. The plates were washed and Merck Ab (Anti-TcdB), Fc-abba (ABAB-Fc), Habab (ABAB-IgG), and $V_HH$ anti-TcdB monomers E3 and 5D were added in the indicated amounts (ng/ml). Appropriate labeled antibodies were used for detection.

As expected, the tetra-specific antibody can bind to TcdA and TcdB simultaneously as determined by sandwich ELISA (FIGS. 9A-9B). In a first set of experiments, plates were coated with 1 ug/ml TcdA (TxA). Serially diluted ABAB-IgG (Habab) was added in concentrations of 0, 1.6, 8, 40, 200 and 1000 ng/ml. The plates were washed and the following amounts of TcdB were added: 1.6, 8, 40, 200, and 1000 ng/ml. Mouse anti-TxB antibodies (500×) and goat anti-mouse-IgG-HRP (3000×) antibodies were used for detection. The results provided in FIG. 9A show that TxB is detected by coating TxA, suggesting IgG-ABAB binds to TxA/B simultaneously. In a second set of experiments, plates were coated with 1 ug/ml TcdB (TxB). Serially diluted ABAB-IgG (Habab) was added in concentrations of 0, 1.6, 8, 40, 200 and 1000 ng/ml. The plates were washed and the following amounts of TcdA were added: 1.6, 8, 40, 200, and 1000 ng/ml. Mouse anti-TxA antibodies (500×) and goat anti-mouse-IgG-HRP (3000×) antibodies were used for detection. The results provided in FIG. 9B show that TxA is detected by coating TxB, again suggesting IgG-ABAB binds to TxA/B simultaneously.

Figure 10A:
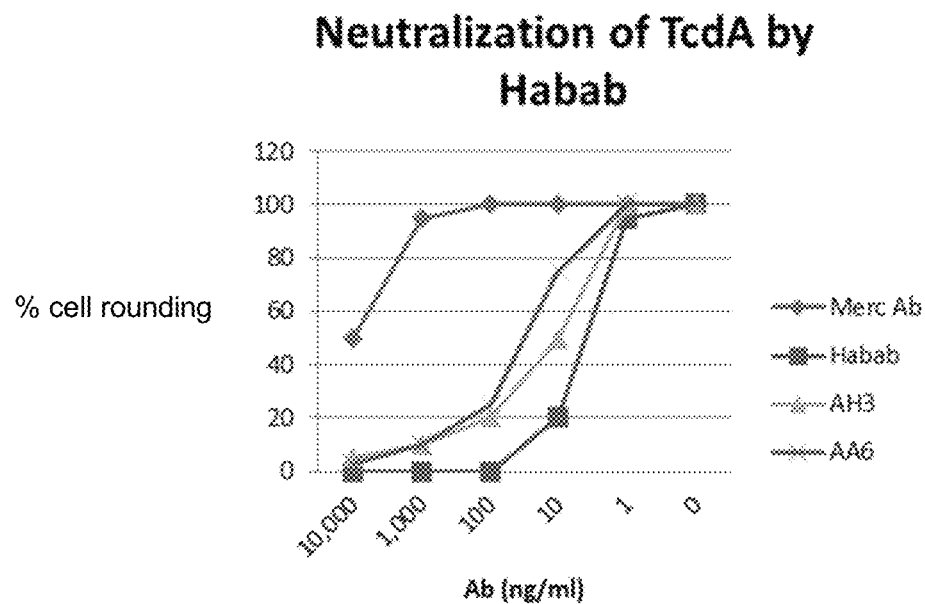
FIGS. 10A-10B. ABAB-IgG neutralizing activities against TcdA (FIG. 10A) and TcdB (FIG. 10B).
Figure 10B:
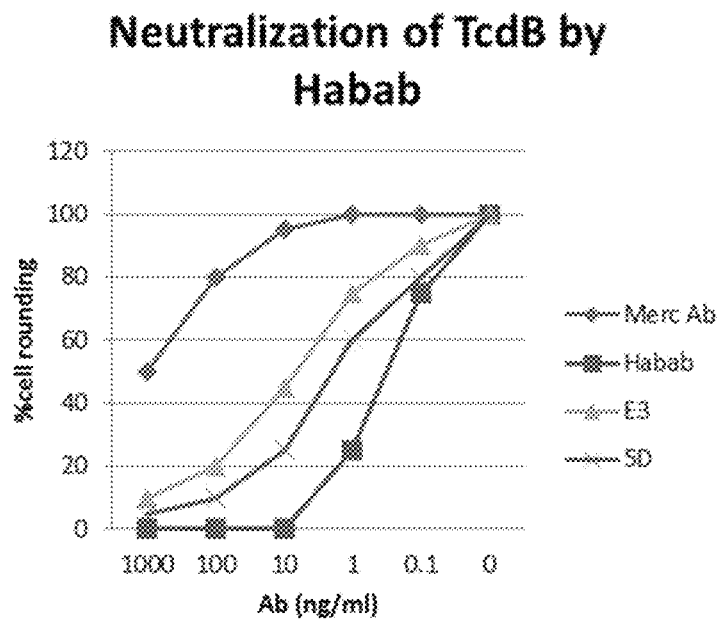

The neutralizing activities of ABAB-IgG1 against cytopathic effects of the toxins on cultured cells were also examined. TcdA (100 ng/ml, FIG. 10A) was mixed with serially diluted Merck anti-TcdA human monoclonal antibody, ABAB-IgG1 (Hababa), and $V_HH$ anti-TcdA monomers AA6 and AH3 before adding to Vero cell monolayers in 100 ul culture medium and incubated at 37° C. for 24 hours. The results provided in FIG. 10A show that ABAB-IgG1 is at least 1000-fold more potent than Merck antibodies in neutralizing TcdA. In similar experiments, TcdB (10 pg/ml, FIG. 10B) was mixed with serially diluted Merck anti-TcdB human monoclonal antibody, ABAB-IgG1 (Hababa), and $V_HH$ anti-TcdB monomers E3 and 5D before adding to Vero cell monolayers in 100 ul culture medium and incubated at 37° C. for 24 hours. The results provided in FIG. 10B show that ABAB-IgG1 is at least 1000-fold more potent than Merck antibodies in neutralizing TcdB.

Figure 11:
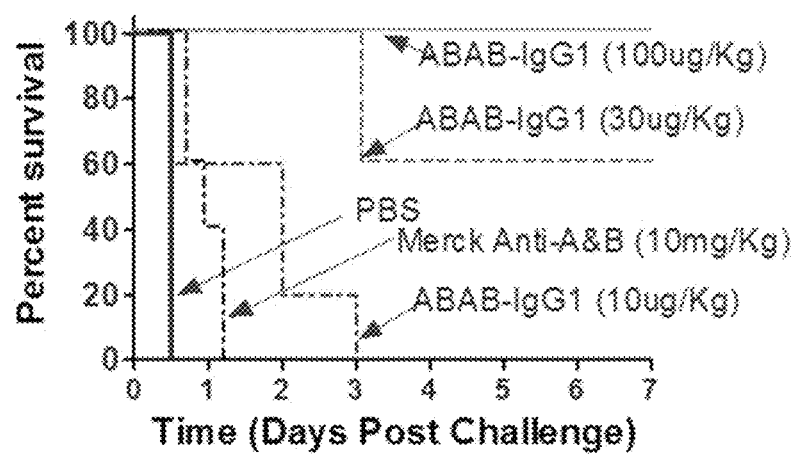
FIG. 11. Graph showing in vivo neutralizing activity of ABAB-IgG against *C. difficile* infection in mice versus Merck antibodies against TcdA and TcdB (actoxumab and bezlotoxumab).

The in vivo neutralizing activities of ABAB-IgG1 were studied in a mouse model of CDI, the results of which are shown in FIG. 11. Mice were challenged with lethal dose of a mixed TcdA and TcdB (25 ng each toxin per mouse) and 4 hour later, ABAB-IgG (10, 30 or 100 ug/kg), a mixture of Merck anti-toxin A and anti-toxin B antibodies (10 mg/kg) or PBS was administered to the mice. The results demonstrate that the neutralizing activity of ABAB-IgG was much greater than the Merck antibody, and at lower concentrations.

Animal Testing of ABAB-IgG

Figure 12:
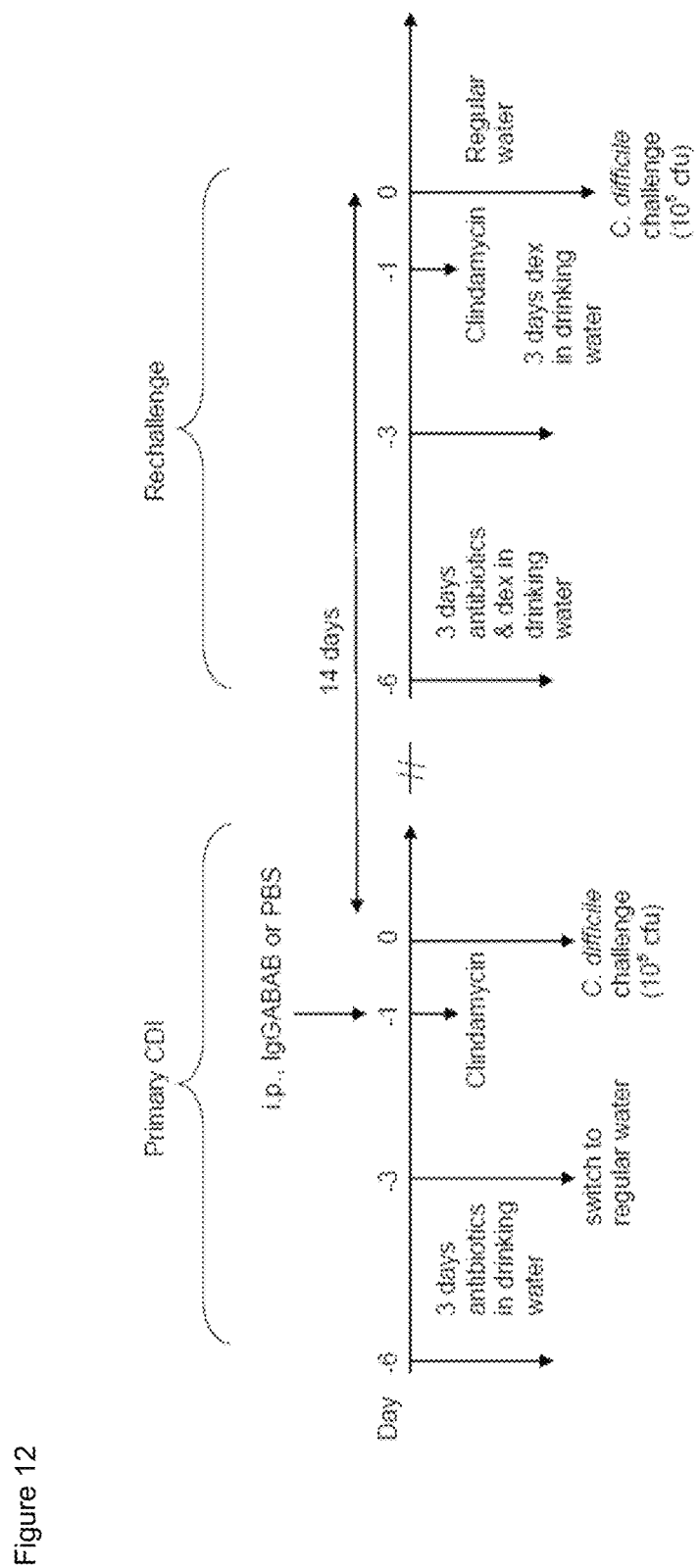
FIG. 12. Design of studies on the effects of prophylactic ABAB-IgG against *C. difficile* infection.

The ABAB-IgG binding agent was tested in both prophylactic treatment and re-challenge survival assays. FIG. 12 provides the experimental design of both studies. 6-8 week old female C57 mice were used, and the conditions included PBS: 10 ml/kg, i.p., n=14; ABAB-IgG: 200 ug/kg, i.p., n=10; ABAB-IgG: 1 mg/kg, i.p., n=10; ABAB-IgG: 5 mg/kg, i.p., n=10.

Table 10 provides a summary of the results seen with prophylactic treatment of mice against *C. difficile* spores (UK1, a 027/BI/NAP1 epidemic strain). ABAB-IgG or PBS was administered one day prior to administrating of *C. difficile* spores. As can be seen, ABAB-IgG showed dose-related prophylactic protection against CDI, where 5 mg/kg showed complete protection on all the parameters examined and 200 ug/kg was found to be more potent than 200 ug/kg of bi-specific $V_HH$ fusion antibody ABA [41].

TABLE 10

|  | Diarrhea | | Weight Change | | | | |
|---|---|---|---|---|---|---|---|
|  | Day 1 Occurrence | Day 2 score | Overall | Day 2 | Day 3 | Day 4 | Survival |
| 200 ug/kg | — | — | — | ✓ | — | ✓ | ✓ |
| 1 mg/kg | ✓ | — | ✓ | — | ✓ | ✓ | — | ✓ |
| 5 mg/kg | ✓ | ✓ | ✓ | ✓ | ✓ | ✓ | ✓ | ✓ |

Table 11 provides a summary of the results seen with re-challenge of mice against *C. difficile* spores. ABAB-IgG or PBS was administered 15 days prior to administrating of *C. difficile* spores. As can be seen, one dose of ABAB-IgG showed some protection against the CDI caused by re-challenge of spores, but the protection was much less efficient compared to that during the primary challenge. This may be due to the drop of the antibody level with time and the generation of antibody in the PBS group following primary challenge.

TABLE 11

| | Diarrhea | | Weight Change | | | | |
|---|---|---|---|---|---|---|---|
| | Occurrence | Day 1 score | Day 2 score | Overall | Day 2 | Day 3 | Day 4 | Survival |
| 200 ug/kg | ✓ | ✓ | — | — | — | — | — | — |
| 1 mg/kg | ✓ | — | — | — | — | — | ✓ | — |
| 5 mg/kg | — | — | — | ✓ | — | — | — | — |

Intestinal delivery of IgG-ABAB was also tested for protection of mice from fulminant CDI. After a single IgG-ABAB injection into mouse ceca after a laparotomy, mice were completely protected against fulminant CDI of death outcomes whereas 50% of control mice succumbed (data not shown). Disease progress and severity were assessed daily using a clinical scoring system modified from a previous publication [62], which included four criteria (activity level, posture, coat, and diarrhea) each graded on a scale from 0 to 4 and added together to generate a score with a maximum value of 16. A normal mouse would score 0 and a mouse found dead was scored as 16. Mice with scores equal to or higher than 11 should be euthanized. Only one mouse in the IgG-ABAB treatment group developed transient diarrhea whereas mice injected with PBS developed severe CDI disease symptoms (data not shown). Thus, Ig-ABAB manually delivered by injection into mouse intestines showed potent therapeutic efficacy.

Expression, Purification and Evaluation of Binding Agents

Figure 3:
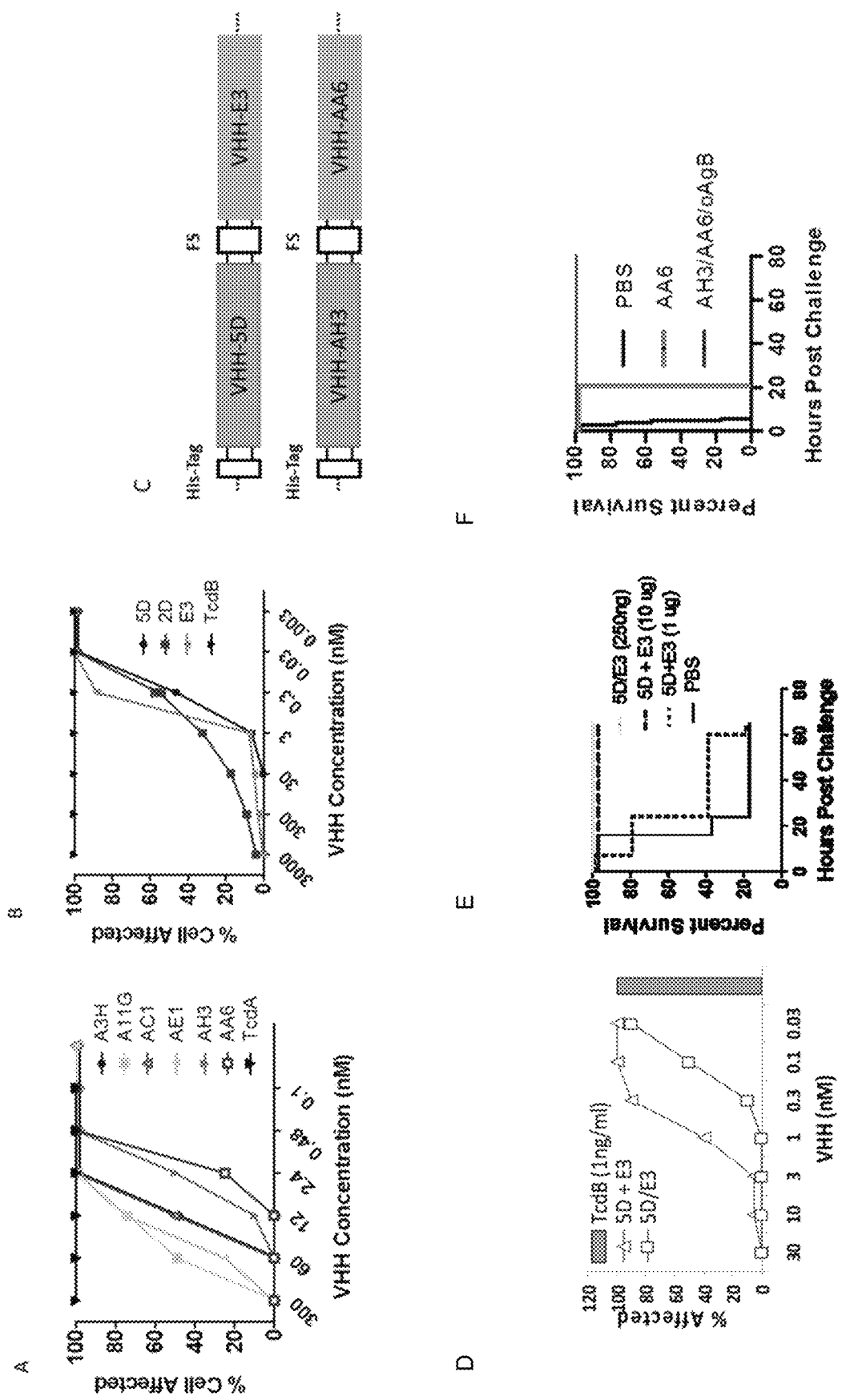
FIGS. 3A-3F. Monomeric or dimeric $V_HH$s possess potent neutralizing activity. $V_HH$s block cell rounding induced by TcdA (FIG. 3A) or TcdB (FIG. 3B) at nM concentrations.

A variety of selection criteria is used to select the binding agents generated in the experiments described in the approaches herein. First, each of the constructs defined herein can be used in transient transfections of 293T cells for making small-scale recombinant proteins by Protein A affinity chromatography. The production yield of each construct can be determined by quantitative ELISA. Second, binding activity of recombinant proteins can be screened using ELISA and surface plasmon resonance (SPR) to select constructs that preserve their original binding activities against the toxins. Third, the proteins are evaluated for neutralizing activity in in vitro assays (FIG. 3).

Accumulating observations indicate that polyreactivity and/or autoreactivity of in vivo recombinant binding agents are potential issues related to their in vivo safety and half-life. The application of the selected ABAB binding agents as a systemic binding agent for preventing primary acute CDI likely requires that the chimeric and humanized ABAB proteins are limited in polyreactivity and/or autoreactivity. Progress in protein proteomics has made it possible to screen for polyreactivity and autoreactivity of recombinant antibodies in vitro, which is a great tool for surrogate therapeutic antibodies. Therefore, selected humanized binding agents with good yield, high binding affinity, and potent neutralizing activity can be further tested for potential polyreactivity and autoreactivity using the auto-antigen microarray test and ProtoArray protein microarrays (Invitrogen).

From the above in vitro assays, candidate ABAB-Fc and ABAB-IgG binding agents can be evaluated for their in vivo toxicity, serum half-life, and immunogenicity.

Generation of S. cerevisiae Secreting ABAB (Sc-ABAB)

Means for in vivo production and delivery of the binding agents to the gut of subjects having CDI or at risk of developing CDI were developed. Because S. cerevisiae is genetically similar to S. boulardii [52,53] and genetic tools are readily available for S. cerevisiae, S. cerevisiae was first used for ABAB secretion validation.

Figure 13:
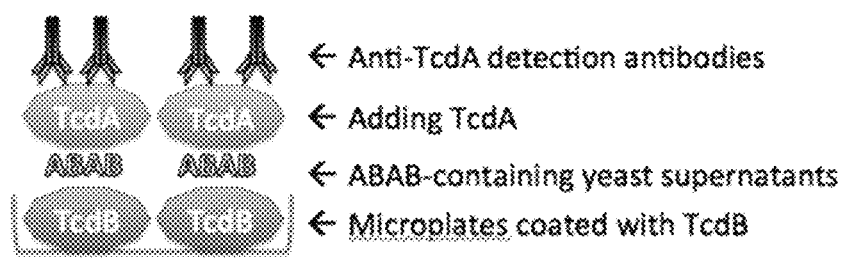
FIGS. 13A-13B. Bi-specific sandwich ELISA.
Figure 13:
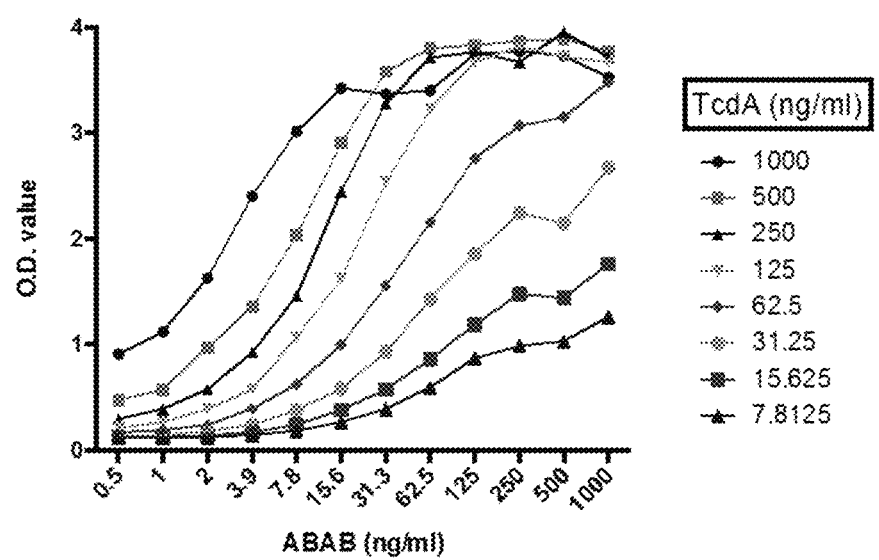

A novel bi-specific sandwich ELISA method was first developed to evaluate ABAB secretion. The setting utilizes purified TcdA and TcdB as binding antigens for ABAB bispecificity and α-TcdA antibodies for detection (FIG. 13A). For standardization, plates were coated with TcdB (1 ug/ml) into which was added serially diluted ABBA ((AH3-E3-E3-AA6)) standard. Serial diluted rTcdA (1 ug/ml to 7.8 ng/ml) was then added. The capture of TcdA was then measured by adding monoclonal antibody against TcdA followed by HRP conjugated secondary antibody. The results for the standard curves are shown in FIG. 13B. Based on these results, a standard curve derived using 125 ng/ml of rTcdA was chosen for determining secretion levels of ABAB in yeast culture supernatants and used for all subsequent ELISA.

A shuttle plasmid (pD1214-FAKS) containing origins of replication from both E. coli (pUC) and yeast (2 micron circle), as well as a yeast auxotrophic selection marker URA3 (conferring the ability to synthesize uracil), was obtained from DNA 2.0 (Newark, Calif.). The sequence encoding ABAB (SEQ ID NO:20), and His tag (SEQ ID NO:66) and D7 tag (SEQ ID NO:112) at the N-terminus and C-terminus of ABAB respectively, was inserted into this plasmid backbone in which transcription was controlled by the strong constitutive yeast translational elongation factor promoter ($P_{TEF}$) and extracellular secretion provided by fusion to the alpha mating factor secretion signal leader sequence (FAKS). The sequence of the resulting plasmid (pD1214-FAKS-His-hABAB-D7) is provided in SEQ ID NO:68.

Plasmid pD1214-FAKS-His-hABAB-D7 was transformed into the S. cerevisiae strain BY4741 (MATa his3Δ1 leu2Δ0 Met15Δ0 ura3Δ0), an URA3 knockout S288C-derivative laboratory strain. Yeast transformants were then cultured in YNB medium containing dropout mix without uracil (6.8 g YNB, 20 g glucose, 2 g dropout mix in 1 L of sterile ddH$_2$O) at 250 rpm at 30° C. overnight to reach O.D. 1 in a shaker. The cells were then centrifuged down and lysed by sonication in 1×SDS loading buffer. After sonication, total cell lysates were treated at 98° C. for 5 minutes before loading on a SDS gel. Same amount of yeast control cell lysates were loaded in each well except the control cells were not viable in YNB medium without uracil and therefore were cultured in YNB complimented with uracil.

Figure 14:
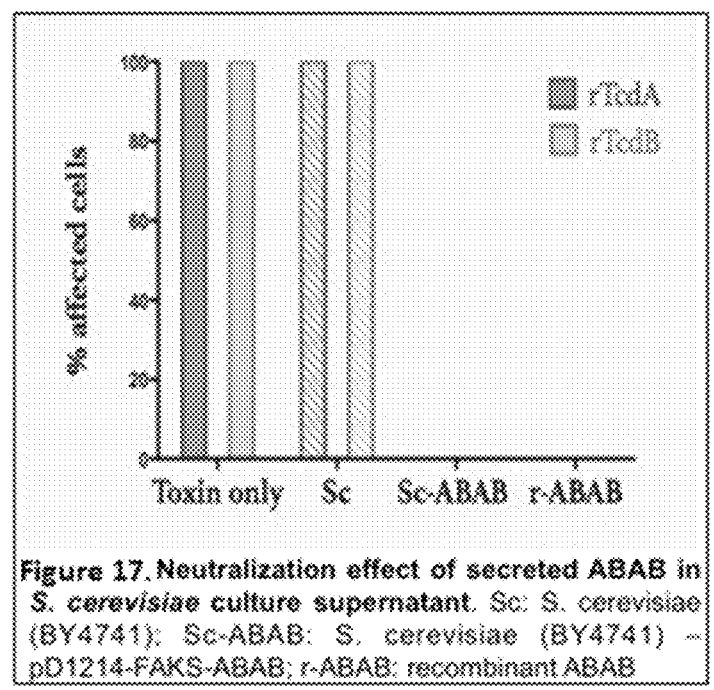
FIGS. 14A-14B. Activity of ABAB secreted by Sc-ABAB.
Figure 14:
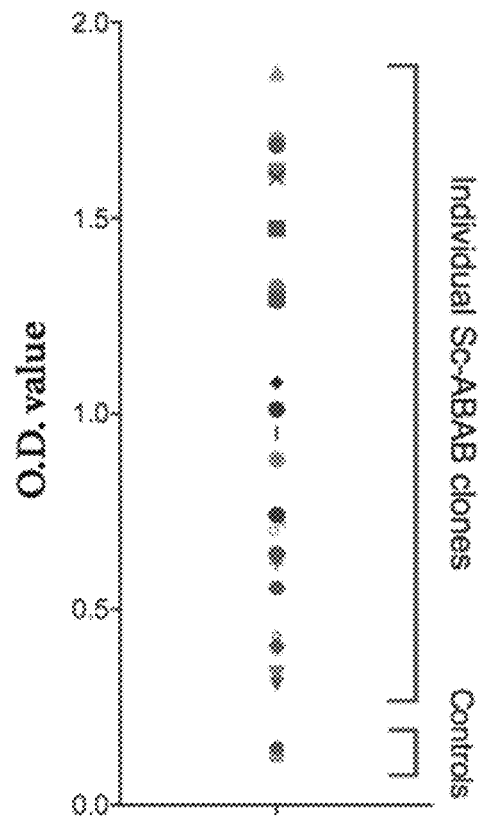

Culture supernatants from 25 yeast transformants as well as 3 yeast control colonies were centrifuged to spin down cells, and the cell-free supernatants were then diluted with 2.5% milk in PBS containing 0.05% of tween 20 at 1:3 ratio and screened by the ELISA as described above after 24 hrs of incubation in a shaker at 250 rpm and 30° C. FIG. 14B shows that all the yeast transformants secreted ABAB in culture supernatant compared to the culture supernatant from the yeast control colonies.

A cell-based neutralizing assay was used to assess the biological activity of secreted ABAB in culture supernatant. In this assay, sufficient amount of toxin A or toxin B to cause 100% cell rounding in 4 hours were added with PBS, cell-free culture supernatant from BY4741 control colony or BY4741-ABAB colony. Recombinant ABAB was used a positive control. The biological activity of secreted ABAB in culture supernatant was determined by the level of neutralizing activity to prevent cell rounding. Full length ABAB secreted from S. cerevisiae indeed retains its neutralizing activity when compared with purified recombinant ABAB (FIG. 14A). These combined results imply the plausibility of ABAB secretion by S. boulardii.

In further experiments, it was demonstrated that oral gavage of mice with Sc-ABAB at doses of $10^{10}$ CFU had no adverse effects on mice, and mice shed live Sc-ABAB as determined by plating feces on Sabouraud CAF-Agar (data not shown). Isolates recovered from mice retained their ability to produce functional ABAB using the assay described above.

ABAB Secretion Optimization

ABAB secretion level is imperatively linked to in vivo therapeutic efficacy. Therefore, the possibility of further optimizing ABAB secretion by replacing the existing FAKS secretion signal with a number of commercially available secretion signals was explored. Secretion sequences facilitate co-translational or post-translational translocation of heterogeneous proteins into the endoplasmic reticulum and Golgi compartments prior to extracellular export. Although α-mating factor is a commonly used signal sequence for heterologous protein secretion that typically generates good yields of the secreted proteins in S. cerevisiae [69,70], studies have shown that other secretion sequences from other proteins such as inulinase or invertase could be more suitable for secreting certain heterologous proteins [71,72].

11 different commercially available secretion signals (Table 4; DNA 2.0, Newark, Calif.) were genetically fused with ABAB individually under the control of TEF promoter in the same pD1214 plasmid backbone. Plasmids encoding ABAB with alternative secretion signals include the following plasmids where the FAKS secretion signal is replaced by the noted new secretion signals from Table 4 and where both the his-tag and D7-tag are removed:

Plasmid pD1214-AKS-hABAB (SEQ ID NO:70)
Plasmid pD1214-AK-hABAB (SEQ ID NO:71)
Plasmid pD1214-AT-hABAB (SEQ ID NO:72)
Plasmid pD1214-AA-hABAB (SEQ ID NO:73)
Plasmid pD1214-GA-hABAB (SEQ ID NO:74)
Plasmid pD1214-IN-hABAB (SEQ ID NO:75)
Plasmid pD1214-IVS-hABAB (SEQ ID NO:76)
Plasmid pD1214-KP-hABAB (SEQ ID NO:77)
Plasmid pD1214-LZ-hABAB (SEQ ID NO:78)
Plasmid pD1214-SA-hABAB (SEQ ID NO:79)

Figure 15:
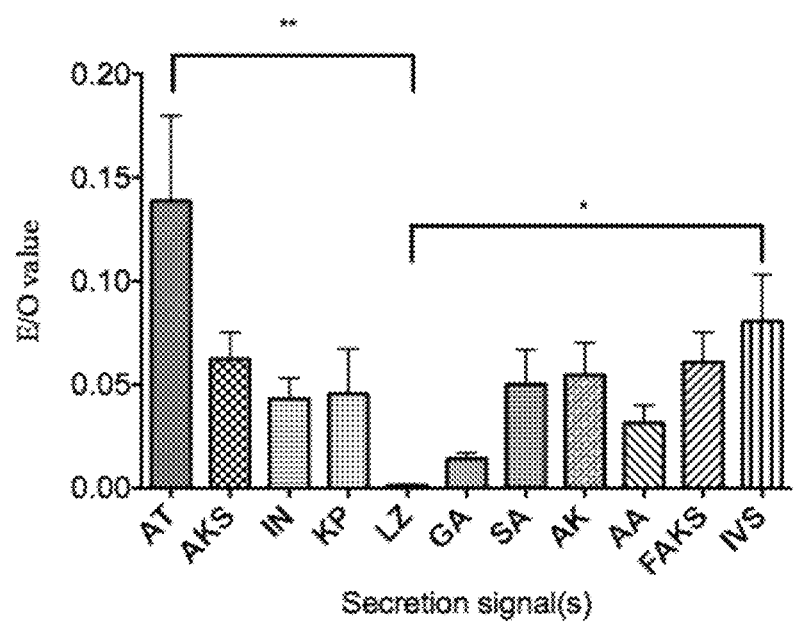
FIGS. 15A-15B. ABAB secretion level with various secretion signals.
Figure 15:
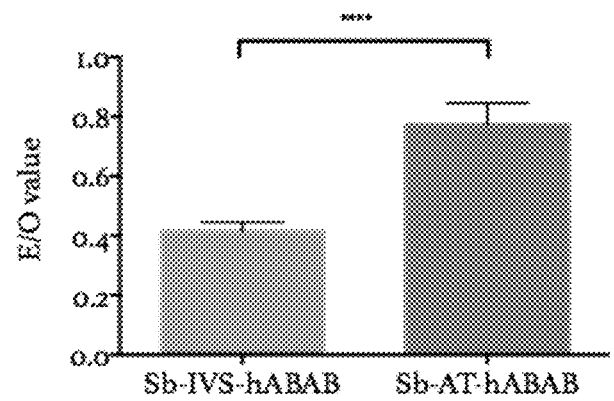

In addition, both the his-tag and D7-tag in the original ABAB construct (pD1214-FAKS-His-hABAB-D7) were removed to produce plasmid pD1214-FAKS-hABAB (SEQ ID NO:69) and culture incubation temperature was raised to 37° C. to better accommodate in vivo and clinical testing relevant scenarios. All 11 plasmids were then transformed in BY4741 and 5 independent colonies from each selective plate were selected to generate culture supernatants. The amount of secreted ABAB was determined by the same ELISA as described above. In addition, E/O value was used to provide a fair comparison across all groups. E/O value is defined by ELISA O.D. value normalizes against culture O.D. value. Two of the best secretion signals for ABAB were found to be AT and IVS (Table 4; FIG. 15A).

Due to the unavailability of an auxotrophic mutant strain for S. boulardii, another 2 um-based plasmid carrying the aphA1 gene encoding resistance to G418 (pCEV-G4-Km; SEQ ID NO:80; a gift from Lars Nielsen & Claudia Vickers (Addgene plasmid #46819)) was used instead of pD1214 plasmids to confirm ABAB secretion in S. boulardii. The best two secretion signals for S. cerevisiae (AT and IVS) were fused with ABAB genetically and inserted in the pCEV-G4-Km plasmid backbone to generate plasmids pCEV-G4-Km-TEF-AT-hABAB* (SEQ ID NO:81) and pCEV-G4-Km-TEF-IVS-hABAB* (SEQ ID NO:82). Both plasmids were used to transform S. boulardii (strain MYA796) and ABAB secretion with AT and IVS in S. boulardii was comparable with S. cerevisiae as determined by ELISA (FIG. 15B). A further construct, pCEV-G4-Km-TEF-AT-hABAB (SEQ ID NO:83), was prepared which differs from pCEV-G4-Km-TEF-AT-hABAB* in that it contains a molecular cloning site between the AT and hABAB sequence.

ABAB secretion was then further optimized by yeast codon optimization (yABAB) at the nucleotide level in the construct having the AT secretion signal, producing plasmid pCEV-G4-Km-TEF-AT-yABAB (SEQ ID NO:84). A sequence containing 40 nucleotides between $P_{TEF}$ and ABAB coding sequence was also found to be dispensable for ABAB secretion and removed resulting in plasmid pCEV-G4-Km-TEF-X40-AT-yABAB (SEQ ID NO:85). A further sequence containing two restriction cloning sites between AT and ABAB sequence was found to negatively impact ABAB secretion and therefore this sequence was also omitted (plasmid pCEV-G4-Km-TEF-AT-$^{RS}$yABAB; SEQ ID NO:115) for subsequent study to maximize ABAB secretion.

Next, the amount of secretion of the individual monomers was measured and AA6 was found to be secreted the least. To improve AA6 secretion, and thus further optimize ABAB secretion, a panel of key amino acid residues was utilized. A T83N mutation was found to improve AA6 secretion. In addition, S. boulardii carrying the hAA6 sequence was found to secrete more AA6 than the one carrying the yeast optimized yAA6 sequence. Therefore, a comparison was undertaken between ABAB carrying the T83N mutation within AA6 (AT-yABAB T83N; plasmid pCEV-G4-Km-TEF-AT-yABAB AA6T83N; SEQ ID NO:116) and ABAB where the yAA6 sequence was replaced by the hAA6 T83N sequence (AT-yABAB hAA6 T83N; plasmid pCEV-G4-Km-TEF-AT-yABAB hAA6T83N, which has the sequence of SEQ ID NO:90 but lacks the coding sequence for c-Myc)) to determined which sequence exhibited better secretion. It was found that there was no significance difference between these constructs and AT-yABAB hAA6 T83N was concluded as the final sequence moving forward. The nucleotide sequence encoding AT-yABAB hAA6 T83N is provided in plasmid pCEV-G4-Km-TEF-AT-yABAB hAA6T83N-tagless (SEQ ID NO:90). The amino acid sequence of AT-yABAB hAA6 T83N is provided in SEQ ID NO:117.

Generation of an Auxotrophic S. boulardii Strain

The expression plasmid encoding ABAB can be cloned into the S. boulardii strain. The S. boulardii strain can tolerate normal body temperature and acidic conditions better than S. cerevisiae, which can improve efficacy as a novel oral yeast-based therapeutic strategy. Two modifications to a wild-type S. boulardii strain can be made to preserve the in vivo stability of the expression plasmid conferred by the yeast URA3 metabolic selection marker: 1) a diploid auxotrophic mutant carrying a deletion in both chromosomal alleles of URA3 can be constructed, and 2) the endogenous 2 micron circle can be cured from *S. boulardii* to prevent unintended recombination from interfering with ABAB expression.

The most straightforward and efficient method for constructing auxotrophic mutants in wild-type *Saccharomyces* strains involves targeted deletion of chromosomally encoded genes by homologous recombination, which occurs at very high frequencies in *Saccharomyces*. Complete deletion of the targeted gene is preferred over selection of spontaneous mutations which can revert back to the wild type. Thus a gene deletion is preferred for the haploid state in *S. cerevisiae* which is typically induced from wild-type diploid via sporulation using a nutritionally poor growth medium and incubating at low temperature (30° C.). However, *S. boulardii* is sporulation deficient and recalcitrant to formation of haploid cells under normal sporulation conditions [64,65]. A two-step process for deletion of both chromosomal gene alleles (e.g. URA3) was used in which each deletion step can be selected for. The process is outlined schematically in FIG. 16.

All chromosomal deletions were carried out by lithium acetate-facilitated genetic transformation [73] of linear DNA deletion cassettes. Lithium acetate-based transformation originated from a *S. cerevisiae* protocol and was found to be compatible with *S. boulardii* although *S. boulardii* was found to be much harder to transform [55,56]. The difference is around 100 fold. Transformation efficiency in *S. cerevisiae* can be improved by adjusting glucose concentration and heat shock time [74]. Therefore various glucose concentrations and heat shock times were incorporated in *S. boulardii* transformation for optimization. The best condition tested for *S. boulardii* was 2% glucose in preculture and 20 minutes of heat shock time at 42° C. and these conditions were used for all transformation procedures in all studies.

Figure 16:
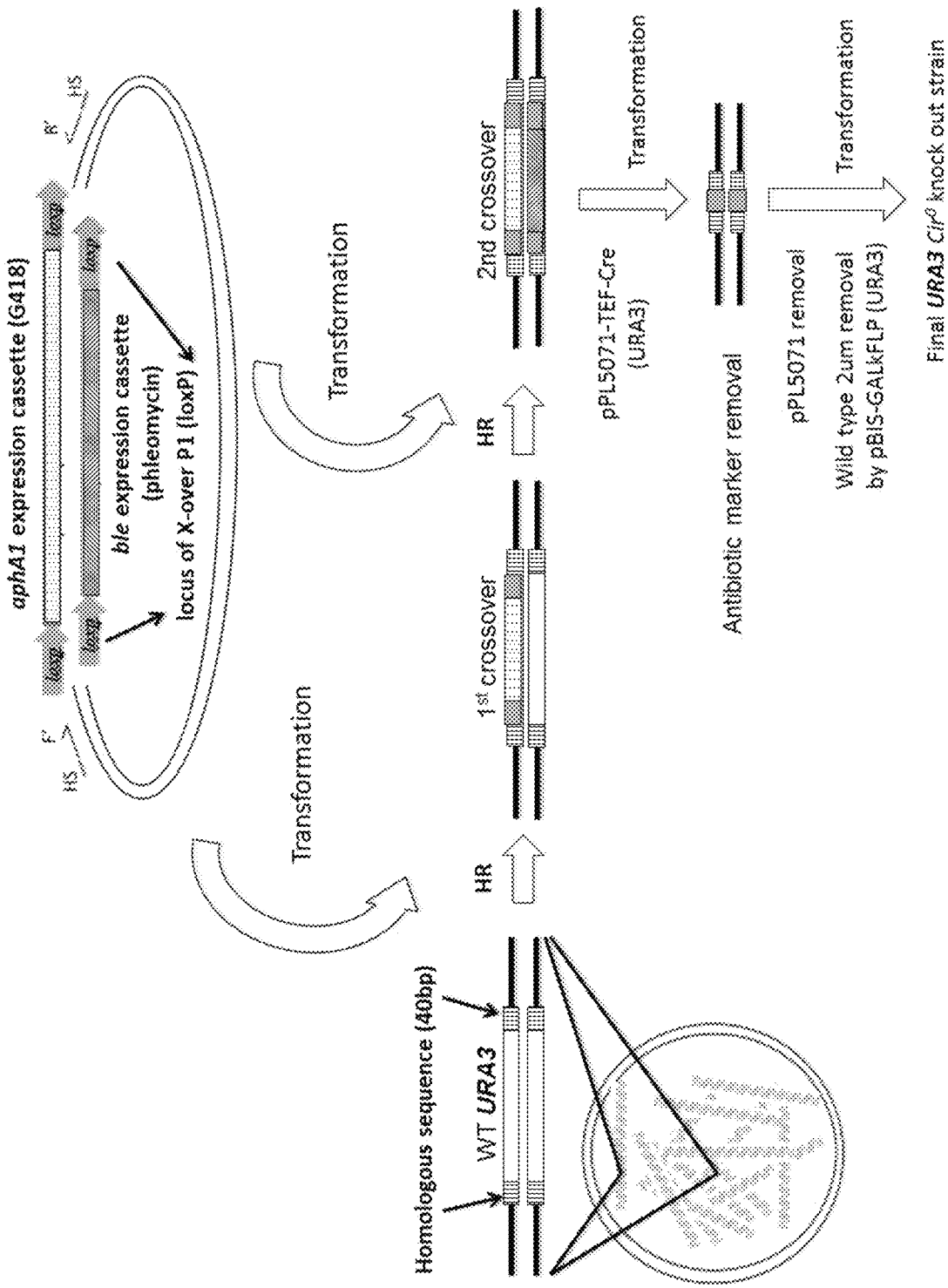
FIG. 16. A diagram of targeted deletion of chromosomally encoded genes by homologous recombination in *S. boulardii*.

Two deletion cassettes containing the genes aphA1 and ble, which confer resistance to G418 and phleomycin in yeast respectively, were generated by PCR using pCEV-G4-Km (SEQ ID NO:80) and pCEV-G4-Ph (SEQ ID NO:86) (a gift from Lars Nielsen & Claudia. Vickers (Addgene plasmid #46820)) as templates. Both deletion cassettes are flanked by two locus of X-over P1 (loxP) in the same direction, allowing for antibiotic resistance genes spin out using Cre-recombinase. 40 base pairs of homologous sequences upstream of URA3 promoter ($P_{URA3}$) and downstream of the stop codon of URA3 were incorporated in PCR primers to generate two final deletion cassettes for site-specific gene deletion in *S. boulardii* (see FIG. 16). The exact sequence and location of URA3 gene on chromosome V on *S. boulardii* was mapped using URA3 gene annotation from online-published sequence from *Saccharomyces* genome database (SGD). Selection for crossover 1 replacing the first URA3 allele with aphA1 deletion cassette is selected for using resistance to G418 [66]; the second crossover replacing the second URA3 allele with ble deletion cassette is selected for using resistance to phleomycin [75] (FIG. 16). The replacement of both URA3 alleles with aphA1 and ble deletion cassettes was evidenced by resistance to both antibiotics (data not shown) as well as lack of growth on minimal synthetic medium plates lacking uracil (data not shown). Yeast phenotype was also confirmed by growth on Sabouraud plate with chloramphenicol (100 ug/ml) (data not shown). In addition, three sets of unique primers targeting the URA3, aphA1 or ble genes in the URA3 chromosomal region was designed and performed PCR using wild type (WT), URA3Δ::aphA1/URA3 ($1^{st}$ crossover) and URA3Δ::aphA1/Δ::ble ($2^{nd}$ crossover) genomic DNA as templates. Expected PCR product sizes targeting the URA3, aphA1 or ble genes in the URA3 chromosomal region are 766 bp, 1183 bp, and 662 bp respectively. DNA electrophoresis of PCR products from WT, $1^{st}$ crossover and $2^{nd}$ crossover clones using these three sets of unique primers confirmed the absence of URA3 alleles and integration of the aphA1 and ble deletion cassettes of the $2^{nd}$ crossover strain.

The $2^{nd}$ crossover strain was then transformed with pPL5071_TEF1-Cre URA3 (pPL5071; SEQ ID NO:95) [76] to remove the aphA1 and ble deletion cassettes. Strain carries pPL5071 expresses Cre recombinase constitutively under $P_{TEF}$. Cre recombinase then targets loxp sequences flanking the aphA1 and ble deletion cassettes; this causes the excision of the aphA1 and ble deletion cassettes, leaving only one loxp site in the URA3 chromosomal region. Strains that underwent successful excision of the aphA1 and ble deletion cassettes cannot grow in the presence of either G418 or phleomycin; yet retain the loss of both URA3 alleles, therefore can only grow on minimal synthetic medium plate in the presence of uracil and showed no growth on minimal synthetic medium plate without uracil supplement.

Removal of pPL5071 was achieved by growth in YPD and selecting for colonies later grown on minimal synthetic medium containing uracil and the pyrimidine analog 5-fluoro-orotic acid (5-FOA) [77]. Strains possessing pPL5071 carry the URA3 gene that can synthesize the toxic intermediate 5-fluorodeoxyuridine a potent inhibitor of thymidylate synthetase, which interrupts DNA synthesis and leads to cell death and allows selection of strains that have lost pPL5071. The absence of pPL5071 also was confirmed by pPL5071 specific primers by PCR and DNA electrophoresis of the PCR product.

The 2 um plasmid is a very stable 6.1 kb plasmid that is ubiquitous in *Saccharomyces* strains. This plasmid confers no selective advantage to the yeast host organism, and it is remarkably stable due to the presence of an efficient REP1-REP2-STB plasmid partitioning system [68]. *S. boulardii* strains used also contain this plasmid as confirmed via PCR. To remove the 2 um plasmid, pBIS-GALkFLP-URA3 (SEQ ID NO:87) [67] was used to cure 2 um plasmid, followed by removal with uracil and 5-FOA. Loss of the 2 um plasmid was confirmed by PCR using primers specific for the origin of replication.

The auxotrophic strain of *S. boulardii* that results from these manipulations is termed *S. boulardii* URA3 Δ/Δ.

Auxotrophic *S. boulardii* Strain for In Situ Delivery of ABAB

Figure 17:
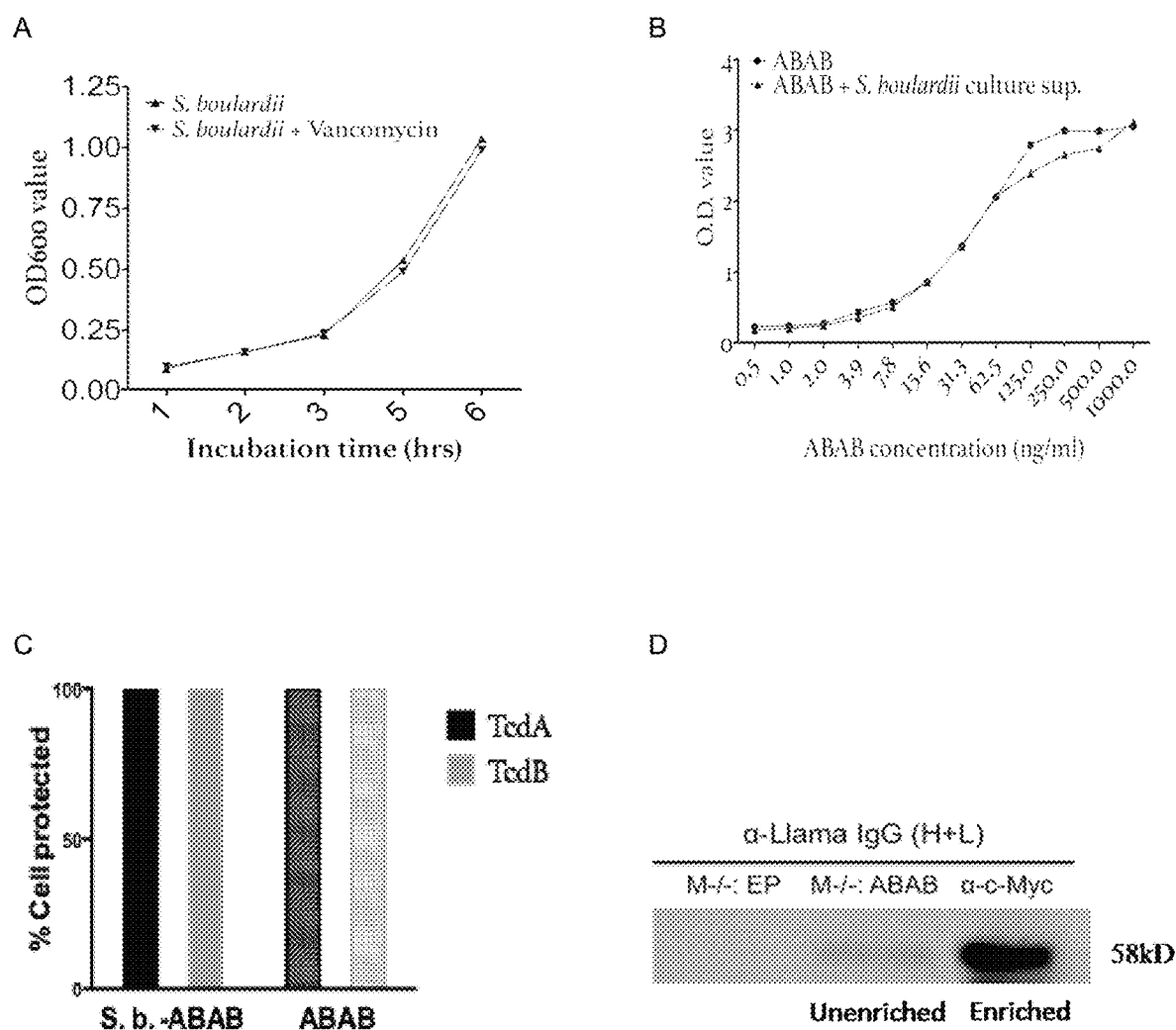
FIGS. 17A-17D. *S. boulardii* URA3Δ/Δ expressing ABAB.

For constructing the auxotrophic *S. boulardii* strain for in situ delivery of ABAB, the aphA1 cassette of the plasmid pCEV-G4-Km-TEF-X40-AT-yABAB (SEQ ID NO:85) was replaced by the URA3 cassette from pD plasmid to generate the plasmid pCEV-URA3-TEF-AT-yABAB-cMyc (SEQ ID NO:88). This plasmid was then used to transform *S. boulardii* URA3 Δ/Δ. The resulting strain secretes fully functional ABAB when compared with purified ABAB in a cell toxicity assay (FIG. 17C). Western blotting showed the corresponding ABAB band from *S. boulardii* culture supernatant using α-Llama antibodies conjugated with HRP (FIG. 17D). C-terminus end of ABAB contains c-Myc tag and can be further pulled down by a-c-Myc antibodies (FIG. 17D).

For empty plasmid (EP) control, AT-yABAB sequence was later removed from pCEV-URA3-TEF-AT-yABAB-cMyc (SEQ ID NO:88) to generate pCEV-URA3-TEF-cMyc (SEQ ID NO:89). *S. boulardii* URA3 Δ/Δ strain transformed with this plasmid results a strain complemented with URA3 but does not secrete ABAB. *S. boulardii* URA3

Δ/Δ strain secreting ABAB also showed no growth inhibition when cultured in YPD containing vancomycin (1 mg/ml) (FIG. 17A). This suggests S. boulardii can be co-administered with vancomycin typically used to treat CDI patients and secretes ABAB to treat ongoing CDI. In addition, purified ABAB is stable in culture supernatant collected from S. boulardii at O.D. 10 over 2 hours period of time suggests secreted ABAB is likely to diffuse out from S. boulardii without being degraded.

Safety Assessment of S. boulardii Delivered Orally to Antibiotic-Treated Mice

Prior to evaluating whether S. boulardii URA3 Δ/Δ expressing ABAB can protect mice in CDI models [20,33, 62,78], a safety assessment was performed to determine safe doses of S. boulardii in antibiotic-treated mice. In this safety assessment mice were first supplied with an antibiotic cocktail in their daily drinking water for three days and then switched to regular water. One day before oral delivery of S. boulardii, mice were injected with clindamycin intraperitoneally. This completes the antibiotic treatment for the mice and S. boulardii was then orally delivered to the mice for safety assessment, which includes monitoring of daily weight change and persistence of S. boulardii in their stool samples of these antibiotic-treated mice. Mice exhibited no signs of illness and steadily weight increase during 6 days of monitoring when $10^{10}$ cells of S. boulardii were delivered orally consistent with the idea of S. boulardii as a GRAS organism. For the subsequent CDI mouse studies, however, only $10^9$ cells of S. boulardii were given due to the ease of pellet resuspension and less variability of the dosing amount to the mice, which can occur with high viscosity present in resuspension. S. boulardii also shows limited colonization in these antibiotic-treated mice GI tracts; three days after the final gavage, no detectable S. boulardii were recovered from Sabouroud plate (data not shown).

Protection of S. boulardii Expressing ABAB Against Primary CDI in Mice

Figure 18:
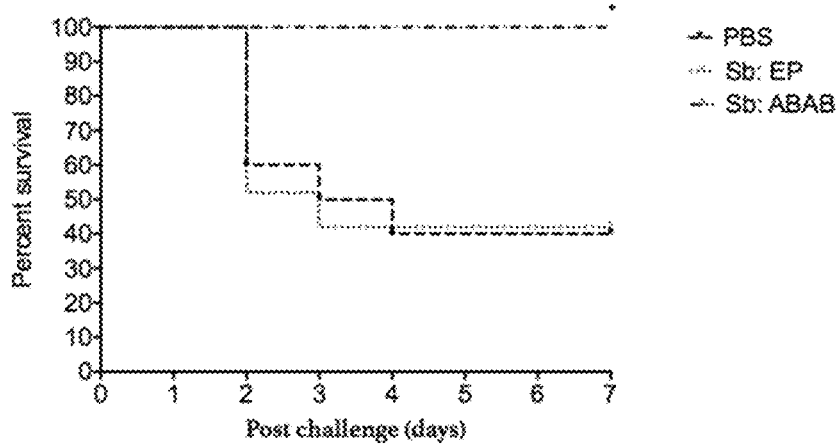
FIGS. 18A-18C. Protection of *S. boulardii* expressing ABAB in CDI prevention in mice.
Figure 18:
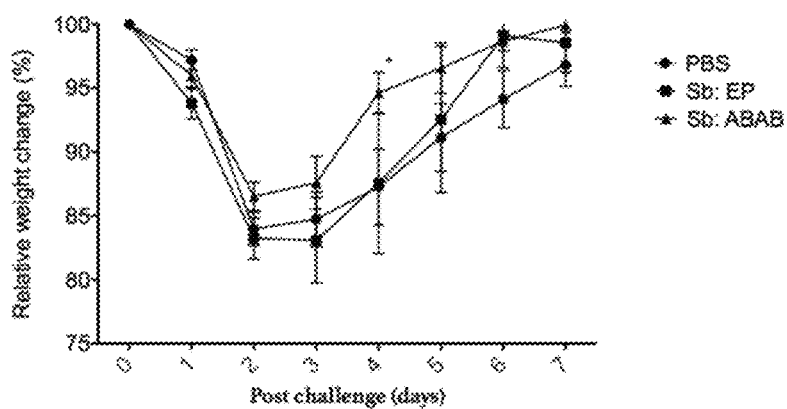
Figure 18:
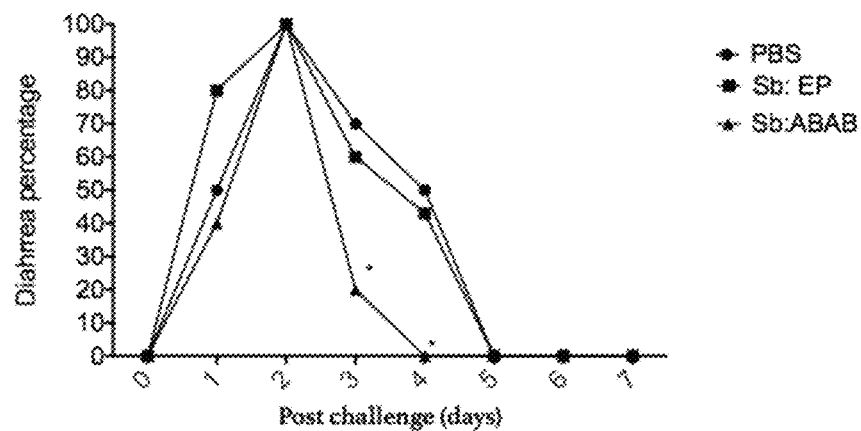
Figure 19:
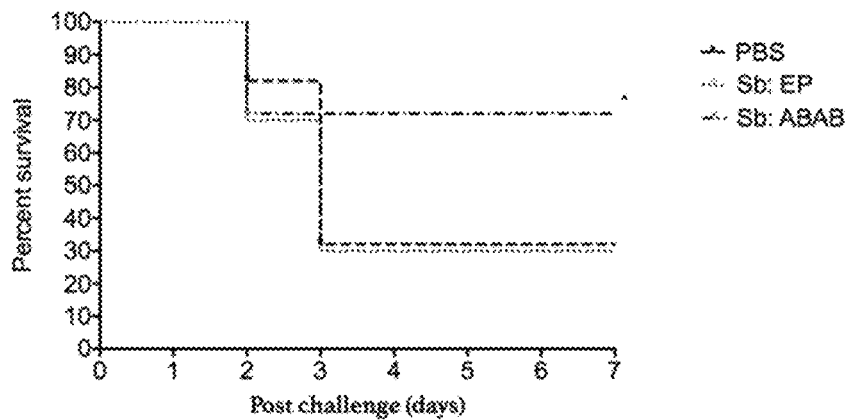
FIGS. 19A-19C. Protection of *S. boulardii* expressing ABAB in treating CDI mice.
Figure 19:
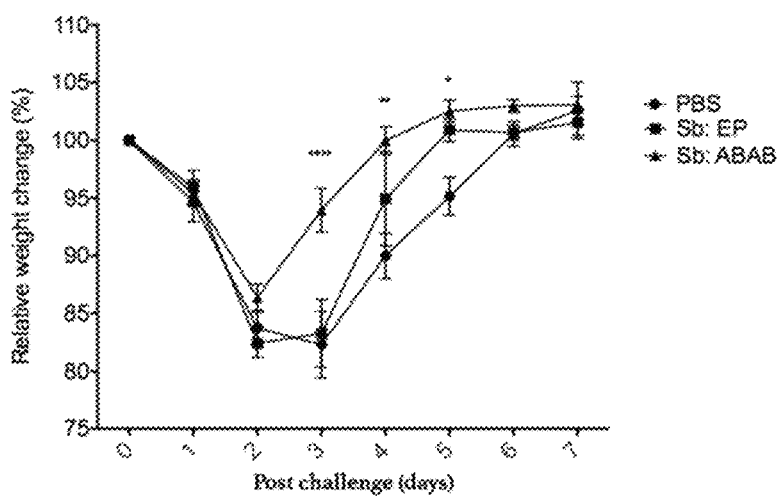
Figure 19:
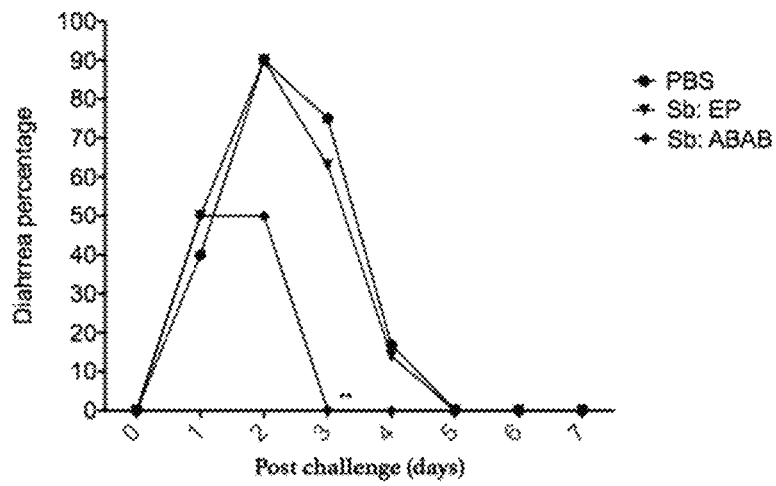

Protection of S. boulardii expressing ABAB was evaluated using established primary mouse CDI models. S. boulardii expressing ABAB was delivered either as preventative or treatment against primary CDI in mice. In brief, primary CDI was established in mice by supplementing a mixture of antibiotic into their drinking water for three days, and then intraperitoneal injection of clindamycin 24 hours prior to C. difficile spore challenge. $10^5$ C. difficile spores (UK1, a 027/BI/NAP1 epidemic strain) were gavaged in the mice to induce CDI. For preventative evaluation, mice started receiving an oral dose of S. boulardii the day after switching to regular drinking water, which continued every day for 7 days. For therapeutic evaluation, mice received an oral dose of S. boulardii at 6, 24, 48, and 72 hours after spore challenge. Controls included PBS and S. boulardii transformed with an empty plasmid. In both methods, mice receiving S. boulardii expressing ABAB were significantly protected against CDI-induced deaths (FIGS. 18A and 19A; PBS: negative control; Sb: EP: S. boulardii transformed with an empty plasmid; Sb: BAB: S. boulardii secreting ABAB). CDI mice typically suffered weight loss with most weight drops around day 2 to day 3 due to diarrhea and gradually recovered. Weights of mice receiving S. boulardii expressing ABAB recovered significantly sooner (FIGS. 18B and 19B) and had significant reduced percentage of diarrhea incidents after day 2 post challenge (FIGS. 18C and 19C).

Protection of S. boulardii Expressing ABAB Against Recurrence CDI in Mice

Figure 20:
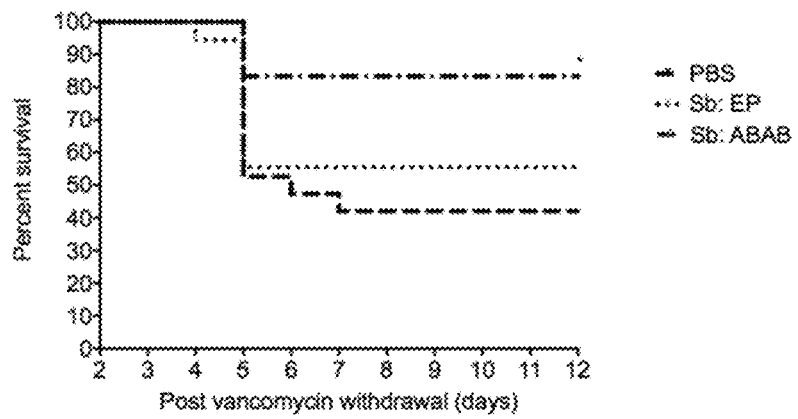
FIGS. 20A-20C. Protection of *S. boulardii* expressing ABAB in CDI recurrent mice.
Figure 20:
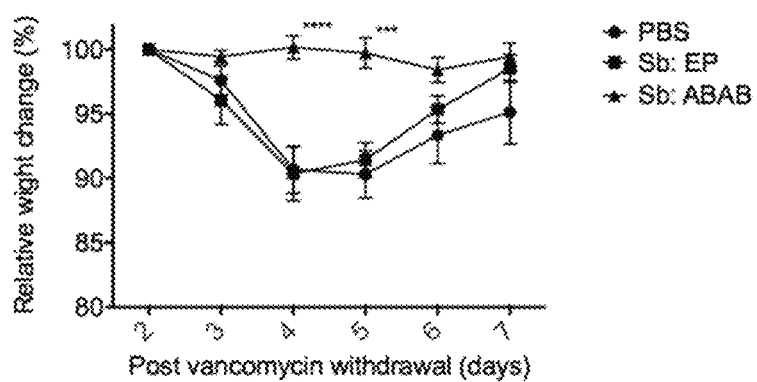
Figure 20:
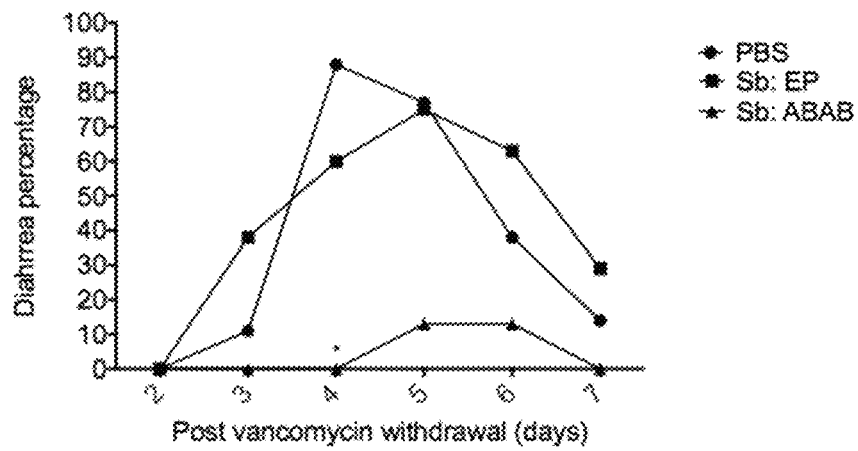

Protection of S. boulardii expressing ABAB was evaluated against recurrence CDI in mice. To induce recurrent CDI, mice were given three days of antibiotic cocktail in their daily drinking water. After three days of antibiotic water, mice were then switched back to drinking regular water. One day before oral delivery of $10^5$ C. difficile spores (UK1, a 027/BI/NAP1 epidemic strain), mice were injected with clindamycin intraperitoneally. Six hours after spore challenge, regular water was changed to water containing 0.5 mg/ml of vancomycin for six days and regular water was switched back again for the rest of study. Mice typically develop signs of CDI after 4 days of vancomycin withdrawal without another C. difficile spore challenge. During the course of recurrence model, S. boulardii was orally delivered along with vancomycin water once every day for 12 days. This model is used to evaluate protection efficacy of S. boulardii expressing ABAB for preventing CDI recurrence in mice. Survival rate, weight loss and diarrhea incident of these mice were monitored on a daily basis. Controls included PBS and S. boulardii transformed with an empty plasmid. Mice receiving S. boulardii expressing ABAB were significantly protected against recurrence-induced CDI deaths (FIG. 20A; PBS: negative control; Sb: EP: S. boulardii transformed with an empty plasmid; Sb: BAB: S. boulardii secreting ABAB). Similar to primary CDI mice, recurrent CDI mice also typically suffered weight loss with most weight drops around day 4 to day 5 after vancomycin water withdrawal. Mice receiving S. boulardii expressing ABAB were significantly protected from weight loss (FIG. 20B) and had significant reduced percentage of diarrhea recurrence incidents (FIG. 20C).

Stability Optimization of ABAB Cassette Through Chromosomal Integration

Genome editing using a CRISPR-Cas9 based system has been recently demonstrated both in S. cerevisiae and S. boulardii [79-81]. In addition, large fragment deletion can be achieved by targeting two guide sequences simultaneously [82]. Foreign genes are typically more steadily maintained when integrated into chromosomes versus introduced via plasmids when there is no selection pressure. However, chromosomal integration often requires multiple rounds of integration to achieve high copies. A protocol reported in a recent publication overcame this hurdle through targeting multiple copies of common sequences such as δ sites in S. cerevisiae genome through CRISPR-induced double stain breaks and achieved concurrent integration of large fragments in these sites [83]. DNA double strain break can be repaired either by non-homologous end joining or homologous recombination; however, when endogenous homologous sequences are present, host preferentially uses homologous sequences to repair DNA double strain break by homologous recombination [83].

δ sites are long terminal repeats (LTRs) belong to the Ty element I and II and are the most abundant LTRs in S. cerevisiae. There are five types of Ty elements (1-5) represented by the class II transposon (retrotransposon) that is more commonly found in S. cerevisiae. It is estimated that there are about 51 retrotransposons (Ty1-5) and 251 δ sites across S. cerevisiae genomes [84]. Such δ sites are appealing target sequences for ABAB expression cassette integration into S. boulardii chromosomes. However, much less is known about δ sites in S. boulardii. Therefore, Ty1-H3 (Genbank accession no. M18706) [84] was first used as a probe to survey Ty1-2 elements in S. boulardii strain MYA796 (ATCC, Manassas, Va.) (draft genome obtained from NCBI) to identify possible Ty1-2 elements and their δ sites in the S. boulardii genome. Surprisingly, no full Ty1-2 elements were found in MYA796. A total of 57 δ sites were found; this includes 44 full δ sites and 12 partial sites as well as a partial Ty element containing 1 full δ site identified across all 16 chromosomes (Table 12).

TABLE 12

Number of δ sites and their distribution on MYA796 chromosomes

|  | Full δ site | Full Ty1, 2 elements | Partial δ site 60 < X < 200 bp | Partial Ty1, 2 element with full δ site |
|---|---|---|---|---|
| Ch I | 0 | 0 | 1 | 0 |
| Ch II | 0 | 0 | 0 | 0 |
| Ch III | 1 | 0 | 0 | 0 |
| Ch IV | 5 | 0 | 1 | 1 |
| Ch V | 2 | 0 | 1 | 0 |
| Ch VI | 2 | 0 | 0 | 0 |
| Ch VII | 8 | 0 | 1 | 0 |
| Ch VIII | 2 | 0 | 0 | 0 |
| Ch IX | 3 | 0 | 0 | 0 |
| Ch X | 3 | 0 | 1 | 0 |
| Ch XI | 0 | 0 | 0 | 0 |
| Ch XII | 8 | 0 | 1 | 0 |
| Ch XIII | 2 | 0 | 1 | 0 |
| Ch XIV | 1 | 0 | 0 | 0 |
| Ch XV | 2 | 0 | 4 | 0 |
| Ch XVI | 5 | 0 | 1 | 0 |
| Total | 44 | 0 | 12 | 1 |

Figure 21:
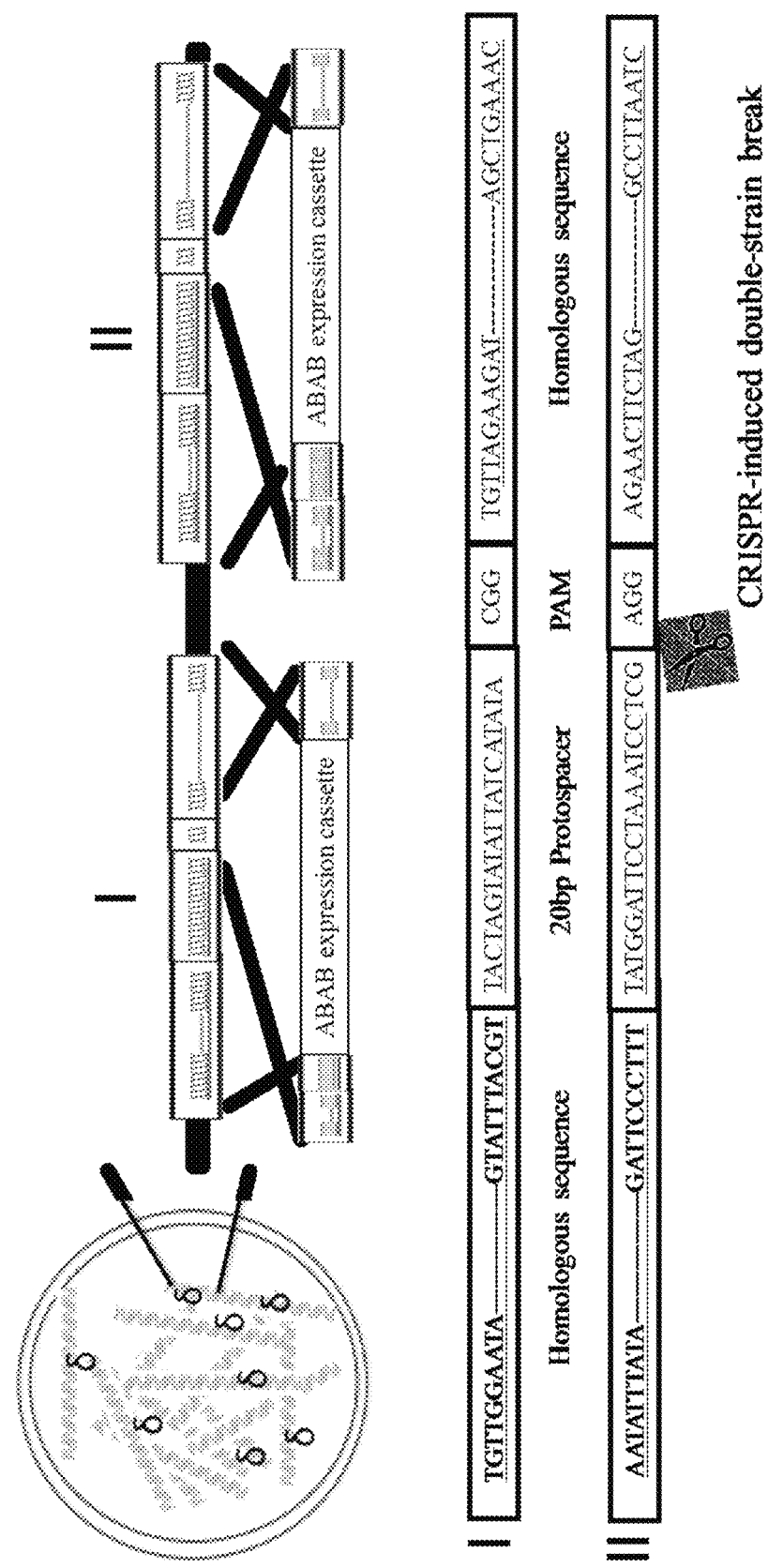
FIG. 21. A diagram of δ site-targeted chromosomal integration using CRISPR. Ty1-H3 (Genbank accession no. M18706) was used to blast against draft genome of MYA796 to obtain δ site sequences. Compiled sequences were used to identify common protospacer adjacent motif (PAM) sites and protospacers. Two PAM site sequences were chosen based on best coverage for multiple sites and common homologous sequences located upstream and downstream of the protospacer and PAM sites for simple integration of ABAB expression cassette. PAM site "I" is provided in SEQ ID NO:93; PAM site "II" is provided in SEQ ID NO:94. Homologous recombination sequences used in primers to generate ABAB expression cassette by PCR are underlined.

Due to *S. boulardii* diploid state; there are about 114 δ sites across the *S. boulardii* genome. To allow simple multiple δ site targeting by CRISPR, all 57 δ site sequences were compiled for multiple sequence alignment using MUSCLE to identify protospacer adjacent motif (PAM) sites that present in high numbers among the 57 δ sequences. Two PAM sites were chosen based on the highest number of δ sequences having uniformity in protospacers as the upstream and downstream sequences. The sequences of these PAM sites are illustrated in FIG. 21 and the specific sequences are as follows:

PAM Site I (SEQ ID NO: 93)
TGTTGGAATAAAAATCAACTATCATCTACTAACTAGTATTTACGTTACTA

GTATATTATCATATACGGTGTTAGAAGATGACGCAAATGATGAGAAATAG

TCATCTAAATTAGTGGAAGCTGAAAC

PAM Site II (SEQ ID NO: 94)
AATATTTATAGAATTGTGTAGAATTGCAGATTCCCTTTTATGGATTCCTA

AATCCTCGAGGAGAACTTCTAGTATATCTACATACCTAATATTATAGCCT

TAATC.

In both Pam Site I and Pam Site II, the sequences underscored by a dashed line correspond to the upstream homologous sequences; the sequences underscored by a single line correspond to the 20 bp protospacers; the sequences underscored by a double line correspond to the PAM sequences; the sequences underscored by a wavy line correspond to the downstream homologous sequences.

These two PAM sites, accompanied by their common upstream and downstream homologous sequences within the δ sites, allow simple chromosomal integration of ABAB expression cassettes into *S. boulardii* genomes. ABAB integration cassettes containing homologous recombination sequences were generated by PCR using primers containing the upstream homologous sequences with the last three nucleotides removed at the 3' end and the downstream homologous sequences with the first two nucleotides removed at the 5' end and the corresponding annealing sequences needed for PCR using plasmid pCEV-G4-Km-TEF-AT-yABAB hAA6T83N-tagless as template (SEQ ID NO:90).

Figure 22:
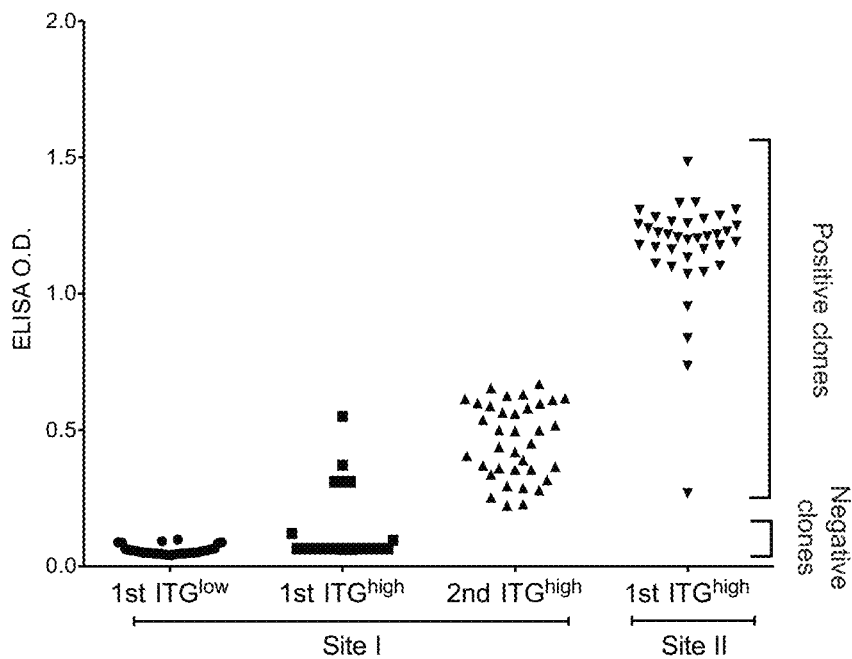
FIGS. 22A-22B. ABAB secretion of *S. boulardii* using CRISPR-based targeting δ site chromosomal integration.
Figure 22:
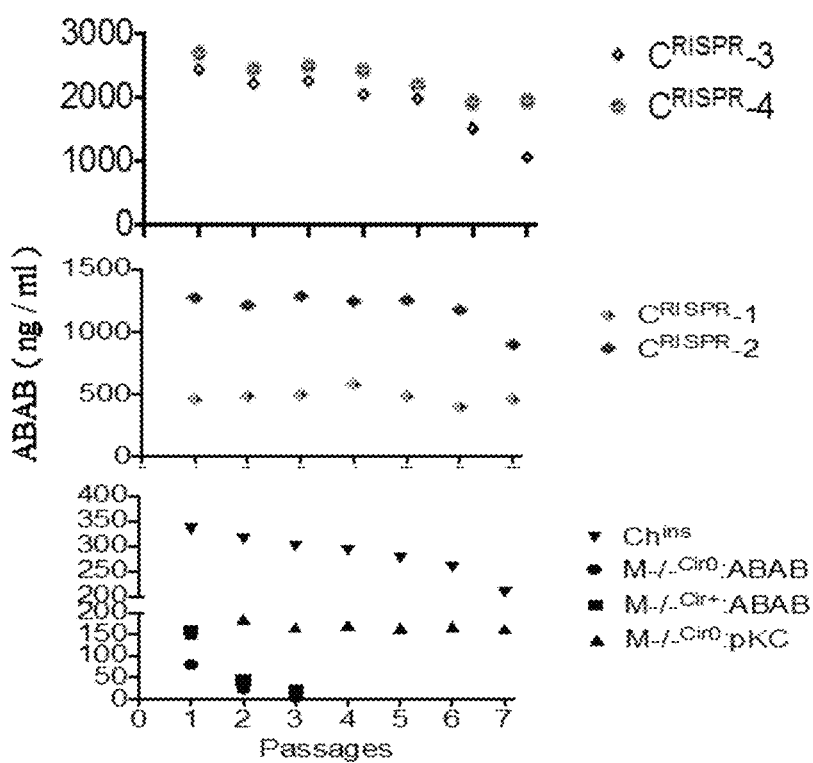
Figure 23:
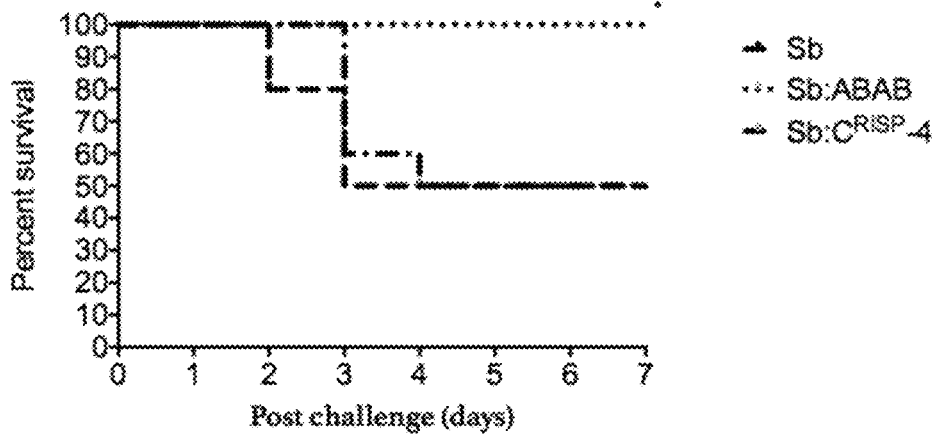
FIGS. 23A-23C. Protection of *S. boulardii* expressing ABAB in treating CDI mice.
Figure 23:
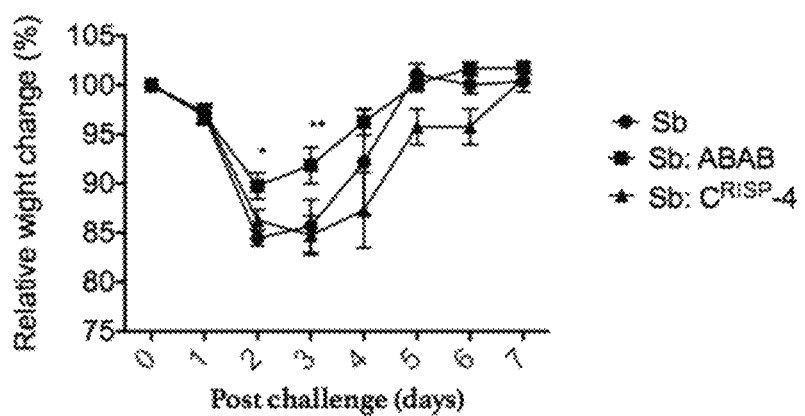
Figure 23:
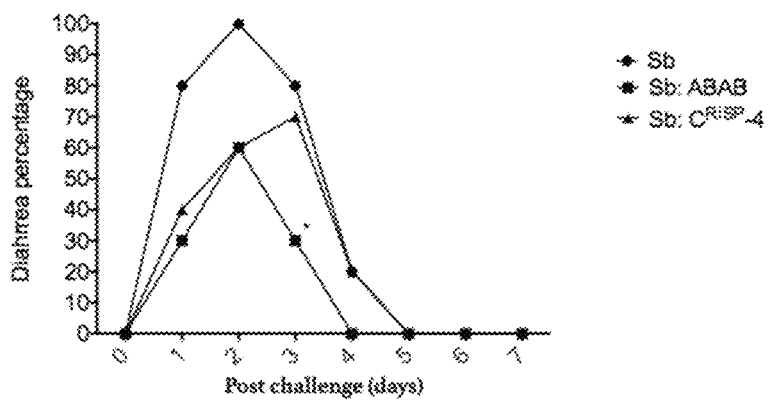

PCR products of the ABAB integration cassette with CRISPR plasmids contain the corresponding guide sequence (pCRI-Sb-δ1 (SEQ ID NO:91) and pCRI-Sb-δ2 (SEQ ID NO:92)) were then cotransformed with *S. bouladii* for ABAB integrations into chromosomes independently and sequentially to target PAM site I and PAM site II. The ratio of PCR product to CRISPR plasmid was found to be important for generating successful integration clones (FIG. 22A; ITG$^{low}$ versus ITG$^{high}$). In addition, a repeat transformation of the highest ABAB secretion clone from ITG$^{high}$ group with the same integration cassette and CRISPR plasmid did not further improve the overall ABAB secretion of independent clones (FIG. 22A; $2^{nd}$ ITG$^{high}$). ABAB secretion of the highest ABAB secretion clone (C$^{RISPR}$-2) from ITG$^{high}$ group was then further improved by cotransforming the second set of ABAB integration cassette containing the homologous recombination sequences and its corresponding guide sequence in CRISPR plasmid targeting site II (FIG. 22A). Two highest ABAB secretion clones, C$^{RISP}$-3 and C$^{RISPR}$-4 were selected. ABAB secretion amount and stability over time of these four representative clones are shown in FIG. 22B. A preliminary mouse CDI study was performed. However, C$^{RISPR}$-4 was found to be not better than previously M−/−:ABAB clone that showed protection in a number of mouse CDI models (FIG. 23).

While the invention has been described with reference to certain particular embodiments thereof, those skilled in the art will appreciate that various modifications may be made without departing from the spirit and scope of the invention. The scope of the appended claims is not to be limited to the specific embodiments described.

REFERENCES

All patents and publications mentioned in this specification are indicative of the level of skill of those skilled in the art to which the invention pertains. Each cited patent and publication is incorporated herein by reference in its entirety. All of the following references have been cited in this application:

1. Cloud, J. & Kelly, C. P. Update on *Clostridium difficile* associated disease. *Curr Opin Gastroenterol* 23, 4-9 (2007).
2. Kelly, C. P. & LaMont, J. T. *Clostridium difficile*—more difficult than ever. *N Engl J Med* 359, 1932-1940 (2008).
3. Barbut, F., et al. Epidemiology of recurrences or reinfections of *Clostridium difficile*-associated diarrhea. *J Clin Microbiol* 38, 2386-2388 (2000).
4. Hassoun, A. & Ibrahim, F. Use of intravenous immunoglobulin for the treatment of severe *Clostridium difficile* colitis. *Am J Geriatr Pharmacother* 5, 48-51 (2007).
5. Shahani, L. & Koirala, J. Intravenous immunoglobulin in treatment of *Clostridium difficile* colitis. *BMJ Case Rep* 2012(2012).
6. Saito, T., et al. Evidence of intravenous immunoglobulin as a critical supportive therapy against *Clostridium difficile* toxin-mediated lethality in mice. *J Antimicrob Chemother* 66, 1096-1099 (2011).

7. Abougergi, M. S. & Kwon, J. H. Intravenous immunoglobulin for the treatment of *Clostridium difficile* infection: a review. *Dig Dis Sci* 56, 19-26 (2011).
8. Sokol, H., Maury, E., Seksik, P., Cosnes, J. & Beaugerie, L. Single immunoglobulin infusion can reverse hemodynamic failure associated with severe *Clostridium difficile* colitis. *Am J Gastroenterol* 104, 2649-2650 (2009).
9. Lowy, I., et al. Treatment with monoclonal antibodies against *Clostridium difficile* toxins. *N Engl J Med* 362, 197-205 (2010).
10. Louie, T. J., et al. Fidaxomicin versus vancomycin for *Clostridium difficile* infection. *The New England journal of medicine* 364, 422-431 (2011).
11. Rao, K. & Young, V. B. Fecal Microbiota Transplantation for the Management of *Clostridium difficile* Infection. *Infectious disease clinics of North America* 29, 109-122 (2015).
12. Vyas, D., Aekka, A. & Vyas, A. Fecal transplant policy and legislation. *World journal of gastroenterology: WJG* 21, 6-11 (2015).
13. Tonna, I. & Welsby, P. D. Pathogenesis and treatment of *Clostridium difficile* infection. *Postgrad Med J* 81, 367-369 (2005).
14. McFarland, L. V., Elmer, G. W. & Surawicz, C. M. Breaking the cycle: treatment strategies for 163 cases of recurrent *Clostridium difficile* disease. *The American journal of gastroenterology* 97, 1769-1775 (2002).
15. O'Neill, G. L., Beaman, M. H. & Riley, T. V. Relapse versus reinfection with *Clostridium difficile*. *Epidemiol Infect* 107, 627-635 (1991).
16. Wilcox, M. H., Fawley, W. N., Settle, C. D. & Davidson, A. Recurrence of symptoms in *Clostridium difficile* infection—relapse or reinfection? *J Hosp Infect* 38, 93-100 (1998).
17. Johnson, S., Adelmann, A., Clabots, C. R., Peterson, L. R. & Gerding, D. N. Recurrences of *Clostridium difficile* diarrhea not caused by the original infecting organism. *J Infect Dis* 159, 340-343 (1989).
18. Tang-Feldman, Y., Mayo, S., Silva Jr, J., Jr. & Cohen, S. H. Molecular analysis of *Clostridium difficile* strains isolated from 18 cases of recurrent *Clostridium difficile*-associated diarrhea. *J Clin Microbiol* 41, 3413-3414 (2003).
19. Johnson, S. Recurrent *Clostridium difficile* infection: causality and therapeutic approaches. *Int J Antimicrob Agents* 33 Suppl 1, S33-36 (2009).
20. Sun, X., et al. Mouse relapse model of *Clostridium difficile* infection. *Infection and immunity* 79, 2856-2864 (2011).
21. Seal, D., et al. Treatment of relapsing *Clostridium difficile* diarrhoea by administration of a non-toxigenic strain. *Eur J Clin Microbiol* 6, 51-53 (1987).
22. Kuehne, S. A., et al. The role of toxin A and toxin B in *Clostridium difficile* infection. *Nature* (2010).
23. Lyras, D., et al. Toxin B is essential for virulence of *Clostridium difficile*. *Nature* 458, 1176-1179 (2009).
24. Libby, J. M. & Wilkins, T. D. Production of antitoxins to two toxins of *Clostridium difficile* and immunological comparison of the toxins by cross-neutralization studies. *Infection and immunity* 35, 374-376 (1982).
25. Katchar, K., et al. Association between IgG2 and IgG3 subclass responses to toxin A and recurrent *Clostridium difficile*-associated disease. *Clinical gastroenterology and hepatology: the official clinical practice journal of the American Gastroenterological Association* 5, 707-713 (2007).
26. Ghose, C., et al. Transcutaneous immunization with *Clostridium difficile* toxoid A induces systemic and mucosal immune responses and toxin A-neutralizing antibodies in mice. *Infection and immunity* 75, 2826-2832 (2007).
27. Sougioultzis, S., et al. *Clostridium difficile* toxoid vaccine in recurrent *C. difficile*-associated diarrhea. *Gastroenterology* 128, 764-770 (2005).
28. Kyne, L., Warny, M., Qamar, A. & Kelly, C. P. Association between antibody response to toxin A and protection against recurrent *Clostridium difficile* diarrhoea. *Lancet* 357, 189-193 (2001).
29. Leav, B. A., et al. Serum anti-toxin B antibody correlates with protection from recurrent *Clostridium difficile* infection (CDI). *Vaccine* 28, 965-969 (2010).
30. Fernie, D. S., Thomson, R. O., Batty, I. & Walker, P. D. Active and passive immunization to protect against antibiotic associated caecitis in hamsters. *Dev Biol Stand* 53, 325-332 (1983).
31. Kim, P. H., Iaconis, J. P. & Rolfe, R. D. Immunization of adult hamsters against *Clostridium difficile*-associated ileocecitis and transfer of protection to infant hamsters. *Infection and immunity* 55, 2984-2992 (1987).
32. Lyerly, D. M., Bostwick, E. F., Binion, S. B. & Wilkins, T. D. Passive immunization of hamsters against disease caused by *Clostridium difficile* by use of bovine immunoglobulin G concentrate. *Infection and immunity* 59, 2215-2218 (1991).
33. Wang, H., et al. A chimeric toxin vaccine protects against primary and recurrent *Clostridium difficile* infection. *Infection and immunity* 80, 2678-2688 (2012).
34. Hamers-Casterman, C., et al. Naturally occurring antibodies devoid of light chains. *Nature* 363, 446-448 (1993).
35. van der Linden, R., et al. Induction of immune responses and molecular cloning of the heavy chain antibody repertoire of *Lama glama*. *J Immunol Methods* 240, 185-195 (2000).
36. Harmsen, M. M. & De Haard, H. J. Properties, production, and applications of camelid single-domain antibody fragments. *Appl Microbiol Biotechnol* 77, 13-22 (2007).
37. Arbabi Ghahroudi, M., Desmyter, A., Wyns, L., Hamers, R. & Muyldermans, S. Selection and identification of single domain antibody fragments from camel heavy-chain antibodies. *FEBS Lett* 414, 521-526 (1997).
38. van der Linden, R. H., et al. Comparison of physical chemical properties of llama VHH antibody fragments and mouse monoclonal antibodies. *Biochim Biophys Acta* 1431, 37-46 (1999).
39. Dumoulin, M., et al. Single-domain antibody fragments with high conformational stability. *Protein Sci* 11, 500-515 (2002).
40. Hussack, G., Hirama, T., Ding, W., Mackenzie, R. & Tanha, J. Engineered single-domain antibodies with high protease resistance and thermal stability. *PloS one* 6, e28218 (2011).
41. Yang, Z., et al. A novel multivalent, single-domain antibody targeting TcdA and TcdB prevents fulminant *Clostridium difficile* infection in mice. *The Journal of infectious diseases* 210, 964-972 (2014).
42. McFarland, L. V. Systematic review and meta-analysis of *Saccharomyces boulardii* in adult patients. *World J Gastroenterol.* 16, 2202-2222 (2010).
43. Elmer, G. W., McFarland, L. V., Surawicz, C. M., Danko, L. & Greenberg, R. N. Behaviour of *Saccharomyces* boulardii in recurrent *Clostridium difficile* disease patients. *Aliment. Pharmacol. Ther.* 13, 1663-1668 (1999).

44. Surawicz, C. M., et al. The search for a better treatment for recurrent *Clostridium difficile* disease: use of high-dose vancomycin combined with *Saccharomyces boulardii*. *Clin. Infect. Dis.* 31, 1012-1017 (2000).

45. McFarland, L. V., et al. A randomized placebo-controlled trial of *Saccharomyces boulardii* in combination with standard antibiotics for *Clostridium difficile* disease. *Jama* 271, 1913-1918 (1994).

46. Czerucka, D., Piche, T. & Rampal, P. Review article: yeast as probiotics—*Saccharomyces boulardii*. *Alimentary pharmacology & therapeutics* 26, 767-778 (2007).

47. Sougioultzis, S., et al. *Saccharomyces boulardii* produces a soluble anti-inflammatory factor that inhibits NF-kappaB-mediated IL-8 gene expression. *Biochemical and biophysical research communications* 343, 69-76 (2006).

48. Qamar, A., et al. *Saccharomyces boulardii* stimulates intestinal immunoglobulin A immune response to *Clostridium difficile* toxin A in mice. *Infection and immunity* 69, 2762-2765 (2001).

49. Chen, X., et al. *Saccharomyces boulardii* inhibits ERK1/2 mitogen-activated protein kinase activation both in vitro and in vivo and protects against *Clostridium difficile* toxin A-induced enteritis. *The Journal of biological chemistry* 281, 24449-24454 (2006).

50. Barc, M. C., et al. Molecular analysis of the digestive microbiota in a gnotobiotic mouse model during antibiotic treatment: Influence of *Saccharomyces boulardii*. *Anaerobe* 14, 229-233 (2008).

51. Gorlani, A., de Haard, H. & Verrips, T. Expression of VHHs in *Saccharomyces cerevisiae*. *Methods in molecular biology* 911, 277-286 (2012).

52. Khatri, I., et al. Gleaning evolutionary insights from the genome sequence of a probiotic yeast *Saccharomyces boulardii*. *Gut Pathog.* 5, 30 (2013).

53. Batista, T. M., Marques, E. T., Jr., Franco, G. R. & Douradinha, B. Draft Genome Sequence of the Probiotic Yeast *Saccharomyces cerevisiae* var. *boulardii* Strain ATCC MYA-796. *Genome announcements* 2, 578-579 (2014).

54. Hamedi, H., et al. Generation of a uracil auxotroph strain of the probiotic yeast *Saccharomyces boulardii* as a host for the recombinant protein production. *Avicenna journal of medical biotechnology* 5, 29-34 (2013).

55. Hudson, L. E., et al. Functional heterologous protein expression by genetically engineered probiotic yeast *Saccharomyces boulardii*. *PLoS One* 9, e112660 (2014).

56. Douradinha, B., et al. Novel insights in genetic transformation of the probiotic yeast *Saccharomyces boulardii*. *Bioengineered* 5, 21-29 (2014).

57. Fietto, J. L., et al. Molecular and physiological comparisons between *Saccharomyces cerevisiae* and *Saccharomyces boulardii*. *Canadian journal of microbiology* 50, 615-621 (2004).

58. Martins, F. S., et al. Screening of yeasts as probiotic based on capacities to colonize the gastrointestinal tract and to protect against enteropathogen challenge in mice. *The Journal of general and applied microbiology* 51, 83-92 (2005).

59. Martins, F. S., Veloso, L. C., Arantes, R. M. & Nicoli, J. R. Effects of yeast probiotic formulation on viability, revival and protection against infection with *Salmonella enterica* ssp. *enterica* serovar *Typhimurium* in mice. *Lett. Appl. Microbiol.* 49, 738-744 (2009).

60. Wu, D., Teng, D., Wang, X., Dai, C. & Wang, J. *Saccharomyces boulardii* prevention of the hepatic injury induced by *Salmonella Enteritidis* infection. *Can. J. Microbiol.* 60, 681-686 (2014).

61. Elmer, G. W. & Corthier, G. Modulation of *Clostridium difficile* induced mortality as a function of the dose and the viability of the *Saccharomyces boulardii* used as a preventative agent in gnotobiotic mice. *Can. J. Microbiol.* 37, 315-317 (1991).

62. Chen, X., et al. A mouse model of *Clostridium difficile*-associated disease. *Gastroenterology* 135, 1984-1992 (2008).

63. Pawlowski, S. W., et al. Murine model of *Clostridium difficile* infection with aged gnotobiotic C57BL/6 mice and a BI/NAP1 strain. *The Journal of infectious diseases* 202, 1708-1712 (2010).

64. McFarland, L. V. *Saccharomyces boulardii* is not *Saccharomyces cerevisiae*. *Clin. Infect. Dis.* 22, 200-201 (1996).

65. Edwards-Ingram, L., et al. Genotypic and physiological characterization of *Saccharomyces boulardii*, the probiotic strain of *Saccharomyces cerevisiae*. *Appl. Environ. Microbiol.* 73, 2458-2467 (2007).

66. Panchal, C. J., Whitney, G. K. & Stewart, G. G. Susceptibility of *Saccharomyces* spp. and *Schwanniomyces* spp. to the aminoglycoside antibiotic G418. *Appl. Environ. Microbiol.* 47, 1164-1166 (1984).

67. Tsalik, E. L. & Gartenberg, M. R. Curing *Saccharomyces cerevisiae* of the 2 micron plasmid by targeted DNA damage. *Yeast* 14, 847-852 (1998).

68. Chan, K. M., Liu, Y. T., Ma, C. H., Jayaram, M. & Sau, S. The 2 micron plasmid of *Saccharomyces cerevisiae*: a miniaturized selfish genome with optimized functional competence. *Plasmid* 70, 2-17 (2013).

69. Brake, A. J., et al. Alpha-factor-directed synthesis and secretion of mature foreign proteins in *Saccharomyces cerevisiae*. *Proceedings of the National Academy of Sciences of the United States of America* 81, 4642-4646 (1984).

70. Porro, D., Sauer, M., Branduardi, P. & Mattanovich, D. Recombinant protein production in yeasts. *Molecular biotechnology* 31, 245-259 (2005).

71. Chung, B. H., Nam, S. W., Kim, B. M. & Park, Y. H. Highly efficient secretion of heterologous proteins from *Saccharomyces cerevisiae* using inulinase signal peptides. *Biotechnology and bioengineering* 49, 473-479 (1996).

72. Hahm, M. S. & Chung, B. H. Secretory expression of human growth hormone in *Saccharomyces cerevisiae* using three different leader sequences. *Biotechnology and Bioprocess Engineering* 6, 306-309 (2001).

73. Gietz, R. D. & Schiestl, R. H. High-efficiency yeast transformation using the LiAc/SS carrier DNA/PEG method. *Nat. Protoc.* 2, 31-4 (2007).

74. Konishi, T. & Harata, M. Improvement of the transformation efficiency of *Saccharomyces cerevisiae* by altering carbon sources in pre-culture. *Biosci. Biotechnol. Biochem.* 78, 1090-1093 (2014).

75. Gatignol, A., Baron, M. & Tiraby, G. Phleomycin resistance encoded by the ble gene from transposon Tn 5 as a dominant selectable marker in *Saccharomyces cerevisiae*. *MGG Mol. Gen. Genet.* 207, 342-348 (1987).

76. Macdonald, C. & Piper, R. C. Puromycin- and methotrexate-resistance cassettes and optimized Cre-recombinase expression plasmids for use in yeast. *Yeast* 32, 423-438 (2015).

77. Boeke, J. D., LaCroute, F. & Fink, G. R. A positive selection for mutants lacking orotidine-5'-phosphate 78. Yang, Z. et al. Intravenous adenovirus expressing a multi-specific, single-domain antibody neutralizing TcdA and TcdB protects mice from *Clostridium difficile* infection. *Pathog. Dis.* 74, ftw078 (2016).
79. DiCarlo, J. E. et al. Genome engineering in *Saccharomyces cerevisiae* using CRISPR-Cas systems. *Nucleic Acids Res.* 41, 4336-43 (2013).
80. Bao, Z. et al. Homology-Integrated CRISPR-Cas (HI-CRISPR) System for One-Step Multigene Disruption in *Saccharomyces cerevisiae*. *ACS Synth. Biol.* 4, 585-594 (2015).
81. Liu, J.-J. et al. Metabolic engineering of a probiotic *Saccharomyces boulardii*. *Appl. Environ. Microbiol.* AEM.00057-16 (2016). doi:10.1128/AEM.00057-16
82. Hao, H. et al. Large fragment deletion using a CRISPR/Cas9 system in *Saccharomyces cerevisiae*. (2016). doi:10.1016/j.ab.2016.07.008.This
83. Shi, S., Liang, Y., Zhang, M. M., Ang, E. L. & Zhao, H. A highly efficient single-step, markerless strategy for multi-copy chromosomal integration of large biochemical pathways in *Saccharomyces cerevisiae*. *Metab. Eng.* 33, 19-27 (2016).
84. Kim, J. M. et al. Transposable Elements and Genome Organization: A Comprehensive Survey of Retrotransposons Revealed by the Complete *Saccharomyces cerevisiae*. *Genome Research.* 8(5): 464-478 (1998).
85. Bao Z, Xiao H, Liang J, Zhang L, Xiong X, Sun N, Si T, Zhao H. Homology-Integrated CRISPR—Cas (HI-CRISPR) System for One-Step Multigene Disruption in *Saccharomyces cerevisiae*. *ACS Synth Biol.* 4(5):585-94 (2015).
86. DiCarlo J E, Norville J E, Mali P, Rios X, Aach J, Church G M. Genome engineering in *Saccharomyces cerevisiae* using CRISPR-Cas systems. *Nucleic Acids Res* 41:4336-43 (2013).
87. Liu J-J, Kong I I, Zhang G-C, Jayakody L N, Kim H, Xia P-F, Kwak S, Sung B H, Sohn J-H, Walukiewicz H E, Rao C V., Jin Y-S. Metabolic engineering of a probiotic *Saccharomyces boulardii*. *Appl Environ Microbiol.* 82(8): 2280-7 (2016).
88. Shi S, Liang Y, Zhang M M, Ang E L, Zhao H. A highly efficient single-step, markerless strategy for multi-copy chromosomal integration of large biochemical pathways in *Saccharomyces cerevisiae*. *Metab Eng* 33:19-27 (2016).

What is claimed is:

1. An engineered strain of *Saccharomyces boulardii* yeast comprising a gene that produces a tetra-specific, tetrameric binding agent integrated into at least two chromosome sites, wherein the binding agent comprises linked first, second, third, and fourth $V_H$H peptide monomers, and wherein the $V_H$H peptide monomers each independently have binding specificity for an epitope of *Clostridium difficile* toxin A (TcdA) or toxin B (TcdB).

2. The engineered strain of *Saccharomyces boulardii* yeast of claim 1, wherein the first, second, third and fourth $V_H$H peptide monomers each has binding specificity for a different epitope.

3. The engineered strain of *Saccharomyces boulardii* yeast of claim 1, wherein two of the $V_H$H peptide monomers have binding specificity for epitopes of TcdA and two of the $V_H$H peptide monomers have binding specificity for epitopes of TcdB.

4. The engineered strain of *Saccharomyces boulardii* yeast of claim 1, wherein the $V_H$H peptide monomers each independently have binding specificity for an epitope in the glucosyltransferase domain, cysteine protease domain, translocation domain or receptor binding domain of TcdA or TcdB.

5. The engineered strain of *Saccharomyces boulardii* yeast of claim 1, wherein the binding agent is ABAB, wherein the first and third monomers have binding specificity for epitopes of TcdA and the first and third monomers are $V_H$H peptide monomers AH3 (SEQ ID NO:7) and AA6 (SEQ ID NO:5), respectively, and wherein the second and forth monomers have binding specificity for epitopes of TcdB and the second and forth monomers are $V_H$H peptide monomers 5D (SEQ ID NO:1) and E3 (SEQ ID NO:3), respectively.

6. The engineered strain of *Saccharomyces boulardii* yeast of claim 5, wherein the ABAB binding agent comprises the amino acid sequence set forth in SEQ ID NO:19, or a sequence variant having at least 95% sequence identity thereto, and wherein the sequence variant retains TcdA and/or TcdB binding specificity, or the sequence variant retains toxin neutralizing activity, or both.

7. The engineered strain of *Saccharomyces boulardii* yeast of claim 5, wherein the ABAB binding agent further comprises an N-terminal secretion signal selected from the AT secretion signal (MRFPSIFTAVLFAASSALA (SEQ ID NO:99)) and the IVS secretion signal (MLLQAFLFLLAGFAAKISA (SEQ ID NO:103)).

8. The engineered strain of *Saccharomyces boulardii* yeast of claim 5, wherein the ABAB binding agent is expressed from a plasmid within the yeast, wherein the ABAB binding agent comprises the amino acid sequence set forth in SEQ ID NO:107, or a sequence variant having at least 95% sequence identity thereto, and wherein the sequence variant retains TcdA and/or TcdB binding specificity, or the sequence variant retains toxin neutralizing activity, or both.

9. The engineered strain of *Saccharomyces boulardii* yeast of claim 8, wherein the plasmid is pCEV-URA3-TEF-AT-yABAB-cMyc (SEQ ID NO:88).

10. The engineered strain of *Saccharomyces boulardii* yeast of claim 5, wherein ABAB binding agent coding sequence is integrated into a chromosome of the yeast, wherein the ABAB binding agent comprises the amino acid sequence set forth in SEQ ID NO:109, or a sequence variant having at least 95% sequence identity thereto, and wherein the sequence variant retains TcdA and/or TcdB binding specificity, or the sequence variant retains toxin neutralizing activity, or both.

11. A pharmaceutical formulation comprising an engineered strain of *Saccharomyces boulardii* yeast of claim 1 and a pharmaceutically acceptable carrier of diluent.

12. The engineered strain of *Saccharomyces boulardii* yeast of claim 1, wherein the yeast expresses an exogenous URA3 gene.

* * * * *